US007608241B2

(12) United States Patent
Chinn et al.

(10) Patent No.: US 7,608,241 B2
(45) Date of Patent: Oct. 27, 2009

(54) RADIOLABELING METHOD

(75) Inventors: Paul Chinn, Vista, CA (US); Ronald A. Morena, El Cajon, CA (US); Michael J. LaBarre, San Diego, CA (US); John E. Leonard, Carlsbad, CA (US)

(73) Assignee: Rit Oncology, LLC, Seattle, WA (US)

( * ) Notice: Subject to any disclaimer, the term of this patent is extended or adjusted under 35 U.S.C. 154(b) by 0 days.

(21) Appl. No.: 11/033,439

(22) Filed: Jan. 12, 2005

(65) Prior Publication Data

US 2005/0169838 A1  Aug. 4, 2005

Related U.S. Application Data

(62) Division of application No. 09/259,337, filed on Mar. 1, 1999, now abandoned.

(51) Int. Cl.
*A61K 39/395* (2006.01)
(52) U.S. Cl. .................. 424/1.53; 424/179.1; 530/391.5
(58) Field of Classification Search ................ 424/1.53, 424/1.69, 179.1; 530/391.5
See application file for complete search history.

(56) References Cited

U.S. PATENT DOCUMENTS

| 3,994,966 A | 11/1976 | Sundberg et al. |
| 4,043,998 A | 8/1977 | Meares et al. |
| 4,315,851 A | 2/1982 | Yoshikumi et al. |
| 4,331,647 A | 5/1982 | Goldenberg |
| 4,348,376 A | 9/1982 | Goldenberg |
| 4,361,544 A | 11/1982 | Goldenberg |
| 4,401,592 A | 8/1983 | Yoshikumi et al. |
| 4,444,744 A | 4/1984 | Goldenberg |
| 4,454,106 A | 6/1984 | Gansow et al. |
| 4,460,559 A | 7/1984 | Goldenberg |
| 4,460,561 A | 7/1984 | Goldenberg |
| 4,472,509 A | 9/1984 | Gansow et al. |
| 4,622,420 A | 11/1986 | Meares et al. |
| 4,636,380 A | 1/1987 | Wong |
| 4,707,352 A | 11/1987 | Stavrianopoulos |
| 4,722,892 A | 2/1988 | Meares et al. |
| 4,735,210 A | 4/1988 | Goldenberg |
| 4,767,609 A | 8/1988 | Stavrianpoulos |
| 4,816,567 A | 3/1989 | Cabilly |
| 4,824,986 A | 4/1989 | Gansow et al. |
| 4,831,175 A | 5/1989 | Gansow et al. |
| 4,855,353 A | 8/1989 | Kurami et al. |
| 4,861,579 A | 8/1989 | Meyer, Jr. et al. |
| 4,921,690 A | 5/1990 | Beatty et al. |
| 4,923,985 A | 5/1990 | Gansow et al. |
| 5,009,069 A | 4/1991 | Molini |
| 5,034,223 A | 7/1991 | Abrams et al. |
| 5,059,518 A | 10/1991 | Kortright et al. |
| 5,101,827 A | 4/1992 | Goldenberg |
| 5,124,471 A | 6/1992 | Gansow et al. |
| 5,130,118 A | 7/1992 | Johnson et al. |
| 5,162,115 A | 11/1992 | Pietronigro |
| 5,208,008 A | 5/1993 | Ranadive et al. |
| 5,217,704 A | 6/1993 | Johnson et al. |
| 5,219,556 A | 6/1993 | Wolfangel |
| 5,246,692 A | 9/1993 | Gansow et al. |
| 5,286,850 A | 2/1994 | Gansoh et al. |
| 5,363,846 A | 11/1994 | Rubin et al. |
| 5,376,356 A | 12/1994 | Morgan, Jr. |
| 5,403,573 A | 4/1995 | Day et al. |
| 5,428,154 A | 6/1995 | Gansow et al. |
| 5,434,287 A | 7/1995 | Gansow et al. |
| 5,460,785 A | 10/1995 | Rhodes et al. |
| 5,500,362 A | 3/1996 | Robinson et al. |
| 5,541,287 A | 7/1996 | Yau et al. |
| 5,545,403 A | 8/1996 | Page |
| 5,545,405 A | 8/1996 | Page |
| 5,595,721 A | 1/1997 | Kaminski et al. |
| 5,620,675 A | 4/1997 | McBride et al. |
| 5,641,637 A | 6/1997 | Hudak et al. |
| 5,650,134 A | 7/1997 | Albert et al. |
| 5,698,178 A | 12/1997 | Goldenberg |
| 5,728,369 A | 3/1998 | Griffiths |
| 5,736,137 A | 4/1998 | Anderson et al. |
| 5,766,571 A | 6/1998 | Ceriani et al. |
| 5,820,845 A | 10/1998 | Dean et al. |
| 5,830,431 A | 11/1998 | Srinivasan et al. |
| 5,874,540 A | 2/1999 | Hansen et al. |
| 5,942,210 A | 8/1999 | Ultee et al. |
| 5,976,492 A | 11/1999 | Griffiths et al. |
| 6,010,680 A | 1/2000 | Govindan et al. |
| 6,994,840 B1 * | 2/2006 | Chinn ........................ 424/1.53 |

FOREIGN PATENT DOCUMENTS

| EP | 0 274 394 | 7/1988 |
| EP | 0315188 A2 | 5/1989 |
| EP | 0 529 645 A | 3/1993 |
| WO | WO 88/04936 | 7/1988 |
| WO | WO 92/07466 | 5/1992 |
| WO | WO 94/11026 A | 5/1994 |
| WO | WO 96/14879 | 5/1996 |

OTHER PUBLICATIONS

Goodwin, D A, et al, Jour. Nucl. Med., 26, 493-502, 1985.*

(Continued)

*Primary Examiner*—David A Saunders
(74) *Attorney, Agent, or Firm*—Lerner, David, Littenberg, Krumholz & Mentlik, LLP

(57) ABSTRACT

Antibody binding assays and radiolabeling kits are disclosed for radiolabeling and testing therapeutic antibodies in the commercial setting. In particular, the kits are designed for making and evaluating radiolabeled anti-CD20 conjugates to be used for the treatment and imaging of B cell lymphoma tumors. All kit reagents are sterile and are designed to achieve a high level of antibody radiolabeling and product stability with results which are highly reproducible.

27 Claims, 39 Drawing Sheets

OTHER PUBLICATIONS

Adams RA, "Formal Discussion: The role of transplantation in the experimental investigation of human leukemia and lymphoma," *Cancer Research*, 1967, 27(1):2479-2482.

Adams RA, et al., "Direct implantation and transplantation of human acute lymphoblastic leukemia in hamsters," 1968, *Cancer Research*, 28:1121-1125.

Antisoma, Internet reference, 16 pp.

Applebaum, "Radiolabled Monoclonal Antibodies in Treatment of NHL," Hematology/Oncology Clinics of North America 5(5):1013-1025 (1991).

Brechbiel et al., "Synthesis of 1-(p-Isothiocyanatobenzyl) derivatives of DTPA and EDTA. Antibody labeling and tumor-imaging studies," *Inorganic Chemistry*, 1986, 25(16):2772-81.

Brechbiel et al., "Synthesis of C-Functionalized trans-Cyclohexyldiethylenetriaminepenta-acetic Acids for Labelling . . . Emitter," J. Chem. Soc. Perkin Trans., 1173-1178, 1992.

Chakrabarti et al., "Prevention of radiolysis of monoclonal antibody during labeling," 1996, J. Nucl. Med., 37:1384-88.

Chinol et al., "Generator-Produced Yttrium-90 for Radioimmunotherapy," J. Nucl. Med. 28(9):1465-1470 (1987).

Cytogen, Internet reference, 15 pp.

DeNardo et al., "Yttrium-90/Indium-111 DOTA peptide chimeric L6: pharmacokinetics, dosimetry and initial therapeutic studies in patients with breast cancer," J. Nucl. Med., 1995, 36:97P.

Gansow et al., "Advanced Methods for Radiolabeling Monoclonal Antibodies with Therapeutic Radionuclides," *Cancer Therapy With Radiolabelled Antibodies*, 1995, Chapter 6, pp. 63-76.

Gansow et al., "Macrocyclic or Conventional Ligands? Selection of Effective Chelators . . . Radioimmunotherapy," Chem. Sect., Radiation Oncol. Branch, Natl. Canc. Inst.

Griffiths, GL, "Antibody Radiolabeling With Isotopes of Rhenium," *Cancer Therapy With Radiolabelled Antibodies*, 1995, Chapter 7, pp. 77-86.

Griffiths et al., "Rapid, facile and quantitative radiolabeling of DOTA-hMAb conjugates with Y-90 cancer radioimmunotherapy," Abstract from AACR Meeting, Noa. 4242.

Grossbard et al., "Monoclonal Antibody-Based Therapies of Leukemia and Lymphoma," Blood 80(4):863-876 (1992).

Hird et al., "Adjuvant therapy of ovarian cancer with radioactive monoclonal antibody," Br. J. Cancer, 68:403-406, 1993.

Hnatowich et al., "The Preparation of DTPA-Coupled Antibodies Radiolabeled with Metallic Radionuclides: an Improved Method," J. Immun. Meth. 65:147-157 (1983).

Huneke et al., "Effective α-Particle-mediated Radioimmunotherapy of Murine Leukimia[1]," Cancer Research, 52:581-5820, 1992.

Izard et al., "An Imiproved Method for Labelling Monoclonal Antibodies with Samarium-153: Use of the Bifunctional Chelate . . . Acid," Bioconjugate Chem., 3(4), 346-350, 1992.

Kaminski et al., "[131]I Anti-b1: Initial Clinical Evaluation in B Cell Lymphoma," third Conference on Radioimmunodetection and . . . Cancer, Abstract No. 144, (1990).

Kaminski et al., "Initial Clinical Radioimmunotherapy Results with [131]I Anti-CD20) in Refractory B cell Lymphoma, Fourth Conference on Radioimmunodetection and Radioimmunotherapy of Cancer Antibody . . . ,I" 5(3) Abstract No. 57.

Kinsey et al., "Efficient Conjugation of DTPA to an IgM Monoclonal Antibody in Ascites Fluid," Nucl., Med. Biol., 15(3):285-292, 1988.

Kobayashi et al., Pharmacokinetics of In-111 and I-125 labeled anti-Tac single-chain Fv recombinant immunotoxin (LMB2), Abstract from AACR Meeting No. 4239.

Kozak et al., "Nature of the bifunctional chelating agent used for radioimmunotherapy with yttrium-90 monoclonal antibodies: critical factors in determining in vivo survival and organ toxicity," *Cancer Research*, 1989, 49:2639-44.

Kukis et al., "Optimized Conditions for Chelation of Yttrium-90-DOTA Immunoconjugates," J. Nucl. Med. 1998, 39:2105-2110.

Larson et al., "Comparison of Bone Marrow Dosimetry and Toxic Effect of High Dose . . . to Man," Nucl. Med. Biol. 16(2):153-158 (1989).

Leland et al., "Electrogenerated chemilumnescence: An oxidative-reduction type ECL reaction sequence using Tripropyl Amine," *Electrochem. Soc.*, 1990, 137, 3127.

Lewis et al., "A facile, water-soluble method for modification of proteins with DOTA," Bioconjugate Chem., 1994, 5:565-76.

Lindmo T., et al., "Determination of the immunoreactive fraction of radiolabeled monoclonal antibodies by linear extrapolation to binding at infinite antigen excess," *Immunol. Methods*, 1984, 72:77-.

Liu a.Y. et al., "Production of a mouse-human chimeric monoclonal antibody to CD20 with potent Fc-dependent biologic activity," J. Immunol., 1987, 139/10:3521-26.

Mather, "Labeling monoclonal antibodies with yttrium-90," Eur. J. Nucl. Med., 1989, 15;307-312.

Mirzadeh et al., "The Chemical Fate of $^{212}$Bi-DOTA Forbed by β-Decay of $^{212}$Pb(DOTA)$^2$," Radiochimica Acta, 60(1):1-10, 1993.

Mirzadeh S. et al., "Radiometal labeling of immunoproteins: Covalent linkage of 2-(4-Isothiocyanatobenzyl) diethylenetriaminepentaacetic acid ligands to immunoglobulin," *Bioconjugate Chemistry*, 1990, 1(1):59.

Motta-Hennessy et al., "Labeling of Monoclonal Antibody Conjugates with $^{90}$Y," Appl. Radiat. Isot., 42(5):421-426, 1991.

Muller RJ, "Calculation of average antibody affinity in anti-hapten sera from data obtained by competitive radioimmunoassay," *Immunological Methods*, 1980, 34;345.

Nicholson et al., "Radioimmunotherapy after chemotherapy compared to chemotherapy alone in the treatment of advanced . . . analysis," Oncology Reports. 5:223-226, 1998.

Pai-Scherf et al., "Imaging and phase I study of $^{111}$In- and $^{90}$Y-labeled anti-Lewis$^Y$ monoclonal antibody," Abstract from AACR Meeting No. 4240.

Parker et al., "Radioimmunotherapy of human B-cell lymphoma with 90Y-conjugated antiidiotype monoclonal antibody," *Cancer Research*, 1990, 50:1022s-28s.

Peitersz et al., "The use of monoclonal antibody conjugates for the diagnosis and treatment of cancer," Immunol. Cell Biol., 1987, 65:111-125.

Pizzarello, Direct and indirect action. In Pizzarello and Witcofski, eds. *Basic Radiation Biology*, 2$^{nd}$ ed. Philadelphia: Lea & Febger, 1975, pp. 20-29.

Reilly, "Radioimmunotherapy of Malignancies," Clin. Pharm. 10(5):359-375 (1991).

Richardson et al., "Optimization and batch production of DTPA-labelled antibody kits for routine use in $^{111}$In immunoscintigraphy," Nucl. Med. Commun. 8:347-356 (1987).

Robinson et al., "Chimeric mouse-human anti-carcinoma antibodies that mediate different anti-tumor cell biological activities," Hum. Antibod. Hybridomas, 1991, 2;84-93.

Salako et al., "Effects of radiolysis on yttrium-90-labeled Lym-1 antibody preparations," J. Nucl. Med., 1998, 39:667-670.

Stewart et al., "Intraperitoneal $^{131}$I- and $^{90}$Y-labeled Monoclonal Antibodies for Ovarian Cancer: Pharmocokinetics and . . . Dosimetry," Int. J. Cancer Suppl., 3:71-76 (1988).

Thomas et al., Gamma-interferon administration after 90Y radiolabeled antibody therapy: survival and hematopoietic toxicity studies, Int. J. Radiat. Oncol. Biol. Phys., 1995, 31:529-534.

Washburn et al., "Preclinical Assessment of $^{30}$Y-Labeled Monoclonal Antibody CO17-1A, a Potential Agent . . . Carcinoma," Nucl. Med. Biol., 15(6):707-711, 1988.

* cited by examiner

RADIOLABELING METHOD

RELATED APPLICATIONS

This is a divisional of U.S. patent application Ser. No. 09/259,337, filed Mar. 1, 1999, now abandoned, the entire contents of which are hereby incorporated by reference.

BACKGROUND OF THE INVENTION

1. Field of the Invention

The present invention relates to antibody binding assays and radiolabeling kits, lyophilized cell preparations, reagents and protocols for testing the clinical efficacy of therapeutic antibodies for the treatment/imaging of tumors and tumor cells. Specifically, the kits of the present invention are used for making and evaluating radiolabeled antibody conjugates that will be used for the treatment and imaging of B-cell lymphoma tumors by targeting the B cell surface antigen BP35 ("CD20").

2. Technology Background

All publications and patent applications herein are incorporated by reference to the same extent as if each individual publication or patent application was specifically and individually indicated to be incorporated by reference.

The immune system of vertebrates (for example, primates, which include humans, apes, monkeys, etc.) consists of a number of organs and cell types which have evolved to: accurately and specifically recognize foreign microorganisms ("antigen") which invade the vertebrate-host; specifically bind to such foreign microorganisms; and, eliminate/destroy such foreign microorganisms. Lymphocytes, as well as other types of cells, are critical to the immune system. Lymphocytes are produced in the thymus, spleen and bone marrow (adult) and represent about 30% of the total white blood cells present in the circulatory system of humans (adult).

There are two major sub-populations of lymphocytes: T cells and B cells. T cells are responsible for cell mediated immunity, while B cells are responsible for antibody production (humoral immunity). However, T cells and B cells can be considered as interdependent—in a typical immune response, T cells are activated when the T cell receptor binds to fragments of an antigen that are bound to major histocompatability complex ("MHC") glycoproteins on the surface of an antigen presenting cell; such activation causes release of biological mediators ("interleukins") which, in essence, stimulate B cells to differentiate and produce antibody (immunoglobulins") against the antigen.

Each B cell within the host expresses a different antibody on its surface—thus one B cell will express antibody specific for one antigen, while another B cell will express antibody specific for a different antigen. Accordingly, B cells are quite diverse, and this diversity is critical to the immune system. In humans, each B cell can produce an enormous number of antibody molecules (i.e. about $10^7$ to $10^8$). Such antibody production most typically ceases (or substantially decreases) when the foreign antigen has been neutralized. Occasionally, however, proliferation of a particular B cell will continue unabated; such proliferation can result in a cancer referred to as "B cell lymphoma."

T cells and B cells both comprise cell surface proteins which can be utilized as "markers" for differentiation and identification. One such human B cell marker is the human B lymphocyte-restricted differentiation antigen Bp35, referred to as "CD20." CD20 is expressed during early pre-B cell development and remains until plasma cell differentiation. Specifically, the CD20 molecule may regulate a step in the activation process which is required for cell cycle initiation and differentiation and is usually expressed at very high levels on neoplastic ("tumor") B cells. CD20, by definition, is present on both "normal" B cells as well as "malignant" B cells, i.e., those B cells whose unabated proliferation can lead to B cell lymphoma. Thus, the CD20 surface antigen has the potential of serving as a candidate for "targeting" of B cell lymphomas.

In essence, such targeting can be generalized as follows: antibodies specific to the CD20 surface antigen of B cells are, e.g., injected into a patient. These anti-CD20 antibodies specifically bind to the CD20 cell surface antigen of (ostensibly) both normal and malignant B cells; the anti-CD20 antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to, e.g., the neoplastic B cells. Irrespective of the approach, a primary goal is to destroy the tumor: the specific approach can be determined by the particular anti-CD20 antibody which is utilized and, thus, the available approaches to targeting the CD20 antigen can vary considerably.

For example, attempts at such targeting of CD20 surface antigen have been reported. Murine (mouse) monoclonal antibody 1F5 (an anti-CD20 antibody) was reportedly administered by continuous intravenous infusion to B cell lymphoma patients. Extremely high levels (>2 grams) of 1F5 were reportedly required to deplete circulating tumor cells, and the results were described as being "transient." Press et al., "Monoclonal Antibody 1F5 (Anti-CD20) Serotherapy of Human B-Cell Lymphomas," Blood 69/2:584-591 (1987).

A potential problem with this approach is that non-human monoclonal antibodies (e.g., murine monoclonal antibodies) typically lack human effector functionality, i.e., they are unable to, inter alia, mediate complement dependent lysis or lyse human target cells through antibody dependent cellular toxicity or Fc-receptor mediated phagocytosis. Furthermore, non-human monoclonal antibodies can be recognized by the human host as a foreign protein; therefore, repeated injections of such foreign antibodies can lead to the induction of immune responses leading to harmful hypersensitivity reactions. For murine-based monoclonal antibodies, this is often referred to as a Human Anti-Mouse Antibody response, or "HAMA" response. Additionally, these "foreign" antibodies can be attacked by the immune system of the host such that they are, in effect, neutralized before they reach their target site.

Lymphocytes and lymphoma cells are inherently sensitive to radiotherapy. Therefore, B cell malignancies are attractive targets for radioimmunotherapy (RIT) for several reasons: the local emission of ionizing radiation of radiolabeled antibodies may kill cells with or without the target antigen (e.g., CD20) in close proximity to antibody bound to the antigen; penetrating radiation, i.e., beta emitters, may obviate the problem of limited access to the antibody in bulky or poly vascularized tumors; and, the total amount of antibody required may be reduced. The radionuclide emits radioactive particles which can damage cellular DNA to the point where the cellular repair mechanisms are unable to allow the cell to continue living; therefore, if the target cells are tumors, the radioactive label beneficially kills the tumor cells. Radiolabeled antibodies, by definition, include the use of a radioactive substance which may require the need for precautions for both the patient (i.e., possible bone marrow transplantation)

as well as the health care provider (i.e., the need to exercise a high degree of caution when working with radioactivity).

Therefore, an approach at improving the ability of murine monoclonal antibodies to effect the treatment of B-cell disorders has been to conjugate a radioactive label to the antibody such that the label or toxin is localized at the tumor site. Toxins (i.e., chemotherapeutic agents such as doxorubicin or mitomycin C) have also been conjugated to antibodies. See, for example, PCT published application WO 92/07466 (published May 14, 1992).

"Chimeric" antibodies, i.e., antibodies which comprise portions from two or more different species (e.g., mouse and human) have been developed as an alternative to "conjugated" antibodies. Mouse/human chimeric antibodies have been created, and shown to exhibit the binding characteristics of the parental mouse antibody, and effector functions associated with the human constant region. See e.g., Cabilly et al., U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397 all of which are incorporated by reference herein. Generally these chimeric antibodies are constructed by preparing a genomic gene library from DNA extracted from pre-existing murine hybridomas. Nishimura et al. (1987) Cancer Research 47: 999. The library is then screened for variable region genes from both heavy and light chains exhibiting the correct antibody fragment rearrangement patterns. The cloned variable region genes are then ligated into an expression vector containing cloned cassettes of the appropriate heavy or light chain human constant region gene. The chimeric genes are then-expressed in a cell line of choice, usually a murine myeloma line.

For example, Liu, A. Y., et al., "Production of a Mouse-Human Chimeric Monoclonal Antibody to CD20 with Potent Fc-Dependent Biologic Activity", J. Immun. 139/10:3521-3526 (1987), describes a mouse/human chimeric antibody directed against the CD20 antigen. See also, PCT Publication No. WO 88/04936. However, no information is provided as to the ability, efficacy or practicality of using Liu's chimeric antibodies for the treatment of B cell disorders in the reference.

It is noted that in vitro functional assays (e.g. complement dependent lysis ("CDC"); antibody dependent cellular cytotoxicity ("ADCC"), etc.) cannot inherently predict the in vivo capability of any antibody to destroy or deplete target cells expressing the specific antigen. See, for example, Robinson, R. D., et al., "Chimeric mouse-human anti-carcinoma antibodies that mediate different antitumor cell biological activities," *Hum. Antibod. Hybridomas,* 2:84-93 (1991) (chimeric mouse-human antibody having undetectable ADCC activity). Therefore, the potential therapeutic efficacy of antibodies can only truly be assessed by in vivo experimentation.

To this end application Ser. No. 08/475,813 (issued as U.S. Pat. No. 6,682,734 B1 on Jan. 27, 2004), Ser. No. 08/475,815 (issued as U.S. Pat. No. 6,399,061 B1 on Jun. 4, 2002), and Ser. No. 08/478,967 (issued as U.S. Pat. No. 5,843,439 on Dec. 1, 1998), herein incorporated by reference in their entirety, disclose radiolabeled ant-CD20 conjugates for diagnostic "imaging" of B cell lymphoma tumors before administration of therapeutic antibody. "In2B8" conjugate comprises a murine monoclonal antibody, 2B8, specific to human CD20 antigen, that is attached to Indium [111] ($^{111}$In) via a bifuncial chelator, i.e., MX-DTPA (diethylenetriaminepentaacetic acid), which comprises a 1:1 mixture of 1-isothiocyanatobenzyl-3-methyl DTPA and 1methyl-3-isothiocyanatobenzyl-DTPA. Indium-[111] is selected as a diagnostic radionuclide because it emits gamma radiation and finds prior usage as an imaging agent.

Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates. These patents are incorporated herein in their entirety.

The specific bifunctional chelator used to facilitate chelation in application Ser. No. 08/475,813, Ser. No. 08/475,815 and Ser. No. 08/478,967 was selected as it possesses high affinity for trivalent metals, and provides for increased tumor-to-non-tumor ratios, decreased bone uptake, and greater in vivo retention of radionuclide at target sites, i.e., B-cell lymphoma tumor sites. However, other bifunctional chelators are known in the art and may also be beneficial in tumor therapy.

Also disclosed in application Ser. Nos. 08/475,813 (issued as U.S. Pat. No. 6,682,734, B1 on Jan. 27, 2004), Ser No. 08/475,815 (issued as U.S. Pat. No. 6,399,061 B1 on Jun. 4, 2002), and antibodies for the targeting and destruction of B cell lymphomas and tumor cells. In particular, the Y2B8 conjugate comprises the same anti-human CD20 murine monoclonal antibody, 2B8, attached to yttrium-[90] ($^{90}$Y) via the same bifunctional chelator. This radionuclide was selected for therapy for several reasons. The 64 hour half-life of $^{90}$Y is long enough to allow antibody accumulation by the tumor and, unlike e.g. $^{131}$I, it is a pure beta emitter of high energy with no accompanying gamma irradiation in its decay, with a range of 100 to 1000 cell diameters. The minimal amount of penetrating radiation allows for outpatient administration of $^{90}$Y-labeled antibodies. Furthermore, internalization of labeled antibodies is not required for cell killing, and the local emission of ionizing radiation should be lethal for adjacent tumor cells lacking the target antigen.

Because the $^{90}$Y radionuclide was attached to the 2B8 antibody using the same bifunctional chelator molecule MX-DTPA, the Y2B8 conjugate possesses the same advantages discussed above, e.g., increased retention of radionuclide at a target site (tumor). However, unlike $^{111}$In, it cannot be used for imaging purposes due to the lack of gamma radiation associated therewith. Thus, a diagnostic "imaging" radionuclide, such as $^{111}$In, can be used for determining the location and relative size of a tumor prior to and/or following administration of therapeutic chimeric or $^{90}$Y-labeled antibodies for the purpose of tumor reduction. Additionally, indium-labeled antibody enables dosimetric assessment to be made.

Depending on the intended use of the antibody, i.e., as a diagnostic or therapeutic reagent, other radiolabels are known in the art and have been used for similar purposes. For instance, radionuclides which have been used in clinical diagnosis include $^{131}$I, $^{125}$I, $^{123}$I, $^{99}$Tc, $^{67}$Ga as well as $^{111}$In. Antibodies have also been labeled with a variety of radionuclides for potential use in targeted immunotherapy (Peirersz et al. (1987) The use of monoclonal antibody conjugates for the diagnosis and treatment of cancer. Immunol. Cell Biol. 65: 111-125). These radionuclides include $^{188}$Re and $^{186}$Re as well as $^{90}$Y, and to a lesser extent $^{199}$Au and $^{67}$Cu. I-[131] has also been used for therapeutic purposes. U.S. Pat. No. 5,460, 785 provides a listing of such radioisotopes and is herein incorparted by reference.

As reported in copending application Ser. Nos. 08/475,813 (issued as U.S. Pat. No. 6,682,734 B1 on Jan. 27, 2004), Ser .No. 08/475,815 (issued as U.S. Pat. No. 6,399,061 B1 on Jun. 4, 2002), and Ser. No. 08/478,967, (issued as U.S. Pat. No. 5,843,439, on Dec. 1, 1998),administration of the radiolabeled Y2B8 conjugate, as well as unlabeled chimeric anti-CD20 antibody, resulted in significant tumor reduction in mice harboring a B cell lymphoblastic tumor. Moreover, human clinical trials reported therein showed significant B cell depletion in lymphoma patients infused with chimeric anti-CD20 antibody. In fact, chimeric 2B8 has recently been heralded the nation's first FDA-approved anti-cancer monoclonal antibody underthe name of Rituxan®. Thus, at least one chimeric anti-CD20 antibody has been shown to demonstrate therapeutic efficacy in the treatment of B cell lymphoma.

In addition, U.S. application Ser. No. 08/475,813 (issued as U.S. Pat. No. 6,682,734, B1 on Jan. 27, 2004), herein incorporated by reference, discloses sequential administration of Rituxan®, a chimeric anti-CD20, with both or either indium-labeled or yttrium-labeled murine monoclonal antibody. Although the radiolabeled antibodies used in these combined therapies are murine antibodies, initial treatment with chimeric anti-CD20 sufficiently depletes the B cell population such that the HAMA response is decreased, thereby facilitating a combined therapeutic and diagnostic regimen.

Thus, in this context of combined immunotherapy, murine antibodies may find particular utility as diagnostic reagents. Moreover, it was shown in U.S. application Ser. No. 08/475,813 (issued as U.S. Pat. No. 6,682,734 B1 on Jan. 27, 2004) that a therapeutically effective dosage of the yttrium-labeled anti-CD20 antibody following administration of Rituxan® is sufficient to
(a) clear any remaining peripheral blood B cells not cleared by the chimeric anti-CD20 antibody;
(b) begin B cell depletion from lymph nodes; or (c) begin B cell depletion from other tissues.

Thus, conjugation of radiolabels to cancer therapeutic antibodies provides a valuable clinical tool which may be used to assess the potential therapeutic efficacy of such antibodies, create diagnostic reagents to monitor the progress of treatment, and devise additional therapeutic reagents which may be used to enhance the initial tumor-killing potential of the chimeric antibody. Given the proven efficacy of an anti-CD20 antibody in the treatment of non-Hodgkin's lymphoma, and the known sensitivity of lymphocytes to radioactivity, it would be highly advantageous for such therapeutic antibodies to become commercially available in kit form whereby they may be readily modified with a radiolabel and administered directly to the patient in the clinical setting.

Although there exist many methods and reagents for accomplishing radiolabeling of antibodies, what is lacking in the art is a convenient vehicle for placing these reagents in the clinical setting, in a way that they may be easily produced and administered to the patient before significant decay of the radiolabel or significant destruction of the antibody due to the radiolabel occurs. The lack of such convenient means to commercialize this valuable technology could be due to the poor incorporation efficiencies demonstrated by some known labeling protocols, and the subsequent need to column purify the reagent following the radiolabeling procedure. The delay in development of such kits might also in part be due to the previously lack of accessibility to pure commercial radioisotopes which may be used to generate efficiently labeled products absent subsequent purification. Alternatively, perhaps the reason such kits are generally unavailable is the actual lack of antibodies which have been able to achieve either the approval or the efficacy that Rituxan® has achieved for the treatment of lymphoma in human patients.

For instance, as discussed in U.S. Pat. No. 4,636,380, herein incorporated by reference, it has been generally believed in the scientific community that for a radiopharmaceutical to find clinical utility, it must endure a long and tedious separation and purification process. Indeed, injecting unbound radiolabel into the patient would not be desirable. The need for additional purification steps renders the process of radiolabeling antibodies in the clinical setting an impossibility, particularly for doctors who have neither the equipment nor the time to purify their own therapeutics.

Furthermore, radiolabeled proteins may be inherently unstable, particularly those labeled with radiolytic isotopes such as $^{90}Y$, which have the tendency to cause damage to the antibody the longer they are attached to it in close proximity. In turn, such radiolysis causes unreliable efficiency of the therapeutic due to loss of radiolabel and/or reduced binding to the target antigen, and may lead to undesired immune responses directed at denatured protein. Yet without the facilities for labeling and purifying the antibodies on site, clinicians have had no choice but to order therapeutic antibodies already labeled, or have them labeled off site at a related facility and transported in following labeling for administration to the patient. All such manipulations add precious time to the period between labeling and administration, thereby contributing to the instability of the therapeutic, while in effect decreasing the utility of radiolabeling kits in the clinical setting.

Others have tried unsuccessfully to develop antibody radiolabeling kits that would be proficient enough to forego a separate purification step of the antibody. For instance, Cytogen has recently launched a commercial kit for radiolabeling a murine monoclonal antibody directed to tumor-associated glycoprotein TAG-72. However, Cytogen's antibody is particularly unamenable to a kit formulation due to the tendency to develop particulates during storage which must later be removed by a further filtration step. Moreover, Cytogen's antibody has caused adverse reactions in patients due to a HAMA responses.

Others have claimed to have developed radiolabeling protocols which would be amenable to kit format in that a separate purification step would not be required (Richardson et al. (1987) Optimization and batch production of DTPA-labeled antibody kits for routine use in $^{111}In$ immunoscintography. Nuc. Med. Commun. 8: 347-356; Chinol and Hnatowich (1987) Generator-produced yttrium-[90] for radioimmunotherapy. J. Nucl. Med. 28(9): 1465-1470). However, such protocols were not able to achieve the level of incorporation that the present inventors have achieved using the protocols disclosed herein, which have resulted in incorporation efficiencies of at least 95%. Such a level of incorporation provides the added benefit of increased safety, in that virtually no unbound label will be injected into the patient as a result of low radioincorporation.

The protocols included in the kits of the present invention allow rapid labeling which may be affected in approximately a half an hour or as little as five minutes depending on the label. Moreover, the kit protocols of the present invention have a labeling efficiency of over 95% thereby foregoing the need for further purification. By foregoing the need for further purification, the half-life of the radiolabel and the integrity of the antibody is reserved for the therapeutic purpose for which it is labeled.

The present application discloses convenient kits and methods whereby diagnostic and therapeutic antibodies may be radiolabeled and administered to a patient in a reproducible, reliable and convenient manner. The kits of the present invention transform the process of radiolabeling antibodies into a hassle-free, worry-free standardized process, which greatly facilitates patient treatment protocols. The present kits provide advantages over the prior art in that the optimum parameters for labeling and administering therapeutic or diagnostic have been determined, thereby-reducing the cost of goods. Since the kits described herein provide the optimum parameters according to the particular label, use of a kit designed for a particular label will also minimize cannibalization, i.e., which occurs when an inappropriate kit is used for a particular label. Avoiding cannibalization in turn also provides for optimum labeling efficiency. Moreover, the protocols and sterile; pyrogen-free ingredients included with each kit make for a more user-friendly process, since sterility, pyrogen testing and post-labeling purification of the reagents are obviated.

SUMMARY OF THE INVENTION

The present invention includes a kit for radiolabeling a diagnostic or therapeutic antibody before administration to a patient comprising at least (i) a vial containing a chelator-conjugated antibody, (ii) a vial containing formulation buffer for stabilizing and administering the radiolabeled antibody, and (iii) instructions for radiolabeling the antibody, wherein said vial components are supplied in such an amount and at such a concentration that when they are combined with a radiolabel of sufficient purity and activity according to the kit instructions, no further purification of the labeled antibody is required before administration to said patient. Moreover, when labeled according to the kit instructions and with a radioisotope of sufficient purity and activity, such isotope incorporation may reach levels higher than 95%, and even as high as 98% or higher.

The antibody included in the kit is most preferably an anti-CD20 antibody. The antibody is supplied in a form whereby it is attached to a bifunctional chelator. Preferably, the antibody is conjugated to MX-DTPA, but other chelators such as phenyl- or benzyl-conjugated DTPA, cyclohexyl-DTPA, EDTA derivatives and DOTA may be used. A chelator according to the present invention may be any chelator that is at least bifunctional, i.e., which possesses at least two binding sites (at least one site for chelating a metallic ion and at least one site for coupling to a protein ligand).

Depending on the antibody used, the conjugated antibody is typically supplied at a concentration of 0.5 to 30 mg/ml, more preferably 2 mg/ml. The volume of conjugated antibody will depend on the concentration and the amount required for optimum labeling depending on the radiolabel. However, the conjugated antibody is to be supplied in such a volume and concentration that the entire volume will be added to the reaction vial using a sterile syringe and aseptic technique. This will allow for increased reproducibility and ease of use. All reagents of the kits disclosed herein are sterile and pyrogen-free, and specifically designed for simplicity and speed in advancing directly from antibody testing to administration. With some labels, the need for testing labeling efficiency may not be required.

A particularly advantageous component of the kit is the formulation buffer for stabilizing against the effects of radiolysis and administering the radiolabeled conjugated antibody to a patient. The formulation buffer is a pharmaceutically acceptable carrier which serves as both a diluent for the labeled antibody and an administration buffer. Although any pharmaceutically acceptable diluent may be used for administering therapeutic or diagnostic antibodies to patient, the formulation buffer of the present invention is particularly suited for administering radiolabeled antibodies.

For instance, the formulation buffer of the present invention comprises a radioprotectant such as human serum albumin (HSA) or ascorbate, which minimize radiolysis due to yttrium, and to a lesser degree, indium. Other radioprotectants are known in the art and could also be used in the formulation buffer of the present invention, i.e., free radical scavengers (phenol, sulfites, glutathione, cysteine, gentisic acid, nicotinic acid, ascorbyl palmitate, $HOP(:O)H_2$, glycerol, sodium formaldehyde sulfoxylate, $Na_2S_2O_5$, $Na_2S_2O_3$, and $SO_2$, etc.).

It should be noted that, while radioprotectants are generally employed in the formulation buffer to protect the antibody from radiolysis, it may be possible to affect further protection by including the radioprotectant in the reaction buffer as well. This has generally not been done before, i.e., with HSA, due to the presence of metals which would interfere with the labeling process. However, it may be possible to "clean" the HSA using a chelating resin such that it could be included in the reaction buffer as well. Ascorbate or other radioprotectants may also need to be treated to remove contaminating metals.

The formulation buffer of the present invention also comprises excess unconjugated chelator. The purpose for including unconjugated chelator is that this chelator serves to scavenge any non-protein bound radiolabel in the patient, and effects excretion of the radiolabel thereby reducing uptake of "bone-seeking" isotopes, i.e., $^{90}Y$, by the bones of the patient. For instance, when the antibody of the kit is conjugated to a DTPA chelator, excess DTPA or any other chelator may be included in the formulation buffer. The formation buffer is also preferably supplied in a volume such that the entire contents are transferred to the reaction vial. As discussed above, this results in increased ease of use and reproducibility because exact volumes do not have to be measured and transferred.

A preferred formulation buffer comprises phosphate buffered or physiological saline, human serum albumin and DTPA. The human serum albumin is preferably at a concentration of between about 1 to 25% (w/v), and more preferably at a concentration of about 7.5% (w/v). The concentration of DTPA is preferably about 1 mM. Ascorbate may be used as an alternative to human serum albumin, and is typically used at a concentration of about 1 to 100 mg/ml. Although a wider range of concentrations may be used without compromising patient safety.

The antibody of the radiolabeling kit is readily labeled with a radioisotope of choice via a bifunctional chelator according to the methods of the present invention. For further simplicity in this regard, the kit of the present invention may also include a vial containing a buffer for adjusting the pH of the radioisotope solution, and a sterile glass reaction vial for performing the labeling and subsequently for resuspending the final radiolabeled antibody in formulation buffer. A 10 ml reaction vial is typically sufficient, but vials capable of holding 5 to 20 mls may also be used. The buffer is preferably a low-metal sodium acetate solution at a concentration of 10 to 1000 mM, most preferably 50 mM.

A specific kit of the present invention comprises the MX-DTPA conjugated antibody, 2B8-MX-DTPA. 2B8 is an anti-CD20 antibody shown to affect B cell depletion upon administration to lymphoma patients. However, it should be apparent to those skilled in the art that the radiolabeling kit of the present invention may be optimized for the radiolabeling of other anti-CD20 antibodies, or any other antibody which has been conjugated to DTPA or other polyvalent chelator. The preferred kit of the present invention may comprise at least (i) a vial containing the MX-DTPA conjugated 2B8 antibody, either in solution or lyophilized (requiring reconstitution); and (ii) a vial containing formulation buffer for administering the radiolabeled antibody to a patient. The preferred kit will also contain (iii) a buffer for adjusting isotope pH, and (iv) a reaction vial. Alternatively, and more preferably, the buffer is supplied in the reaction vial, thereby eliminating the steps of measuring and transferring the buffer and increasing the simplicity, consistency and sterility of the kit components, However, other embodiments are also envisioned, i.e., whereby the buffer is added to the isotope vial first, and the buffered isotope is then transferred to the reaction vial. In this case, the reaction vial could be supplied with the required antibody volume. Alternatively, the isotope/buffer vial could be made large enough to accommodate addition of the antibody conjugate, i.e., directly to the supplier's vial. This would eliminate the need for the reaction vial.

As described above, another preferred kit configuration is encompassed whereby the reaction vial itself contains the required volume of conjugated antibody (i.e., 1 or 1.5 mL for $^{111}$In and $^{90}$Y, respectively). The antibody may be supplied in a buffer that provides the appropriate radiolabeling pH according to the specific desired isotope (i.e., pH 3-6 for $^{111}$In, pH 3-5 for $^{90}$Y). Different buffers may be used, depending on the isotope (i.e., sodium acetate for $^{90}$Y, sodium citrate for $^{111}$In). The pH and composition of the buffer may also vary depending on the nature of the binding ligand to be labeled (i.e., labeling peptides may permit <pH 3 to be used). Essentially then, the isotope would be transferred directly to the reaction vial, as would the formulation buffer. Limiting use of the kit to two transfer steps would further increase reproducibility and simplicity, and further decrease the chance for contamination of sterility during manipulation of the kit components.

The radiolabeling kits of the present invention may further comprise a vial of radioisotope, or radioisotope may be ordered separately from an appropriate supplier. Preferred radioisotopes of the present invention are $^{111}$In chloride and $^{90}$Y chloride in HCl although the disclosed methods are not limited to these isotopes. Other radionuclides that have been used for imaging applications are known in the art, i.e., as described in U.S. Pat. Nos. 4,634,586, 5,460,785 and 5,766,571, which are herein incorporated by reference. Indium-[111] is particularly advantageous for imaging B cell tumors and beta emitters such as $^{90}$Y are particularly useful as radiotherapeutic agents. Although other radioisotopes suitable for these or other purposes, i.e., alpha emitters, may be used depending on the chelator used for antibody conjugation.

Given the proven efficacy of the combined therapeutic regimens disclosed in U.S. application Ser. No. 08/475,813 (issued as U.S. Pat. No. 6,682,734 B1 on Jan. 27, 2004), a further kit embodiment will also include a separate vial of chimeric antibody, i.e., Rituxan®, to be administered before or after the radiolabeled anti-CD20 antibody. When the chimeric antibody is administered before the radiolabeled antibody, the HAMA response which might generally occur in response to administration of a murine anti-CD20 antibody may be significantly decreased, thereby increasing the therapeutic utility of radiolabeled murine antibodies. Moreover, when chimeric anti-CD20 is employed to clear circulating B cells, subsequent diagnostic images achieved with $^{111}$In-labeled antibodies may be much clearer.

It should also be apparent that both a diagnostic radiolabeled antibody and a therapeutic radiolabeled antibody may be used together in a combined therapeutic regimen. In this regard, the diagnostic antibody may be used either before or after the therapeutic antibody to visualize tumor size before and after treatment. In this case, the kit of the present invention may include separate, perhaps color-coded, buffer vials specifically formulated according to the optimum pH requirements for radiolabeling antibodies with the specific radioisotopes to be used. Such a system would ensure that the appropriate buffer was used for each label, and would allow the clinician the same ease in radiolabeling the two antibodies as if two kits had been purchased. Such a kit in effect combines the components from two radiolabeling kits into one.

The components of the radiolabeling kit of the present invention are supplied at the appropriate concentration and pH so that sterility is readily maintained before antibody administration and there is little need for additional buffers or media. However, it should be apparent to those of skill in the art that some of the reagents can be prepared, sterilized and tested for sterility on site. Thus, variations of the kit of the invention are envisioned depending on the budget and preference of the consumer.

The radiolabeling kit of the present invention may be used in a method for radiolabeling a chelator-conjugated antibody for administration to a patient. According to the present invention, such a method comprises, in general, (i) mixing a chelator-conjugated antibody with a solution containing a radioisotope; (ii) incubating the mixture for an appropriate amount of time at appropriate temperature; and (iii) diluting the labeled antibody to an appropriate concentration in formulation buffer, such that the radiolabeled antibody may be administered directly to a patient without further purification.

Most preferably the antibody is an anti-CD20 antibody, and in particular, the anti-CD20 antibody may be 2B8. The antibody may be conjugated to any appropriate chelator, i.e., MX-DTPA, CHX-DTPA, phenyl- or benzyl-DTPA, DOTA, EDTA derivatives, etc. MX-DTPA is preferred. Methods for affecting antibody conjugation are known in the art (Kozak et al. (1989); Mirzadeh et al. (1990), Brachbiel et al. (1986)).

The present inventors have found that the method of radiolabeling a chelator-conjugated antibody works best wherein the solution containing the radiolabel is adjusted to a pH of between about 3.0 and 6.0, and more preferably to about 4.2 before it is mixed with the chelator-conjugated antibody. Low-metal sodium acetate is particularly preferred for adjusting the pH, although other buffers may be used. Preferably, the sodium acetate is at a concentration of between about 10 and 1000 mM, and more preferably 50 mM.

When the radioisotope is $^{111}$In chloride, the volume quantity of $^{111}$In chloride which should be used to prepare a single administrative dose is typically about 5.5 mCi divided by the radioactivity concentration at the time of labeling. For patient administration, a typical diagnostic dose of $^{111}$In is about 2 to 10 mCi. The quantity of sodium acetate used for adjusting the pH varies depending on the sodium acetate concentration and the isotope carrier solution, and may therefor be quite broad. When the concentration of sodium acetate is 50 mM, the amount required for adjusting the pH is typically about 1.2 times the volume quantity of $^{111}$In chloride used although larger volumes may be used. It should be appreciated that the ratio of sodium acetate to HCl is what is important, and the amount of sodium acetate used would change depending on the amount and concentration of HCl in the buffer. About 1 ml of a chelator-conjugated antibody at a concentration of about 2 mg/ml is then mixed with the radiolabel acetate solution, and the mixture is incubated for about 30 minutes, or for a time sufficient to achieve optimal labeling of the antibody. Such time may range from about 30 seconds to about 60 minutes. Formulation buffer is then added in an amount necessary to achieve a total final volume of about 10 ml.

The optimum time required for labeling the antibody may vary depending on the antibody, the particular radiolabel and the particular conjugate employed. An underlying factor in the optimization of the time allotted for radiolabeling is the chelator to antibody ratio of the reagent which is to be labeled. For instance, the chelator to antibody ratio must be high enough to achieve a therapeutically useful level of incorporation, i.e., 90 to 95% depending on the radioisotope, but must also not be too high such that the structural integrity or immunoreactivity of the antibody is compromised. This requires a certain balancing process that in some cases may lead to a lower level of conjugated chelator and longer labeling time.

For instance, for 2B8 and MX-DTPA, it has been discovered that labeling may be accomplished in under five minutes for $^{90}$Y and in about thirty minutes for $^{111}$In to achieve the desired level of radioincorporation, with only about a 1½ to 1 molar ratio of chelator to antibody. It was not necessary, therefor, to increase the chelator to antibody ratio, because a desirable level of radioincorporation was achieved. Moreover, it was not advantageous to increase the quantity of conjugated chelator because this could effect antibody immunoreactivity. Such parameters could be empirically determined for other antibodies for the design of kits such as those described in the present invention.

When the radioisotope is $^{90}$Y chloride, the volume quantity of $^{90}$Y chloride used for preparing a single administrative dose typically ranges from about 10 to 50 mCi, and is preferably about 45 mCi, divided by the radioactivity concentration at the time of labeling. The quantity of sodium acetate used for adjusting the pH varies depending on the sodium acetate concentration and the concentration of isotope carrier, and may therefor be quite broad. When the concentration of sodium acetate is 50 mM and the $^{90}$Y is supplied in 50 mM HCl, the amount required for adjusting the pH is typically about 1.2 times the volume quantity of $^{90}$Y chloride used. About 1.5 ml of a chelator-conjugated antibody at a concentration of about 2 mg/ml is then mixed with the radiolabel acetate solution, and incubated for about 5 minutes, or for a time sufficient to achieve optimal labeling of the antibody. Such time may range from about 30 seconds to about 60 minutes. Formulation buffer is added in an amount necessary to achieve a total final volume of about 10 ml.

Preferably, the radiolabeling method of the invention is performed using the radiolabeling kit described herein. However, it should be apparent to those of skill in the art that the preferred components and conditions are merely acceptable guidelines for practicing the method of the invention, and may be altered to some degree with appropriate optimization. Conditions which depart from those preferred but still accomplish the purpose of the method are considered to be within the scope of the invention.

The radiolabeling kit of the present invention may also be supplied with reagents suitable for conveniently verifying the binding affinity of the antibody following radiolabeling. In such a case, the kit of the invention may also be used for determining the percent binding of a radiolabeled antibody to its target cell before administering the antibody to a patient. The present inventors have also found that the particular binding assay kit disclosed may be useful for testing the affinity of any antibody generally for which purified antigen is not available. Accordingly, the binding assay components may also be sold as a separate kit.

In general, a binding assay and radiolabeling kit comprises (i) at least one vial of lyophilized cells which express the antigen which is recognized by the antibody in the kit; (ii) a vial containing chelator-conjugated antibody; (iii) a vial containing formulation buffer, and (iv) instructions for radiolabeling the antibody such that the radiolabeled antibody may be administered directly to a patient without the need for subsequent purification. As described above for the radiolabeling kit, this kit may also comprise a vial containing a buffer for adjusting the pH of the radioisotope, and a sterile glass reaction vial. Preferably the buffer is a low-metal sodium acetate solution at a concentration of between about 10 and 1000 mM, and the glass reaction vial holds a volume of at least 5 ml. The antibody is preferably an anti-CD20 antibody, and the chelator is preferably MX-DTPA. Other chelators may be used as described previously. The preferred conjugated antibody is 2B8-MX-DTPA, although any chelator-conjugated antibody may be labeled and its affinity assessed. The formulation buffer is phosphate buffered saline comprising a radioprotectant and unconjugated chelator as described above, and radioisotope may or may not be included and is preferably $^{111}$In chloride or $^{90}$Y chloride. Other radioisotopes may be used depending on the chelator.

The difference between the binding assay/radiolabeling kit and the radiolabeling kit described above is the inclusion of antigen-positive cells to serve as a substrate target for testing antibody affinity. When the antigen is CD20, preferred CD20-positive cells are SB cells (ATCC# CCL 120) but any CD20-positive cells may be used. The binding assay and radiolabeling kit may further include antigen-negative cells for use as a negative control. Preferred CD20-negative cells are HSB cells (ATCC# CCL 120.1) but any CD20-negative cells may be used.

Of course, the combined radiolabeling and binding assay kit may further comprise a vial of chimeric anti-CD20 antibody in addition to the antibody to be labeled for the purposes of affecting a combined therapeutic regimen, or for clearing peripheral B cells prior to diagnostic imagery. Such separate antibody is preferably Rituxan®, but may be any antibody shown to effectuate tumor cell killing. In fact, two different types of antibodies may be combined in one kit, i.e., antibodies directed to two different B cell antigens, so long as the combined therapeutic regimen serves to target the same type of cell, i.e., the B cell lymphoma.

Just as the components of the kit may be used to label other antibodies, other cells for testing antibody affinity may be prepared depending on the target antigen. However, for anti-CD20 antibodies, the binding assay and radiolabeling kit of the present invention is particularly suited for the commercial setting in that the target cells are provided in lyophilized form. This allows the verification of antibody efficacy to proceed simply and systematically, and negates the hassle and expense involved in maintaining tissue culture facilities. The lyophilized cells are generally supplied in aliquots of between 0.5 and 500×10$^6$ cells per vial according to the methods of the invention.

It is possible that particular facilities will prefer to order antibody which has already been radiolabeled, in which case such a facility might desire the binding assay reagents in order to ensure that the antibodies retain target affinity. In this case, the present invention also provides for a binding assay kit for determining the percent binding of a radiolabeled antibody to its target cell. Such a kit includes at least one vial of fixed and/or lyophilized antigen-positive cells, and may optionally contain antigen-negative cells as described above for the binding assay and radiolabeling kit. Moreover, it should be apparent that variations of such a kit may include an unlabeled control antibody for verifying the binding specificity of the consumer's antibody via a competitive assay.

Again, when the antigen is CD20, the CD20-positive cells are preferably SB cells (ATCC # CCL 120) and the CD20-negative cells are preferably HSB cells (ATCC # CCL120.1), which are supplied in lyophilized form in aliquots of between 0.5 and 50×10$^6$ cells. In this case, the antibody is preferably an MX-DTPA conjugate of 2B8 labeled with $^{111}$In or $^{90}$Y.

In view of the additional kit embodiments disclosed herein, it should be stressed that one of the advantages of the radiolabeling kit and method of the present invention is that no further purification step is necessary, and the radiolabeled antibody may be administered directly to the patient, thereby saving valuable time and increasing antibody stability. Therefore, it is emphasized that, while it might be desirable for the clinician to test or verify the binding specificity and affinity of the radiolabeled antibody prior to administration, such test may be foregone with particular radioisotopes if antibody stability and the inhibition of radiolysis are particular concerns, i.e., as with yttrium. By providing kit embodiments whereby the binding affinity and specificity may be tested, the present inventors are in no way suggesting that such tests are absolutely required in the methods or kits of the invention. The option to test such antibody validity is purely at the option of the clinician.

The present inventors have also found that the method used for preparing fixed and lyophilized cells for the binding assay kits of the present invention is particularly suitable for preparing cells for commercial kits. Cells may be fixed prior to lyophilization to improve structure/stability. In particular, the cells of the present invention demonstrate high reproducibility when used for antibody binding assays.

In particular, the present invention includes a method of preparing lyophilized cells comprising (i) harvesting cells at a cell density of 0.5 to $2\times10^6$ cells per ml by centrifugation; (ii) washing cells at least one time in a balanced salt solution, i.e., HBSS; (iii) resuspending pelleted cells in a lyophilization buffer comprising a balanced salt solution containing carrier protein and at least one type of sugar; (iv) dispensing an aliquot of resuspended cells into a microfuge tube or a glass vial; and (v) lyophilizing the cells 12-96 h and more preferably 24-72 h at about 30-60 millitor. The method is particularly suitable for preparing lyophilized cells wherein said cells are SB cells (ATCC # CCL 120) or HSB cells (ATCC # CCL 120.1), but is likely applicable to other cell types as well.

Preferably, the buffer generally contains bovine serum albumin as the carrier protein at a concentration of 1% (w/v) and mannitol at a concentration of 10%. However, conceivably other carrier proteins, i.e., HSA, and other sugars may be used. The cells are harvested by centrifugation at a speed of about 1300 rpm, and the salt solution HBSS (Hank's balanced salt solution) is added. The cells are generally resuspended at a concentration of $50\times10^6$ cells per ml. However, it should be apparent to those of skill in the art that the above conditions may be modified slightly without significantly compromising cell viability. Moreover, the above conditions may be supplemented by additional procedures designed to optimize the process for larger quantities of cells, e.g., tangential flow diafiltration to exchange cells into the lyophilization buffer.

The binding assay kits of the present invention may be used in an assay for assessing the binding affinity of a radiolabeled antibody. Such an assay is also a subject of the present invention. A binding assay for determining the percent binding of a radiolabeled antibody to its target cell comprises in general the following steps: (i) mixing at least one aliquot of a radiolabeled antibody with at least one aliquot of antigen positive cells; (ii) mixing at least one aliquot of a radiolabeled antibody identical to the aliquot of step (i) with at least one aliquot of dilution buffer of the same volume as the aliquot of antigen-positive cells in step (i) as a control; (iii) pelleting the cells by centrifugation; (iv) measuring the radioactivity in the supernatant of the pelleted cells and the control; and (v) comparing the quantity of radioactivity in the cell supernatant to the quantity of radioactivity in the control.

Just as the radiolabeling kits of the present invention optionally contain $^{111}$In chloride or $^{90}$Y chloride, the binding assay of the present invention is typically performed with antibodies labeled with $^{111}$In or $^{90}$Y. When $^{111}$In is the radiolabel, radioactivity in the assay tubes is measure using a gamma counter. When $^{90}$Y is the label, radioactivity is measured using a scintillation counter, although a gamma counter could be used.

For the binding assay of the present invention, the preferred antibody is an anti-CD20 antibody, and the anti-CD20 antibody is preferably 2B8, wherein the 2B8 antibody is labeled using the radiolabeling kit of the present invention. However, any radiolabeled antibody may be tested provided cells expressing the particular antigen are available. When CD20 is the antigen the preferred cells for performing the assay are SB cells (ATCC # CCL 120), however, the assay may also be optimized and performed with any radiolabeled antibody and appropriate target cell.

The dilution buffer used for the assay should maintain binding of the antibody, i.e., physiological buffer, possibly containing a carrier protein, e.g. BSA, to minimize non-specific binding to cells. Although the tube with dilution buffer serves as a control, a further control may be included in the assay by using antigen-negative cells. In this case, the binding assay further comprises the following steps: (i) mixing at least one aliquot of a radiolabeled antibody with at least one aliquot of antigen-negative cells; (ii) pelleting the antigen-negative cells by centrifugation; (iv) measuring the radioactivity in the supernatant of the antigen-negative pelleted cells; and (v) comparing the quantity of radioactivity in the antigen-negative cell supernatant to the quantity of radioactivity in the supernatant of the antigen-positive cell supernatant and the control. Comparing the radioactivity obtained from this tube to the dilution buffer control will serve as a measure of the amount of non-specific binding to antigen-positive cells. When CD20 is the antigen, and the CD20-positive cells are SB cells, CD20 negative cells are preferably HSB cells (ATCC # CCL 120.1).

As described above, the lyophilized cells of the present invention provide a simple, efficient and reproducible standard for testing the binding efficacy of a radiolabeled antibody. Therefore, the binding assay of the present invention is preferably performed using the lyophilized cells included in the binding assay kits of the present invention. In addition, the radiolabeling assays of the present invention may be combined with the binding assays of the present invention, wherein the antibody is first labeled by the method of labeling an chelator-conjugated antibody as described in the present invention. Most preferably, the binding assay of the present invention is performed using one of the binding assay and radiolabeling kits described herein.

There may be some instances where the affinity of an antibody should be tested or verified but a radiolabel has not been attached. For instance, under certain circumstances, i.e., trouble-shooting, it may be advantageous to test the binding affinity of an antibody before radiolabeling. For such a case, the present invention also encompasses a competitive binding assay for assessing affinity of a test antibody to a target cell, comprising (i) preparing a ruthenium-labeled control antibody using a known antibody specific for the same antigen; (ii) incubating increasing amounts of test antibody and increasing amounts of unlabeled control antibody with a fixed concentration of target cells and a trace amount of ruthenium-labeled antibody wherein each separate concentration of test antibody and each separate concentration of control antibody are in separate tubes, respectively; (iii) determining the quantity of binding in each reaction tube based on relative electrochemiluminescence (ECL) using ORIGEN instrumentation; and (iv) calculating the average affinity value of the test antibody. The average affinity value may be calculated from the EC50 values and the known concentration of trace antibody using the method of Muller (J. Immunological Methods (1980) 34:345) or any other appropriate method. It should be noted that this assay may also be used to test the affinity of radiolabeled antibodies, or any antibody for which antigen cannot be purified and cells are required as an antigen source. The fixed, lyophilized cells of the present invention may be used as target cells.

When the competitive binding assay of the present invention is performed to test the affinity of anti-CD20 antibodies, the control antibody may be 2B8, or any other unconjugated anti-CD20 antibody. The control antibody may be a chelator-conjugated antibody. The test antibody may also be a chelator-conjugate of the control antibody. Alternatively, the test antibody may be another anti-CD20 antibody whose binding affinity to CD20 as compared to 2B8 is of interest. However, the assay may be adapted for use with antibodies having other specificities so long as an appropriate target cell is available.

In the competitive binding assay of the present invention, the preferred target cells are CD20-positive cells, more preferably SB cells (ATCC # CCL 120), and are more preferably resuspended lyophilized SB cells prepared according to the method of the present invention. Cells lyophilized using other methods or fixed cells may also be used. The ruthenium-labeled antibody is typically prepared by a process comprising incubating the control antibody with N-hydroxysuccinimide ester of ruthenium (II) tris-bypyridine chelator (TAG-NHS), although other known method of labeling antibodies are also envisioned. For labeling, the control antibody and TAG-NHS are preferably incubated at about a 1:15 molar ratio.

These and other aspects of the present invention will become clearly understood by reference to the following figures, examples and description of the invention.

BRIEF DESCRIPTION OF THE DRAWINGS

FIG. 6A) A constant amount of radiolabeled antibody (5 ng/mL) was incubated with increasing volumes of SB cells (20×10$^6$ cells/mL). The amount of radioactivity (cpm) bound to cells was plotted against the volume of cell suspension added. FIG. 6B) Total applied radioactivity over bound radioactivity (AT/B) was plotted. Linear extrapolation allowed calculation of the y-intercept (0.997). The reciprocal of the y-intercept X 100 yielded an immunoreactivity value of 100% at infinite antigen excess.

As shown in FIG. 22A, the antibody exhibited at β $t_{1/2}$ value of approximately 4.5 days. The clearance of the 2B8 antibody and its MX-DTPA conjugate from the circulation of BALB/c mice are shown in FIG. 22B. Mice were injected intravenously with 25 µg of native or conjugated 2B8 and blood samples taken at various times up to 264 hours following injection; sera was subsequently analyzed by enzyme immunoassay using SB cells as the capture agent. Both the native and conjugated antibodies exhibited clearance values of 8.75 days.

Figure 26A:
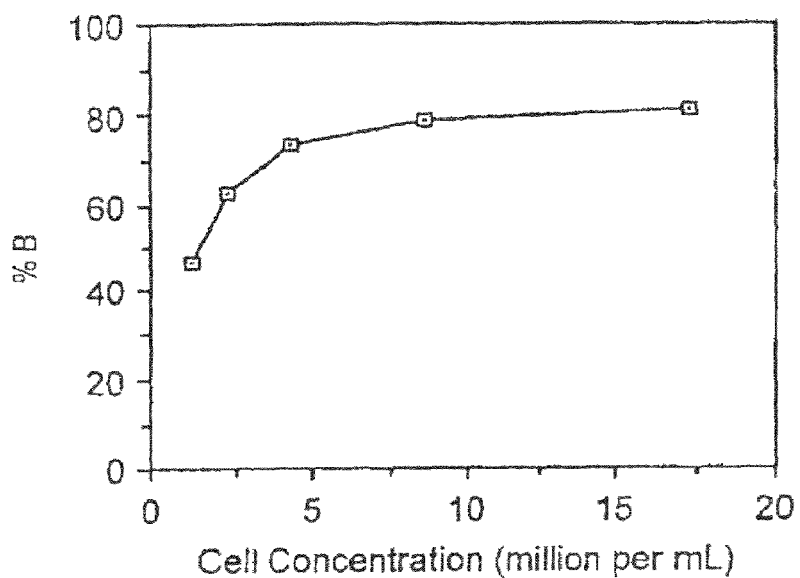
Figure 26B:
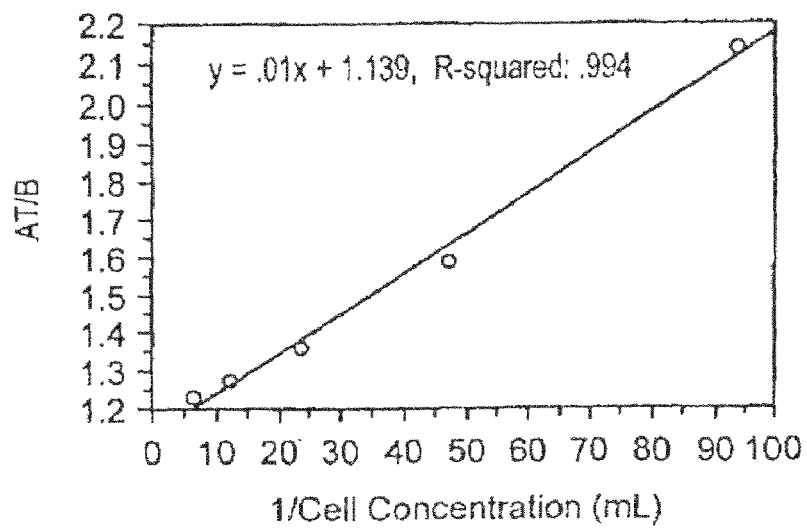

FIG. 26 FIG. 26A and 26B. Binding assay for determination of immunoreactivity of "mix-&-shoot" $^{90}$Y-labeled 2B8-MX-DTPA incubated in PBS, pH 7.4 containing 50-75 mg/M1 human serum albumin (48 h incubation). Panel A FIG. 26A) A constant amount of $^{90}$Y-labeled antibody (approximately 1 ng/ml) was incubated with increasing amounts of SB cells. The amount of radioactivity (cpm) bound to cells was plotted against the cell concentration. Panel B FIG. 26B) Total applied $^{90}$Y radioactivity over bound radioactivity (AT/B) was plotted. Linear extrapolation allowed calculation of the y-intercept (1.139). The reciprocal of the y-intercept×100 yielded an immunoreactivity value of 87.9% at infinite antigen excess. No binding was observed with CD20-negative cells (HSB).

Figure 27:
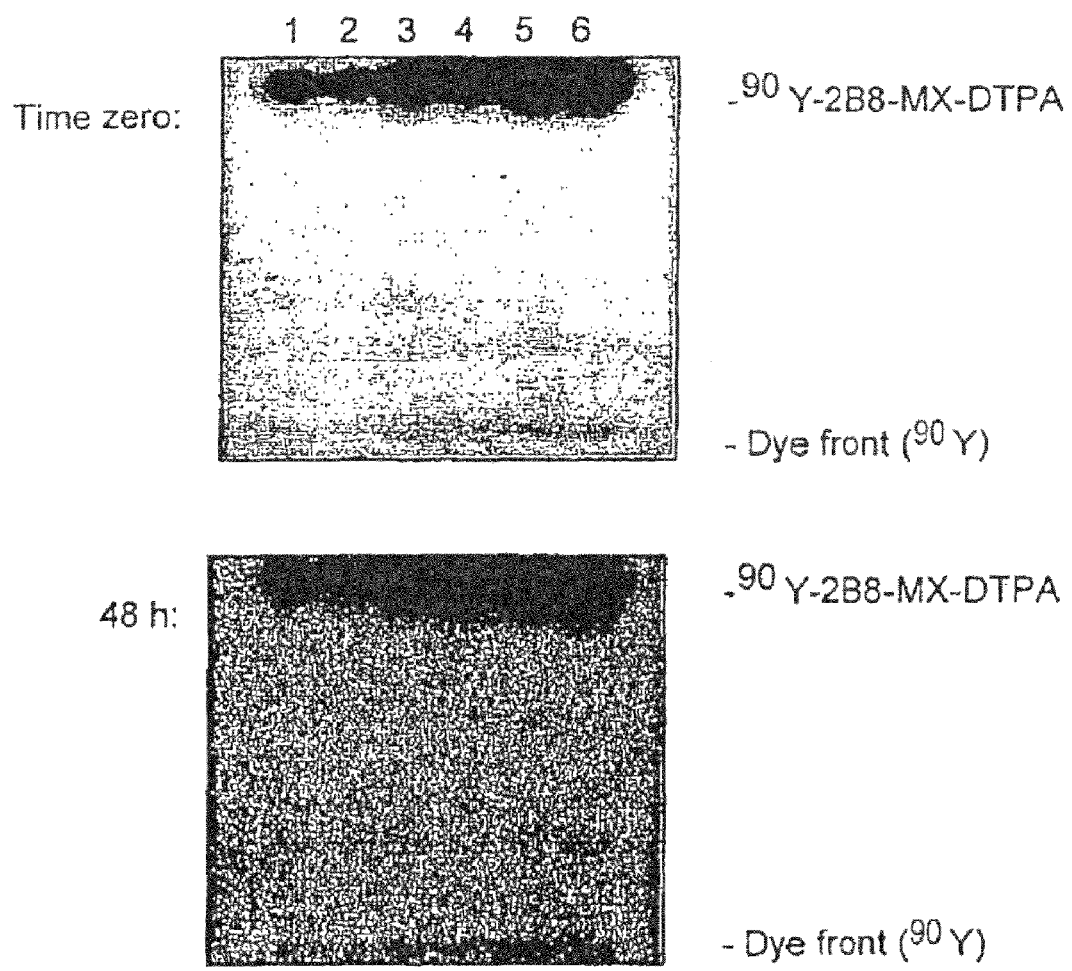

FIG. 27. Autoradiograms obtained from SDS-PAGE analysis of $^{90}$Y-labeled 2B8-MX-DTPA incubated at 4° C. in PBS, pH 7.4 containing 75 mg/mL human serum albumin and 1 mM DTPA. At the indicated times, samples were electrophoresed on 4-20% Tris-glycine gels using non-reducing conditions, denaturing conditions (SDS). The samples were loaded at 5 µL (lanes 1, 2), 10 µL (lanes 5, 6). The gels were exposed to x-ray film for approximately 15 min at ambient temperature and photographed.

Figure 28:
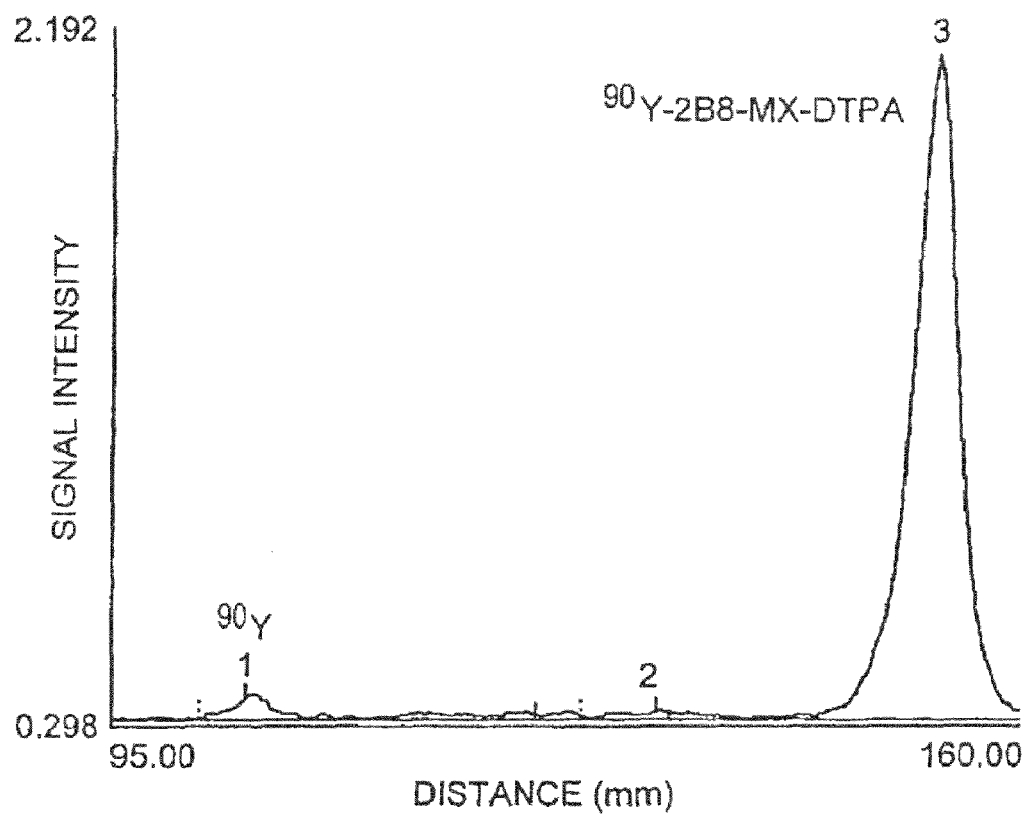

FIG. 28. Densitometric scan of time zero autoradiogram obtained from SDS-PAGE analysis of $^{90}$Y-labeled 2B8-MX-DTPA incubated at 4° C. in PBS, pH 7.4 containing 75 mg/mL human serum albumin and 1 mM DTPA. The sample was electrophoresed on a 4-20% Trib-glycine gel using non-reducing conditions. Samples were loaded at 5 µL, 10 µL, and 20 µL in duplicate wells. The gel was exposed to x-ray film for approximately 15 min at ambient temperature and one of the lanes was scanned using a densitometer. The relative area of the radiolabeled conjugate peak (#2) was 96.1%.

Figure 29:
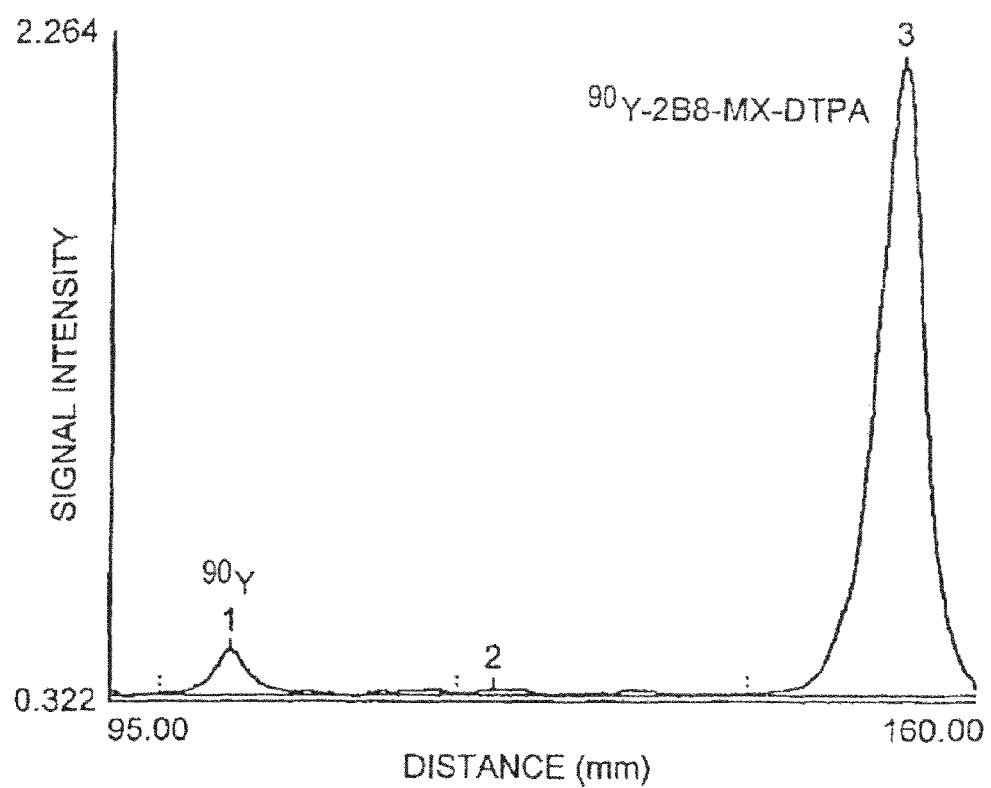

FIG. 29. Densitometric scan of 48 h autoradiogram obtained from SDS-PAGE analysis of $^{90}$Y-labeled 2B8-MX-DTPA incubated at 4° C. in PBS, pH 7.4 containing 75 mg/mL human serum albumin and 1 mM DTPA. The sample was electrophoresed on a 4-20% Tris-glycine gel using non-reducing conditions. Samples were loaded at 5 µL, 10 µL, and 20 µL in duplicate wells. The gel was exposed to x-ray film for approximately 15 min at ambient temperature and one of the lanes was scanned using a densitometer. The relative area of the radiolabeled conjugate peak (#2) was 94.1%.

Figure 30:
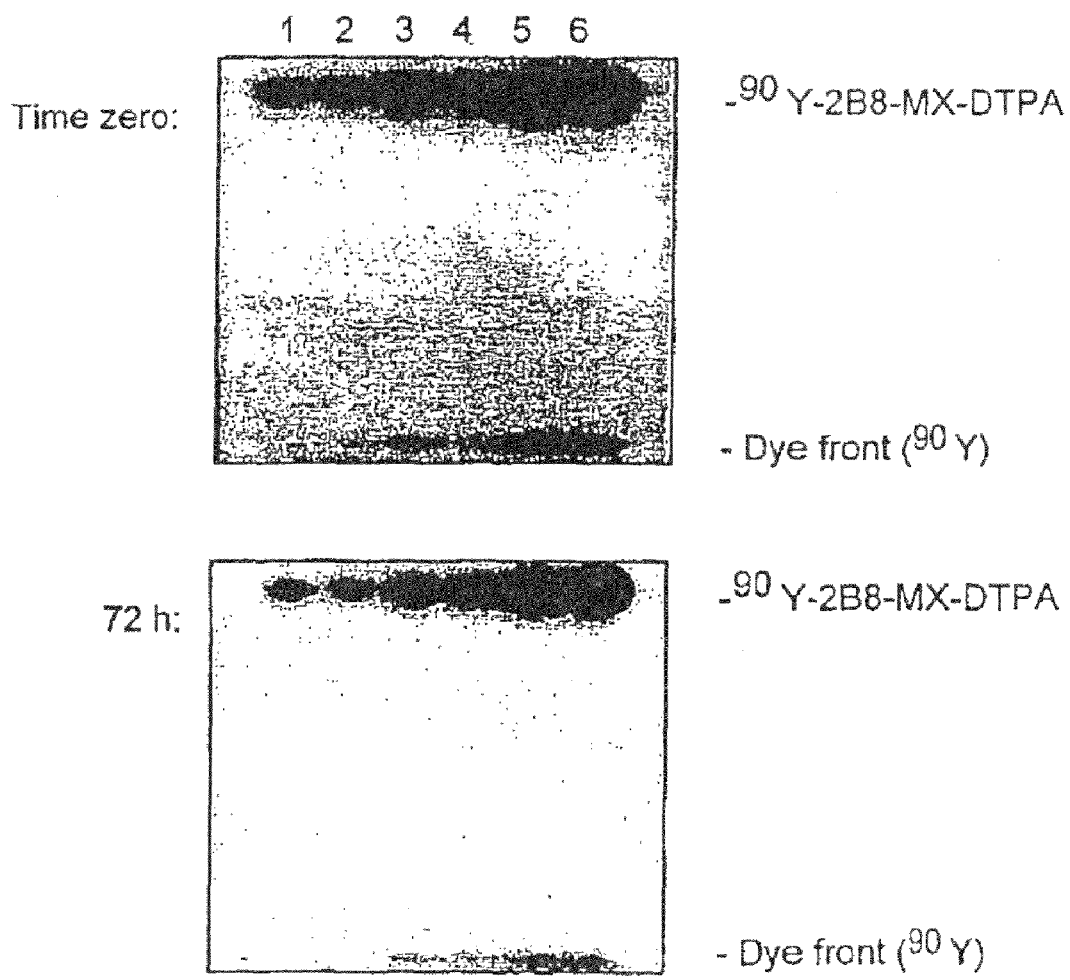

FIG. 30. Autoradiograms obtained from SDS-PAGE analysis of "mix-&-shoot" $^{90}$Y-labeled 2B8-MX-DTPA incubated at 37° C. in human serum. At the indicated times, samples were electrophoresed on 4-20% Tris-glycine gels using non-reducing conditions. The samples were loaded at 5 µL (lanes 1, 2), 10 µL (lanes 3, 4), and 20 µL (lanes 5, 6). The gels were exposed to x-ray film for approximately 15 min at ambient temperature and photographed.

Figure 31:
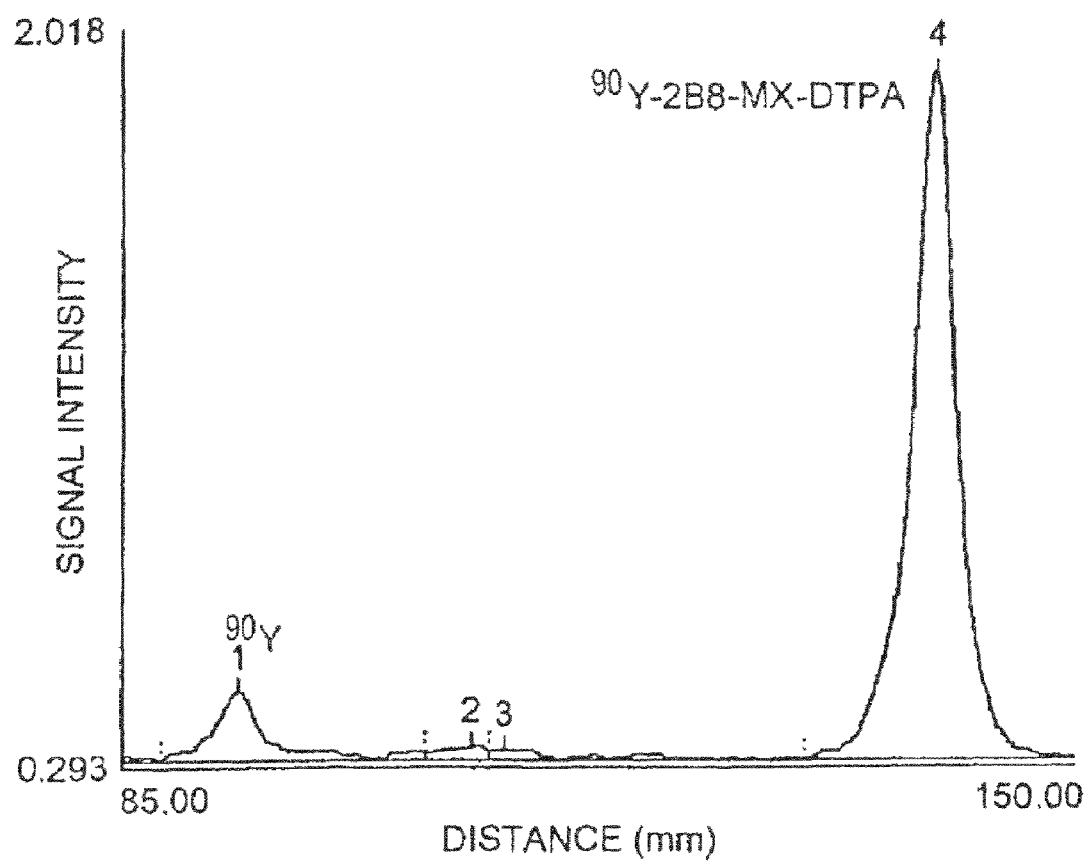

FIG. 31. Densitometric scan of time zero autoradiogram obtained from SDS-PAGE analysis of "mix-&-shoot" $^{90}$Y-labeled 2B8-MX-DTPA incubated at 37° C. in human serum. The sample was electrophoresed on a 4-20% Tris-glycine gel using non-reducing conditions. The sample was loaded at 5 µL, 10 µL, and 20 µL in duplicate wells. Gels were exposed to x-ray film for approximately 15 min at ambient temperature and one of the lanes was scanned using a densitometer. The relative area of the radiolabeled conjugate peak (#2) was 89.1%.

Figure 32:
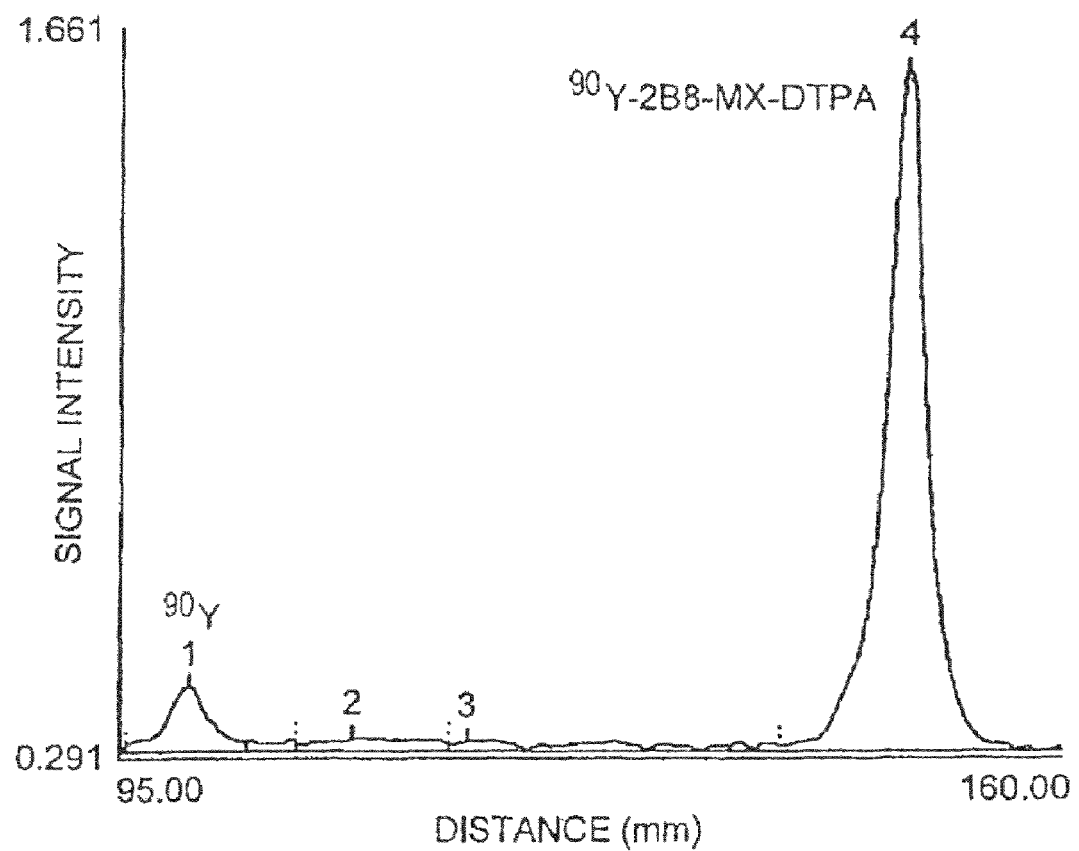

FIG. 32. Densitometric scan of 72 h autoradiogram obtained from SDS-PAGE analysis of "mix-&-shoot" $^{90}$Y-labeled 2B8-MX-DTPA incubated at 37° C. in human serum. The sample was electrophoresed on a 4-20% Tris-glycine gel using non-reducing conditions. The sample was loaded at 5 µL, 10 µL, and 20 µL in duplicate wells. Gels were exposed to x-ray film for approximately 15 min at ambient temperature and one of the lanes was scanned using a densitometer. The relative area of the radiolabeled conjugate peak (#2) was 88.8%.

Figure 33:
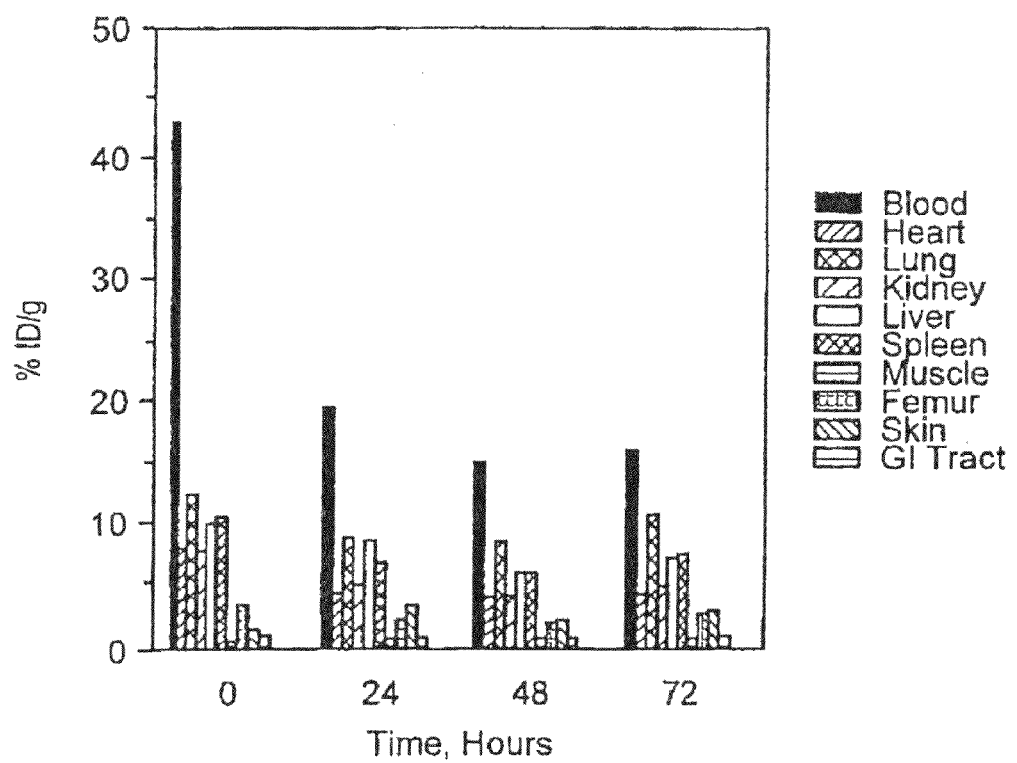

FIG. 33. Twenty BALB/c mice were each injected intravenously with 5 µCi $^{90}$Y-labeled 2B8-MX-DTPA formulated in 1× PBS, pH 7.4, containing 75 mg/mL human serum albumin and 1 mM DTPA. Groups of five mice each were sacrificed at 1, 24, 48 and 72 hours and their blood and various tissues prepared and analyzed for associated radioactivity.

Figure 34:
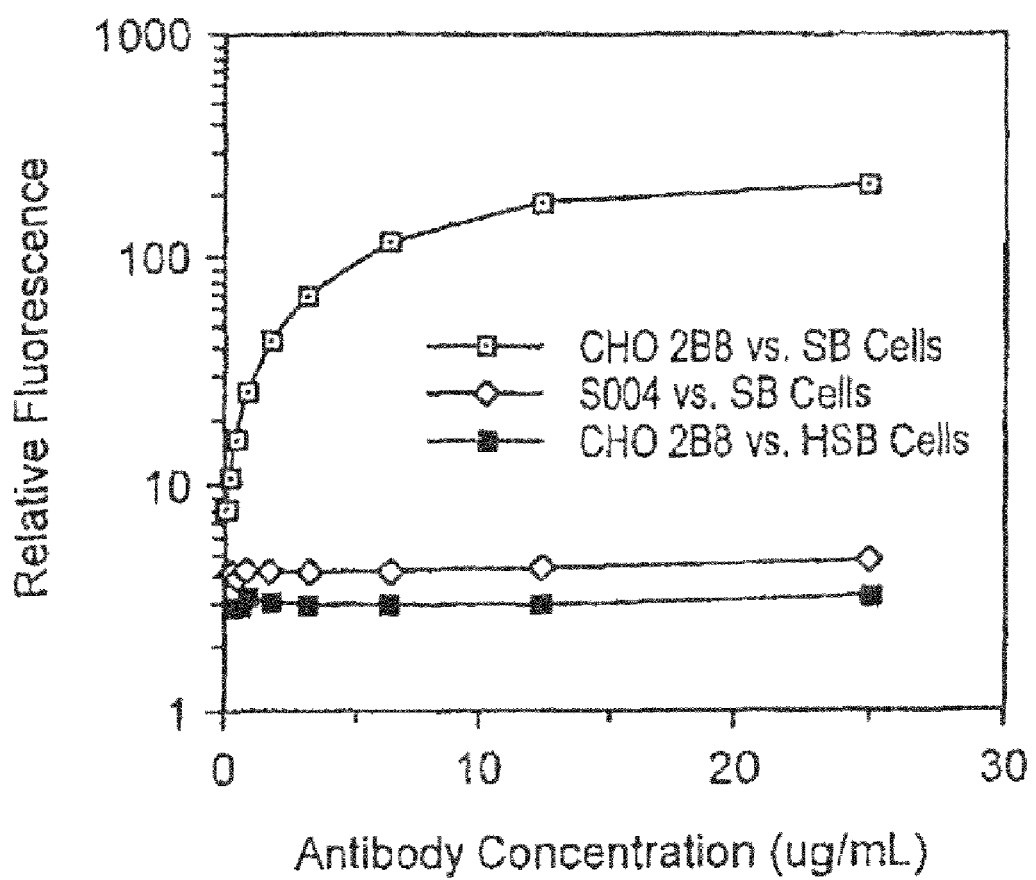

FIG. 34. Increasing amounts of CHO-derived 2B8 antibody labeled were incubated with a fixed concentration of freshly harvested CD20-positive B-cells (SB) or CD20-negative T-cells (HSB). Antibody binding to cells was quantified using FACS analysis using goat anti-mouse IgG-FITC F(ab)'$_2$ as described herein. Comparison was made to an irrelevant isotype antibody (S004). Only the CHO-derived 2B8 antibody showed any appreciable binding to CD20-positive SB cells.

Figure 35:
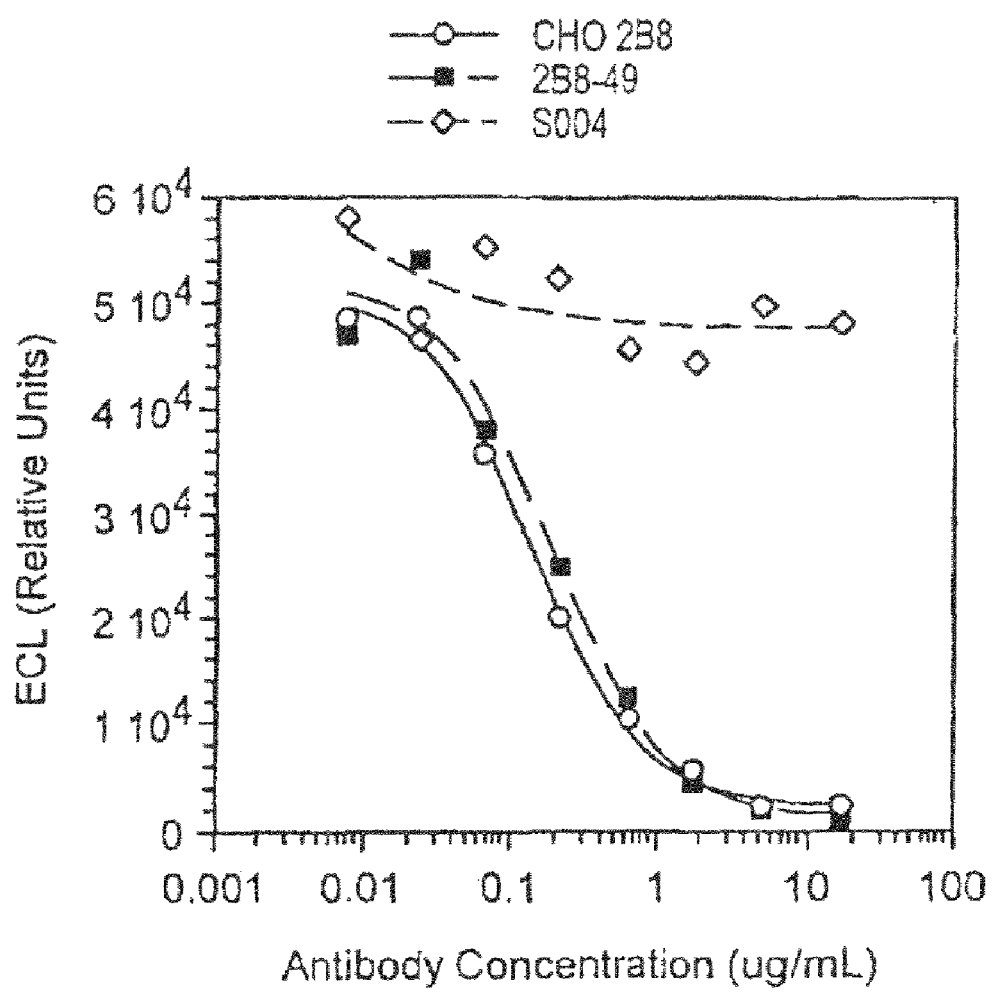

FIG. 35. The immunoreactivity of CHO-derived 2B8 was compared to the 2B849 parent antibody produced in a hybridoma cell line by direct competition in an ORIGEN assay. Increasing amounts of antibody was incubated with a fixed concentration of CD20-positive B-cells (SB) and a trace amount of ruthenium-labeled CHO 2B8. After incubation for three hours at ambient temperature, binding, expressed as relative electrochemiluminescence (ECL), was determined using the ORIGEN instrument as described in the Materials and Methods. Values represent the means of duplicate determinations. Average affinity constants for CHO 2B8 and 2B849 were calculated to be 1.3×10$^{-10}$ M and 2.5×10$^{-10}$ M, respectively. An irrelevant isotype antibody (S004), was included for comparison.

Figure 36:
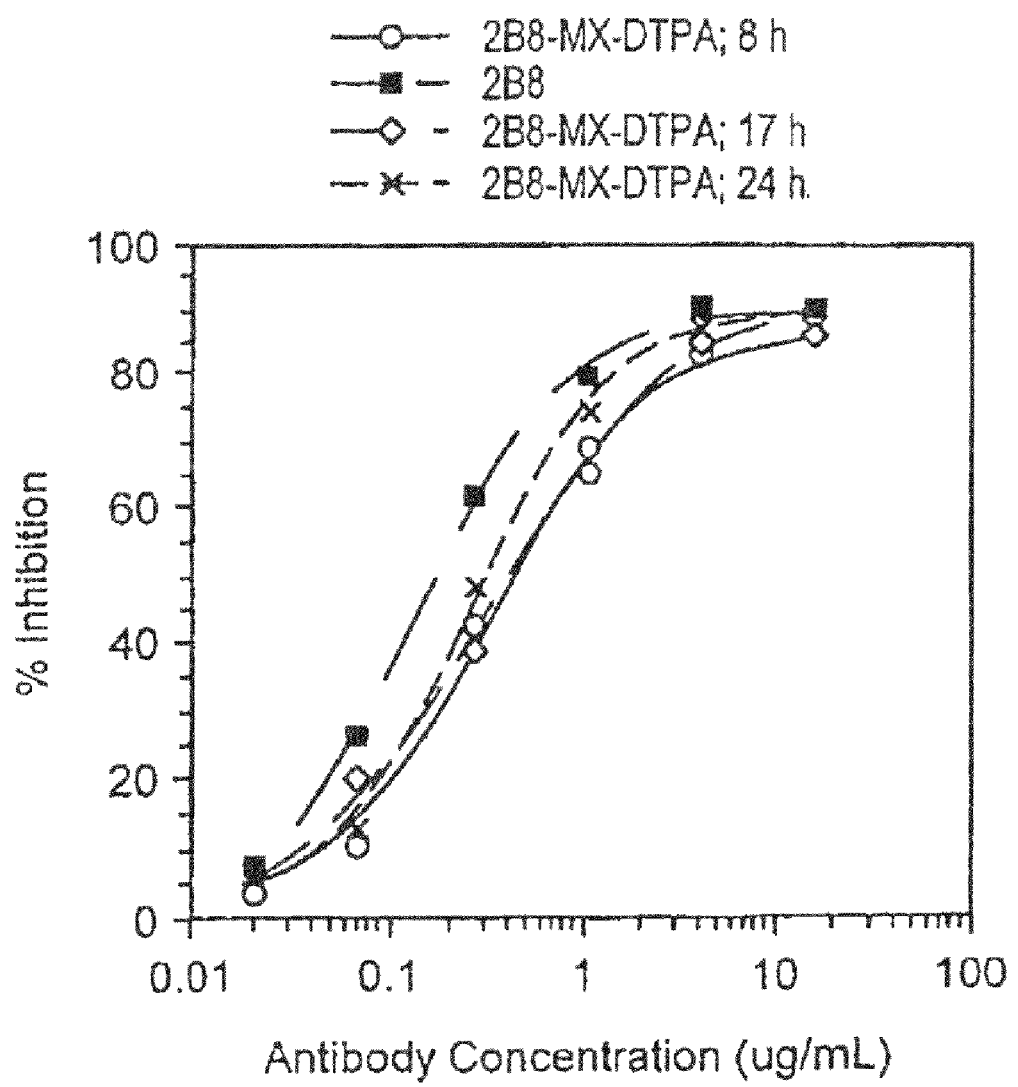

FIG. 36. The binding of 2B8-MX-DTPA conjugates prepared from CHO-derived 2B8 was compared to the unconjugated antibody by direct competition in an ORIGEN assay. Conjugates were prepared by incubation of 2B8 with MX-DTPA for 8, 17, and 24 h before removal of unreacted chelate. For binding assessment, antibodies were incubated with a fixed concentration of CD20-positive B-cells (SB) and a trace amount of ruthenium-labeled CHO 2B8. After incubation for three hours at ambient temperature, binding, expressed as relative electrochemiluminescence (ECL), was determined using the ORIGEN instrument as described in the Materials and Methods. Values represent the means of duplicate determinations. Conjugate preparations exhibited similar binding compared to unconjugated 2B8 antibody.

Figure 37A:
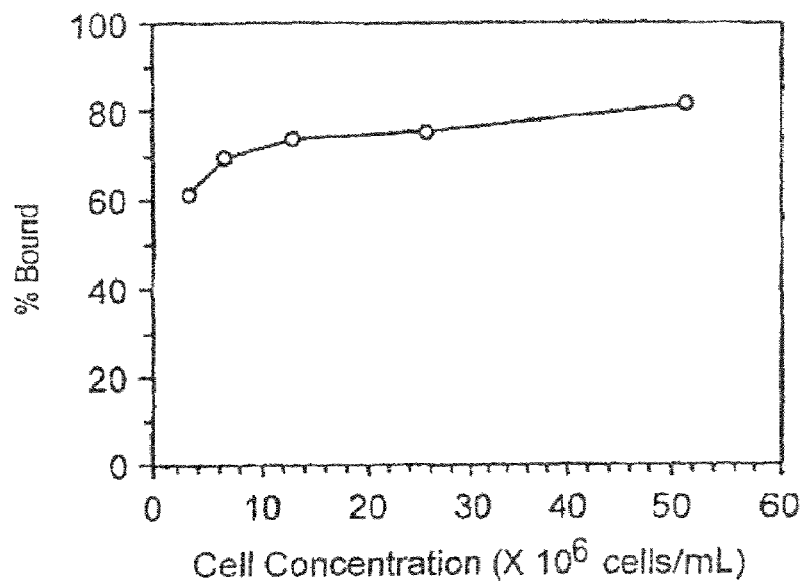
Figure 37B:
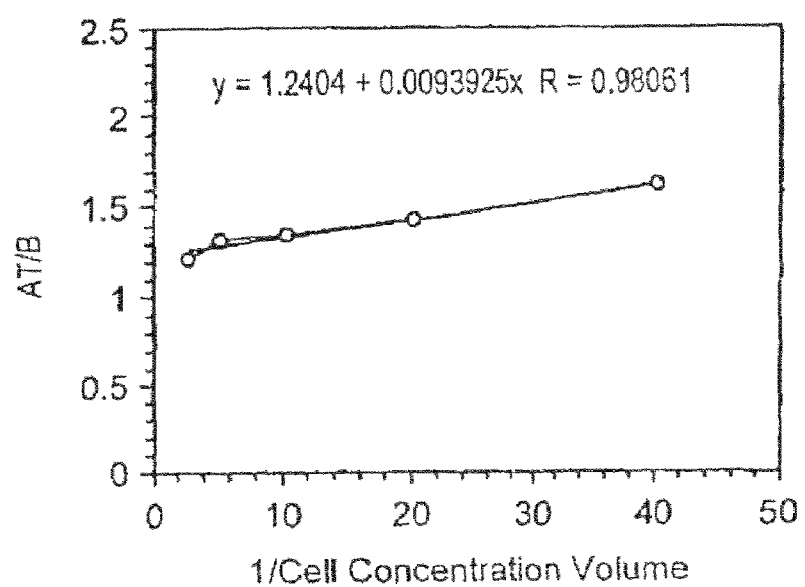

FIGS. 37A and 37B. FIG. 37A) SB cells were washed and resuspended to 90×10$^6$ cells/mL with dilution buffer (1× PBS, pH 7.4 containing 1% (w/v) bovine serum albumin. Increasing concentrations of cells were incubated for 3 h with 7.5 ng/mL In2B8 prepared using 2B8-MX-DTPA lot 0165A. FIG. 37B) Double-inverse plot of cell concentration vs. bound radioactivity/total radioactivity (B/AT). Immunoreactivity was calculated as 1/y-intercept×100. Immunoreactivity and correlation coefficient (R) values were 80.6% and 0.981, respectively.

Figure 38A:
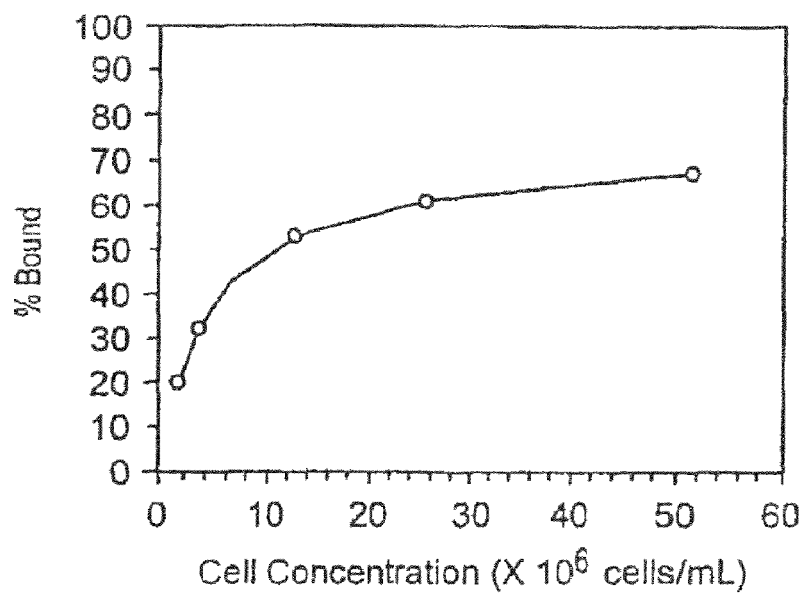
Figure 38B:
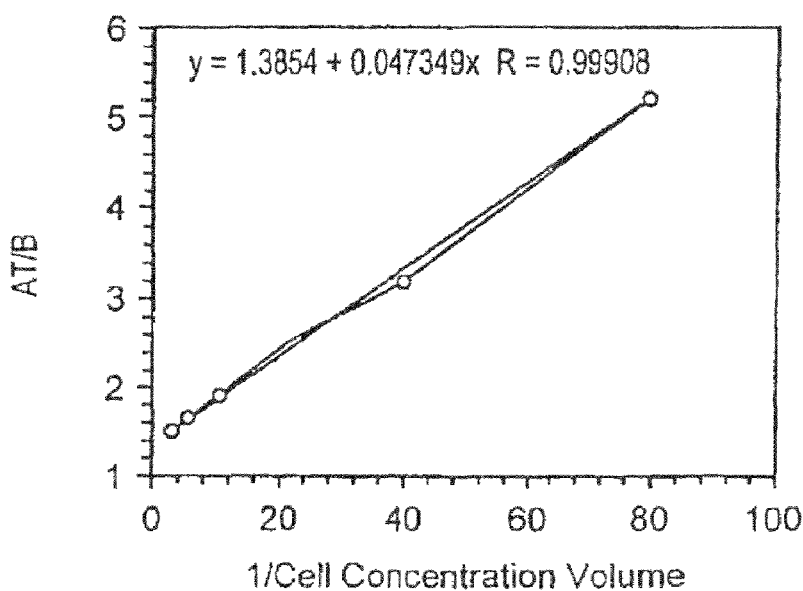

FIGS. 38A and 38B. FIG. 38A) SB cells were washed and resuspended to 90×10$^6$ cells/mL with dilution buffer (1× PBS, pH 7.4 containing 1% (w/v) bovine serum albumin. Increasing concentrations of cells were incubated for 3 h with 2 ng/mL Y2B8 prepared using 2B8-MX-DTPA lot #0165A. FIG.38B) Double-inverse plot of cell concentration vs. bound radioactivity/total radioactivity (B/AT). Immunoreactivity was calculated as 1/y-intercept×100. Immunoreactivity and correlation coefficient (R) values were 72.2% and 0.999, respectively.

DETAILED DESCRIPTION OF THE INVENTION

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defied below.

low metal—refers to reagents treated to reduce metal contamination to a level which does not impact radioincorporation antigen positive—means expresses antigen that is recognized by particular antibody of the invention in such a way that the antibody is capable of binding.

% radioincorporation—refers to the amount of radiolabel from a radiolabeling reaction that is conjugated to the antibody relative to the total amount of radiolabel initially added to the reaction.

% binding—refers to the amount of antibody from a sample which binds to the target antigen, with or without specificity.

% immunoreactivity or binding specificity—refers to that amount of an antibody sample which binds to the target antigen with specificity.

diagnostic antibody—refers to an antibody conjugated to a radiolabel such us $^{111}$I which can effect diagnostic imaging of tumors and antigen positive cells.

therapeutic antibody—refers to an antibody conjugated to a alpha or beta emitting radiolabel (such as 90Y) which can effect cell killing when bound to the targeted antigen.

DESCRIPTION OF THE INVENTION

Pre-Clinical Development of Murine Monoclonal Anti-CD20 Antibody 2B8, Conjugated 2B8, $^{111}$In and $^{90}$Y-Labeled 2B8

I. Materials and Methods for Development of Murine Monoclonal Anti-CD20 Antibody 2B8, Conjugate 2B8-MX-DTPA, $^{111}$In-Labeled 2B8-MX-DTPA and HPLC-Purified $^{90}$Y-MX-DTPA A. Materials.

1. Cells.

The human cell lines SB and HSB were obtained from the American Type Culture Collection and cultured in RPMI-1640 containing 10% fetal bovine serum. The CD20-positive SB cell line is a B lymphoblastoid cell line derived from the peripheral blood buffy coat of a patient with acute lymphoblastic leukemia (1). The antigen-negative cell line HSB is a T lymphoblastoid cell line developed from tumors induced in newborn Syrian hamsters (2). The murine myeloma cell line SP2/0 was similarly maintained in RPMI-1640 containing 10% fetal bovine serum.

2. Antibodies.

The anti-CD20 antibodies B1 and Leu 16 were purchased from Coulter Immunology and Becton/Dickinson, respectively. The $^{125}$I-labeled goat anti-mouse IgG and goat anti-human IgG antibodies were obtained from ICN. Goat F(ab')2 anti-mouse IgG was obtained from Cappel.

3. Reagents

Freund's complete and incomplete adjuvants were purchased from Sigma Chemical Company. Polyethylene glycol, HAT concentrate, and HT concentrate were all obtained from Boehringer Mannheim. Fluorescein isothiocyanate (FITC) was purchased from Sigma Chemical Company. Indium-[111] chloride and $^{90}$Y chloride were obtained from Amersham or NEN Dupont. Yttrium-[89] chloride was purchased from Aldrich Chemical Company. All other reagents were obtained from standard sources.

Reagents used for conjugation and radiolabeling protocols were processed, to remove contaminating heavy metal ions which could compete with the radioisotopes during the radiolabeling step. Reagents were typically processed by passing the solutions through a column of Chelex 100 ion exchange resin (BioRad Industries) or batch processing by addition of Chelex 100 to a prepared solution. Low metal-containing water, either Milli-Q-purified or Water for Irrigation (WFIr) was used for all preparations and dilutions. The metal-free solutions were sterile-filtered and collected in sterile plastic containers.

B. Methods.

1. Production and Screening of 2B8 Hybridoma Supernatants by RIA.

Ten BALB/c mice were immunized with 20 million SB cells suspended in PBS containing Freunds complete adjuvant. The cells were injected both s.c and i.p at multiple sites on the animal. After a 2 week rest period the mice were injected a second time with SB cells emulsified in Freund's incomplete adjuvant. Subsequent immunization boosters were performed on a weekly schedule with SB cells suspended in PBS. Mice were immunized for a period of 6 weeks to 4 months.

Two animals at a time were sacrificed by cervical dislocation and their spleens removed for fusion with the murine myeloma SP2/0. Animals were chosen based on the ability of post-immune sera to effectively inhibit the binding of radiolabeled Coulter B1 anti-CD20 antibody to human SB cells. Three days prior to each fusion the selected animals were given one last intravenous (tail vein) injection of 20 million SB cells in PBS. Upon sacrifice the spleens were removed under aseptic conditions and the splenocytes fused with SP2/0 cells at a ratio of 5:1 (splenocytes:SP2/0). Fused cells were washed in tissue culture media and distributed into 96 well plates containing HAT selection media. Hybridomas were screened by inhibition radioimmunoassay using Coulter B1 antibody after 10-14 days.

Screening of hybrids secreting anti-CD20 antibody was accomplished using established radioimmunoassay methods. Briefly, Coulter B1 anti-CD20 antibody was purified by Protein A affinity chromatography. Fifty micrograms of purified antibody was coupled to $^{125}$I by brief oxidation in the presence of Iodobeads (Pierce Chemical Co.), following the manufacturer's procedure. The radiolabeled antibody was desalted on amberlite resin and stored in dilution buffer (PBS, pH 7.4, containing 0.2% gelatin, 0.02% sodium azide, and 1.0% BSA). Ten nanograms of radiolabeled antibody was placed in each well of a previously blocked filter assay plate (blocking buffer: dilution buffer containing 10% FBS) along with 50 μL of hybridoma supernatant from test wells and 100,000 SB cells suspended in 50 μL dilution buffer. The suspension was incubated for one hour at ambient temperature. The plates were washed thoroughly with wash buffer (PBS, pH 7.4, containing 0.2% gelatin and 0.02% sodium azide) on a V&P Scientific vacuum manifold and filter bottoms containing trapped SB cells were transferred to a gamma counter. Wells containing only HAT media and labeled B1 antibody were used as background controls and identical wells containing SB cells were used as positive controls. Inhibition controls contained radiolabeled B1 and various amounts of unlabeled B1 antibody ranging from 2 μg to 2 ng.

2. Flow Cytometry Studies.

a. Cell Lines

Preliminary flow cytometry studies were performed with supernatants from 2B8 hybridoma cultures. One hundred microliters of hybridoma supernatant was incubated with SB cells for one hour at ambient temperature; a secondary antibody (goat F(ab')2 anti-mouse IgG; Cappel), used at a 1/400 dilution, was added subsequently and the incubation continued for 1 hour in the dark. The cells were washed for 5 times. Controls included cells only (no primary or secondary antibody) from which autofluorescence was determined, cells with secondary antibody only to determine non-specific binding and commercially available fluorescein isothiocyanate-conjugated B1 (B1-FITC) for a CD20 population control.

For some experiments, fluorescein was coupled to purified 2B8 antibody through the reaction of amino groups with fluorescein isothiocyanate (FITC). Briefly, 2B8 antibody (1.2 mg/mL) was incubated in pH 9.5, 0.1M sodium carbonate buffer with 150-200 µg FITC per mg protein. The solution was incubated at room temperature for 2 hours and the resulting 2B8-FITC conjugate was purified on a Sephadex G-25 column. Other reagents used in these studies such as B1 and Leu 16 were purchased as fluorescein conjugates directly from Coulter or Becton Dickinson.

Cells to be analyzed were harvested and washed three times with PBS containing 0.2% BSA and 0.1% sodium azide. Viability was determined by trypan blue exclusion with a viability requirement of >90%. Cell concentrations were adjusted to 3 million per ml with 50 µL added per well into 96 well U-bottom plates. Primary antibody (50 µL) was added to appropriate wells and the mixture incubated for 30 min. to 1 h. at ambient temperature; subsequently the cells were washed 5 times with 200 µL/well of PBS containing 0.2% BSA and 0.02% sodium azide. Cells were centrifuged in the plates at 1300 RPM for 1 min. in a Sorvall centrifuge and the supernatants removed by gently "flicking" the plates. Secondary antibody, if needed, was added and incubated for an additional 30 min to 1 h at ambient temperature in the dark; wells were then washed as above. Finally, 200 µL of fixing buffer (0.15 M sodium chloride containing 1% paraformaldehyde, pH 7.4) was added to each sample and the treated cells transferred to 12×75 mm tubes for analysis.

b. Whole Blood from Cynomolgus Monkeys.

After removal of plasma, the cells were washed twice by centrifugation and resuspension in HBSS. Fetal bovine serum (2 mL) was added and the cells resuspended. One hundred microliters of the resuspended cells were then distributed to each of 6, 15 ml conical centrifuge tubes. Fluorescently-labeled monoclonal antibodies were added as follows:

Tube #1: Murine anti-CD2-FITC (AMAC), 2.5 µg/mL, 5 µg;
Tube #2: Goat anti-Human IGM-FITC (Fisher) 2.5 µg/mL, 5 µg;
Tube #3: Goat anti-mouse IgG-RPE (Fisher) 2.5 µg/mL, 5 µg;
Tube #4: Goat anti-Human IgM-FITC+Goat anti-mouse IgG-RPE (absorbed), 2.5 µg/mL, 5 µg;
Tube #5: anti-human CD20-FITC (anti-Leu 16, Becton Dickinson), 5 µg;
Tube #6: Cells only (auto-fluorescence).

Labeled antibodies and cells were centrifuged for 2 min at 1500 rpm to mix cells and antibodies and all 6 samples were then placed on ice and incubated for 30 min. Subsequently the tubes were removed from the ice and lysing buffer (pre-warmed to 37° C.) was added to a volume of 12 mL. The samples were then incubated for 15 min at room temperature, centrifuged for 5 min at 4° C. at 1500 rpm, and the supernatants removed. Cell pellets were then washed twice in labeling buffer (PBS containing 1% BSA and 0.05% sodium azide).

Subsequently the cells were fixed by the addition of 0.5 mL of fixation buffer (0.15 M sodium chloride, pH 7.4, containing 1% paraformaldehyde) per tube and analyzed on a Becton Dickinson FACScan instrument using autocompensation and precalibration with Calibrite beads. Green fluorescence from fluorescein was measured in FL1 mode and red fluorescence from phycoeretherin was measured in FL2 mode. Data were expressed in log form. Viable lymphocyte populations were initially identified by forward vs. right angle light scatter in a dot plot bitmap. The total lymphocyte population was then isolated by gating out all other events. Subsequent fluorescence measurements reflected only those specific events which occurred within the gated area.

For high-dose pharmacology/toxicology studies the pre-study lymphocyte levels were determined for each cynomolgus monkey and used as baseline values. The percentage of T- and B-cells and T:B ratios were calculated and used as depletion references. The pre-study B cell population was enumerated with Leu 16 and anti-human IgM antibodies.

After injection of 2B8 into the monkeys, when the CD20 antigen was saturated with 2B8, the percentage of B cells in the total population was approximated using goat anti-human IgM-FITC, anti-mouse IgG-RPE and the double staining population containing these two markers. The double staining population was used for quantitation until all of the 2B8 was cleared from the peripheral blood of the animals. The percentage of T cells in the total lymphocyte population was estimated using anti-CD2-FITC. Data were averaged from three, 10,000 event measurements made with each sample. Cells from each of the designated blood samples were evaluated subsequently, enumerating in each case the T- and B-cell subpopulations within the total lymphocyte population. The T:B ratios were also examined. Depletion of B-cells was calculated as the percent of reduction of B-cells relative to original B-cell levels for each individual monkey.

3. Radioiodination and Immunoprecipitation of CD20.

One hundred million SB cells were divided into two equal parts after surface iodination with $^{125}I$ and Iodobeads (Pierce Chemical Co.). The cells were washed repeatedly by centrifugation until radioactivity levels in the supernatant returned to background. One hundred micrograms of 2B8 or B1 (Coulter Immunology) antibody were added to either of the two samples of labeled B cells. The antibodies and SB cells were incubated overnight and then washed three times by centrifugation until all of the unbound antibody was removed. The cell pellets containing bound 2B8 and B1 were then lysed and extracted by addition of 1% NP-40 detergent in 0.1 M Tris-HCl, pH 8.0, followed by incubation at room temperature for 1 h. The extract was centrifuged in a microfuge at high speed for 30 min and the supernatants were transferred to new tubes. Protein A-Sepharose (300 µL) was added to each tube and the resin pelleted by centrifugation. The protein A-Sepharose was then washed 20 times to remove non specifically bound iodinated protein. When the bead-to-supernatant radioactivity ratio reached a value of 100, the pellet was extracted with SDS PAGE sample buffer and heated to boiling. After cooling, approximately 15,000 cpm of each of the extracts were added to wells of a 10% polyacrylamide gel. A low molecular weight pre-stained standard (BioRad Inc.) was added to a separate well and used for molecular weight estimation. The proteins were resolved by electrophoresis and the gel was dried and exposed to a sheet of X-ray film for 24 hours at −70° C.; subsequently the film was developed and analyzed.

4. Scatchard Analysis of 2B8 Binding.

Purified 2B8 was evaluated for apparent affinity by Scatchard analysis. Radiolabeled 2B8 was prepared by reaction with $^{125}$I in the presence of Iodobeads. Following removal of free iodine the radiolabeled antibody was incubated in various concentrations, in duplicate, ranging from 5000 ng per well to 35 ng/well with 10,000 SB cells. The amount of antibody binding to cells was calculated from the specific activity of the $^{125}$I-labeled 2B8; The ratio of bound/free antibody was plotted against the molar concentration of bound antibody and the apparent affinity constant was determined from the ratio of the X and Y axis intercepts.

5. Preparation of 2B8-MX-DTPA a. Source of MX-DTPA

For some pre-clinical studies, carbon-14-labeled 1-isothiocyanatobenzyl-3-methyldiethylenetriaminepentaacetic acid (MX-DTPA) was provided as a dry solid by Dr. Otto Gansow at the National Institute of Health and stored desiccated at 4° C. protected from light. Stock solutions of the chelate were prepared in Milli-Q water and the concentration determined by assessing the radioactivity and using the specific activity of the compound. Stock solutions were generally 2-5 mM and were stored at −70° C. in polypropylene tubes. For other studies, MX-DTPA was obtained from Coulter Immunology as the disodium salt in water and stored at −70° C.

b. Maintenance of Metal-Free Conditions

In addition to using metal-free reagents, all manipulations of reagents were performed so as to minimize the possibility of metal contamination. When possible, polypropylene plastic containers such as flasks, beakers and graduated cylinders were used. These were washed with Alconox and exhaustively rinsed with Milli-Q water before use. In addition, metal-free pipette tips (BioRad) were used for accurately manipulating small volumes. For manipulating larger volumes of reagents, sterile, plastic serological pipettes (available in 1 to 25 mL sizes) were used. Reactions were conveniently performed in screw-top, polypropylene microfuge tubes (Sardstedt Industries; 1.5 mL capacity) or polypropylene conical tubes (Costar; 15 mL and 50 μL). When dialysis tubing was manipulated, disposable surgical gloves, previously rinsed with Milli-Q water, were worn.

c. Preparation of Antibody

The murine anti-CD20 antibody 2B8 was purified initially from ascites by Protein A and QAE chromatography. For later experiments 2B8 was purified from hollow-fiber bioreactor supernatants using the same purification process. The hollow-fiber-derived antibody has now been replaced for commercialization purposes with the CHO-derived antibody described in Example 2.

The antibody was prepared for conjugation by transferring it into metal-free 50 mM bicine-NaOH, pH 8.6, containing 150 mM NaCl, using dialysis or repetitive buffer exchange. In some-studies, buffer exchange was effected using repetitive ultrafiltration with Centricon 30 (Amicon) spin filters (30,000D MWCO). In general, 50-200 μL of protein (10 mg/mL) was added to the filter unit and 2 mL of bicine buffer added. The filter was centrifuged at 4° C. in a Sorval SS-34 rotor at 6,000 rpm for 45 min. Retentate volume was approximately 50-100 μL. This process was repeated twice with the same filter. Retentate was transferred to a polypropylene 1.5 mL screw cap tube, assayed for protein, diluted to 10.0 mg/mL and stored at 4° C. until used for conjugation. For some studies, the protein was transferred into 50 mM sodium citrate, pH 5.5 containing 150 mM NaCl and 0.05% sodium azide using the same protocol described above.

d. Conjugation Protocol

Conjugation of 2B8 with MX-DTPA was performed in polypropylene tubes at ambient temperature. Frozen stock solutions of MX-DTPA were thawed immediately before use. Typically, 50-200 μL of antibody at 10 mg/mL were reacted with chelate at a molar ratio of chelate-to-protein of 4:1. Reactions were initiated by adding the chelate stock solution and gently mixing; the conjugation was allowed to proceed overnight, generally for 14 to 20 h, at ambient temperature. Unreacted chelate was removed from the conjugate by dialysis or repetitive ultrafiltration, as described above, into metal-free normal saline (0.9% w/v) containing 0.05% sodium azide. The protein concentration was adjusted to 10 mg/mL and stored at 4° C. in a polypropylene tube until radiolabeled.

e. Determination of Chelate Incorporation

Chelate incorporation was determined by scintillation counting and comparing the value obtained with the purified conjugate to the specific activity of the carbon-[14]-labeled chelate. For later studies, in which non-radioactive chelate obtained from Coulter Immunology was used, chelate incorporation was assessed by incubating the conjugate with an excess of a radioactive carrier solution of $^{90}$Y of known concentration and specific activity.

Briefly, a stock solution of yttrium chloride of known concentration was prepared in metal-free 0.05 N HCl to which carrier-free $^{90}$Y (chloride salt) was added. An aliquot of this solution was analyzed by liquid scintillation counting to determine an accurate specific activity for this reagent. A volume of the yttrium chloride reagent equal to 3-times the number of mols of chelate expected to be attached to the antibody, typically 2 mol/mol antibody, was added to a polypropylene tube, and the pH adjusted to 4.0-4.5 with 2 M sodium acetate. Conjugated antibody was subsequently added and the mixture incubated 15-30 min at ambient temperature. The reaction was quenched by adding 20 mM EDTA to a final concentration of 1 mM and the pH of the solution adjusted to approximately pH 6 with 2M sodium acetate.

After a 5 min incubation the entire volume was purified by high-performance size-exclusion chromatography as described below. The eluted protein-containing fractions were combined, the protein concentration determined, and an aliquot assayed for radioactivity. The chelate incorporation was calculated using the specific activity of the $^{90}$Y chloride preparation and the protein concentration.

f. Immunoreactivity of 2B8-MX-DTPA

The immunoreactivity of conjugated 2B8 was assessed using whole-cell ELISA. Mid-log phase SB cells were harvested from culture by centrifugation and washed two times with 1× HBSS. Cells were diluted to 1-2×10$^6$ cells/mL in HBSS and aliquoted into 96-well polystyrene microliter plates at 50,000-100,000 cells/well. The plates were dried under vacuum for 2 h at 40-45° C. to fix the cells to the plastic. The plates were stored dry at −20° C. until used. For assay the plates were warmed to ambient temperature immediately before use, then blocked with 1× PBS, pH 7.2-7.4 containing 1% BSA (2 h). Samples for assay were diluted in 1× PBS/1% BSA, applied to plates and serially diluted (1:2) into the same buffer. After incubating plates for 1 h at ambient temperature, the plates were washed three times with 1× PBS. Secondary antibody (goat anti-mouse IgG1-specific HRP conjugate) (50 μL) was added to wells (1:1500 dilution in 1×PBS/1% BSA) and incubated 1 h at ambient temperature. Plates were washed four times with 1× PBS followed by the addition of ABTS substrate solution (50 mM sodium citrate, pH 4.5 containing 0.01% ATBS and 0.001% $H_2O_2$). Plates were read at 405 nm after 15-30 min incubation. Antigen-negative HSB cells were included in assays to monitor non-specific binding. Immunoreactivity of the conjugate was calculated by plotting the absorbance values vs. the respective dilution factor and comparing these to values obtained using native antibody (representing 100% immunoreactivity) tested on the same plate. Several values on the linear portion of the titration profile were compared and a mean value determined.

g. In Vitro Stability of Native 2B8 and 2B8-MX-DTPA

For this 12-week assessment of antibody and conjugate stability, aliquots of 2B8 antibody and 2B8-MX-DTPA were formulated in either normal saline or normal saline containing 10 mM glycine-HCl, pH 6.8. Duplicate sets of samples were incubated at both 4° and 30° C. and samples assayed weekly using the following methods: SDS-PAGE (both reducing and nonreducing), immunoreactivity by whole-cell enzyme immunoassay using either SB (antigen-positive) or HSB (antigen-negative) cells as capture, and isoelectric focusing gel, electrophoresis (pH range, 3-10). In addition, the radiolabeling efficiency of the conjugate was assessed at weeks 4, 8, and 12 by radiolabeling the conjugate with $^{90}$Y and analyzing the product by SDS-PAGE and autoradiographic analysis. Finally, in a separate study, aliquots of 2B8-MX-DTPA incubated at 4° and 30° C. for 10 weeks were radiolabeled with $^{111}$In and evaluated in a biodistribution study in BALB/c mice as described below.

h. Immunohistology Studies.

Immunohistology studies with both the native and conjugated (2B8-MX-DTPA) antibodies were performed by IMPATH Laboratories using sections of human tissues fixed with acetone. The antibody was purified from hollow-fiber bioreactor supernatants by chromatography on protein A and Q Sepharose. Clinical-grade conjugate was prepared using MX-DTPA from Coulter Immunology according to the protocol described above.

i. In Vitro Immunoreactivity of Radiolabeled 2B8-MX-DTPA.

For some experiments, the whole-cell ELISA protocol used for unlabeled 2B8-MX-DTPA was used. In later experiments, immunoreactivity of $^{111}$In and $^{90}$Y-labeled conjugates (each prepared at IDEC Pharmaceuticals or, alternatively, at MPI Pharmacy Services, Inc.) was determined using a modified version of the whole-cell binding assay described by Lindmo (3). Briefly, increasing concentrations of mid-log phase, antigen-positive SB cells or antigen-negative HSB cells [20-30×10$^6$ cells/mL in dilution buffer (PBS, pH 7.4 containing 1% BSA, 0.1% gelatin, and 0.02% sodium azide)] were added to duplicate sets of tubes. The radiolabeled conjugate was diluted to a final antibody concentration of 1-5 ng/mL with dilution buffer and 0.35 mL was added to each tube. Following a 75-90 min incubation period at ambient temperature the cells were pelleted by centrifugation and the supernatants collected. Radioactivity remaining in the supernatant fraction was determined with a gamma or scintillation counter. The data were plotted as the quotient of the total radioactivity added divided by the cell-associated radioactivity, versus the inverse of the cell number per tube. The y axis intercept thus represents the immunoreactive fraction.

j. In Vitro Stability of Radiolabeled 2B8-MX-DTPA in Human Serum.

The in vitro stability of $^{111}$In- and $^{90}$Y-labeled 2B8-MX-DTPA was assessed by incubation in human serum at 37° C. for 96 hours. The conjugated antibody was prepared and radiolabeled with $^{111}$In ("mix-and-shoot" protocol) or $^{90}$Y as described above. The specific activities of the $^{111}$In and $^{90}$Y-labeled conjugates were 2.5 and 14.6 mCi/mg, respectively; the radiolabeled conjugates were suspended in buffer containing 75 mg/mL human serum albumin (HSA) and 1 mM DTPA (yttrium-labeled conjugate) or buffer containing 50 mg/mL HSA (indium-labeled conjugate). The radiolabeled conjugates were diluted 1:10 with normal human serum (non-heat-inactivated) and aliquots placed aseptically into sterile capped tubes; these tubes were then incubated at 37° C. for periods up to 96 hours. At selected times conjugate samples were removed and analyzed by non-reducing SDS-PAGE in 4-20% gradient gels followed by autoradiography, and by instant thin layer chromatography.

k. In Vitro Stability of Clinically-Formulated $^{111}$In-2B8-MX-DTPA.

The 2B8-MX-DTPA conjugate was radiolabeled with $^{111}$In and used without HPLC purification ("mix-and-shoot" protocol). The radiolabeled antibody was diluted into PBS and human serum albumin (HSA) added to a final concentration of 50 mg/mL. The specific activity of the formulated radiolabeled conjugate was 2.2 mCi/mg. The formulated conjugate was subsequently incubated at 4° C. for 48 hours and aliquots analyzed at time 0, 24 h and 48 hours using non-reducing SDS-PAGE in 4-20% gradient gels followed by autoradiography, and by instant thin layer chromatography. The immunoreactivity at each time point was assessed using the wholecell suspension assay described in section 1 above.

l. In Vitro Stability of Clinically-Formulated $^{90}$Y-2B8-MX-DTPA.

The 2B8-MX-DTPA conjugate was radiolabeled with $^{90}$Y and purified by size-exclusion chromatography on HPLC using 1× PBS as an elution buffer. The radiolabeled conjugate fractions were pooled and human serum albumin and DTPA were added to final concentrations of 75 mg/mL and 1 mM, respectively. The specific activity of the formulated radiolabeled conjugate was 14.6 mCi/mg. The formulated conjugate was subsequently incubated at 4° C. for 48 hours and aliquots analyzed at time 0, 24 h and 48 hours using non-reducing SDS-PAGE in 4-20% gradient gels followed by autoradiography, and instant thin layer chromatography. Immunoreactivity at each time point was assessed using the whole-cell suspension assay described in section 1 above.

2. Animal Studies.

a. Primate High Dose Pharmacology/Toxicology Study Using 2B8.

Antibody 2B8 was evaluated in a high-dose pharmacology study performed under GLP regulations at White Sands Research Center (Study Number 920111). Adult *Macaca fascicularis* (cynomolgus) monkeys were used; study groups each consisted of one male and one female. The antibody was injected intravenously every 48 hours for a total of seven injections. The study consisted of five groups: Group I (saline); Group II (0.6 mg/kg); Group III (2.5 mg/kg); Group IV (10 mg/kg); and, Group V (10 mg/kg on day 0 only).

Prior to initiation of the study, blood was obtained from all 10 animals and used to determine reagent backgrounds and initial B cell populations. All subsequent blood samples were drawn prior to each antibody injection. Groups III and IV were sacrificed at day 13 for complete necropsy and histopathology.

Animals in groups I, II, and V were bled on days 0, 1, 3, 7, 13, 21, 37 and 52; approximately 5 mL whole blood was drawn in heparinized tubes. Whole blood was kept at 4° C. and analyzed within 24 hours. Blood from each animal was centrifuged at 2000 rpm for 5 min. and the supernatant plasma was removed for assay of serum 2B8 levels by RIA (see RIA procedure for specific assay methods). The pelleted material containing PBLs and RBCs was resuspended in FCS for FACS analysis.

b. Pharmacokinetic Studies with 2B8 and 2B8-MX-DTPA.

The mean serum beta half life of 2B8 in cynomolgus monkeys was determined using Group V animals (above). Goat anti-mouse IgG1 (Fisher Scientific) was diluted to 2.0 µg per ml in 10 mM borate buffer, pH 9.6, and 50 µL was added to each well of a 96-well plate. The antibody was allowed to bind to the plate during an overnight incubation at 4° C., or for 2 h at ambient temperature. Each plate was blocked for 30 min. at ambient temperature with 150 µL per well of PBS containing 1% BSA. The plates were washed with distilled water and serum or plasma samples were applied in triplicate to individual wells at 1:100 initial dilution followed by serial 1:2 dilutions. Purified 2B8 was added to pre-bleed sera and diluted for use as a standard curve beginning with 0.5 mg/mL; samples were diluted 1:100 and then serially diluted as with the other samples. The plates were incubated for 1 h at ambient temperature and washed 4 times with distilled water. The secondary reagent (goat anti-mouse IgG1-HRPO) was then added at 1:4000 dilution and incubated at ambient temperature for an additional hour. The plates were washed again in distilled water and 0.1 mL peroxidase substrate was added containing hydrogen peroxide. Color was allowed to develop from the reaction for 20 min.; the absorbance was subsequently determined at 405 nm using a microplate ELISA reader. The results were plotted in µg antibody per mL serum.

In addition, the $\beta\ t_{1/2}$ values of 2B8 and 2B8-MX-DTPA were determined in BALB/c mice. Unconjugated 2B8 stored at −70° C. in 1× PBS, pH 7.4/10% glycerol was thawed, diluted to 0.5 mg/mL and sterile filtered. Conjugated antibody was prepared following standard protocols but with carbon-[14]-labeled chelate; chelate incorporation was 1.5 mol/mol antibody. The purified conjugate was diluted to 0.5 mg/mL in normal saline (0.9%), sterile filtered, and stored at 4° C. with the native antibody until used.

Six-to-eight week old mice were injected with 100 µL of purified 2B8 antibody at a concentration of 250 µg/mL. Mice were subsequently bled by retro-orbital puncture at various times ranging from 0 to 264 hours and their sera analyzed for the presence of the native and conjugated 2B8 antibody by whole-cell enzyme immunoassay using the antigen-positive B-cell line SB as the capture. The resulting data were plotted as the concentration of 2B8 or 2B8-MX-DTPA versus time; from these results a linear regression plot was generated and the slope used to determine the $\beta\ t_{1/2}$ values.

c. Pharmacology/Toxicology Study of [89]-Y-2B8-MX-DTPA in Cynomolgus Monkeys.

Yttrium-[89]-bearing 2B8-MX-DTPA was prepared using the protocol described for insertion of $^{90}$Y, except that HPLC purification was not used. The non-radioactive, metal-bearing conjugate was formulated in 1× PBS containing 75 mg/mL HSA and 1 mM DTPA and evaluated in GLP study number 920611 at White Sands Research Center. One male and one female monkey were included in each of four groups. The animals were injected intravenously every 48 hours for a total of 7 injections with the following amounts of drug: group 1 (saline); group II (0.003 mg/kg); group III (0.03 mg/kg); and, group IV (0.3 mg/kg). The animals were evaluated during the study by determining body weights and temperatures, food and water consumption, elimination, serum chemistries, hematology, urinalysis, and physical examinations. Animals in groups I through IV were bled prior to infusion on days 0, 2, 7, 10 and 14 and the blood analyzed for circulating B-cell levels by FACS analyses.

d. Biodistribution of Radiolabeled 2B8-MX-DTPA

In a preliminary study $^{111}$In-labeled 2B8-MX-DTPA was evaluated for tissue biodistribution in six-to-eight week old BALB/c mice. The radiolabeled conjugate was prepared using clinical-grade 2B8-MX-DTPA following the "mix and shoot" protocol described above. The specific activity of the conjugate was 2.3 mCi/mg and the conjugate was formulated in PBS, pH 7.4 containing 50 mg/mL HSA. Mice were injected intravenously with 100 µL of $^{111}$In-labeled 2B8-MX-DTPA (approximately 21 µCi) and groups of three mice were sacrificed by cervical dislocation at 0, 24, 48, and 72 hours. After sacrifice, the tail, heart, lungs, liver, kidney, spleen, muscle, and femur were removed, washed, weighed; a sample of blood was also removed for analysis. Radioactivity associated with each specimen was determined by gamma counting and the percent injected dose per gram tissue subsequently determined. No attempt was made to discount the activity contribution represented by the blood associated with individual organs.

In a separate protocol, aliquots of 2B8-MX-DTPA incubated at 4° and 30° C. for 10 weeks were radiolabeled with $^{111}$In to a specific activity of 2.1 mCi/mg for both preparations. These conjugates were then used in biodistribution studies in mice as described above.

For dosimetry determinations, 2B8-MX-DTPA was radiolabeled with $^{111}$In to a specific activity of 2.3 mCi/mg and approximately 1.1 µCi was injected into each of 20 BALB/c mice. Subsequently, groups of five mice each were sacrificed at 1, 24, 48 and 72 hours and their organs removed and prepared for analysis. In addition, portions of the skin, muscle, and bone were removed and processed for analysis; the urine and feces were also collected and analyzed for the 24-72 hour time points.

Using a similar approach, 2B8-MX-DTPA was also radiolabeled with $^{90}$Y and its biological distribution evaluated in BALB/c mice over a 72-hour time period. Following purification by HPLC size exclusion chromatography, four groups of five mice each were injected intravenously with approximately 1 µCi of clinically-formulated conjugate (specific activity: 12.2 mCi/mg); groups were subsequently sacrificed at 1, 24, 48 and 72 hours and their organs and tissues analyzed as described above. Radioactivity associated with each tissue specimen was determined by measuring bremstrahlung energy with a gamma scintillation counter. Activity values were subsequently expressed as percent injected dose per gram tissue or percent injected dose per organ. While organs and other tissues were rinsed repeatedly to remove superficial blood, the organs were not perfused. Thus, organ activity values were not discounted for the activity contribution represented by internally associated blood.

e. Tumor Localization of $^{111}$In-Labeled 2B8-MX-DTPA.

The localization of radiolabeled 2B8-MX-DTPA was determined in athymic mice bearing Ramos B-cell tumors. Six-to-eight week old athymic mice were injected subcutaneously (left-rear flank) with 0.1 mL of RPMI-1640 containing 1.2×10$^7$ Ramos tumor cells which had been previously adapted for growth in athymic mice. Tumors arose within two weeks and ranged in weight from 0.07 to 1.1 grams. Mice were injected intravenously with 100 µL of $^{111}$In-labeled 2B8-MX-DTPA (16.7 µCi) and groups of three mice were sacrificed by cervical dislocation at 0, 24, 48, and 72 hours. After sacrifice the tail, heart, lungs, liver, kidney, spleen, muscle, femur, and tumor were removed, washed, weighed; a sample of blood was also removed for analysis. Radioactivity associated with each specimen was determined by gamma counting and the percent injected dose per gram tissue determined.

3. Dosimetry Calculations

Using the biodistribution data obtained using BALB/c mice injected with either the $^{111}$In or $^{90}$Y-labeled 2B8-MX-DTPA (Tables 1-4 and 5-8), estimates of the radiation dose absorbed from a 1.0 mCi dose administered to a 70 Kg patient were calculated using the approach formalized by Medical Internal Radiation Dose (MIRD) Committee of the Society of Nuclear Medicine. The biological half-lives of the radiolabeled conjugates were determined from the injected dose per organ values determined from the biodistribution data for each radioimmunoconjugate. For some tissues, e.g. blood, it was assumed that the biological decay of the radioconjugate followed a two-compartment model with an exponential decay from these compartments. For other tissues, e.g. the liver, whose activity levels remained roughly constant throughout the 72-hour biodistribution study, it was assumed that the biological half-life was very long and assigned a value of 1000 hours.

TABLE 1

Distribution of Activity 1.0 Hour Following I.V. Injection of $^{111}$In-2B8-MX-DTPA Into Normal BALB/c Mice
Mean Values ± SD

| Sample | Organ Weight Gram | % ID/ Gram | % ID per Organ |
|---|---|---|---|
| Blood | 1.47 ± 0.17 | 40.3 ± 5.32 | 58.4 ± 3.1 |
| Heart | 0.087 ± 0.01 | 5.88 ± 0.76 | 0.51 ± 0.05 |
| Lung (2) | 0.149 ± 0.01 | 14.2 ± 1.4 | 2.10 ± 0.17 |
| Kidney (1) | 0.127 ± 0.02 | 9.82 ± 0.86 | 1.22 ± 0.12 |
| Liver | 1.06 ± 0.20 | 10.32 ± 1.58 | 10.76 ± 1.93 |
| Spleen | 0.090 ± 0.01 | 6.94 ± 1.17 | 0.61 ± 0.03 |
| Muscle | 8.39 ± 0.98 | 0.70 ± 0.25 | 5.67 ± 1.35 |
| Bone | 3.15 ± 0.35 | 2.97 ± 0.71 | 9.10 ± 1.09 |
| Skin | 3.15 ± 0.35 | 0.96 ± 0.29 | 3.0 ± 1.12 |
| GI Tract | 2.58 ± 0.31 | 6.10 ± 2.00 | 7.80 ± 1.80 |
| Urine | | | — |
| Feces | | | — |
| TOTAL | | | 99.04 ± 4.8 |

No. Mice = 5
Mean Weight = 20.97 ± 2.46 grams

TABLE 2

Distribution of Activity 24 Hours Following I.V. Injection of $^{111}$In-2B8-MX-DTPA Into Normal BALB/c Mice
Mean Values ± SD

| Sample | Organ Weight Gram | % ID/ Gram | % ID per Organ |
|---|---|---|---|
| Blood | 1.47 ± 0.07 | 21.97 ± 1.87 | 32.22 ± 1.35 |
| Heart | 0.128 ± 0.03 | 4.02 ± 0.23 | 0.38 ± 0.01 |
| Lung (2) | 0.152 ± 0.02 | 7.90 ± 1.61 | 1.20 ± 0.18 |
| Kidney (1) | 0.128 ± 0.01 | 5.94 ± 0.40 | 0.76 ± 0.04 |
| Liver | 1.11 ± 0.10 | 10.08 ± 1.83 | 11.20 ± 2.23 |
| Spleen | 0.082 ± 0.01 | 5.04 ± 0.75 | 0.40 ± 0.02 |
| Muscle | 8.41 ± 0.38 | 1.24 ± 0.05 | 10.44 ± 0.76 |
| Bone | 3.15 ± 0.14 | 2.02 ± 0.33 | 6.31 ± 0.81 |
| Skin | 3.15 ± 0.14 | 3.75 ± 0.39 | 11.77 ± 1.09 |
| GI Tract | 2.91 ± 0.27 | 4.50 ± 0.52 | 6.65 ± 0.56 |
| Urine | | | 0.98 |
| Feces | | | 2.54 |
| TOTAL | | | 87.10 ± 1.68 |

No. Mice = 5
Mean Weight = 21.03 ± 0.94 grams

TABLE 3

Distribution of Activity 48 Hours Following I.V. Injection of $^{111}$In-2B8-MX-DTPA Into Normal BALB/c Mice
Mean Values ± SD

| Sample | Organ Weight Gram | % ID/ Gram | % ID per Organ |
|---|---|---|---|
| Blood | 1.45 ± 0.13 | 22.41 ± 3.95 | 31.90 ± 2.89 |
| Heart | 0.090 ± 0.01 | 4.05 ± 0.94 | 0.36 ± 0.06 |
| Lung (2) | 0.155 ± 0.02 | 8.45 ± 0.53 | 1.31 ± 0.19 |
| Kidney (1) | 0.125 ± 0.01 | 6.16 ± 1.15 | 0.76 ± 0.07 |
| Liver | 1.040 ± 0.11 | 9.41 ± 2.33 | 9.84 ± 3.18 |
| Spleen | 0.082 ± 0.01 | 5.32 ± 0.71 | 0.48 ± 0.11 |
| Muscle | 8.26 ± 0.77 | 1.42 ± 0.58 | 11.62 ± 4.67 |
| Bone | 3.10 ± 0.29 | 2.08 ± 0.16 | 6.41 ± 0.44 |
| Skin | 3.10 ± 0.29 | 3.43 ± 0.59 | 10.54 ± 1.69 |
| GI Tract | 2.96 ± 0.20 | 5.05 ± 0.63 | 7.46 ± 0.60 |
| Urine | | | 1.46 |
| Feces | | | 6.41 |
| TOTAL | | | 88.49 ± 6.87 |

No. Mice = 5
Mean Weight = 20.65 ± 1.93 grams

TABLE 4

Distribution of Activity 72 Hours Following I.V. Injection of $^{111}$In-2B8-MX-DTPA Into Normal BALB/c Mice
Mean Values ± SD

| Sample | Organ Weight Gram | % ID/ Gram | % ID per Organ |
|---|---|---|---|
| Blood | 1.52 ± 0.06 | 18.97 ± 1.31 | 28.51 ± 2.03 |
| Heart | 0.094 ± 0.01 | 3.71 ± 0.31 | 0.35 ± 0.04 |
| Lung (2) | 0.161 ± 0.01 | 7.60 ± 0.30 | 1.18 ± 0.09 |
| Kidney (1) | 0.135 ± 0.01 | 5.55 ± 0.53 | 0.76 ± 0.09 |
| Liver | 1.11 ± 0.11 | 9.90 ± 1.77 | 11.00 ± 2.03 |
| Spleen | 0.095 ± 0.01 | 5.12 ± 0.75 | 0.48 ± 0.04 |
| Muscle | 8.58 ± 0.34 | 1.04 ± 0.09 | 8.95 ± 0.68 |
| Bone | 3.22 ± 0.12 | 1.73 ± 0.34 | 6.04 ± 0.51 |
| Skin | 3.22 ± 0.12 | 3.16 ± 0.60 | 10.19 ± 2.03 |
| GI Tract | 2.79 ± 0.19 | 4.53 ± 0.83 | 6.37 ± 1.38 |
| Urine | | | 2.49 |
| Feces | | | 11.50 |
| TOTAL | | | 87.80 ± 4.79 |

No. Mice = 5
Mean Weight = 21.46 ± 0.84 grams

TABLE 5

Distribution of Activity 1.0 Hour Following I.V. Injection of $^{90}$Y-2B8-MX-DTPA Into Normal BALB/c Mice
Mean Values ± SD

| Sample | Organ Weight Gram | % ID/ Gram | % ID per Organ |
|---|---|---|---|
| Blood | 1.27 ± 0.06 | 39.23 ± 2.45 | 49.77 ± 1.72 |
| Heart | 0.086 ± 0.01 | 5.80 ± 0.84 | 0.50 ± 0.09 |
| Lung (2) | 0.137 ± 0.01 | 12.11 ± 1.08 | 1.66 ± 0.17 |
| Kidney (1) | 0.120 ± 0.01 | 10.23 ± 1.30 | 1.15 ± 0.12 |
| Liver | 0.921 ± 0.05 | 12.12 ± 1.72 | 11.17 ± 1.66 |
| Spleen | 0.080 ± 0.01 | 9.27 ± 0.46 | 0.74 ± 0.07 |
| Muscle | 7.27 ± 0.32 | 0.78 ± 0.13 | 5.72 ± 1.05 |
| Bone | 2.73 ± 0.12 | 4.35 ± 0.39 | 11.89 ± 1.47 |
| Skin | 2.73 ± 0.12 | 2.12 ± 0.78 | 5.82 ± 2.24 |
| GI Tract | 2.22 ± 0.06 | 3.52 ± 1.12 | 4.22 ± 0.84 |
| Urine | — | — | — |
| Feces | — | — | — |
| TOTAL | | | 94.85 ± 3.47 |

No. Mice = 5
Mean Weight = 18.17 grams ± 0.81 grams

TABLE 6

Distribution of Activity at 24 Hours Following I.V. Injection of $^{90}$Y-2B8-MX-DTA Into Normal BALB/c Mice
Mean Values ± SD

| Sample | Organ Weight Gram | % ID/ Gram | % ID per Organ |
|---|---|---|---|
| Blood | 1.517 ± 0.090 | 8.35 ± 2.547 | 12.83 ± 4.60 |
| Heart | 0.092 ± 0.005 | 2.63 ± 0.142 | 0.240 ± 0.006 |
| Lung | 0.141 ± 0.005 | 4.56 ± 0.393 | 0.644 ± 0.047 |
| Kidney | 0.138 ± 0.007 | 5.63 ± 0.222 | 0.779 ± 0.040 |
| Liver | 0.438 ± 0.098 | 5.22 ± 0.335 | 2.259 ± 0.399 |
| Spleen | 0.081 ± 0.003 | 4.23 ± 0.180 | 0.345 ± 0.011 |
| Muscle | 8.668 ± 0.514 | 0.976 ± 0.164 | 8.55 ± 1.945 |
| Bone | 3.246 ± 0.186 | 1.326 ± 0.102 | 4.289 ± 0.154 |

No. Mice = 3
Mean Weight = 21.671 ± 1.11 gram

TABLE 7

Distribution of Activity at 48 Hours Following I.V. Injection of $^{90}$Y-2B8-MX-DTPA Into Normal BALB/c Mice
Mean Values ± SD

| Sample | Organ Weight Gram | % ID/ Gram | % ID per Organ |
|---|---|---|---|
| Blood | 1.33 ± 0.06 | 17.34 ± 2.0 | 23.03 ± 1.95 |
| Heart | 0.088 ± 0.01 | 3.56 ± 0.31 | 0.31 ± 0.04 |
| Lung (2) | 0.139 ± 0.01 | 7.54 ± 0.88 | 1.05 ± 0.15 |
| Kidney (1) | 0.122 ± 0.01 | 6.53 ± 0.42 | 0.79 ± 0.01 |
| Liver | 0.968 ± 0.04 | 9.05 ± 1.70 | 8.92 ± 1.57 |
| Spleen | 0.087 ± 0.01 | 6.52 ± 1.13 | 0.57 ± 0.07 |
| Muscle | 7.26 ± 0.36 | 1.05 ± 0.18 | 8.01 ± 1.17 |
| Bone | 2.86 ± 0.14 | 3.34 ± 0.42 | 9.53 ± 1.08 |
| Skin | 2.86 ± 0.14 | 4.13 ± 0.76 | 11.75 ± 1.82 |
| GI Tract | 2.84 ± 0.19 | 2.74 ± 0.34 | 3.80 ± 0.30 |
| Urine | — | — | 4.29 |
| Feces | — | — | 7.67 |
| | | TOTAL | 79.72 ± 3.23 |

No. Mice = 5
Mean Weight = 19.07 ± 0.91 grams

TABLE 8

Distribution of Activity at 72 Hours Following I.V. Injection of $^{90}$Y-2B8-MX-DTPA Into Normal BALB/c Mice
Mean Values ± SD

| Sample | Organ Weight Gram | % ID/ Gram | % ID per Organ |
|---|---|---|---|
| Blood | 1.35 ± 0.02 | 15.40 ± 1.63 | 20.71 ± 2.13 |
| Heart | 0.088 ± 0.01 | 3.12 ± 0.24 | 0.28 ± 0.01 |
| Lung (2) | 0.142 ± 0.01 | 8.23 ± 1.05 | 1.17 ± 0.20 |
| Kidney (1) | 0.123 ± 0.01 | 6.45 ± 0.57 | 0.79 ± 0.07 |
| Liver | 0.02 ± 0.06 | 8.39 ± 1.04 | 8.58 ± 1.31 |
| Spleen | 0.103 ± 0.01 | 5.90 ± 1.19 | 0.59 ± 0.08 |
| Muscle | 7.68 ± 0.11 | 1.01 ± 0.15 | 7.73 ± 1.05 |
| Bone | 2.88 ± 0.05 | 3.20 ± 0.25 | 9.20 ± 0.61 |
| Skin | 2.88 ± 0.05 | 3.97 ± 0.49 | 11.42 ± 1.36 |
| GI Tract | 2.86 ± 0.18 | 2.90 ± 0.65 | 4.06 ± 0.93 |
| Urine | — | — | 3.00 |
| Feces | — | — | 11.08 |
| | | TOTAL | 78.62 ± 2.63 |

No. Mice = 5
Mean Weight = 19.21 ± 0.27 grams

In a similar manner the other biological half-life values were assigned or calculated using the standard equation for calculating the $t_{1/2}$ for an exponential decay. Once these values had been determined, the variables for $T_{ue}$, $T_{e1}$, $T_{e2}$, $A_1$, $A_2$, and A, listed in Tables 9 and 10, were determined for each radiolabeled conjugate using the equations provided at the top of these tables (output variables). These values, as well as those shown in the subsequent tables, were calculated using a program written in the Symphony spreadsheet (Lotus Development Corp.) by Mr. Phillip Hagan, MS, Nuclear Medicine Service, VA Medical Center, La Jolla, Calif. 92161.

TABLE 9

| INPUT VARIABLES | OUTPUT VARIABLES |
|---|---|
| A0 = Administered dose | |
| Tue = Effective uptake half-time | |
| Tp = Physical half-life of radionuclide | Te1 = Effective disappearance half-time of first component |
| Tu = Biologic uptake half-time | Te2 = Effective disappearance half-time of second component |
| Tb1 = Biological disappearance half-time of first component | A1 = Cumulated activity of first component |
| Tb2 = Biological disappearance half-time of second component | A2 = Cumulated activity of second component |
| f1 = Fraction of A0 with biological half-time of Tb1 | A = Total cumulated activity |
| f2 = Fraction of A0 with biological half-time of Tb2 | Tue = Tu * Tp/(Tu + Tp) A1 − 1.44*f1*A0*Tel*(Tue/Tu) |
| S = Mean Dose/Unit Cumulated Activity | Te1 = Tb1 * Tp/(Tb1 + Tp) A2 − 1.44*f2*A0*Te2 |
| | Te2 = Tb2 * Tp/(Tb2 + Tp) A − A1 + A2 |

Example. Al FOR LIVER − 1.44 * 11.000% * 1000 * 63.2 * 1.00 = 10007.5 microcuries cumulated activity
TABLE OF INPUT AND OUTPUT VALUES USED TO EVALUATE CUMULATED ACTIVITY (A)

| | Tu (hr) | f1 | f2 | Tb1 (hr) | Tb2 (hr) | Tue (hr) | Te1 (hr) | Te2 (hr) | A1 (uCi-hr) | A2 (uCi-hr) | A (uCi-hr) |
|---|---|---|---|---|---|---|---|---|---|---|---|
| ADRENALS | 2.78E−04 | 0.000% | 0.00% | 1000 | 0 | 2.78E−04 | 63.2 | 0.0 | 0.0 | 0.0 | 0 |
| BLAD CONTENTS | 2.78E−04 | 1.000% | 0.00% | 4 | 0 | 2.78E−04 | 3.8 | 0.0 | 54.4 | 0.0 | 54 |
| STOMACH CONTENTS | 2.78E−04 | 6.650% | 0.00% | 1.5 | 0 | 2.78E−04 | 1.5 | 0.0 | 140.5 | 0.0 | 141 |
| SM. INT. CONTENTS | 2.78E−04 | 6.650% | 0.00% | 3.5 | 0 | 2.78E−04 | 3.3 | 0.0 | 318.6 | 0.0 | 319 |
| ULI_CONTENTS | 2.78E−04 | 6.650% | 0.00% | 4.5 | 0 | 2.78E−04 | 4.2 | 0.0 | 404.0 | 0.0 | 404 |
| LLI_CONTENTS | 2.78E−04 | 6.650% | 0.00% | 4.2 | 0 | 2.78E−04 | 4.0 | 0.0 | 378.6 | 0.0 | 379 |
| KIDNEYS | 2.78E−04 | 1.220% | 0.00% | 35 | 0 | 2.78E−04 | 23.0 | 0.0 | 404.8 | 0.0 | 405 |
| LIVER | 2.78E−04 | 11.000% | 0.00% | 1000 | 0 | 2.78E−04 | 63.2 | 0.0 | 10007.5 | 0.0 | 10008 |
| LUNGS | 2.78E−04 | 2.100% | 1.20% | 30 | 1000 | 2.78E−04 | 20.8 | 63.2 | 627.9 | 1091.7 | 1720 |
| OTH TISS (TOTAL) | 2.78E−04 | 0.000% | | | | | | | | | |
| MUSCLE | 2.78E−04 | 10.400% | 0.00% | 1000 | 0 | 2.78E−04 | 63.2 | 0.0 | 9461.7 | 0.0 | 9462 |

TABLE 9-continued

| | | | | | | | | | | | |
|---|---|---|---|---|---|---|---|---|---|---|---|
| ADIPOSE | 2.78E−04 | 0.000% | 0.00% | 1000 | 0 | 2.78E−04 | 63.2 | 0.0 | 0.0 | 0.0 | 0 |
| BLOOD | 2.78E−04 | 58.400% | 32.22% | 15 | 1000 | 2.78E−04 | 12.3 | 63.2 | 10319.2 | 29313.1 | 39632 |
| BRAIN | 2.78E−04 | 0.000% | 0.00% | 1000 | 0 | 2.78E−04 | 63.2 | 0.0 | 0.0 | 0.0 | 0 |
| HEART | 2.78E−04 | 0.510% | 0.38% | 57 | 1000 | 2.78E−04 | 30.9 | 63.2 | 226.9 | 345.7 | 573 |
| PVARIES | 2.78E−04 | 0.000% | 0.00% | 1000 | 0 | 2.78E−04 | 63.2 | 0.0 | 0.0 | 0.0 | 0 |
| PANCREAS | 2.78E−04 | 0.000% | 0.00% | 1000 | 0 | 2.78E−04 | 63.2 | 0.0 | 0.0 | 0.0 | 0 |
| SKELETON (TOTAL) | 2.78E−04 | 0.000% | | | | | | | | | |
| CORTICAL BONE | 2.78E−04 | 0.000% | 0.00% | 1000 | 0 | 2.78E−04 | 63.2 | 0.0 | 0.0 | 0.0 | 0 |
| TRABECULAR BONE | 2.78E−04 | 9.100% | 6.30% | 45 | 1000 | 2.78E−04 | 27.0 | 63.2 | 3536.8 | 5731.6 | 9268 |
| NARROW (RED) | 2.78E−04 | 0.000% | 0.00% | 1000 | 0 | 2.78E−04 | 63.2 | 0.0 | 0.0 | 0.0 | 0 |
| MARROW (YELLOW) | 2.78E−04 | 0.000% | 0.00% | 1000 | 0 | 2.78E−04 | 63.2 | 0.0 | 0.0 | 0.0 | 0 |
| CARTILAGE | 2.78E−04 | 0.000% | 0.00% | 1000 | 0 | 2.78E−04 | 63.2 | 0.0 | 0.0 | 0.0 | 0 |
| OTHER CONSTIT. | 2.78E−04 | 0.000% | 0.00% | 1000 | 0 | 2.78E−04 | 63.2 | 0.0 | 0.0 | 0.0 | 0 |
| SKIN | 2.78E−04 | 11.770% | 0.00% | 1000 | 0 | 2.78E−04 | 63.2 | 0.0 | 10708.1 | 0.0 | 10708 |
| SPLEEN | 2.78E−04 | 0.610% | 0.40% | 39 | 1000 | 2.78E−04 | 24.7 | 63.2 | 217.1 | 363.9 | 581 |
| TESTES | 2.78E−04 | 0.000% | 0.00% | 1000 | 0 | 2.78E−04 | 63.2 | 0.0 | 0.0 | 0.0 | 0 |
| THYROID | 2.78E−04 | 0.000% | 0.00% | 1000 | 0 | 2.78E−04 | 63.2 | 0.0 | 0.0 | 0.0 | 0 |
| TOTAL BODY | 2.78E−04 | 0.000% | 0.00% | 1000 | | | | | | | |

TABLE 10

| INPUT VARIABLES | OUTPUT VARIABLES |
|---|---|
| A0 = Administered dose | Tue = Effective uptake half-time |
| Tp = Physical half-life of radionuclide | Te1 = Effective disappearance half-time of first component |
| Tu = Biologic uptake half-time | Te2 = Effective disappearance half-time of second component |
| Tb1 = Biological disappearance half-time of first component | A1 = Cumulated activity of first component |
| Tb2 = Biological disappearance half-time of second component | A2 = Cumulated activity of second component |
| f1 = Fraction of A0 with biological half-time of Tb1 | A = Total cumulated activity |
| f2 = Fraction of A0 with biological half-time of Tb2 | Tue = Tu * Tp/(Tu + Tp) A1 − 1.44*f1*A0*Te1*(Tue/Tu) |
| S = Mean Dose/Unit Cumulated Activity | Te1 = Tb1 * Tp/(Tb1 + Tp) A2 − 1.44*f2*A0*Te2 |
| | Te2 = Tb2 * Tp/(Tb2 + Tp) A − A1 + A2 |

Example. A1 FOR LIVER − 1.44 * 9.000% * 1000 * 60.2 * 1.00 = 7795.5 microcuries cumulated activity
TABLE OF INPUT AND OUTPUT VALUES USED TO EVALUATE CUMULATED ACTIVITY (A)

| | Tu (hr) | f1 | f2 | Tb1 (hr) | Tb2 (hr) | Tue (hr) | Te1 (hr) | Te2 (hr) | A1 (uCi-hr) | A2 (uCi-hr) | A (uCi-hr) |
|---|---|---|---|---|---|---|---|---|---|---|---|
| ADRENALS | 2.78E−04 | 0.000% | 0.00% | 1000 | 0 | 2.78E−04 | 60.2 | 0.0 | 0.0 | 0.0 | 0 |
| BLAD CONTENTS | 2.78E−04 | 1.000% | 0.00% | 4 | 0 | 2.78E−04 | 3.8 | 0.0 | 54.2 | 0.0 | 54 |
| STOMACH CONTENTS | 2.78E−04 | 4.220% | 0.00% | 1.5 | 0 | 2.78E−04 | 1.5 | 0.0 | 89.1 | 0.0 | 89 |
| SM. INT. CONTENTS | 2.78E−04 | 4.220% | 0.00% | 3.5 | 0 | 2.78E−04 | 3.3 | 0.0 | 201.7 | 0.0 | 202 |
| ULI_CONTENTS | 2.78E−04 | 4.220% | 0.00% | 4.5 | 0 | 2.78E−04 | 4.2 | 0.0 | 255.5 | 0.0 | 255 |
| LLI_CONTENTS | 2.78E−04 | 4.220% | 0.00% | 4.2 | 0 | 2.78E−04 | 3.9 | 0.0 | 239.5 | 0.0 | 240 |
| KIDNEY | 2.78E−04 | 1.150% | 0.87% | 70 | 1000 | 2.78E−04 | 33.4 | 60.2 | 553.6 | 753.6 | 1307 |
| LIVER | 2.78E−04 | 9.000% | 0.00% | 1000 | 0 | 2.78E−04 | 60.2 | 0.0 | 7795.5 | 0.0 | 7795 |
| LUNGS | 2.78E−04 | 1.200% | 0.00% | 1000 | 0 | 2.78E−04 | 60.2 | 0.0 | 1039.4 | 0.0 | 1039 |
| OTH TISS (TOTAL) | 2.78E−04 | 0.000% | | | | | | | | | |
| MUSCLE | 2.78E−04 | 8.720% | 0.00% | 1000 | 0 | 2.78E−04 | 60.2 | 0.0 | 7552.9 | 0.0 | 7553 |
| ADIPOSE | 2.78E−04 | 0.000% | 0.00% | 1000 | 0 | 2.78E−04 | 60.2 | 0.0 | 0.0 | 0.0 | 0 |
| BLOOD | 2.78E−04 | 49.770% | 25.90% | 13 | 1000 | 2.78E−04 | 10.8 | 60.2 | 7743.9 | 22433.7 | 30178 |
| BRAIN | 2.78E−04 | 0.000% | 0.00% | 1000 | 0 | 2.78E−04 | 60.2 | 0.0 | 0.0 | 0.0 | 0 |
| HEART | 2.78E−04 | 0.500% | 0.36% | 51 | 1000 | 2.78E−04 | 28.4 | 60.2 | 204.4 | 311.8 | 516 |
| OVARIES | 2.78E−04 | 0.000% | 0.00% | 1000 | 0 | 2.78E−04 | 60.2 | 0.0 | 0.0 | 0.0 | 0 |
| PANCREAS | 2.78E−04 | 0.000% | 0.00% | 1000 | 0 | 2.78E−04 | 60.2 | 0.0 | 0.0 | 0.0 | 0 |
| SKELETON (TOTAL) | 2.78E−04 | 0.000% | | | | | | | | | |
| CORTICAL BONE | 2.78E−04 | 0.000% | 0.00% | 1000 | 0 | 2.78E−04 | 60.2 | 0.0 | 0.0 | 0.0 | 0 |
| TRABECULAR BONE | 2.78E−04 | 11.890% | 9.28% | 67 | 1000 | 2.78E−04 | 32.7 | 60.2 | 5604.4 | 8038.0 | 13642 |
| MARROW (RED) | 2.78E−04 | 0.000% | 0.00% | 1000 | 0 | 2.78E−04 | 60.2 | 0.0 | 0.0 | 0.0 | 0 |
| MARROW (YELLOW) | 2.78E−04 | 0.000% | 0.00% | 1000 | 0 | 2.78E−04 | 60.2 | 0.0 | 0.0 | 0.0 | 0 |
| CARTILAGE | 2.78E−04 | 0.000% | 0.00% | 1000 | 0 | 2.78E−04 | 60.2 | 0.0 | 0.0 | 0.0 | 0 |
| OTHER CONSTIT. | 2.78E−04 | 0.000% | 0.00% | 1000 | 0 | 2.78E−04 | 60.2 | 0.0 | 0.0 | 0.0 | 0 |
| SKIN | 2.78E−04 | 15.600% | 0.00% | 1000 | 0 | 2.78E−04 | 60.2 | 0.0 | 13512.1 | 0.0 | 13512 |
| SPLEEN | 2.78E−04 | 0.740% | 0.56% | 60 | 1000 | 2.78E−04 | 31.0 | 60.2 | 330.0 | 485.1 | 815 |
| TESTES | 2.78E−04 | 0.000% | 0.00% | 1000 | 0 | 2.78E−04 | 60.2 | 0.0 | 0.0 | 0.0 | 0 |
| THYROID | 2.78E−04 | 0.000% | 0.00% | 1000 | 0 | 2.78E−04 | 60.2 | 0.0 | 0.0 | 0.0 | 0 |
| TOTAL BODY | 2.78E−04 | 0.000% | 0.00% | 1000 | 0 | 2.78E−04 | 60.2 | 0.0 | 0.0 | 0.0 | 0 |

Using the Total Cumulated Activity (A) values from Tables 9 and 10, and the S values provided from MIRD Pamphlet Number 11 (Tables 11 and 12, and 13 and 14), the radiation absorbed dose estimates were determined for each of the radiolabeled conjugates for the listed tissues (Tables 15, 16, 17 and 18). In determining the summary radiation dose estimates for the indium-labeled conjugate provided in Table 19, the self-dose of a given organ was summed with the absorbed dose produced by activity in adjacent organs or tissues. However, in calculating the radiation dose estimate values attributed to the yttrium-labeled conjugate (Table 20), certain of the values are absent for the listed tissues (e.g. adrenals). This is due to the shorter path length of the released 13 particle, relative to the path-length of the emitted g particle, hence providing a negligible activity contribution from adjacent tissues, and to the absence of primary biodistribution data for these tissues.

TABLE 11

S. ABSORBED DOSE PER UNIT CUMULATED ACTIVITY, (RAD/UCI-H)
INDIUM-[111] HALF-LIFE 67.44 HOURS

| | SOURCE ORGANS | | | | | | | | |
|---|---|---|---|---|---|---|---|---|---|
| | | Bladder | Intestinal Tract | | | | | | Other |
| Target Organs | Adrenals | Contents | Stomach Contents | Si Contents | Uli Contents | Lli Contents | Kidneys | Liver | Lungs | Tissue (Muscle) |
| ADRENALS | 7.4E-03 | 5.7E-07 | 7.3E-06 | 4.4E-06 | 2.8E-06 | 1.3E-06 | 3.4E-05 | 1.5E-05 | 7.6E-06 | 4.8E-06 |
| BLADDER WALL | 3.6E-07 | 4.5E-04 | 7.5E-07 | 8.0E-06 | 6.4E-06 | 2.0E-05 | 9.3E-07 | 5.2E-07 | 1.5E-07 | 5.5E-06 |
| BONE | 5.2E-06 | 2.3E-06 | 2.3E-06 | 3.2E-06 | 2.9E-06 | 4.2E-06 | 3.7E-06 | 2.9E-06 | 3.8E-06 | 3.2E-06 |
| GI (STOM WALL) | 8.8E-06 | 8.5E-07 | 3.4E-04 | 1.1E-05 | 1.2E-05 | 5.4E-06 | 1.0E-05 | 5.8E-06 | 5.7E-06 | 4.3E-06 |
| GI (SI) | 2.5E-06 | 8.6E-06 | 7.9E-06 | 2.1E-04 | 5.4E-05 | 3.0E-05 | 8.6E-06 | 5.0E-06 | 6.1E-07 | 4.8E-06 |
| GI (ULI WALL) | 2.8E-06 | 6.9E-06 | 1.1E-05 | 8.3E-05 | 3.3E-04 | 1.4E-05 | 8.6E-06 | 7.5E-06 | 7.4E-07 | 5.0E-06 |
| GI (LLI WALL) | 7.1E-07 | 2.2E-05 | 3.8E-06 | 2.4E-05 | 9.5E-06 | 4.7E-04 | 2.5E-06 | 7.3E-07 | 3.0E-07 | 5.2E-06 |
| KIDNEYS | 3.7E-05 | 8.5E-07 | 1.1E-05 | 9.2E-06 | 8.3E-06 | 2.8E-06 | 5.2E-04 | 1.2E-05 | 2.7E-06 | 4.4E-06 |
| LIVER | 1.5E-05 | 6.3E-07 | 5.9E-06 | 5.6E-06 | 7.8E-06 | 8.4E-07 | 1.2E-05 | 1.3E-04 | 7.7E-06 | 3.4E-06 |
| LUNGS | 7.6E-06 | 8.2E-08 | 5.2E-06 | 7.5E-07 | 8.3E-07 | 2.6E-07 | 2.5E-06 | 7.8E-06 | 1.4E-04 | 4.2E-06 |
| MARROW (RED) | 9.4E-06 | 5.3E-06 | 4.0E-06 | 1.1E-05 | 9.1E-06 | 1.3E-05 | 9.6E-06 | 4.1E-06 | 4.8E-06 | 5.3E-06 |
| OTH TISS (MUSC) | 4.8E-06 | 5.5E-06 | 4.3E-06 | 4.8E-06 | 4.5E-06 | 5.2E-06 | 4.4E-06 | 3.4E-06 | 4.4E-06 | 7.5E-06 |
| OVARIES | 1.8E-06 | 2.3E-05 | 1.3E-06 | 3.3E-05 | 3.7E-05 | 6.4E-05 | 3.6E-06 | 1.4E-06 | 3.6E-07 | 6.3E-06 |
| PANCREAS | 2.6E-05 | 8.6E-07 | 5.7E-05 | 6.1E-06 | 7.1E-06 | 2.1E-06 | 2.0E-05 | 1.2E-05 | 7.7E-06 | 5.7E-06 |
| SKIN | 1.8E-06 | 1.7E-06 | 1.4E-06 | 1.4E-06 | 1.4E-06 | 1.6E-06 | 1.8E-06 | 1.6E-06 | 1.8E-06 | 2.5E-06 |
| SPLEEN | 2.0E-05 | 7.6E-07 | 3.1E-05 | 4.6E-06 | 4.2E-06 | 2.4E-06 | 2.8E-05 | 2.8E-06 | 7.1E-06 | 4.6E-06 |
| TESTES | 1.4E-07 | 1.4E-05 | 1.8E-07 | 1.0E-06 | 9.8E-07 | 5.9E-06 | 3.4E-07 | 2.5E-07 | 3.9E-08 | 3.6E-06 |
| THYROID | 4.7E-07 | 1.2E-08 | 3.5E-07 | 6.9E-08 | 7.5E-08 | 2.7E-08 | 2.0E-07 | 6.2E-07 | 2.6E-06 | 4.3E-06 |
| UTERUS (NONGRVD) | 5.8E-06 | 4.9E-05 | 2.4E-06 | 2.9E-05 | 1.5E-05 | 2.1E-05 | 3.1E-06 | 1.2E-06 | 2.8E-07 | 7.4E-06 |
| TOTAL BODY | 6.6E-06 | 6.2E-06 | 6.1E-06 | 7.3E-06 | 6.8E-06 | 6.9E-06 | 6.6E-06 | 6.6E-06 | 5.9E-06 | 5.6E-06 |

REFERENCE - MIRD PAMPHLET NO. 11, PAGE 164

TABLE 12

S. ABSORBED DOSE PER UNIT CUMULATED ACTIVITY, (RAD/UCI-H)
INDIUM-[111] HALF-LIFE 67.44 HOURS

| | SOURCE ORGANS | | | | | | | | |
|---|---|---|---|---|---|---|---|---|---|
| Target | | | Skeleton | | | | | | Total |
| Organs | Ovaries | Pancreas | R Marrow | Cort Bone | TRA Bone | Skin | Spleen | Testes | Thyroid | Body |
| ADRENALS | 1.1E-06 | 2.6E-05 | 7.9E-06 | 3.9E-06 | 3.9E-06 | 2.4E-06 | 2.0E-05 | 1.4E-07 | 4.7E-07 | 7.0E-06 |
| BLADDER WALL | 2.1E-05 | 4.7E-07 | 2.4E-06 | 1.5E-06 | 1.5E-06 | 1.6E-06 | 4.7E-07 | 1.5E-05 | 1.2E-08 | 6.9E-06 |
| BONE | 3-8E-06 | 3.6E-06 | 1.2E-05 | 3.0E-05 | 2.6E-05 | 2.9E-06 | 2.9E-06 | 2.4E-06 | 2.6E-06 | 6.9E-06 |
| GI (STOM WALL) | 2.4E-06 | 5.9E-05 | 3.2E-06 | 1.7E-06 | 1.1E-06 | 1.7E-06 | 3.0E-05 | 1.5E-07 | 1.5E-07 | 7.1E-06 |
| GI (SI) | 3.8E-05 | 5.5E-06 | 7.9E-06 | 2.3E-06 | 2.3E-06 | 1.5E-06 | 4.2E-06 | 1.2E-06 | 4.2E-08 | 7.5E-06 |
| GI (ULI WALL) | 3.7E-05 | 6.6E-06 | 6.4E-06 | 2.2E-06 | 2.2E-06 | 1.4E-06 | 3.8E-06 | 1.1E-06 | 3.3E-08 | 7.0E-06 |
| GI (LLI WALL) | 4.8E-05 | 1.7E-06 | 9.0E-06 | 3.2E-06 | 3.2E-06 | 1.5E-06 | 1.9E-06 | 8.3E-06 | 2.2E-08 | 6.7E-06 |
| KIDNEYS | 2.9E-06 | 1.9E-05 | 6.8E-06 | 2.7E-06 | 2.7E-06 | 2.0E-06 | 2.8E-05 | 1.7E-07 | 1.2E-07 | 6.6E-06 |
| LIVER | 1.7E-06 | 1.3E-05 | 2.9E-06 | 2.0E-06 | 2.0E-06 | 1.7E-06 | 3.0E-06 | 1.2E-07 | 3.5E-07 | 6.5E-06 |
| LUNGS | 2.2E-07 | 7.6E-06 | 3.7E-06 | 3.0E-06 | 3.0E-06 | 1.9E-06 | 6.9E-06 | 3.4E-08 | 2.9E-06 | 5.9E-06 |
| MARROW (RED) | 1.3E-05 | 6.8E-06 | 7.5E-05 | 1.3E-05 | 2.6E-05 | 2.7E-06 | 4.4E-06 | 1.9E-06 | 2.9E-06 | 7.7E-06 |
| OTH TISS (MUSC) | 6.3E-06 | 5.7E-06 | 3.8E-06 | 3.2E-06 | 3.2E-06 | 2.5E-06 | 4.6E-06 | 3.6E-06 | 4.3E-06 | 5.6E-06 |
| OVARIES | 1.0E-02 | 1.0E-06 | 7.7E-06 | 2.2E-06 | 2.2E-06 | 1.4E-06 | 1.7E-06 | 0.0E+00 | 1.7E-08 | 7.0E-06 |
| PANCREAS | 1.5E-06 | 1.6E-03 | 4.9E-06 | 3.1E-06 | 3.1E-06 | 1.7E-06 | 6.1E-05 | 2.1E-07 | 3.0E-07 | 7.8E-06 |
| SKIN | 1.4E-06 | 1.3E-06 | 2.0E-06 | 2.3E-06 | 2.3E-06 | 3.7E-05 | 1.5E-06 | 4.9E-06 | 2.5E-06 | 3.7E-06 |
| SPLEEN | 1.6E-06 | 6.2E-05 | 2.7E-06 | 2.0E-06 | 2.0E-06 | 1.7E-06 | 9.1E-04 | 8.9E-08 | 3.5E-07 | 6.8E-06 |
| TESTES | 0.0E+00 | 2.1E-07 | 1.0E-06 | 1.9E-06 | 1.9E-06 | 3.4E-06 | 2.0E-07 | 3.6E-03 | 3.3E-09 | 4.9E-06 |
| THYROID | 2.5E-08 | 4.5E-07 | 2.2E-06 | 2.8E-06 | 2.8E-06 | 2.4E-06 | 3.4E-07 | 3.3E-09 | 5.8E-03 | 5.2E-06 |
| UTERUS (NONGRVO) | 6.5E-05 | 1.9E-06 | 6.7E-06 | 1.8E-06 | 1.8E-06 | 1.2E-06 | 1.2E-06 | 0.0E+00 | 2.4E-08 | 7.8E-06 |
| TOTAL BODY | 7.7E-06 | 7.5E-06 | 6.4E-06 | 5.9E-06 | 5.9E-06 | 3.8E-06 | 6.6E-06 | 5.6E-06 | 5.3E-06 | 5.8E-06 |

REFERENCE - MIRD PAMPHLET NO. 11. PAGE 165

TABLE 13

S. ABSORBED DOSE PER UNIT CUMULATED ACTIVITY, (RAD/UCI-H)
YTTRIUM-[90] HALF-LIFE 64 HOURS

| | | | SOURCE ORGANS | | | | | | | |
|---|---|---|---|---|---|---|---|---|---|---|
| | | | | Intestinal Tract | | | | | | Other |
| Target Organs | Adrenals | Bladder Contents | Stomach Contents | SI Contents | ULI Contents | LLI Contents | Kidneys | Liver | Lungs | Tissue (Muscle) |
| ADRENALS | 1.4E−01 | 0.0 | 0.0 | 0.0 | 0.0 | 0.0 | 0.0 | 0.0 | 0.0 | 0.0 |
| BLADDER WALL | 0.0 | 5.0E−03 | 0.0 | 0.0 | 0.0 | 0.0 | 0.0 | 0.0 | 0.0 | 0.0 |
| BONE | 0.0 | 0.0 | 0.0 | 0.0 | 0.0 | 0.0 | 0.0 | 0.0 | 0.0 | 0.0 |
| GI (STOM WALL) | 0.0 | 0.0 | 4.0E−03 | 0.0 | 0.0 | 0.0 | 0.0 | 0.0 | 0.0 | 0.0 |
| GI (SI) | 0.0 | 0.0 | 0.0 | 2.5E−03 | 0.0 | 0.0 | 0.0 | 0.0 | 0.0 | 0.0 |
| GI (ULI WALL) | 0.0 | 0.0 | 0.0 | 0.0 | 4.5E−03 | 0.0 | 0.0 | 0.0 | 0.0 | 0.0 |
| GI (LLI WALL) | 0.0 | 0.0 | 0.0 | 0.0 | 0.0 | 7.4E−03 | 0.0 | 0.0 | 0.0 | 0.0 |
| KIDNEYS | 0.0 | 0.0 | 0.0 | 0.0 | 0.0 | 0.0 | 6.4E−03 | 0.0 | 0.0 | 0.0 |
| LIVER | 0.0 | 0.0 | 0.0 | 0.0 | 0.0 | 0.0 | 0.0 | 1.1E−03 | 0.0 | 0.0 |
| LUNGS | 0.0 | 0.0 | 0.0 | 0.0 | 0.0 | 0.0 | 0.0 | 0.0 | 2.0E−03 | 0.0 |
| MARROW (RED) | 0.0 | 0.0 | 0.0 | 0.0 | 0.0 | 0.0 | 0.0 | 0.0 | 0.0 | 0.0 |
| OTH TISS (MUSC) | 0.0 | 0.0 | 0.0 | 0.0 | 0.0 | 0.0 | 0.0 | 0.0 | 0.0 | 7.1E−05 |
| OVARIES | 0.0 | 0.0 | 0.0 | 0.0 | 0.0 | 0.0 | 0.0 | 0.0 | 0.0 | 0.0 |
| PANCREAS | 0.0 | 0.0 | 0.0 | 0.0 | 0.0 | 0.0 | 0.0 | 0.0 | 0.0 | 0.0 |
| SKIN | 0.0 | 0.0 | 0.0 | 0.0 | 0.0 | 0.0 | 0.0 | 0.0 | 0.0 | 0.0 |
| SPLEEN | 0.0 | 0.0 | 0.0 | 0.0 | 0.0 | 0.0 | 0.0 | 0.0 | 0.0 | 0.0 |
| TESTES | 0.0 | 0.0 | 0.0 | 0.0 | 0.0 | 0.0 | 0.0 | 0.0 | 0.0 | 0.0 |
| THYROID | 0.0 | 0.0 | 0.0 | 0.0 | 0.0 | 0.0 | 0.0 | 0.0 | 0.0 | 0.0 |
| UTERUS (NONGRVD) | 0.0 | 0.0 | 0.0 | 0.0 | 0.0 | 0.0 | 0.0 | 0.0 | 0.0 | 0.0 |
| TOTAL BODY | 2.8E−05 | 3.2E−06 | 8.5E−05 | 2.3E−05 | 1.4E−05 | 1.7E−05 | 2.8E−05 | 2.8E−05 | 2.8E−05 | 2.8E−05 |

REFERENCE - MIRD PAMPHLET NO. 11, PAGE 144

TABLE 14

S. ABSORBED DOSE PER UNIT CUMULATED ACTIVITY, (RAD/UCI-H)
YTTRIUM-[90] HALF-LIFE 64 HOURS

| | | | SOURCE ORGANS | | | | | | | |
|---|---|---|---|---|---|---|---|---|---|---|
| Target Organs | Ovaries | Pancreas | Skeleton | | | Skin | Spleen | Testes | Thyroid | Total Body |
| | | | R Marrow | Cort Bone | TRA Bone | | | | | |
| ADRENALS | 0.0 | 0.0 | 0.0 | 0.0 | 0.0 | 0.0 | 0.0 | 0.0 | 0.0 | 2.8E−05 |
| BLADDER WALL | 0.0 | 0.0 | 0.0 | 0.0 | 0.0 | 0.0 | 0.0 | 0.0 | 0.0 | 2.8E−05 |
| BONE | 0.0 | 0.0 | 1.1E−04 | 4.0E−04 | 2.3E−04 | 0.0 | 0.0 | 0.0 | 0.0 | 2.8E−05 |
| GI (STOM WALL) | 0.0 | 0.0 | 0.0 | 0.0 | 0.0 | 0.0 | 0.0 | 0.0 | 0.0 | 2.8E−05 |
| GI (SI) | 0.0 | 0.0 | 0.0 | 0.0 | 0.0 | 0.0 | 0.0 | 0.0 | 0.0 | 2.8E−05 |
| GI (ULI WALL) | 0.0 | 0.0 | 0.0 | 0.0 | 0.0 | 0.0 | 0.0 | 0.0 | 0.0 | 2.8E−05 |
| GI (LLI WALL) | 0.0 | 0.0 | 0.0 | 0.0 | 0.0 | 0.0 | 0.0 | 0.0 | 0.0 | 2.8E−05 |
| KIDNEYS | 0.0 | 0.0 | 0.0 | 0.0 | 0.0 | 0.0 | 0.0 | 0.0 | 0.0 | 2.8E−05 |
| LIVER | 0.0 | 0.0 | 0.0 | 0.0 | 0.0 | 0.0 | 0.0 | 0.0 | 0.0 | 2.8E−05 |
| LUNGS | 0.0 | 0.0 | 0.0 | 0.0 | 0.0 | 0.0 | 0.0 | 0.0 | 0.0 | 2.8E−05 |
| MARROW (RED) | 0.0 | 0.0 | 8.6E−04 | 3.3E−05 | 5.7E−04 | 0.0 | 0.0 | 0.0 | 0.0 | 2.8E−05 |
| OTH TISS (MUSC) | 0.0 | 0.0 | 0.0 | 0.0 | 0.0 | 0.0 | 0.0 | 0.0 | 0.0 | 2.8E−05 |
| OVARIES | 1.8E−01 | 0.0 | 0.0 | 0.0 | 0.0 | 0.0 | 0.0 | 0.0 | 0.0 | 2.8E−05 |
| PANCREAS | 0.0 | 2.0E−02 | 0.0 | 0.0 | 0.0 | 0.0 | 0.0 | 0.0 | 0.0 | 2.8E−05 |
| SKIN | 0.0 | 0.0 | 0.0 | 0.0 | 0.0 | 7.6E−04 | 0.0 | 0.0 | 0.0 | 2.8E−05 |
| SPLEEN | 0.0 | 0.0 | 0.0 | 0.0 | 0.0 | 0.0 | 1.1E−02 | 0.0 | 0.0 | 2.8E−05 |
| TESTES | 0.0 | 0.0 | 0.0 | 0.0 | 0.0 | 0.0 | 0.0 | 5.7E−02 | 0.0 | 2.8E−05 |
| THYROID | 0.0 | 0.0 | 0.0 | 0.0 | 0.0 | 0.0 | 0.0 | 0.0 | 9.9E−02 | 2.8E−05 |
| UTERUS (NONGRVO) | 0.0 | 0.0 | 0.0 | 0.0 | 0.0 | 0.0 | 0.0 | 0.0 | 0.0 | 2.8E−05 |
| TOTAL BODY | 2.8E−05 | 2.8E−05 | 2.8E−05 | 2.8E−05 | 2.8E−05 | 2.8E−05 | 2.8E−05 | 2.8E−05 | 2.8E−05 | 2.8E−05 |

REFERENCE - MIRD PAMPHLET NO. 11, PAGE 145

TABLE 15

RADIATION ABSORBED DOSE (RAD = A * S)
INDIUM-[111] HALF-LIFE 67.44 HOURS

SOURCE ORGANS

| Target Organs | Adrenals | Bladder Contents | Intestinal Tract Stomach Contents | SI Contents | ULI Contents | LLI Contents | Kidneys | Liver | Lungs | Other Tissue |
|---|---|---|---|---|---|---|---|---|---|---|
| ADRENALS | 0.0E+00 | 3.1E−05 | 1.0E−03 | 1.4E−03 | 1.1E−03 | 4.9E−04 | 1.4E−02 | 1.5E−01 | 1.3E−02 | 2.4E−01 |
| BLADDER WALL | 0.0E+00 | 2.4E−02 | 1.1E−04 | 2.SE−03 | 2.6E−03 | 7.6E−03 | 3.8E−04 | 5.2E−03 | 2.6E−04 | 2.7E−01 |
| GI (STOM WALL) | 0.0E+00 | 4.6E−05 | 4.8E−02 | 3.5E−03 | 2.2E−02 | 2.0E−03 | 4.0E−03 | 5.8E−02 | 9.8E−03 | 2.1E−01 |
| GI (SI) | 0.0E+00 | 4.7E−04 | 1.1E−03 | 6.7E−03 | 2.2E−03 | 1.1E−02 | 3.5E−03 | 5.0E−02 | 1.0E−03 | 2.4E−01 |
| GI (ULI WALL) | 0.0E+00 | 3.8E−04 | 1.5E−03 | 2.6E−02 | 1.3E−01 | 5.3E−03 | 3.5E−03 | 7.5E−02 | 1.3E−03 | 2.5E−01 |
| GI (LLI WALL) | 0.0E+00 | 1.2E−03 | 5.3E−04 | 7.6E−03 | 3.8E−03 | 1.8E−01 | 1.0E−03 | 7.3E−03 | 5.2E−04 | 2.6E−01 |
| KIDNEYS | 0.0E+00 | 4.6E−05 | 1.5E−03 | 2.9E−03 | 3.4E−03 | 1.1E−03 | 2.1E−01 | 1.2E−01 | 4.6E−03 | 2.2E−01 |
| LIVER | 0.0E+00 | 3.4E−05 | 8.3E−04 | 1.8E−03 | 3.2E−03 | 3.2E−03 | 4.9E−03 | 1.3E+00 | 1.3E−02 | 1.7E−01 |
| LUNGS | 0.0E+00 | 4.5E−06 | 7.3E−04 | 2.4E−04 | 3.4E−04 | 9.8E−05 | 1.0E−03 | 7.8E−02 | 2.4E−01 | 2.1E−01 |
| OTHER TISSUES | | | | | | | | | | |
| MUSCLE | 0.0E+00 | 3.0E−04 | 6.0E−04 | 1.5E−03 | 1.8E−03 | 2.0E−03 | 1.8E−03 | 3.4E−02 | 7.6E−03 | 3.7E−01 |
| ADIPOSE | 0.0E+00 | 3.0E−04 | 6.0E−04 | 1.5E−03 | 1.8E−03 | 2.0E−03 | 1.8E−03 | 3.4E−02 | 7.6E−03 | 3.7E−01 |
| BLOOD | 0.0E+00 | 3.0E−04 | 6.0E−04 | 1.5E−03 | 1.8E−03 | 2.0E−03 | 1.8E−03 | 3.4E−02 | 7.6E−03 | 3.7E−01 |
| BRAIN | 0.0E+00 | 3.0E−04 | 6.0E−04 | 1.5E−03 | 1.8E−03 | 2.0E−03 | 1.8E−03 | 3.4E−02 | 7.6E−03 | 3.7E−01 |
| HEART | 0.0E+00 | 4.1E−05 | 4.4E−03 | 1.5E−03 | 1.7E−03 | 9.1E−04 | 1.1E−02 | 2.8E−02 | 1.2E−02 | 3.7E−01 |
| OVARIES | 0.0E+00 | 1.3E−03 | 1.8E−04 | 1.1E−02 | 1.5E−02 | 2.4E−02 | 1.5E−03 | 1.4E−02 | 6.2E−04 | 2.8E−01 |
| PANCREAS | 0.0E+00 | 4.7E−05 | 8.0E−03 | 1.9E−03 | 2.9E−03 | 8.0E−04 | 8.1E−03 | 1.2E−01 | 1.3E−02 | 1.2E−01 |
| SKELETON | | | | | | | | | | |
| CORTICAL BONE | 0.0E+00 | 1.3E−04 | 3.2E−04 | 1.0E−03 | 1.2E−03 | 1.6E−03 | 1.5E−03 | 2.9E−02 | 6.5E−03 | 1.6E−01 |
| TRABECULAR BONE | 0.0E+00 | 1.3E−04 | 3.2E−04 | 1.0E−03 | 1.2E−03 | 1.6E−03 | 1.5E−03 | 2.9E−02 | 6.5E−03 | 1.6E−01 |
| MARROW (RED) | 0.0E+00 | 2.9E−04 | 5.6E−04 | 3.5E−03 | 3.7E−03 | 4.6E−03 | 3.9E−03 | 4.1E−02 | 8.3E−03 | 2.6E−01 |
| MARROW (YELLOW) | 0.0E+00 | 2.9E−04 | 5.6E−04 | 3.5E−03 | 3.7E−03 | 4.9E−03 | 3.9E−03 | 4.1E−02 | 8.3E−03 | 2.6E−01 |
| CARTILAGE | 0.0E+00 | 1.3E−04 | 3.2E−04 | 1.0E−03 | 1.2E−03 | 1.6E−03 | 1.5E−03 | 2.9E−02 | 6.5E−03 | 1.6E−01 |
| OTHER CONSTIT. | 0.0E+00 | 1.3E−04 | 3.2E−04 | 1.0E−03 | 1.2E−03 | 1.6E−03 | 1.5E−03 | 2.9E−02 | 6.5E−03 | 1.6E−01 |
| SKIN | 0.0E+00 | 9.2E−05 | 2.0E−04 | 4.5E−04 | 5.7E−04 | 6.1E−04 | 7.3E−04 | 1.6E−02 | 3.1E−03 | 1.2E−01 |
| SPLEEN | 0.0E+00 | 4.1E−05 | 4.4E−03 | 1.5E−03 | 1.7E−03 | 9.1E−04 | 1.1E−02 | 2.8E−02 | 1.2E−02 | 2.3E−01 |
| TESTES | 0.0E+00 | 7.6E−04 | 2.5E−05 | 3.2E−04 | 4.0E−04 | 2.2E−03 | 1.4E−04 | 2.5E−03 | 6.7E−05 | 1.8E−01 |
| THYROID | 0.0E+00 | 6.SE−07 | 4.9E−05 | 2.2E−05 | 3.0E−05 | 1.0E−05 | 8.1E−05 | 6.2E−03 | 4.5E−03 | 3.7E−01 |
| UTERUS (NONGRVD) | 0.0E+00 | 3.4E−04 | 8.6E−04 | 2.3E−03 | 2.7E−03 | 2.6E−03 | 2.7E−03 | 6.6E.02 | 1.0E−02 | 3.7E−01 |
| TOTAL BODY | 0.0E+00 | 2.7E.03 | 3.4E.04 | 9.2E−03 | 6.1E−03 | 8.0E.03 | 1.3E−03 | 1.2E−02 | 4.8E−04 | 2.8E−01 |

TABLE 16

RADIATION ABSORBED DOSE (RAD = A * S)
INDIUM-[111] HALF-LIFE 67.44 HOURS

SOURCE ORGANS

| Target Organs | Ovaries | Pancreas | Skeleton R Marrow | Cort Bone | TRA Bone | Skin | Spleen | Testes | Thyroid | Total Body |
|---|---|---|---|---|---|---|---|---|---|---|
| ADRENALS | 0.0E+00 | 0.0E+00 | 0.0E+00 | 0.0E+00 | 3.6E−02 | 2.6E−02 | 1.2E−02 | 0.0E+00 | 0.0E+00 | 0.0E+00 |
| BLADDER WALL | 0.0E+00 | 0.0E+00 | 0.0E+00 | 0.0E+00 | 1.4E−02 | 1.7E−02 | 2.7E−04 | 0.0E+00 | 0.0E+00 | 0.0E+00 |
| GI (STOM WALL) | 0.0E+00 | 0.0E+00 | 0.0E+00 | 0.0E+00 | 1.6E−02 | 1.8E−02 | 1.7E−02 | 0.0E+00 | 0.0E+00 | 0.0E+00 |
| GI (SI) | 0.0E+00 | 0.0E+00 | 0.0E+00 | 0.0E+00 | 2.1E−02 | 1.6E−02 | 2.4E−03 | 0.0E+00 | 0.0E+00 | 0.0E+00 |
| GI (ULI WALL) | 0.0E+00 | 0.0E+00 | 0.0E+00 | 0.0E+00 | 2.0E−02 | 1.5E−02 | 2.2E−03 | 0.0E+00 | 0.0E+00 | 0.0E+00 |
| GI (LLI WALL) | 0.0E+00 | 0.0E+00 | 0.0E+00 | 0.0E+00 | 3.0E−02 | 1.6E−02 | 1.1E−03 | 0.0E+00 | 0.0E+00 | 0.0E+00 |
| KIDNEYS | 0.0E+00 | 0.0E+00 | 0.0E+00 | 0.0E+00 | 2.5E−02 | 2.1E−02 | 1.6E−02 | 0.0E+00 | 0.0E+00 | 0.0E+00 |
| LIVER | 0.0E+00 | 0.0E+00 | 0.0E+00 | 0.0E+00 | 1.9E−02 | 1.8E−02 | 1.7E−03 | 0.0E+00 | 0.0E+00 | 0.0E+00 |
| LUNGS | 0.0E+00 | 0.0E+00 | 0.0E+00 | 0.0E+00 | 2.8E−02 | 2.0E−02 | 4.0E−03 | 0.0E+00 | 0.0E+00 | 0.0E+00 |
| OTHER TISSUES | | | | | | | | | | |
| MUSCLE | 0.0E+00 | 0.0E+00 | 0.0E+00 | 0.0E+00 | 3.0E−02 | 2.7E−02 | 2.7E−03 | 0.0E+00 | 0.0E+00 | 0.0E+00 |
| ADIPOSE | 0.0E+00 | 0.0E+00 | 0.0E+00 | 0.0E+00 | 3.0E−02 | 2.7E−02 | 2.7E−03 | 0.0E+00 | 0.0E+00 | 0.0E+00 |
| BLOOD | 0.0E+00 | 0.0E+00 | 0.0E+00 | 0.0E+00 | 3.0E−02 | 2.7E−02 | 2.7E−03 | 0.0E+00 | 0.0E+00 | 0.0E+00 |
| BRAIN | 0.0E+00 | 0.0E+00 | 0.0E+00 | 0.0E+00 | 3.0E−02 | 2.7E−02 | 2.7E−03 | 0.0E+00 | 0.0E+00 | 0.0E+00 |
| HEART | 0.0E+00 | 0.0E+00 | 0.0E+00 | 0.0E+00 | 3.0E−02 | 2.7E−02 | 2.7E−03 | 0.0E+00 | 0.0E+00 | 0.0E+00 |
| OVARIES | 0.0E+00 | 0.0E+00 | 0.0E+00 | 0.0E+00 | 2.0E−02 | 1.5E−02 | 9.9E−04 | 0.0E+00 | 0.0E+00 | 0.0E+00 |
| PANCREAS | 0.0E+00 | 0.0E+00 | 0.0E+00 | 0.0E+00 | 2.9E−02 | 1.8E−02 | 3.5E−02 | 0.0E+00 | 0.0E+00 | 0.0E+00 |
| SKELETON | | | | | | | | | | |
| CORTICAL BONE | 0.0E+00 | 0.0E+00 | 0.0E+00 | 0.0E+00 | 2.4E−01 | 3.1E−02 | 1.7E−03 | 0.0E+00 | 0.0E+00 | 0.0E+00 |
| TRABECULAR BONE | 0.0E+00 | 0.0E+00 | 0.0E+00 | 0.0E+00 | 2.4E−01 | 3.1E−02 | 1.7E−03 | 0.0E+00 | 0.0E+00 | 0.0E+00 |

TABLE 16-continued

RADIATION ABSORBED DOSE (RAD = A * S)
INDIUM-[111] HALF-LIFE 67.44 HOURS

SOURCE ORGANS

| Target Organs | Ovaries | Pancreas | Skeleton | | | Skin | Spleen | Testes | Thyroid | Total Body |
| --- | --- | --- | --- | --- | --- | --- | --- | --- | --- | --- |
| | | | R Marrow | Cort Bone | TRA Bone | | | | | |
| MARROW (RED) | 0.0E+00 | 0.0E+00 | 0.0E+00 | 0.0E+00 | 2.4E−01 | 2.9E−02 | 2.6E−03 | 0.0E+00 | 0.0E+00 | 0.0E+00 |
| MARROW (YELLOW) | 0.0E+00 | 0.0E+00 | 0.0E+00 | 0.0E+00 | 2.4E−01 | 2.9E−02 | 2.6E−03 | 0.0E+00 | 0.0E+00 | 0.0E+00 |
| CARTILAGE | 0.0E+00 | 0.0E+00 | 0.0E+00 | 0.0E+00 | 2.4E−01 | 3.1E−02 | 1.7E−03 | 0.0E+00 | 0.0E+00 | 0.0E+00 |
| OTHER CONSTIT. | 0.0E+00 | 0.0E+00 | 0.0E+00 | 0.0E+00 | 2.4E−01 | 3.1E−02 | 1.7E−03 | 0.0E+00 | 0.0E+00 | 0.0E+00 |
| SKIN | 0.0E+00 | 0.0E+00 | 0.0E+00 | 0.0E+00 | 2.1E−02 | 4.0E−01 | 8.7E−04 | 0.0E+00 | 0.0E+00 | 0.0E+00 |
| SPLEEN | 0.0E+00 | 0.0E+00 | 0.0E+00 | 0.0E+00 | 1.9E−02 | 1.8E−02 | 5.3E−01 | 0.0E+00 | 0.0E+00 | 0.0E+00 |
| TESTES | 0.0E+00 | 0.0E+00 | 0.0E+00 | 0.0E+00 | 1.8E−02 | 3.6E−02 | 1.2E−04 | 0.0E+00 | 0.0E+00 | 0.0E+00 |
| THYROID | 0.0E+00 | 0.0E+00 | 0.0E+00 | 0.0E+00 | 2.6E−02 | 2.6E−02 | 2.0E−04 | 0.0E+00 | 0.0E+00 | 0.0E+00 |
| UTERUS (NONGRVO) | 0.0E+00 | 0.0E+00 | 0.0E+00 | 0.0E+00 | 1.7E−02 | 0.0E+00 | 7.0E−04 | 0.0E+00 | 0.0E+00 | 0.0E+00 |
| TOTAL BODY | 0.0E+00 | 0.0E+00 | 0.0E+00 | 0.0E+00 | 5.5E−02 | 4.1E−02 | 3.8E−03 | 0.0E+00 | 0.0E+00 | 0.0E+00 |

TABLE 17

RADIATION ABSORBED DOSE (RAD = A * S)
YTTRIUM-[90] HALF-LIFE 64 HOURS

SOURCE ORGANS

| Target Organs | Adrenals | Bladder Contents | Intestinal Tract | | | | Kidneys | Liver | Lungs | Other Tissue |
| --- | --- | --- | --- | --- | --- | --- | --- | --- | --- | --- |
| | | | Stomach Contents | SI Contents | ULI Contents | LLI Contents | | | | |
| ADRENALS | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| BLADDER WALL | 0.0E+00 | 2.7E−01 | 0.0E+00 | 0.0E+00 | 0.0E+00 | 0.0E+00 | 0.0E+00 | 0.0E+00 | 0.0E+00 | 0.0E+00 |
| GI (STOM WALL) | 0.0E+00 | 0.0E+00 | 3.6E−01 | 0.0E+00 | 0.0E+00 | 0.0E+00 | 0.0E+00 | 0.0E+00 | 0.0E+00 | 0.0E+00 |
| GI (SI) | 0.0E+00 | 0.0E+00 | 0.0E+00 | 5.0E−01 | 0.0E+00 | 0.0E+00 | 0.0E+00 | 0.0E+00 | 0.0E+00 | 0.0E+00 |
| GI (ULI WALL) | 0.0E+00 | 0.0E+00 | 0.0E+00 | 0.0E+00 | 1.1E+00 | 0.0E+00 | 0.0E+00 | 0.0E+00 | 0.0E+00 | 0.0E+00 |
| GI (LLI WALL) | 0.0E+00 | 0.0E+00 | 0.0E+00 | 0.0E+00 | 0.0E+00 | 1.8E+00 | 0.0E+00 | 0.0E+00 | 0.0E+00 | 0.0E+00 |
| KIDNEYS | 0.0E+00 | 0.0E+00 | 0.0E+00 | 0.0E+00 | 0.0E+00 | 0.0E+00 | 8.4E+00 | 0.0E+00 | 0.0E+00 | 0.0E+00 |
| LIVER | 0.0E+00 | 0.0E+00 | 0.0E+00 | 0.0E+00 | 0.0E+00 | 0.0E+00 | 0.0E+00 | 8.6E+00 | 0.0E+00 | 0.0E+00 |
| LUNGS | 0.0E+00 | 0.0E+00 | 0.0E+00 | 0.0E+00 | 0.0E+00 | 0.0E+00 | 0.0E+00 | 0.0E+00 | 2.1E+00 | 0.0E+00 |
| OTHER TISSUES | | | | | | | | | | |
| MUSCLE | 0.0E+00 | 0.0E+00 | 0.0E+00 | 0.0E+00 | 0.0E+00 | 0.0E+00 | 0.0E+00 | 0.0E+00 | 0.0E+00 | 2.7E+00 |
| ADIPOSE | 0.0E+00 | 0.0E+00 | 0.0E+00 | 0.0E+00 | 0.0E+00 | 0.0E+00 | 0.0E+00 | 0.0E+00 | 0.0E+00 | 2.7E+00 |
| BLOOD | 0.0E+00 | 0.0E+00 | 0.0E+00 | 0.0E+00 | 0.0E+00 | 0.0E+00 | 0.0E+00 | 0.0E+00 | 0.0E+00 | 2.7E+00 |
| BRAIN | 0.0E+00 | 0.0E+00 | 0.0E+00 | 0.0E+00 | 0.0E+00 | 0.0E+00 | 0.0E+00 | 0.0E+00 | 0.0E+00 | 2.7E+00 |
| HEART | 0.0E+00 | 0.0E+00 | 0.0E+00 | 0.0E+00 | 0.0E+00 | 0.0E+00 | 0.0E+00 | 0.0E+00 | 0.0E+00 | 2.7E+00 |
| OVARIES | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| PANCREAS | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| SKELETON | | | | | | | | | | |
| CORTICAL BONE | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| TRABECULAR BONE | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| MARROW (RED) | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| MARROW (YELLOW) | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| CARTILAGE | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| OTHER CONSTIT. | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| SKIN | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| SPLEEN | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| TESTES | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| THYROID | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| UTERUS (NONGRVD) | 0.0E+00 | 1.7E−04 | 7.6E−03 | 4.6E−03 | 3.6E−03 | 4.1E−03 | 3.7E−02 | 2.2E−01 | 2.9E−02 | 0.0E+00 |
| TOTAL BODY | 0.0E+00 | 0.0E+00 | 0.0E+00 | 0.0E+00 | 0.0E+00 | 0.0E+00 | 0.0E+00 | 0.0E+00 | 0.0E+00 | 1.1E+00 |

TABLE 18

RADIATION ABSORBED DOSE (RAD = A * S)
YTTRIUM-[90] HALF-LIFE 64.00 HOURS

SOURCE ORGANS

| Target Organs | Ovaries | Pancreas | Skeleton R Marrow | Skeleton Cort Bone | Skeleton TRA Bone | Skin | Spleen | Testes | Thyroid | Total Body |
|---|---|---|---|---|---|---|---|---|---|---|
| ADRENALS | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| BLADDER WALL | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| GI (STOM WALL) | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| GI (SI) | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| GI (ULI WALL) | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| GI (LLI WALL) | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| KIDNEYS | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| LIVER | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| LUNGS | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| OTHER TISSUES | | | | | | | | | | |
| MUSCLE | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| ADIPOSE | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| BLOOD | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| BRAIN | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| HEART | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| OVARIES | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| PANCREAS | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| SKELETON | | | | | | | | | | |
| CORTICAL BONE | 0.0E+00 | 0.0E+00 | 0.0E+00 | 0.0E+00 | 3.1E+00 | 0.0E+00 | 0.0E+00 | 0.0E+00 | 0.0E+00 | 0.0E+00 |
| TRABECULAR BONE | 0.0E+00 | 0.0E+00 | 0.0E+00 | 0.0E+00 | 3.1E+00 | 0.0E+00 | 0.0E+00 | 0.0E+00 | 0.0E+00 | 0.0E+00 |
| MARROW (RED) | 0.0E+00 | 0.0E+00 | 0.0E+00 | 0.0E+00 | 7.8E+00 | 0.0E+00 | 0.0E+00 | 0.0E+00 | 0.0E+00 | 0.0E+00 |
| MARROW (YELLOW) | 0.0E+00 | 0.0E+00 | 0.0E+00 | 0.0E+00 | 7.8E+00 | 0.0E+00 | 0.0E+00 | 0.0E+00 | 0.0E+00 | 0.0E+00 |
| CARTILAGE | 0.0E+00 | 0.0E+00 | 0.0E+00 | 0.0E+00 | 3.1E+00 | 0.0E+00 | 0.0E+00 | 0.0E+00 | 0.0E+00 | 0.0E+00 |
| OTHER CONSTIT. | 0.0E+00 | 0.0E+00 | 0.0E+00 | 0.0E+00 | 3.1E+00 | 0.0E+00 | 0.0E+00 | 0.0E+00 | 0.0E+00 | 0.0E+00 |
| SKIN | 0.0E+00 | 0.0E+00 | 0.0E+00 | 0.0E+00 | 0.0E+00 | 1.0E+01 | 0.0E+00 | 0.0E+00 | 0.0E+00 | 0.0E+00 |
| SPLEEN | 0.0E+00 | 0.0E+00 | 0.0E+00 | 0.0E+00 | 0.0E+00 | 0.0E+00 | 9.0E+00 | 0.0E+00 | 0.0E+00 | 0.0E+00 |
| TESTES | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| THYROID | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| UTERUS (NONGRVO) | 0.0E+00 | 0.0E+00 | 0.0E+00 | 0.0E+00 | 0.0E+00 | 0.0E+00 | 0.0E+00 | 0.0E+00 | 0.0E+00 | 0.0E+00 |
| TOTAL BODY | 0.0E+00 | 0.0E+00 | 0.0E+00 | 0.0E+00 | 3.8E−01 | 3.8E+01 | 2.3E−02 | 0.0E+00 | 0.0E+00 | 0.0E+00 |

TABLE 19

Radiation Dosimetry Estimates Resulting from the Administration of Indium-[111] Labeled 2B8-MX Uniformly Distributed in Standard Man(70 Kg) and Based on Animal Distribution Data Over 72 Hours after Injection

AMOUNT OF ACTIVITY = 1000 MICROCURIES/PATIENT DOSE

| | RADS | | RADS |
|---|---|---|---|
| ADRENALS | 0.493 | OVARIES | 0.387 |
| BLADDER WALL | 0.348 | PANCREAS | 0.362 |
| STOMACH WALL | 0.412 | SKELETON | |
| SMALL INTESTINE | 0.434 | CORTICAL BONE | 0.474 |
| UL INTEST. WALL | 0.533 | TRABECULAR BONE | 0.474 |
| LL INTEST. WALL | 0.505 | MARROW (RED) | 0.602 |
| KIDNEYS | 0.625 | MARROW (YELLOW) | 0.602 |
| LIVER | 1.533 | CARTILAGE | 0.474 |
| LUNGS | 0.582 | OTHER CONSTIT. | 0.474 |
| OTHER TISSUES | | SKIN | 0.564 |
| MUSCLE | | SPLEEN | 0.854 |
| ADIPOSE | | TESTES | 0.239 |
| BLOOD | | THYROID | 0.276 |
| BRAIN | | UTERUS (NONGRVD) | 0.473 |
| HEART | | TOTAL BODY | 0.417 |

Ref: A Schema for Absorbed-dose Calculation for Biologically Distributed Radionuclides, MIRD J. of Nucl. Med./Suppl. #1, 2/68

Calculations Performed Using a Spreadsheet Template in Symphony (Lotus Development Corporation) and Created by Phillip L. Hagan, MS Nuclear Medicine Service VA Hospital San Diego, CA 92161

TABLE 20

Radiation Dosimetry Estimates Resulting from the Administration of Yttrium-[90] Labeled 2B8-MX Uniformly Distributed in Standard Man(70 Kg) and Based on Animal Distribution Data Over 72 Hours After Injection

| AMOUNT OF ACTIVITY = | | 1000 MICROCURIES/PATIENT DOSE | |
|---|---|---|---|
| | RADS | | RADS |
| ADRENALS | 0.000 | OVARIES | 0.000 |
| BLADDER WALL | 0.271 | PANCREAS | 0.000 |
| STOMACH WALL | 0.356 | SKELETON | |
| SMALL INTESTINE | 0.504 | CORTICAL BONE | 3.138 |
| UL INTEST. WALL | 1.150 | TRABECULAR BONE | 3.138 |
| LL INTEST. WALL | 1.772 | MARROW (RED) | 7.776 |
| KIDNEYS | 8.366 | MARROW (YELLOW) | 7.776 |
| LIVER | 8.575 | CARTILAGE | 3.138 |
| LUNGS | 2.079 | OTHER CONSTIT. | 3.138 |
| OTHER TISSUES | | SKIN | 10.269 |
| MUSCLE | 2.716 | SPLEEN | 8.965 |
| ADIPOSE | 2.716 | TESTES | 0.000 |
| BLOOD | 2.716 | THYROID | 0.000 |
| BRAIN | 2.716 | UTERUS (NONGRVD) | 0.304 |
| HEART | 2.176 | TOTAL BODY | 1.854 |

Ref: A Schema for Absorbed-dose Calculation for Biologically Distributed Radionuclides, MIRD J. of Nucl. Med./Suppl. #1, 2/68
Calculations Performed Using a Spreadsheet Template in Symphony (Lotus Development Corporation) and Created by
Phillip L. Hagan, MS
Nuclear Medicine Service
VA Hospital
San Diego, CA 92161

II. Results

A. In Vitro Studies with 2B8 and 2B8-MX-DTPA

1. Production and Characterization of the Anti-CD20 Antibody 2B8

A total of nine fusions resulted in three hybridomas producing antibodies which effectively competed with radiolabeled Coulter B1 antibody. In each case, the hybridoma was expanded into a 24 well plate. The first two antibodies isolated from fusions 3 and 4, were isotyped and both identified as IgM. The third antibody, produced in fusion 5 and designated 2B8, was determined to be an IgG1 kappa isotype and was selected for continuation studies. Clone 2B8.Hll was expanded and placed in long term storage in liquid nitrogen. Clone 2B8.Hll was subcloned to produce clone 2B8.Hll.G3 and again to produce clone 2B8.Hll.G3.G9. This clone was expanded for further study and the antibody was purified by protein A affinity chromatography.

Figure 1:
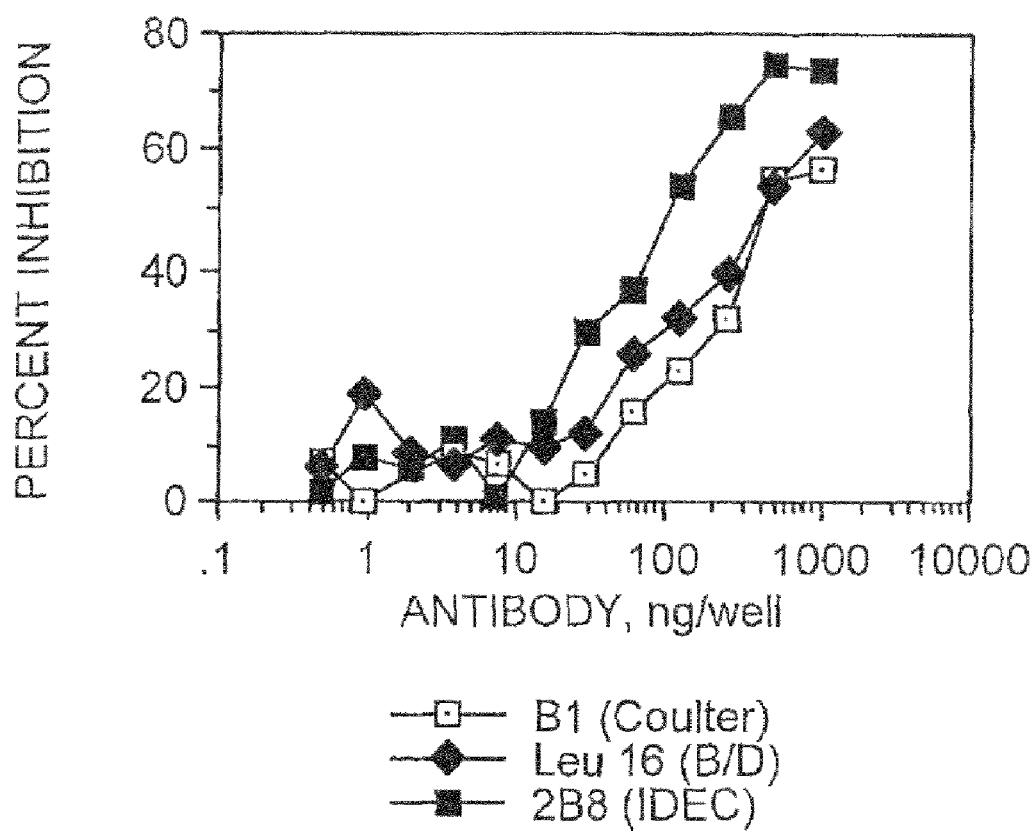
FIG. 1. Immunoreactivity of native 2B8 was compared to commercially available anti-CD20 antibodies B1 (Coulter) and Leu 16 (Becton Dickinson) by direct competition in a radioimmunoassay using $^{125}$I-labeled B1. Antigen-positive SB cells (100,000) were added to each well of V&P filter plates; 10 ng of radiolabeled B1 was mixed with various concentrations of unlabeled competition and the mixture added to the cells. The antibodies were incubated with the cells for one hour at ambient temperature; determinations were performed in triplicate. Subsequently, the wells were washed, dried and the filter-associated radioactivity determined. The data shown were corrected for background radioactivity and are the means of triplicate determinations.

Competition assays using unlabeled 2B8, B1 and Leu 16 and radiolabeled Coulter B1 demonstrated that 2B8 was able to inhibit B1 binding to CD20 more effectively than equal concentrations of either B1 or Leu 16 (FIG. 1). Similar results were obtained (data not shown) in a competition study using FITC-conjugated 2B8, native B1 and the irrelevant antibodies UPC-10 and S-003 (IgG 2a and 1 isotypes, respectively).

Direct binding to cellular CD20 antigen by 2B8 and B1 antibodies was compared by FACS analysis using CD20-positive SB cells and CD20-negative HSB cells. The results shown in FIG. 2 indicate that for comparable amounts of antibody, more 2B8 than B1 was bound to the SB cells. No significant binding to SB cells was observed with the irrelevant antibodies. Only background fluorescence was observed with any reagent used with HSB cells. These results confirm the specificity of interaction of 2B8 with the CD20 antigen and suggest that 2B8 may have higher affinity for the cell-surface antigen than B1.

Figure 3:
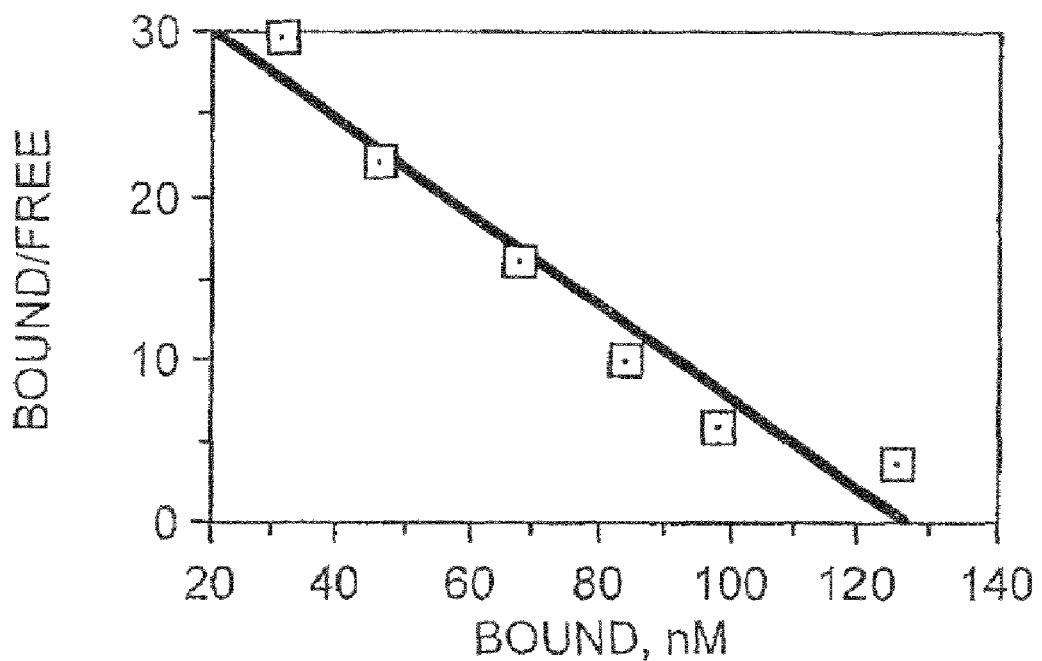
FIG. 3. Human B-cells (SB) were incubated with increasing amounts of $^{125}$I-labeled 2B8. Triplicate samples were incubated for one hour and cell-bound radioactivity was determined after filtration to collect cells. Scatchard analysis allowed calculation of an apparent affinity constant of 4.3× $10^{-9}$ M.

To determine the apparent affinity of 2B8, purified antibody was radiolabeled with $^{125}$I and increasing concentrations of the labeled antibody were incubated with antigen-positive SB cells; cell-associated radioactivity was determined following a 1 hour incubation period (FIG. 3). The results suggest that the 2B8 antibody binds to the CD20 antigen with an apparent affinity constant of $4.3 \times 10^{-9}$ M.

Flow cytometry studies with human normal peripheral blood lymphocytes indicated that 2B8 was specific for B-cells and did not react with other types of lymphocytes (e.g. T-cells, monocytes, macrophages). FITC-labeled 2B8 was compared to B1-FITC and Leu 16-FITC using the same population of human lymphocytes. The results shown in Table 21 indicate that 2B8 reacted with approximately 14 percent of the peripheral blood lymphocytes versus approximately 12 percent for Leu 16 and 11 percent for B1. The lymphocyte population based on another B lymphocyte marker (CD-19) was between 11 and 14 percent. Finally, when human peripheral blood lymphocytes were incubated with 2B8 and either B1 or Leu 16 and then counterstained with the CD19 marker (Becton/Dickinson) the double staining population of B lymphocytes was 9 percent with 2B8, and 10 percent with either B1 or Leu 16. These results confirm the similarity of these reagents.

TABLE 21

Comparison of Binding of 2B8 to Human Peripheral Blood Lymphocytes with other B- and T-Lymphocyte Specific Reagents
Antibody Marker

| | Percent of CD45 Gated Lymphocytes |
|---|---|
| A. Single Staining: | |
| None (autofluorescence) | 0 |
| B1-FITC (Coulter Immunology, (IgG2a, k) | 11 |
| Leu 16-FITC (Becton Dickinson, IgG1, k) | 12 |
| 2B8-FITC (EDEC, IgG1, k) | 14 |
| B72.3-FITC (IgG1, k irrelevant control) | 4 |
| anti-CD4-FITC (Coulter Immunology | 37 |
| anti-CD3-FITC (Becton Dickinson) | 59 |
| anti-CD19-RPE (Becton Dickinson) | 11 |
| anti-CD19-FITC (Becton Dickinson) | 14 |
| B. Double Staining: | |
| B1-FITC/anti CD19-RPE | 10 |
| Leu 16-FITC/anti CD19-RPE | 10 |
| 2B8 FITC/anti CD19-RPE | 9 |
| anti-CD19 FITC/anti CD19-RPE | 13 |
| B1-FITC/anti Hu Ig RPE | 10 |
| 2B8-FITC/anti Hu Ig RPE | 10 |
| B72.3-FITC/anti Hu Ig RPE | 2 |
| Leucogate Simultest | 99 |

Immunoprecipitation of radiolabeled cellular CD20 antigen by either 2B8 or B1 resulted in the precipitation of indistinguishable doublet protein species with molecular weights of approximately 33 and 35 KD (data not shown).

2. Production and Characterization of 2B8-.MX-DTPA

The 2B8-MX-DTPA conjugate was produced by reacting the antibody with a 4:1 molar excess of isothiocyanatobenzyl-3-methyldiethylene-triaminepentaacetic acid (4). Typically, 1-2 mol of MX-DTPA chelate were introduced per mol of 2B8-antibody. As shown by the results presented in FIG. 4, the 2B8-MX-DTPA conjugate exhibited no apparent loss in immunoreactivity, vis a vis native 2B8, as both the native and conjugated 2B8 antibodies exhibited virtually identical B1 inhibition profiles; the IC50 values for 2B8 and 2B8-MX-DTPA were approximately 3 and 4 μg/mL, respectively.

These results were obtained using $^{125}$I-labeled B1 antibody in a whole-cell radioimmunoassay performed using SB cells. Similar results were obtained using 2B8 or 2B8-MX-DTPA as inhibitors of $^{125}$I-labeled 2B8 binding to SB cells; both 2B8 and its MX-DTPA conjugate inhibited $^{125}$I-2B8 binding to SB cells at concentrations of approximately 3-4 μg/mL (data not shown).

Figure 5A:
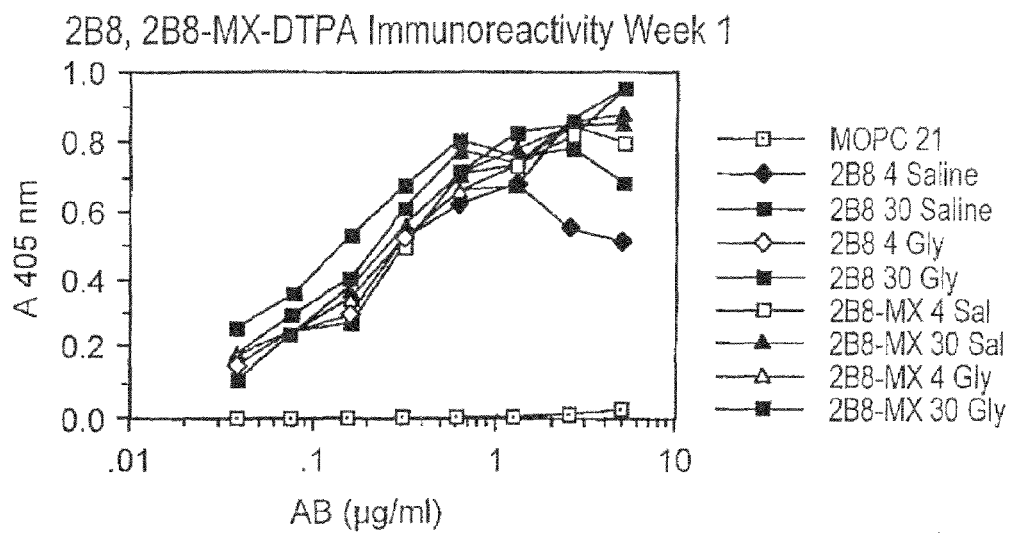
FIG. 5A-5C. Antibody 2B8 was formulated at a final concentration of 10 mg/mL in normal saline or normal saline containing 10 mM glycine-HCl, pH 6.8. Duplicate sets of samples were then placed in screw-capped vials, the vials purged with nitrogen, and then capped. The samples were then incubated at 4° C. or 30° C. for 12 weeks; the immunoreactivity of the samples was evaluated weekly. No loss of immunoreactivity was observed with any of the 2B8 samples throughout the 12-week study. Immunoreactivities at week 1 (FIG. 5A), week 6 (FIG. 5B) and week 12 (FIG. 5C) are depicted.
Figure 5B:
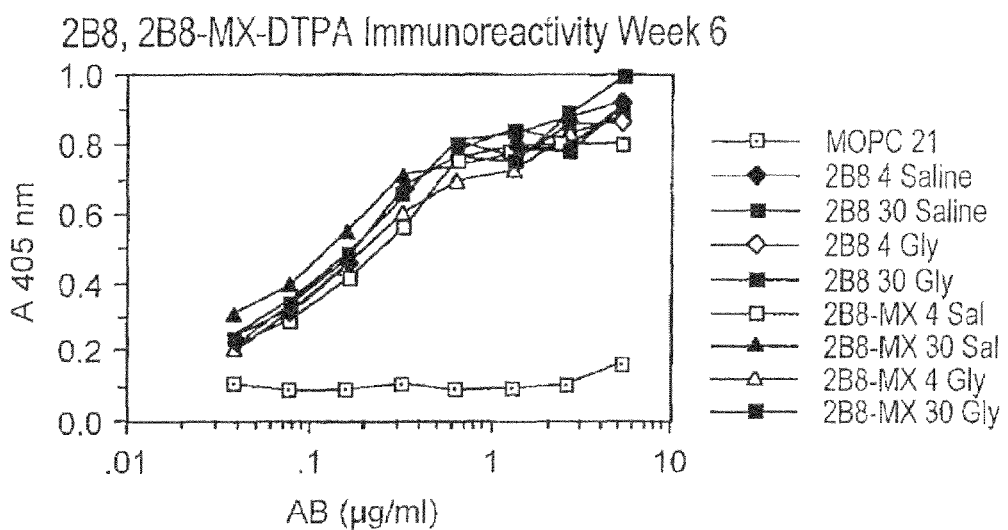
Figure 5C:
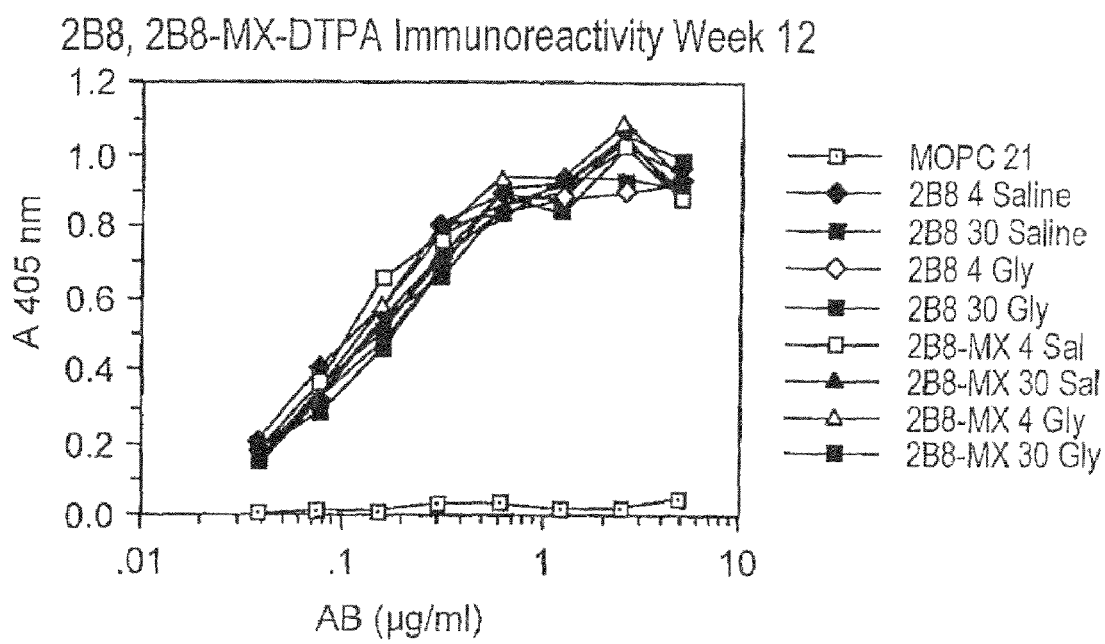

To assess the in vitro stability of the native 2B8 antibody and the 2B8-.MX-DTPA conjugate, samples in normal saline or saline containing 10 mM glycine-HCl, pH 6.8, were incubated at 4° and 30° C. for 12 weeks and aliquots were assayed weekly using the following assays: immunoreactivity by whole-cell enzyme immunoassay, SDS-PAGE under reducing and non-reducing conditions, and isoelectric focusing gel electrophoresis. While immunoreactivity assays detected no loss of antigen recognition by antibody samples incubated at either temperature (FIG. 5), the isoelectric focusing range for the antibody (pH 7.30-8.40 at week zero), which was stable at 4° C., did exhibit a decrease of 0.2 pH unit at 30° C. after week six (Table 22). This result may be equivocal, however, as it is at the limit of experimental error for the assay.

TABLE 22

2B8/2B8-MX-DTPA pI SUMMARY

| WEEK | 2B8 4 SAL | 2B8 30 SAL | 2B8 4 GLY | 2B8 30 GLY | 2B8-MX 4 SAL | 2B8-MX 30 SAL | 2B8-MX 4 GLY | 2B8-MX 30 GLY |
|---|---|---|---|---|---|---|---|---|
| 0 | 7.46-8.37 |  | 7.46-8.37 |  | 6.30-8.21 |  | 6.30-8.21 |  |
| 1 | 7.39-8.24 | 7.42-8.27 | 7.46-8.31 | 7.46-8.24 | 6.39-8.26 | 6.39-8.26 | 6.32-8.24 | 6.25-8.24 |
| 2 | 7.38-8.27 | 7.45-8.34 | 7.45-8.40 | 7.45-8.34 | 6.02-8.40 | 6.02-8.34 | 6.02-8.40 | 5.95-8.27 |
| 3 | 7.47-8.35 | 7.33-8.35 | 7.40-8.29 | 7.33-8.29 | 6.0-8.29 | 6.0-8.29 | 6.0-8.22 | 6.0-8.15 |
| 4 | 7.38-8.24 | 7.38-8.24 | 7.38-8.35 | 7.38-8.28 | 5.99-8.28 | 5.99-8.35 | 5.99-8.35 | 5.99-8.35 |
| 5 | 7.29-8.25 | 7.29-8.25 | 7.37-8.32 | 7.37-8.32 | 5.90-8.32 | 5.90-8.27 | 5.90-8.32 | 5.90-8.27 |
| 6 | 7.24-8.12 | 7.20-8.27 | 7.27-8.27 | 7.20-8.12 | 5.85-8.27 | 5.85-8.27 | 5.85-8.27 | 5.85-7.95 |
| 7 | 7.39-8.32 | 7.17-8.32 | 7.35-8.25 | 7.17-8.47 | 6.02-8.25 |  | 5.95-8.32 | 5.95-8.32 |
| 8 | 7.33-8.29 | 7.26-8.36 | 7.40-8.36 |  | 5.86-8.36 | 5.86-8.36 | 5.86-8.36 | 5.86-8.21 |
| 9 | 7.49-8.53 | 7.26-8.45 | 7.41-8.45 | 7.34-8.30 | 5.93-8.45 | 5.93-8.45 | 5.93-8.45 | 5.93-8.23 |
| 10 | 7.26-8.27 | 7.19-8.27 | 7.26-8.27 | 7.19-8.27 | 5.95-8.35 | 5.95-8.35 | 5.88-8.35 | 5.95-8.13 |
| 11 | 7.40-8.27 | 7.18-8.27 | 7.40-8.35 | 7.18-8.13 | 5.93-8.35 | 5.93-8.27 | 5.93-8.27 | 5.93-8.13 |
| 12 | 7.26-8.18 | 7.04-8.18 | 7.26-8.18 | 7.19-8.11 | 5.90-8.26 | 5.90-8.18 | 5.90-8.26 | 5.90-8.18 |

Samples of native 2B8 and 2B8-MX-DTPA were formulated in different buffers and incubated at either 40 or 30° C. for 12 weeks. During this period various assays, including isoelectric point determinations, were performed. The values shown above show the isoelectric point range for the native and conjugated antibody incubated at each temperature, in each of the formulations, and for each of the twelve weeks during the stability study. The headings represent: 2B8 4 SAL, 2B8 incubated at 4° C. in saline; 2B8 30 SAL, 2B8 incubated at 30° C. in saline; 2B8 4 GLY, 2B8 incubated at 4° C. in normal saline containing 10 mM glycine; 2B8 30 GLY, 2B8 incubated at 30° C. in normal saline containing 10 mM glycine; 2B8-MX 4 SAL; 2B8-MX-DTPA (conjugate) incubated at 4° C. in saline; 2B8-MX 30 SAL, conjugate incubated at 30° C. in saline; 2B8-MX 4'GLY, conjugate incubated at 4° C. in normal saline containing 10 mM glycine; and, 2B8-MX 30 GLY, conjugate incubated at 30° C. in normal saline containing 10 mM glycine.

Finally, using non-reducing SDS-PAGE, the 30° C. antibody samples exhibited high molecular weight aggregates after week 1 (Table 23). Densitometric analyses of the gels indicated that the aggregates represented between 8 and 17% of the samples (Table 23). However, when these samples were analyzed by reducing SDS-PAGE, no evidence of the high molecular weight species was found, suggesting the formation of covalent antibody aggregates at 30° C. Again, no loss of immunoreactivity was observed.

TABLE 23

In Vitro Stability of 2B8

| Sample | Percentage | | |
|---|---|---|---|
|  | High MW | Monomer | Low MW |
| A. Desensitometric Scans of Non-Reducing SDS Gels | | | |
| Reference | 0 | 100.00 | 0 |
| 12 wk/4° C./saline | 0 | 95.42 | 4.58 |
| 12 wk/4° C./glycine | 0 | 100.00 | 0 |
| 12 wk/30° C./saline | 7.63 | 83.34 | 9.03 |
| 12 wk/30° C./glycine | 16.70 | 72.11 | 11.18 |
| B. Desensitometric Scans of Reducing SDS Gels | | | |
| Reference | 0 | 100.00 | 0 |
| 12 wk/30° C./saline | 0 | 100.00 | 0 |
| 12 wk/30° C./glycine | 0 | 10.00 | 0 |

During the course of this stability study, samples of 2B8-MX-DTPA, incubated at both 4° and 30° C. were also tested for radiometal incorporation using $^{90}$Y. Samples assayed at weeks 4, 8, and 12 incorporated >90% of the $^{90}$Y, regardless of the incubation temperature.

Finally, in a separate study, aliquots of 2B8-MX-DTPA incubated at 4° and 30° C. for 10 weeks were radiolabeled with $^{111}$In and their tissue biodistribution assessed in BALB/c mice. Conjugate from both incubation temperatures produced similar biodistributions (data not shown). Moreover, the results obtained were similar to biodistribution results obtained in BALB/c mice using $^{111}$I-labeled conjugate stored at 4° C. (see below).

The radiolabeling protocols for both $^{111}$In and $^{90}$Y were found to be reproducible. Typically, radioincorporations of >95% for $^{111}$In and >90% for $^{90}$Y were obtained. Specific activities for $^{111}$I- and $^{90}$Y-labeled conjugates were routinely in the range of 2-3 and 10-15 mCi/mg antibody, respectively. In initial development of the $^{111}$I- and $^{90}$Y radiolabeling protocols, uncomplexed radioisotopes were removed from the radiolabeled 2B8-MX-DTPA using HPLC gel permeation chromatography. In later experiments, HPLC purification of the indium-labeled conjugate was eliminated because of the high radioincorporations obtained (>95%) with this isotope.

Figure 6A:
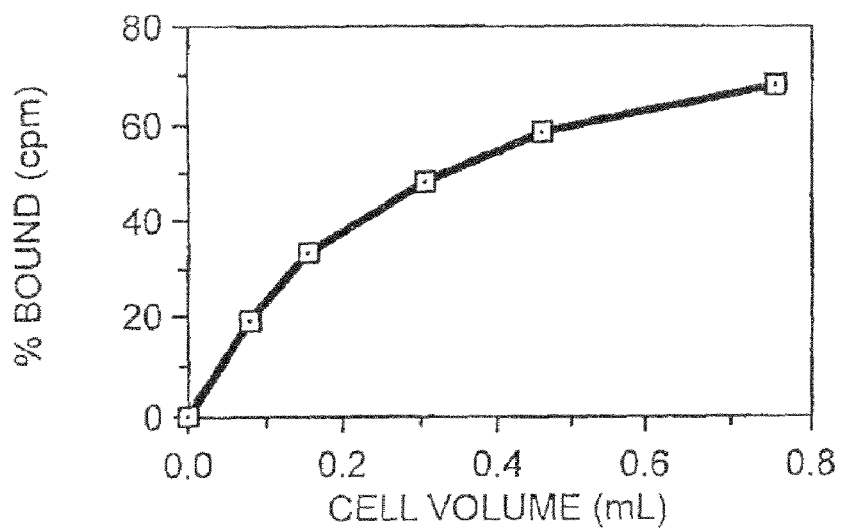
FIGS. 6A and 6B. Binding assay for determination of immunoreactivity of "In-labeled 2B8-MX-DTPA incubated in PBS, pH 7.4 containing 50 mg/mL human serum albumin (48 h incubation).
Figure 6B:
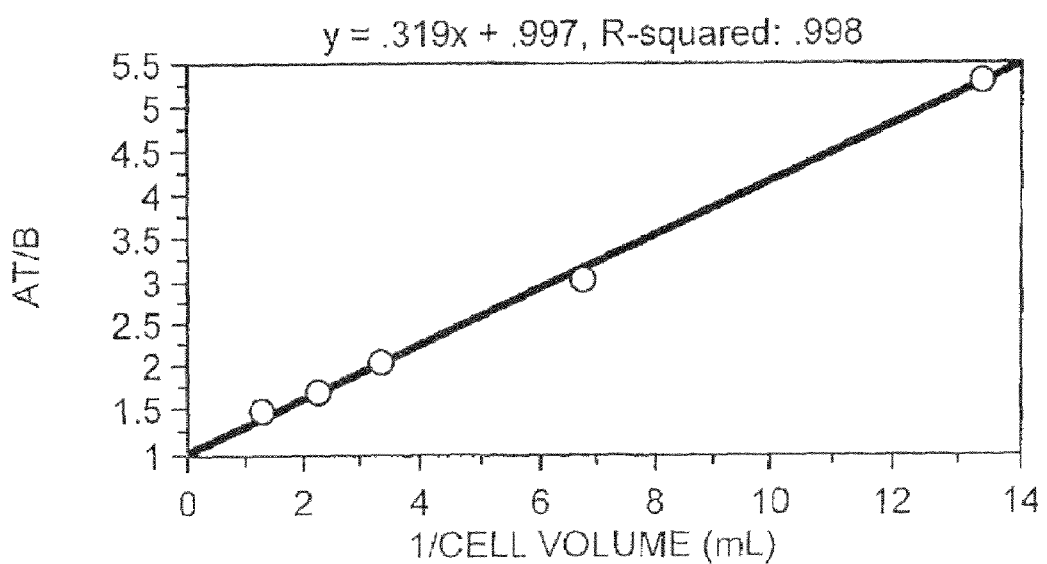

The immunoreactivity of $^{111}$In and $^{90}$Y-labeled preparations of 2B8-MX-DTPA were analyzed by the method of Lindmo (3). The $^{111}$In labeled 2B8-MX-DTPA was found to be 100% immunoreactive (FIG. 6), and the $^{90}$Y-labeled conjugate was determined to be 60% immunoreactive (data not shown).

3. Characterization of $^{111}$I- and $^{90}$Y-Labeled 2B8-MX-DTPA

Figure 7:
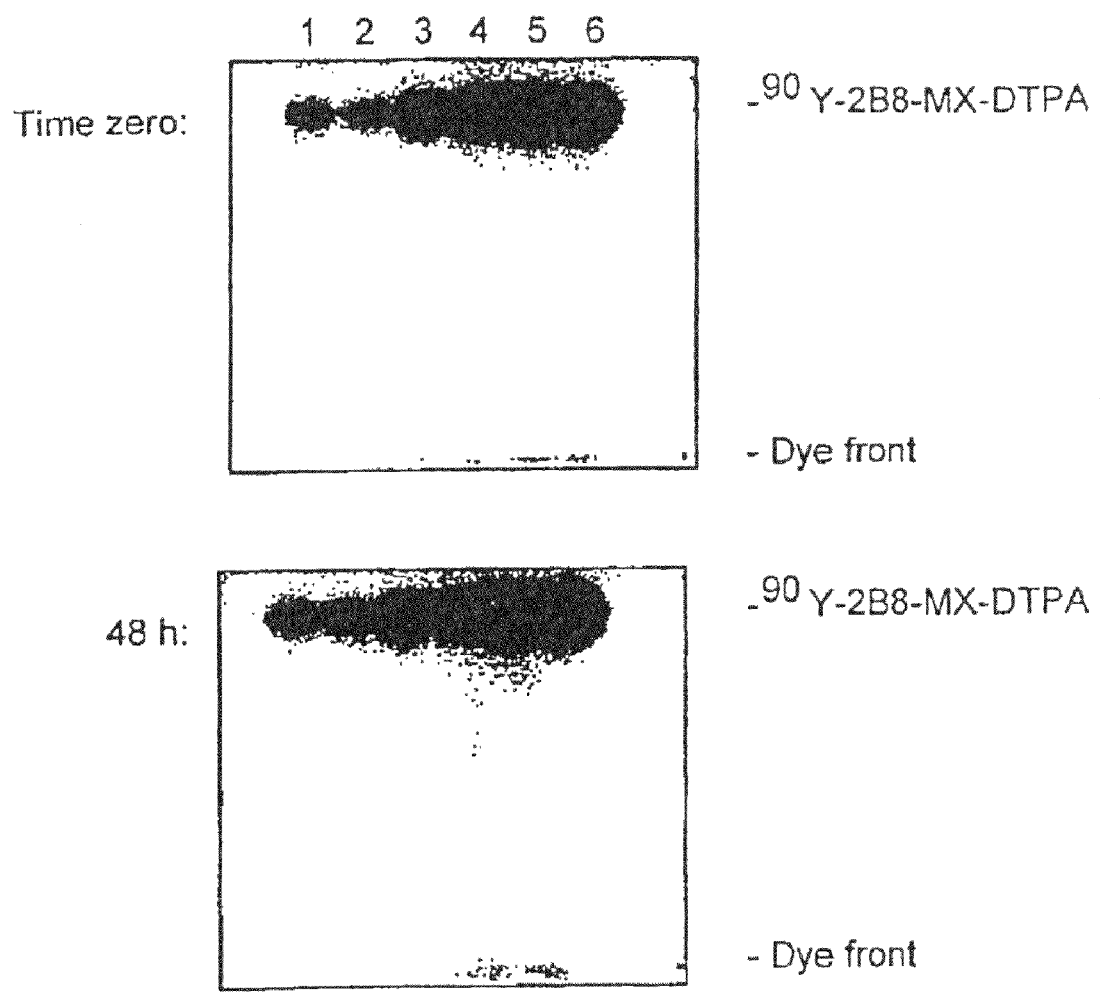
FIG. 7. Autoradiograms obtained from SDS-PAGE analysis of $^{90}$Y-labeled 2B8-MX-DTPA incubated at 4° C. in PBS, pH 7.4 containing 75 mg/mL human serum albumin and 1 mM DTPA. At the indicated times, samples were electrophoresed on 4-20% Tris-glycine gels using non-reducing conditions, denaturing conditions (SDS). The samples were loaded at 5 μL (lanes 1, 2), 10 μL (lanes 5, 6). The gels were exposed to x-ray film for approximately 15 min at ambient temperature and photographed.
Figure 8:
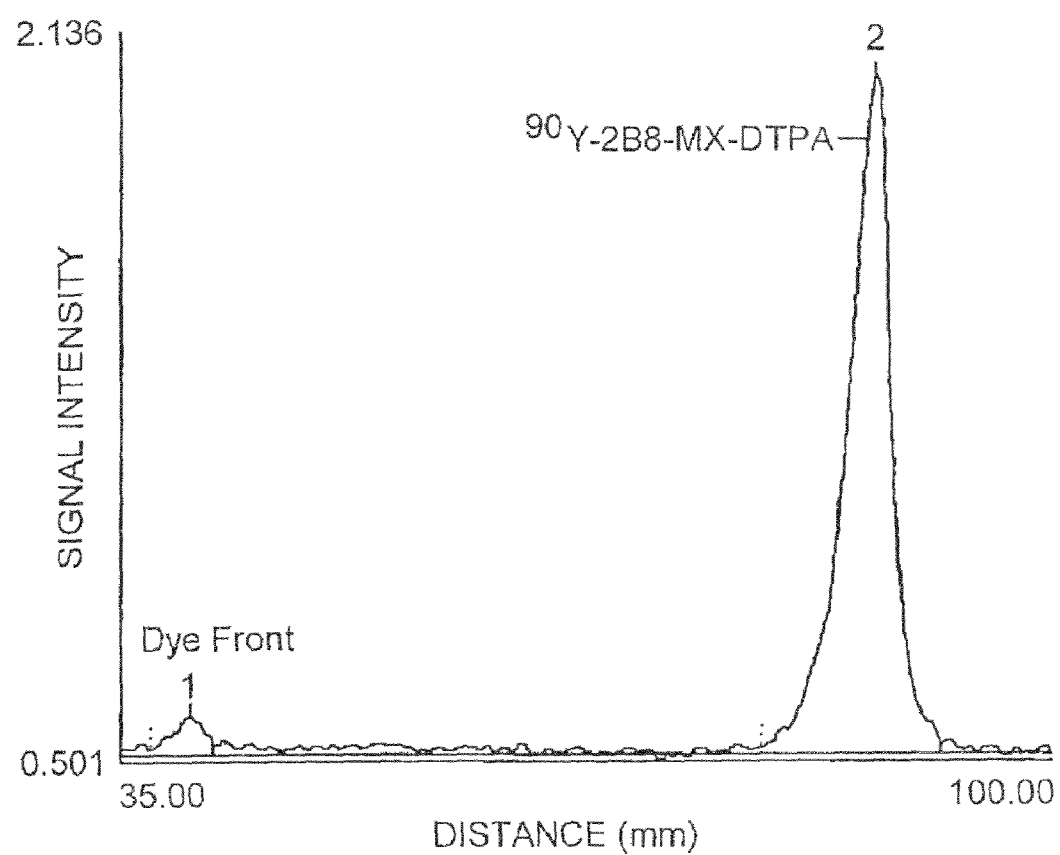
FIG. 8. Densitometric scan of time zero autoradiogram obtained from SDS-PAGE analysis of $^{90}$Y-labeled 2B8-MX-DTPA incubated at 4° C. in PBS, pH 7.4 containing 75 mg/mL human serum albumin and 1 mM DTPA. The sample was electrophoresed on a 4-20% Trib-glycine gel using non-reducing conditions. Samples were loaded at 5 μL, 10 μL, and 20 μL in duplicate wells. The gel was exposed to x-ray film for approximately 15 min at ambient temperature and one of the lanes was scanned using a densitometer. The relative area of the radiolabeled conjugate peak (#2) was 96.2%.
Figure 9:
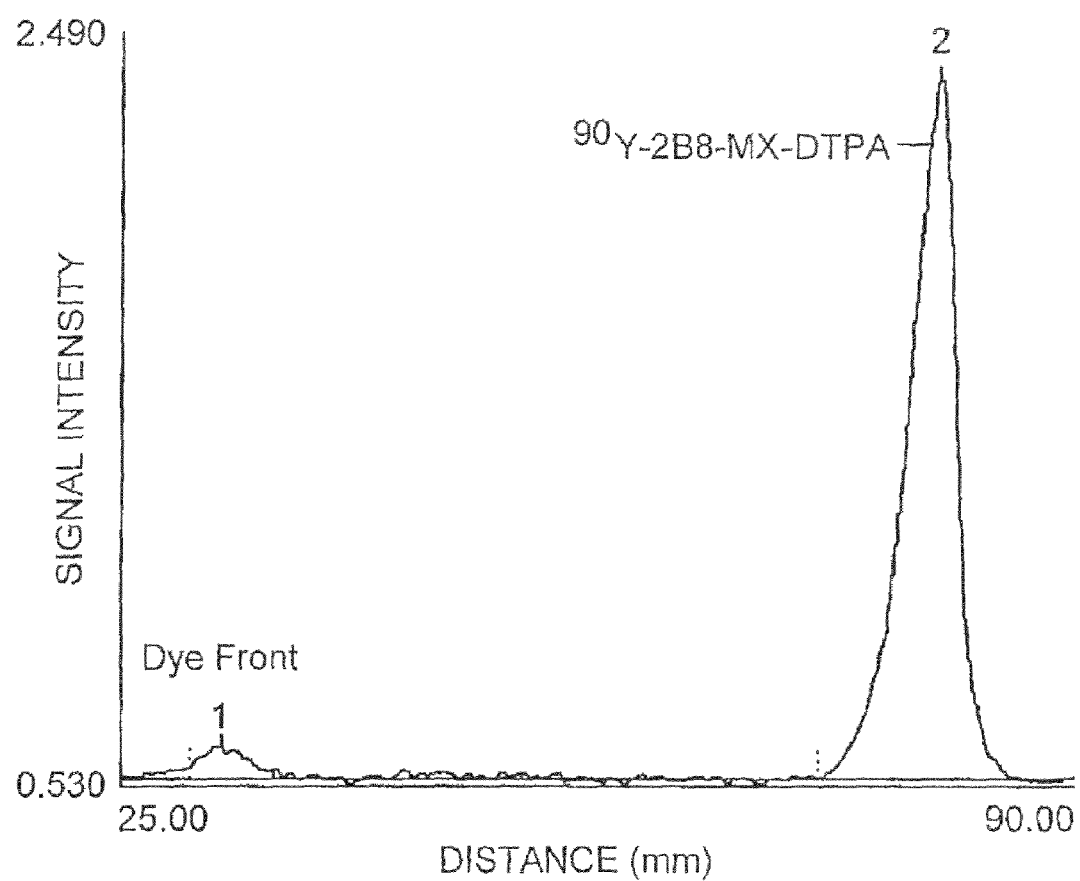
FIG. 9. Densitometric scan of 48 h autoradiogram obtained from SDS-PAGE analysis of $^{90}$Y-labeled 2B8-MX-DTPA incubated at 4° C. in PBS, pH 7.4 containing 75 mg/mL human serum albumin and 1 mM DTPA. The sample was electrophoresed on a 4-20% Tris-glycine gel using non-reducing conditions. Samples were loaded at 5 μL, 10 μL, and 20 μL in duplicate wells. The gel was exposed to x-ray film for approximately 15 min at ambient temperature and one of the lanes was scanned using a densitometer. The relative area of the radiolabeled conjugate peak (#2) was 95.5%.

Preliminary experiments with the $^{90}$Y-labeled conjugate demonstrated that significant antibody degradation and loss of immunoreactivity occurred at specific activities >10 mCi/mg antibody. Therefore, a formulation was developed to minimize the effects of radiolysis. While a number of low molecular weight free-radical scavengers were evaluated and found to be effective, high concentrations of human serum albumin (HSA) were the most effective in preserving antibody integrity and immunoreactivity (FIGS. 7-9).

The $^{90}$Y-labeled antibody was formulated in 1× PBS, pH 7.4 containing 75 mg/mL HSA; diethylenetriaminepentaacetic acid (DTPA) was also added to a final concentration of 1 mM to insure that any $^{90}$Y which may be lost from the antibody would be chelated. Degradation of 2B8-MX-DTPA, radiolabeled to a specific activity of 14.6 mCi/mg was evaluated at 0 and 48 hours using SDS-PAGE and autoradiography. FIGS. 8 and 9 show that the radiolabeled antibody exhibited no significant degradation over a period of 48 h when incubated at 4° C. Analysis using instant thin layer chromatography showed that the loss of $^{90}$Y was less than 2% during the 48 h incubation (Table 24). The immunoreactivity was also relatively constant at 60% (Table 24).

TABLE 24

Stability of Clinically-Formulated $^{90}$Y-2B8-MX-DTPA

| Time (Hours at 4° C.) | Percent Conjugate-Associated Radioactivity | Percent Immunoreactivity |
| --- | --- | --- |
| 0 | 97.2 | 62 |
| 24 | 96.2 | 60 |
| 48 | 96.2 | 60 |

Radiolabeled conjugate (14.6 mCi/mg specific activity) was formulated in PBS, pH 7.4, containing 75 mg/mL human serum albumin and 1 MM DTPA and aliquots incubated at 4° C. Conjugate stability was analyzed at the times shown by SDS-PAGE and autoradiography, instant thin-layer chromatography and by whole-cell binding assay. The results show that approximately 96% of the radiometal remained associated with the conjugate after 48 hours at 4° C., and that antibody immunoreactivity remained constant at approximately 60%.

Figure 10:
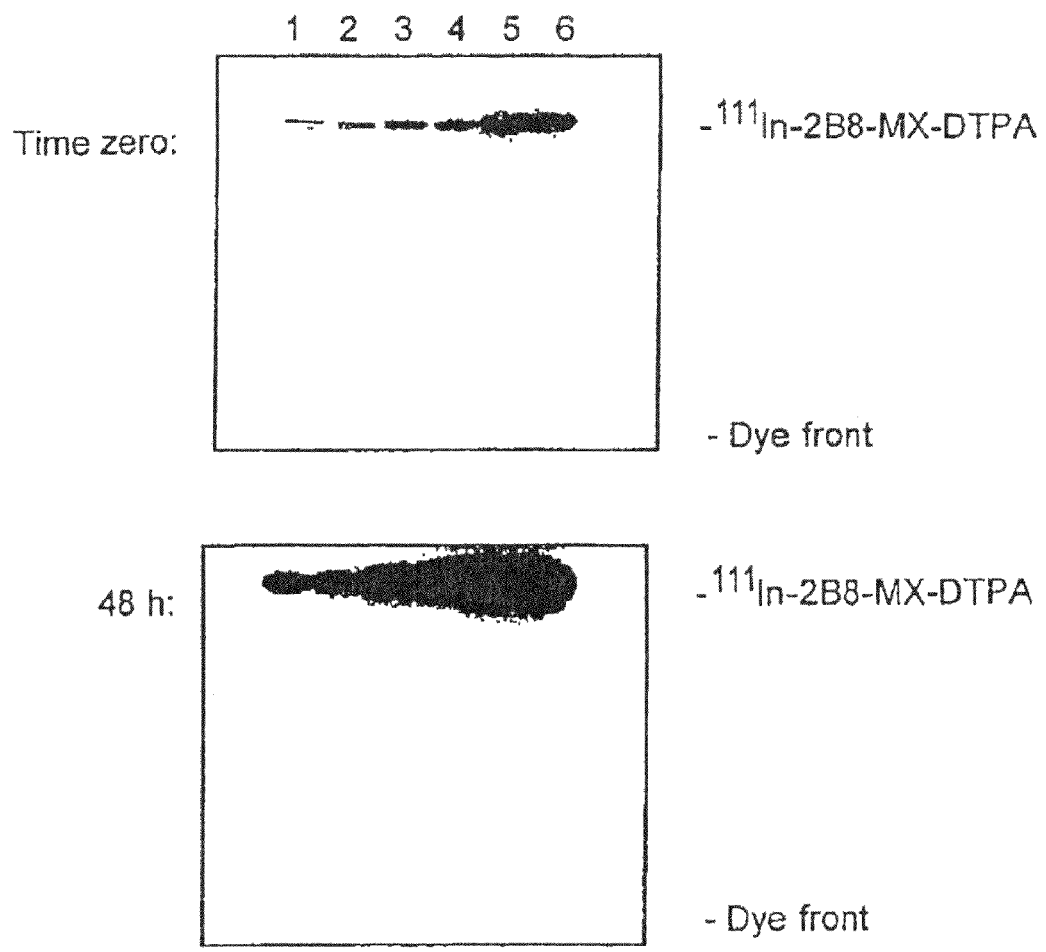
FIG. 10. Autoradiograms obtained from SDS-PAGE analysis of $^{111}$In-labeled 2B8-MX-DTPA incubated at 4° C. in PBS, pH 7.4 containing 50 mg/mL human serum albumin. At the indicated times, samples were electrophoresed on 4-20% Tris-glycine gels using non-reducing conditions. The samples were loaded at 5 μL (lanes 1, 2), 10 μL (lanes 3, 4), and 20 μL (lanes 5, 6). The gels were exposed to x-ray film for approximately 15 min at ambient temperature and photographed. (Note: The 48 h autoradiogram was obtained using intensifying screens resulting in a more intense signal compared to the time zero autoradiogram).
Figure 11:
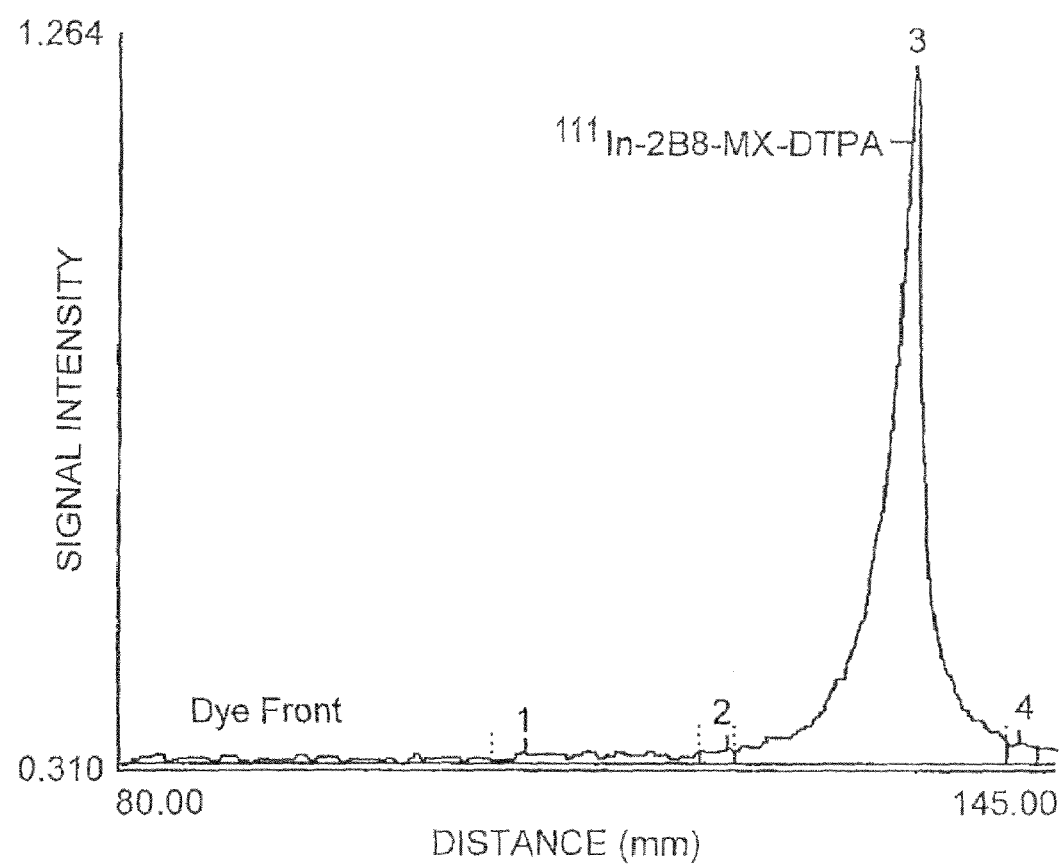
FIG. 11. Densitometry scan of time zero autoradiogram obtained from SDS-PAGE analysis of $^{111}$In-labeled 2B8-MX-DTPA incubated at 4° C. in PBS, pH 7.4 containing 50 mg/mL human serum albumin. The sample was electrophoresed on a 4-20% Tris-glycine gel under non-reducing conditions. The sample was loaded at 5 µL, 10 µL, and 20 µL in duplicate wells. The gel was exposed to x-ray film for approximately 15 min at ambient temperature and one of the lanes scanned using a densitometer. The relative area of the radiolabeled conjugate peak (#3) was 95.9%.
Figure 12:
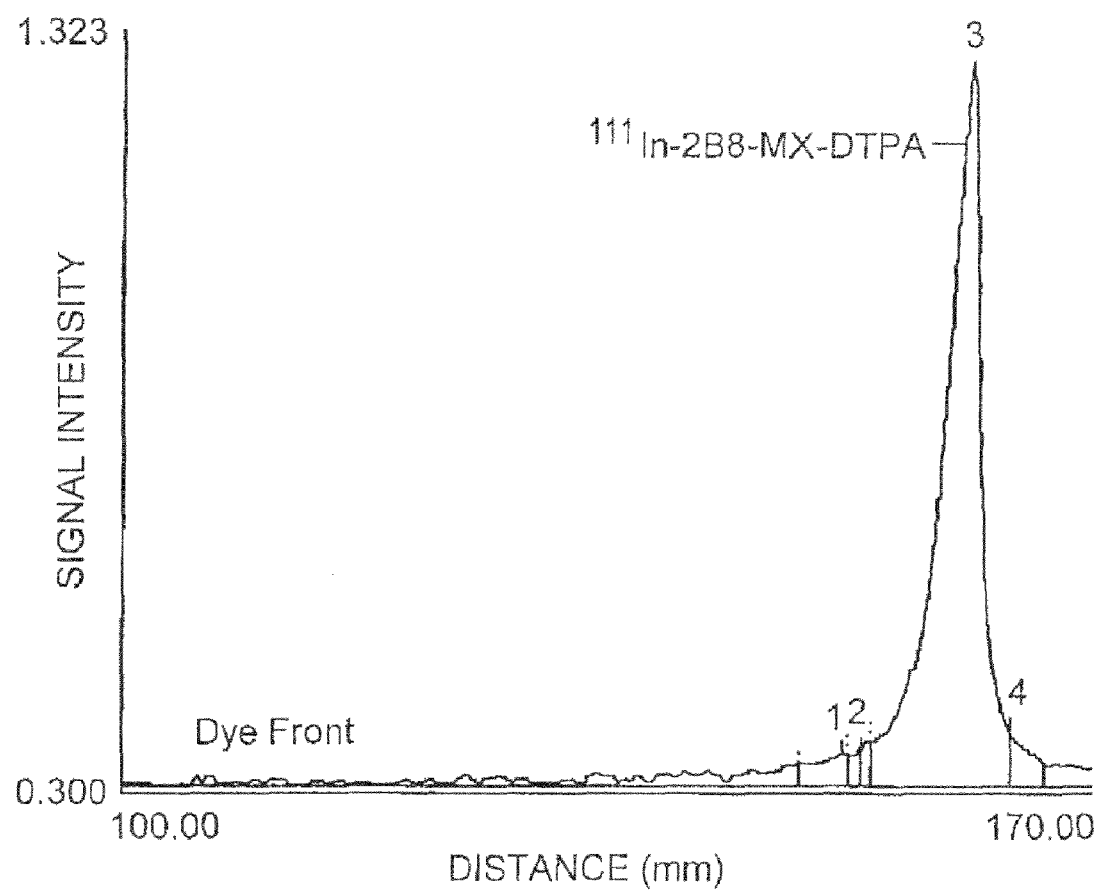
FIG. 12. Densitometry scan of 48 h autoradiogram obtained from SDS-PAGE analysis of $^{111}$In-labeled 2B8-MX-DTPA incubated at 4° C. in PBS, pH 7.4 containing 50 mg/mL human serum albumin. The sample was electrophoresed on a 4-20% Tris-glycine gel under non-reducing conditions. The sample was loaded at 5 µL, 10 µL, and 20 µL in duplicate wells. The gel was exposed to x-ray film for approximately 15 min at ambient temperature and one of the lanes scanned using a densitometer. The relative area of the radiolabeled conjugate was 97.0% (combined areas of peaks #2, 3, and 4).

Formulation studies were also performed with the $^{111}$In-labeled conjugate; the specific activity was 2.2 mCi/mg. The radiolabeled antibody was evaluated in 1× PBS, pH 7.4 containing 50 mg/mL HSA. FIG. 10 shows photographs of the autoradiograms for time zero and 48 h incubation samples; densitometric analysis of the autoradiograms indicate that there was no degradation of the radiolabeled antibody over the course of the study (FIGS. 11, 12). Instant thin-layer chromatography analysis of the samples demonstrated no loss of $^{111}$In (Table 25); moreover, immunoreactivity was maintained at approximately 100% (Table 25).

TABLE 25

Stability of Clinically-Formulated $^{111}$In-2B8-MX-DTPA

| Time (Hours at 4° C.) | Percent Conjugate-Associated Radioactivity | Percent Immunoreactivity |
| --- | --- | --- |
| 0 | 94.0 | 105 |
| 24 | 96.5 | 104 |
| 48 | 96.0 | 100 |

The radiolabeled conjugate (2.2 mCi/mg specific activity) was formulated in PBS, pH 7.4, containing 50 mg/mL human serum albumin and aliquots incubated at 4° C. Conjugate stability was analyzed by SDS-PAGE and autoradiography, by instant thin-layer chromatography, and by whole-cell binding assay. The results show that approximately 96% of the radiolabel was retained with the conjugate after 48 hours at 4° C., and that antibody immunoreactivity remained constant at approximately 100%.

Figure 13:
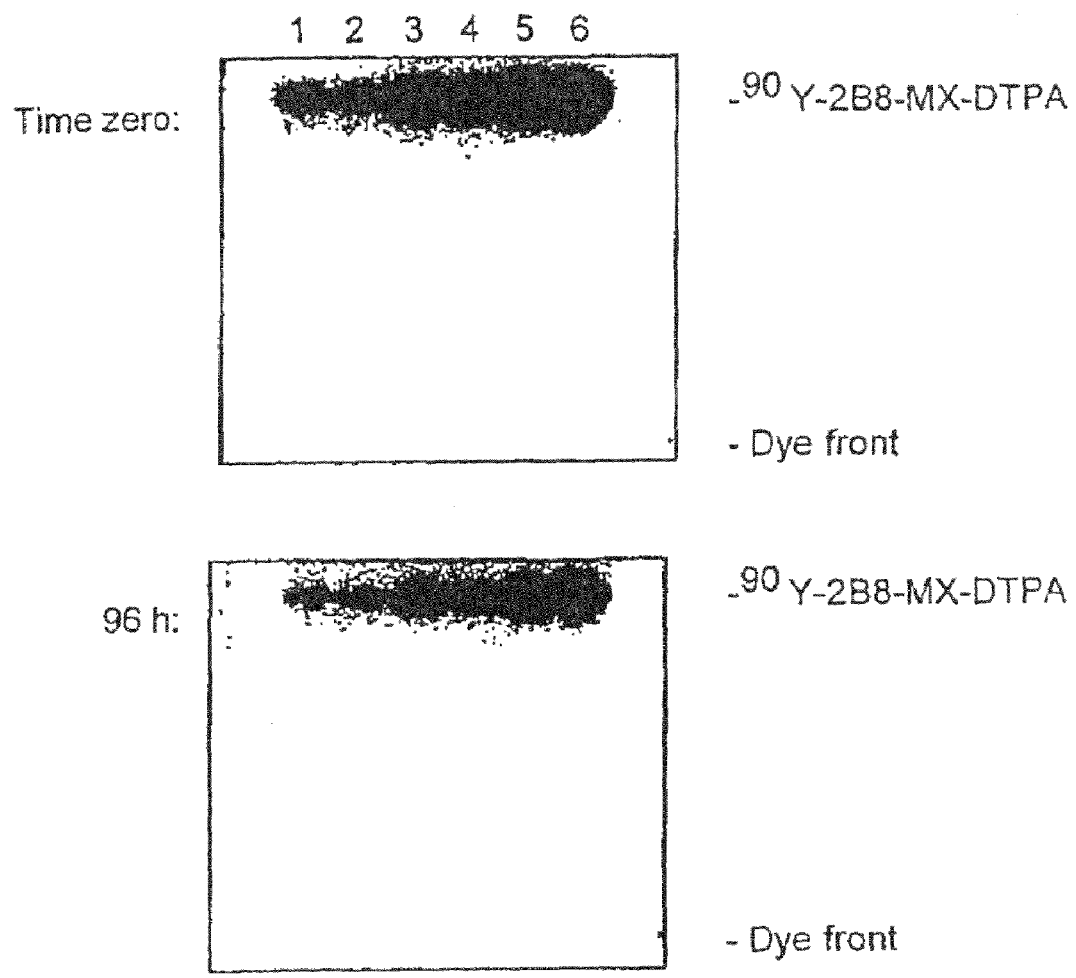
FIG. 13. Autoradiograms obtained from SDS-PAGE analysis of $^{90}$Y-labeled 2B8-MX-DTPA incubated at 37° C. in human serum. At the indicated times, samples were electrophoresed on 4-20% Tris-glycine gels using non-reducing conditions. The samples were loaded at 5 µL (lanes 1, 2), 10 µL (lanes 3, 4), and 20 µL (lanes 5, 6). The gels were exposed to x-ray film for approximately 15 min at ambient temperature and photographed.
Figure 14:
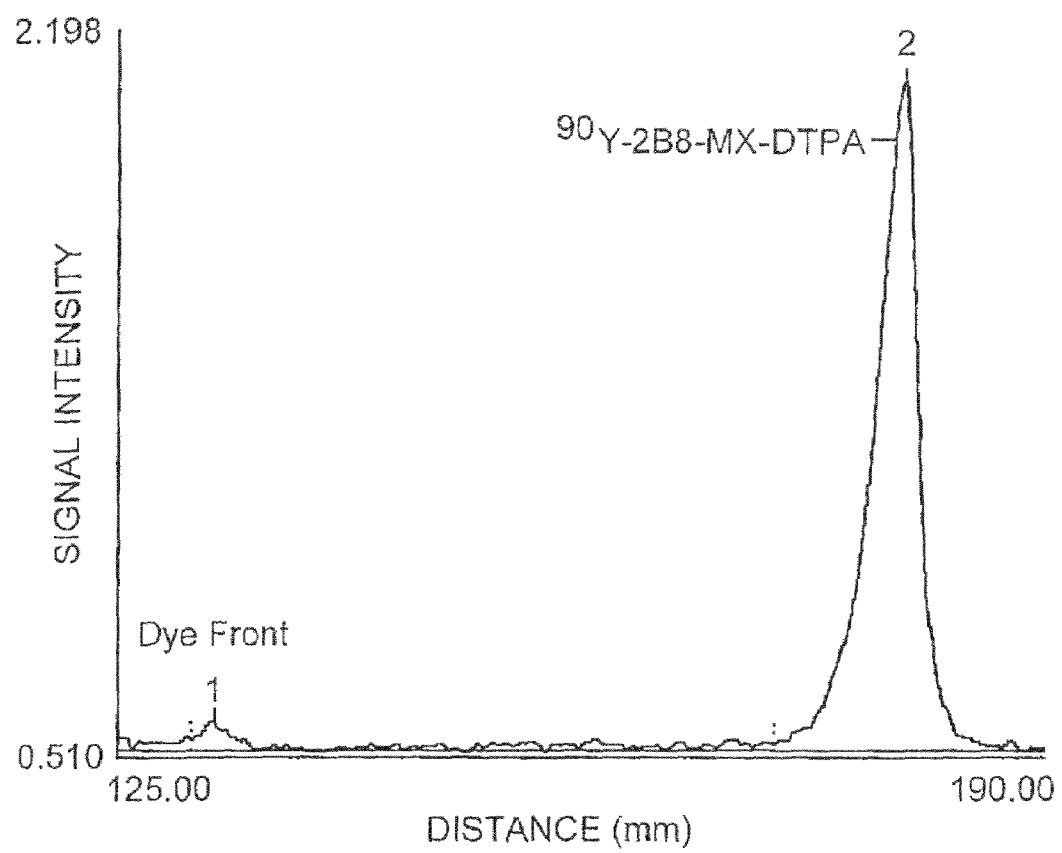
FIG. 14. Densitometric scan of time zero autoradiogram obtained from SDS-PAGE analysis of $^{90}$Y-labeled 2B8-MX-DTPA incubated at 37° C. in human serum. The sample was electrophoresed on a 4-20% Tris-glycine gel using non-reducing conditions. The sample was loaded at 5 µL, 10 µL, and 20 µL in duplicate wells. Gels were exposed to x-ray film for approximately 15 min at ambient temperature and one of the lanes was scanned using a densitometer. The relative area of the radiolabeled conjugate peak (#2) was 97.9%.
Figure 15:
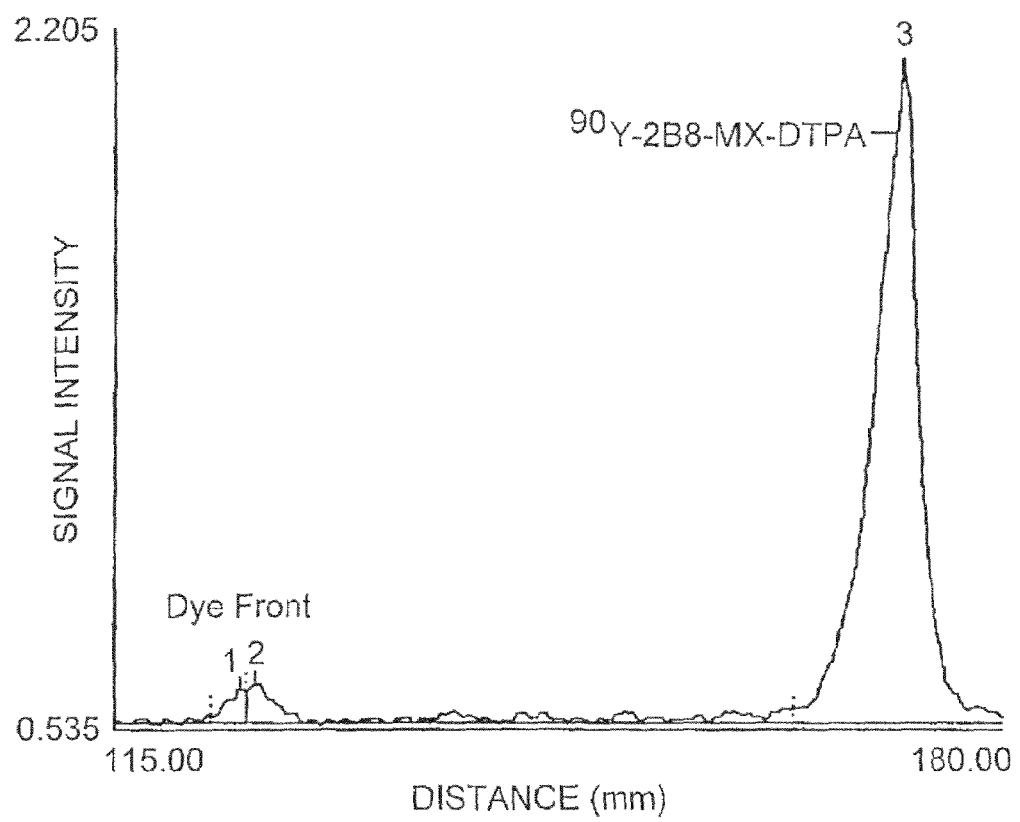
FIG. 15. Densitometric scan of 98 h autoradiogram obtained from SDS-PAGE analysis of $^{90}$Y-labeled 2B8-MX-DTPA incubated at 37° C. in human serum. The sample was electrophoresed on a 4-20% Tris-glycine gel using non-reducing conditions. The sample was loaded at 5 µL, 10 µL, and 20 µL in duplicate wells. Gels were exposed to x-ray film for approximately 15 min at ambient temperature and one of the lanes was scanned using a densitometer. The relative area of the radiolabeled conjugate peak (#2) was 94.7%.
Figure 16:
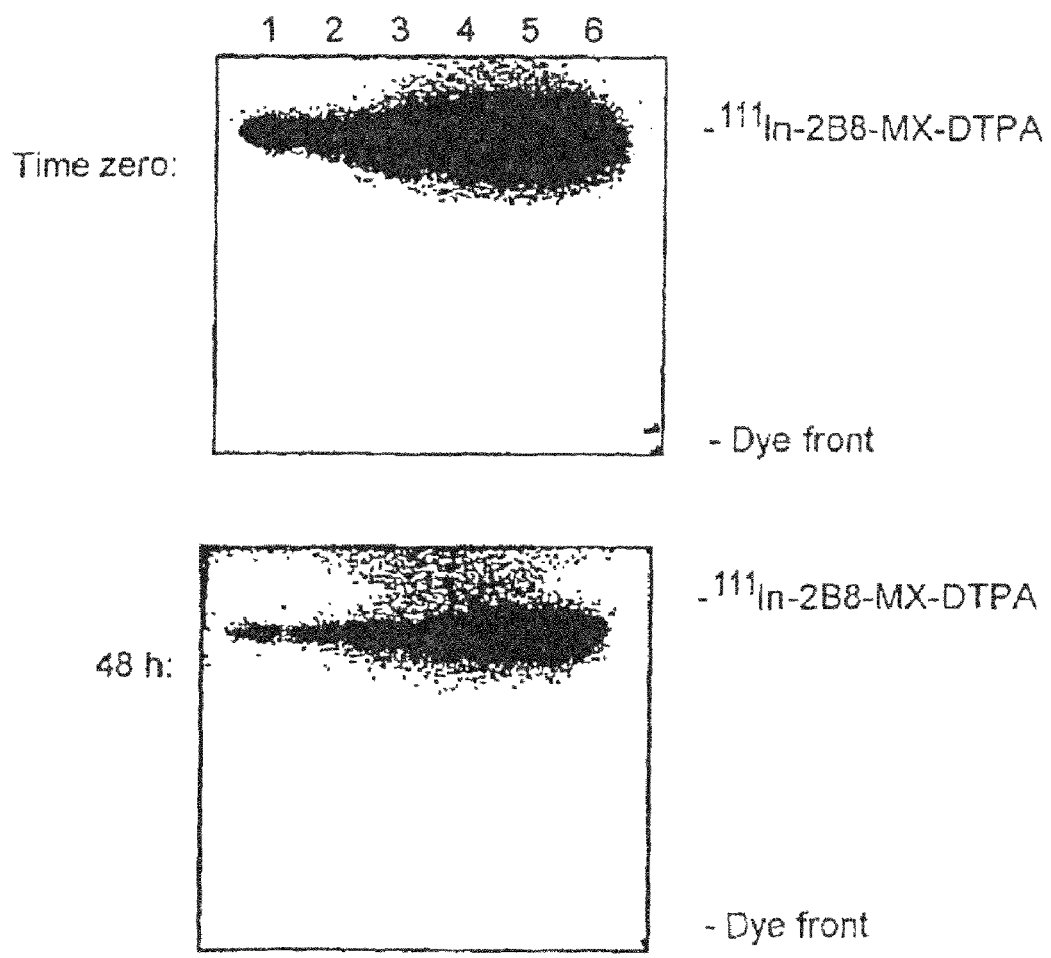
FIG. 16. Autoradiograus obtained from SDS-PAGE analysis of $^{111}$In labeled 2B8-MX-DTPA incubate at 37° C. in human serum. At the indicated times, samples were electrophoresed on 4-20% Tris-glycine gels using non-reducing conditions. The samples were loaded at 5 µL (lanes 1, 2), 10 µL (lanes 3, 4), and 20 µL (lanes 5, 6). The gels were exposed to x-ray film for approximately 16-20 h at ambient temperature and photographed.
Figure 17:
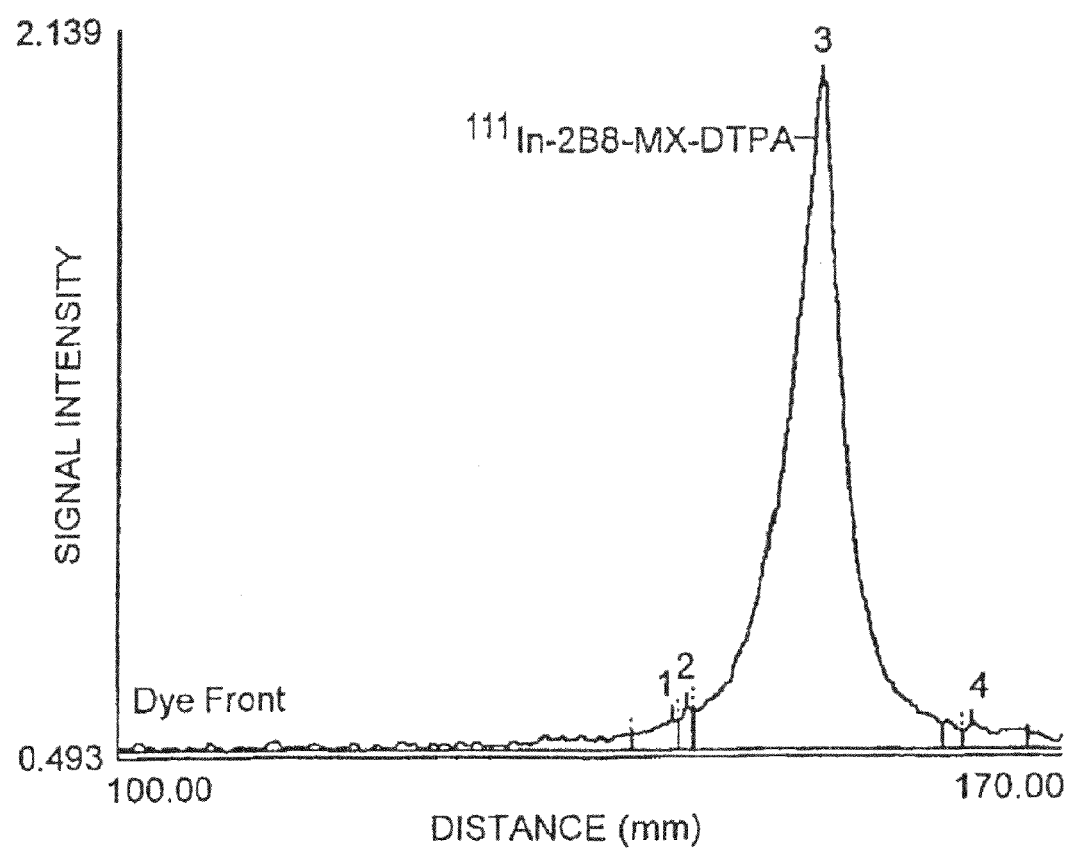
FIG. 17. Densitometric scan of time zero autoradiogram obtained from SDS-PAGE analysis of $^{111}$In-labeled 2B8-MX-DTPA incubated at 37° C. in human serum. The sample was electrophoresed on a 4-20% Tris-glycine gel using non-reducing conditions. The sample was loaded at 5 µL, 10 µL, and 20 µL in duplicate wells. The gel was exposed to x-ray film for approximately 16-20 h at ambient temperature and one of the lanes was scanned using a densitometer. The relative area of the radiolabeled conjugate peak (#3) was 95.3%.
Figure 18:
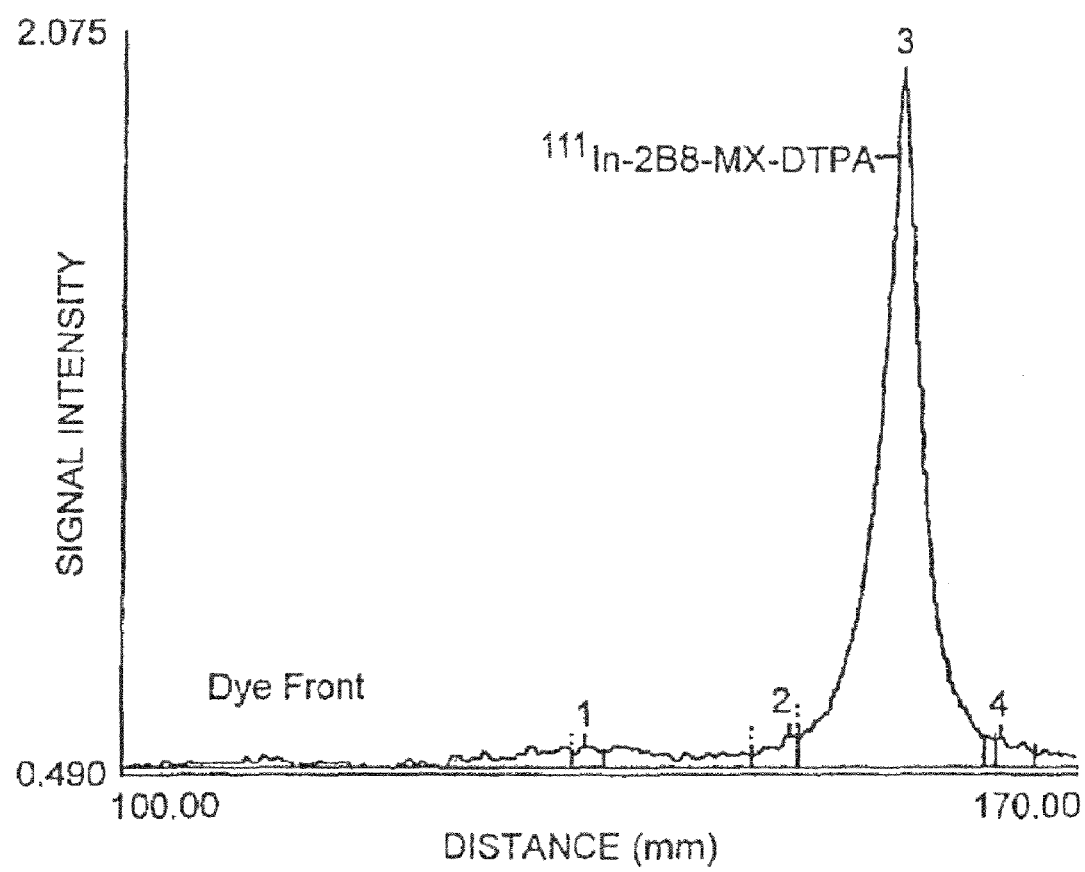
FIG. 18. Densitometric scan of the 96 h autoradiogram obtained from SDS-PAGE analysis of $^{111}$In-labeled 2B8-MX-DTPA incubated at 37° C. in human serum. The sample was electrophoresed on a 4-20% Tris-glycine gel using non-reducing conditions. The sample was loaded at 5 µL, 10 µL, and 20 µL in duplicate wells. The gel was exposed to x-ray film for approximately 16-20 h at ambient temperature and one of the lanes was scanned using a densitometer. The relative area of the radiolabeled conjugate peak (#3) was 94.0%.

When a clinically-formulated preparation of 2B8-MX-DTPA, radiolabeled with $^{90}$Y to a specific activity 14.6 mCi/mg, was incubated for 96 hours at 37° C. in human serum and analyzed by non-reducing SDS-PAGE and autoradiography, less than 4% of the radioisotope was lost during the course of the incubation period. Densitometric scans of the autoradiograms at time zero and 96 h indicated no significant degradation of the radiolabeled conjugate (FIGS. 13-15). These results were corroborated by analytical thin-layer chromatographic analyses of the time zero and 96-hour samples (Table 26). Taken together these results suggest that the yttrium-labeled conjugate is stable under the conditions used in this study. Similar results were obtained with the $^{111}$In labeled 2B8-MX-DTPA conjugate (FIGS. 16-18).

TABLE 26

Analytical Thin-Layer Chromatographic Analysis of $^{90}$Y-2B8-MX-DTPA Conjugate Incubated in Human Serum for 96 Hours at 37° C.

| Time (Hours at 37° C.) | Percent Conjugate-Associated Radioactivity |
| --- | --- |
| 0 | 95.1 |
| 24 | 95.2 |
| 48 | 93.2 |
| 72 | 92.0 |
| 96 | 91.4 |

Human serum samples containing $^{90}$Y-2B8-MX-DTPA (specific activity 14.6 mCi/mg) were analyzed at the times shown by spotting 1 µl of a 1:20 dilution of samples on instant thin-layer chromatography strips; samples were analyzed in triplicate. Chromatography strips were developed by ascending chromatography in 10% ammonium acetate in methanol:water (1:1; v/v), dried, and cut in half crosswise. The radioactivity associated with the bottom and top halves of each strip was then determined and the percent conjugate-associated radioactivity calculated. (Free radiometal migrates with the solvent front while protein-associated radioactivity remains at the origin.) The means of each determination of conjugate-associated radioactivity are shown.

B. Animal Studies.

1. High-Dose Pharmacology/Toxicology Studies with 2B8 and 2B8-MX-DTPA

In a GLP study performed at White Sands Research Center (Study Number 920111), cynomolgus monkeys were given intravenous injections of various doses of 2B8. Blood samples were taken before each new injection and the blood was processed for flow cytometric evaluation of the lymphocyte populations (Table 27).

TABLE 27

Primate B cell Populations Determined by Flow Cytometry, Following Infusion of Anti-CD20 Murine Monoclonal Antibody 2B8

| Animal # | Dose | Day | B cells[a,b] | % Depletion |
| --- | --- | --- | --- | --- |
| Group I | | | | |
| 452 | saline | 0 | 20.1 | 0 |
|  |  | 1 | 18.3 | 9 |
|  |  | 7 | 21.6 | 0 |
|  |  | 13 | 14.6 | 27 |
|  |  | 38 | 15.5 | 23 |
|  |  | 52 | 18.6 | 7 |
| 424 | saline | 0 | 12.4 | 0 |
|  |  | 1 | 11.6 | 6 |
|  |  | 7 | 11.2 | 10 |
|  |  | 13 | 8.4 | 32 |
|  |  | 38 | 7.7 | 38 |
|  |  | 52 | 13.1 | 0 |
| Group II | | | | |
| 540 | 0.6 mg/kg | 0 | 16.1 | 0 |
|  |  | 1 | 7.1 | 54 |

TABLE 27-continued

Primate B cell Populations Determined by Flow Cytometry, Following Infusion of Anti-CD20 Murine Monoclonal Antibody 2B8

| Animal # | Dose | Day | B cells[a,b] | % Depletion |
|---|---|---|---|---|
| | | 7 | 6.0 | 63 |
| | | 13 | 5.7 | 65 |
| | | 38 | 10.8 | 33 |
| | | 52 | 14.4 | 11 |
| 804 | 0.6 mg/kg | 0 | 17.6 | 0 |
| | | 1 | 8.3 | 53 |
| | | 7 | 6.1 | 65 |
| | | 13 | 6.6 | 62 |
| | | 38 | 5.1 | 71 |
| | | 52 | 5.2 | 68 |
| Group III | | | | |
| 701 | 2.5 mg/kg | 0 | 21.6 | 0 |
| | | 1 | 10.7 | 50 |
| | | 7 | 3.0 | 86 |
| | | 13 | 10.7 | 50 |
| 754 | 2.5 mg/kg | 0 | 19.9 | 0 |
| | | 1 | 11.2 | 44 |
| | | 7 | 10.5 | 47 |
| | | 13 | 9.0 | 55 |
| Group IV | | | | |
| 782 | 10 mg/kg | 0 | 15.9 | 0 |
| | | 1 | 3.0 | 81 |
| | | 7 | 3.5 | 78 |
| | | 13 | 6.5 | 59 |
| 164 | 10 mg/kg | 0 | 17.7 | 0 |
| | | 1 | 8.4 | 47 |
| | | 7 | 7.9 | 50 |
| | | 13 | 7.7 | 42 |
| Group V | | | | |
| 705 | 10 mg/kg | 0 | 17.2 | 0 |
| | | 1 | 5.2 | 70 |
| | | 7 | 1.3 | 69 |
| | | 13 | 8.2 | 52 |
| | | 38 | 17.1 | 1 |
| | | 52 | 13.3 | 22 |
| 716 | 10 mg/kg | 0 | 34.7 | 0 |
| | | 1 | 18.6 | 46 |
| | | 7 | 8.1 | 77 |
| | | 13 | 3.5 | 90 |
| | | 38 | 6.9 | 80 |
| | | 52 | 9.2 | 61 |

[a]Percent of total lymphocytes.
[b]B cell population quantitated by double staining marker reagents anti mouse IGG-RPE + anti human IG-FITC (anti mouse IgG RPE detects 2B8 blocked CD20 and anti human IgG FITC detects monkey B cell surface Ig) Animals in groups I through IV were injected every 48 hours for a total of seven injections; animals in group V were injected once on day 0. The animals in Groups III and IV were sacrificed on day 14.

No significant pharmacotoxic effects related to the administration of the anti-CD20 antibody 2B8 were noted in any clinical parameter evaluated during or following the study. Similarly, no abnormalities were noted during analysis of the various histopathology specimens obtained from animals in groups III and IV.

The study duration was 14 days and the animals were evaluated during the study in the following categories: clinical observations, body weights, body temperature, food and water intake, fecal elimination, serum chemistries, hematology, urinalysis, and physical examinations. Additionally, the animals in each group were bled on days 0, 1, 7, and 13 and the blood analyzed for serum antibody (2B8) levels and for T- and B-cell levels. On day 13 the animals in Groups III and IV were sacrificed and selected tissues examined by light microscopy following specimen preparation. The tissues evaluated were: heart, spleen, liver, kidney, lung, cerebral cortex, spinal cord, lymph node, stomach, ileum, colon, skeletal muscle, testis/ovary, pancreas, and bone marrow.

Figure 19:
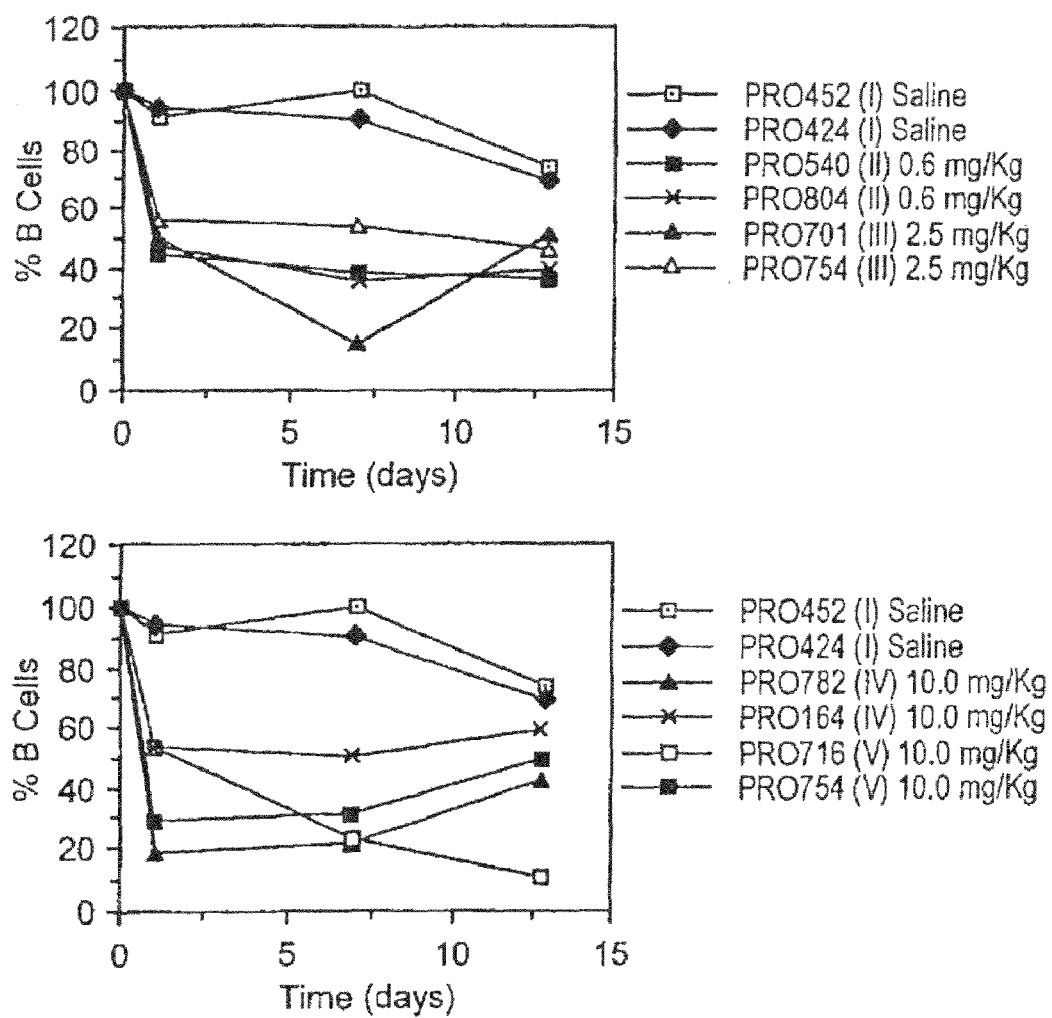
FIG. 19. Cynomolgus monkeys were injected intravenously every 48 hours for a total of seven injections; the amounts administered are shown. Circulating T- and B-cell levels were determined by FACS analysis using anti-CD2 (T-cell), anti-Mo-IgG (2B8), anti-CD20 (Leu 16), and anti-human-IgG (B-cell). No effect was observed on circulating T-cell levels. (Group V animals were given a single dose).

When the blood from the treated animals was analyzed for levels of circulating T- and B-cells, animals in groups II through V exhibited >50% loss of circulating B-cells through day 13 (FIG. 19); administration of the antibody had no effect on T-cell levels (data not shown). All groups receiving 2B8 showed saturation of B-cells and excess antibody in the plasma (not shown). The animals in group V, which received a single 10.0 mg/Kg dose of 2B8 also exhibited reduction in circulating B-cell levels equivalent to that observed in animals in the other groups.

Figure 20:
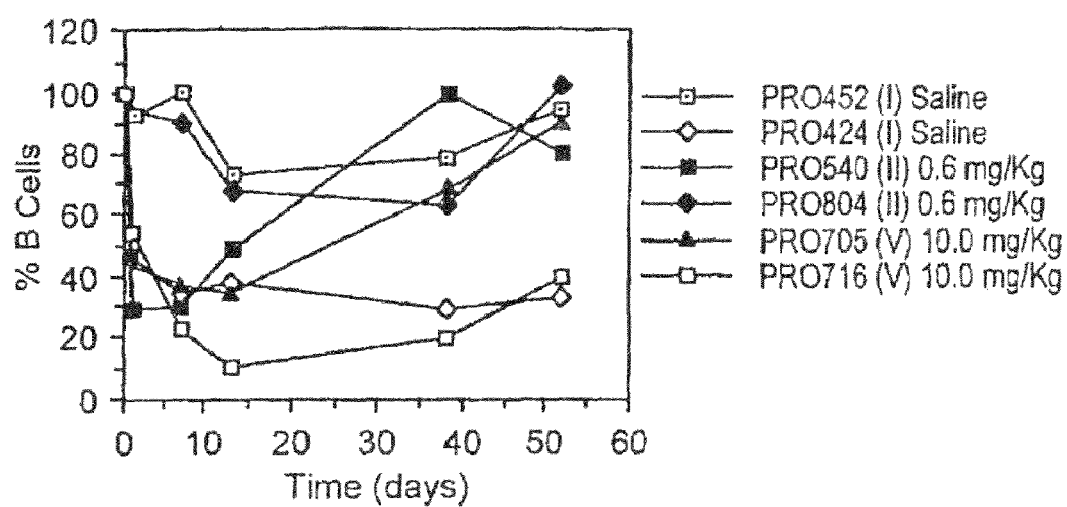
FIG. 20. The recovery of circulating B-cell levels in animals receiving 2B8 was followed by FACS analysis using the fluorescently-labeled antibodies described in the brief description of FIG. 19. The animals in Groups III and IV were not monitored as they were sacrificed on day 13.

The animals in groups I, II, and V were examined through day 52 (FIG. 20). The levels of B-cells returned to >70% of normal by day 38, except for one animal in Group II (PRO804) and one animal in Group V (PRO716). The levels of circulating B-cells in these animals remained at approximately 40% of normal levels after 52 days.

In addition to this study, the pharmacotoxic effects of [89]Y-2B8-MX-DTPA were assessed in cynomolgus monkeys in a GLP study performed at White Sands Research Center (Study No. 920611). Clinical-grade conjugate was loaded with non-radioactive [89]Y. The yttrium-bearing conjugate was formulated in PBS pH 6.8, containing 75 mg/mL human serum albumin and 1 mM DTPA (clinical formulation) and administered intravenously as described in the Methods Section.

Figure 21:
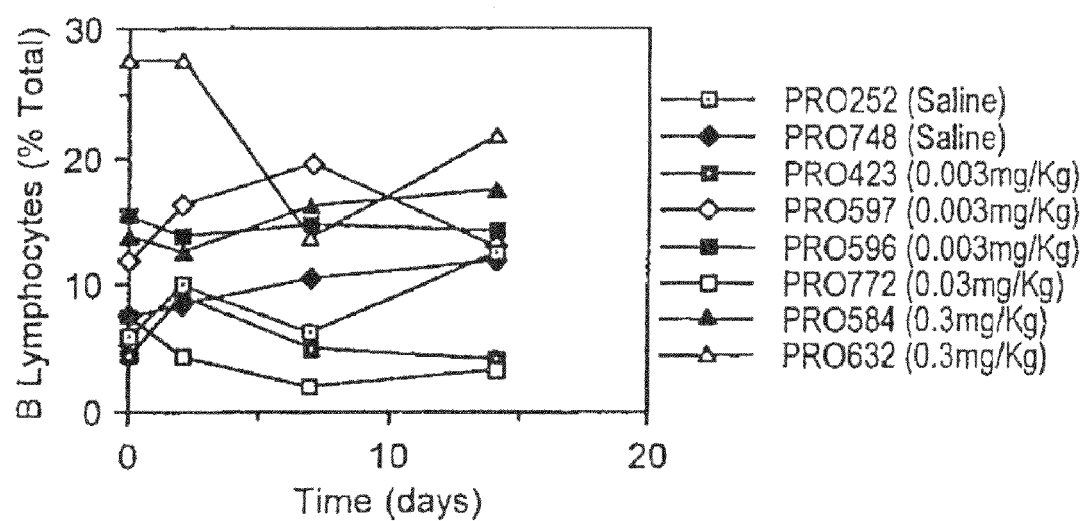
FIG. 21. Cynomolgus monkeys were injected intravenously with $^{89}$Y-2B8-MX-DTPA which had been prepared using clinical-grade 2B8-MX-DTPA. The animals were dosed every 48 hours with the amounts shown above for a total of seven doses. On days 0, 2, 7, 10 and 14 the monkeys were bled and evaluated for serum chemistries hematology and circulating B-cell levels (day 10 sera were not analyzed for B-cell content). Other than decreased total lymphocyte count in all animals, except one individual in groups II, no significant abnormalities were noted during the course of the study.

As shown by the results in FIG. 21, the [89]Y-labeled 2B8-MX-DTPA had little, if any, effect on circulating B-cells in these animals, regardless of the dose administered. In addition, other than a general depletion of lymphocytes (20-43%), no significant abnormalities were found in any clinical parameter evaluated, including serum chemistry, urinalysis, body weights and temperatures.

2. Pharmacokinetic Studies with 2B8 and 2B8-MX-DTPA

Figure 22A:
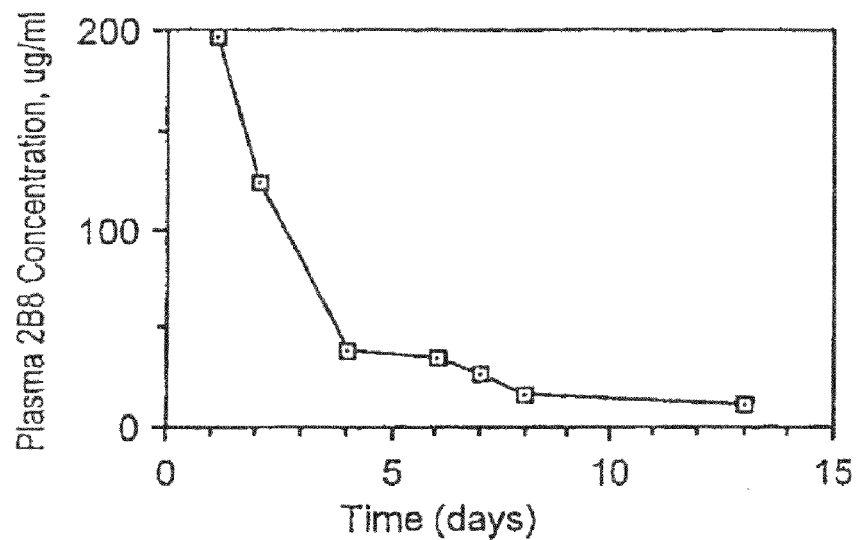
FIGS. 22A and 22B. The clearance of murine anti-CD20 antibody 2B8 from cynomolgus monkeys was determined by ELISA following a single injection of 10 mg/kg on day zero.
Figure 22B:
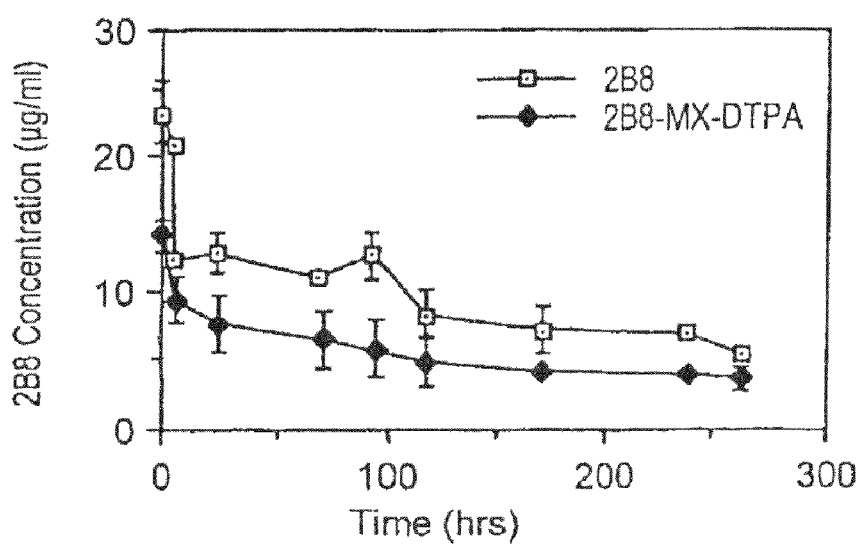

As described above, the animals in group V of the GLP study received a single dose of 10.0 mg/Kg of 2B8. Linear regression analysis of the data suggest that the native antibody was cleared from the circulation of these monkeys with a 13 t1/2 value of approximately 4.5 days. In a similar study using BALB/c mice, the $\beta$ $t_{1/2}$ values for native and conjugated 2B8 were determined by linear regression analysis (not shown) to be 8.75 days (FIG. 22). These results suggest that conjugation of 2B8 had no effect on its clearance from BALB/c mice.

3. Biodistribution and Tumor Localization Studies with Radiolabeled 2B8-MX-DTPA

Figure 23:
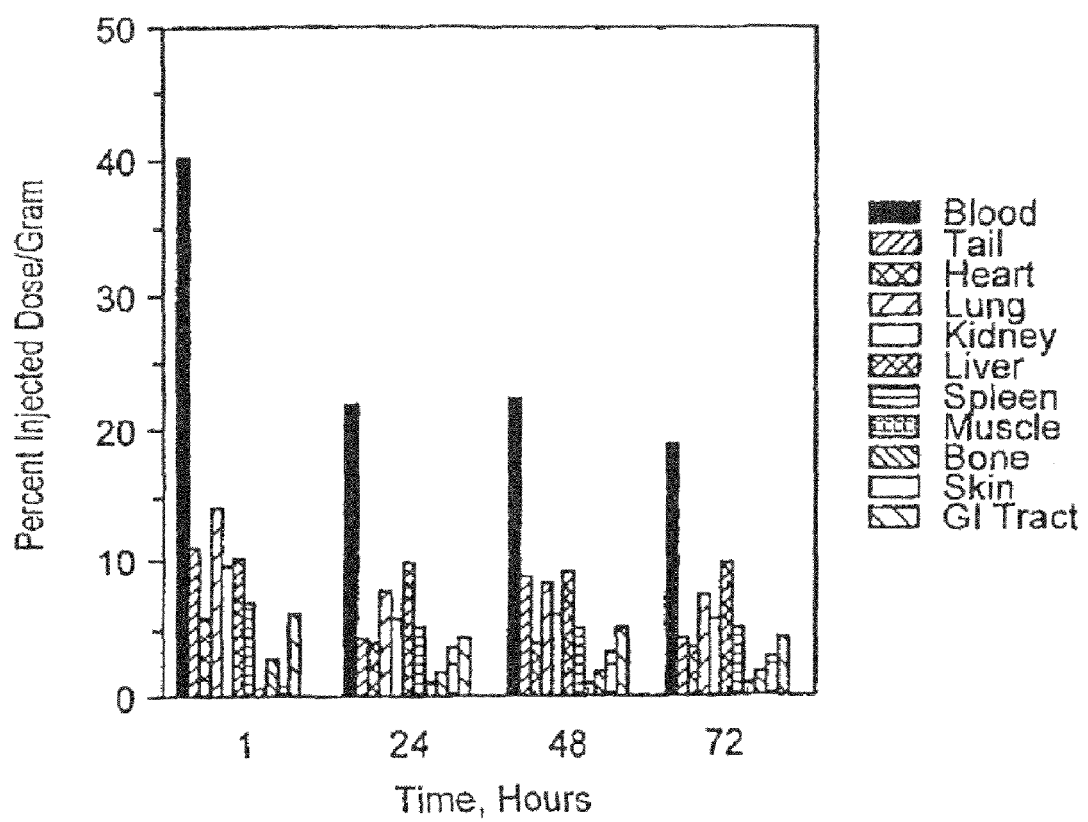
FIG. 23. Twenty BALB/c mice were each injected with 1.1 µCi of radiolabeled conjugate (100 µL) formulated in PBS, pH 7.4, containing 50 mg/mL HSA. Groups of five mice each were sacrificed at 1, 24, 48, and 72 hours and then blood and various tissues prepared and analyzed for associated radioactivity.

Building on the preliminary biodistribution experiment described above (Section 2d), conjugated 2B8 was radiolabeled with $^{111}$In to a specific activity of 2.3 mCi/mg and roughly 1.1 µCi was injected into each of twenty BALB/c mice to determine biodistribution of the radiolabeled material. Subsequently, groups of five mice each were sacrificed at 1, 24, 48 and 72 hours and their organs and a portion of the skin, muscle and bone were removed and processed for analysis. In addition, the urine and feces were collected and analyzed for the 24-72 hour time-points. The level of radioactivity in the blood dropped from 40.3% of the injected dose per gram at 1 hour to 18.9% at 72 hours (Tables 1-4; FIG. 23). Values for the heart, kidney, muscle and spleen remained in the range of 0.7-9.8% throughout the experiment. Levels of radioactivity found in the lungs decreased from 14.2% at 1 hour to 7.6% at 72 hours; similarly the respective liver injected dose per gram values were 10.3% and 9.9%. These data were used in determining radiation absorbed dose estimates [111]In-2B8-MX-DTPA (Table 19).

Figure 24:
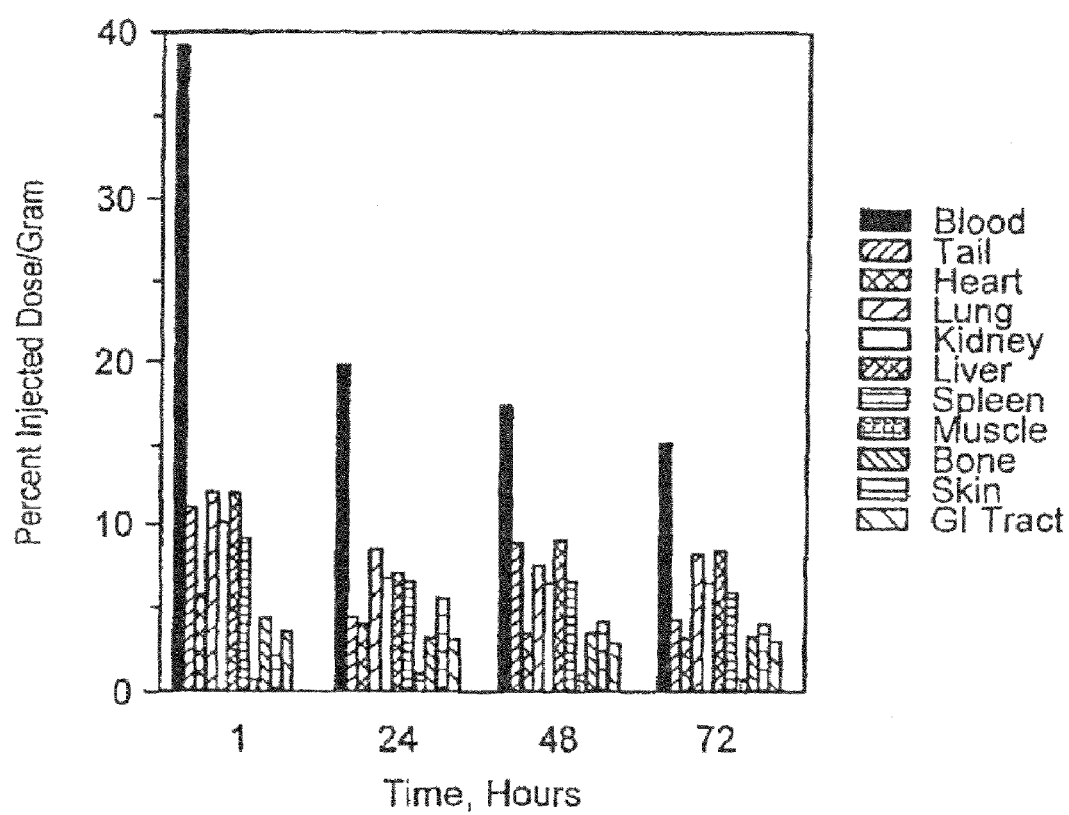
FIG. 24. Twenty BALB/c mice were each injected intravenously with approximately 1.0 µCi (in 100 µl) of radiolabeled conjugate formulated in 1× PBS, pH 7.4, containing 75 mg/mL human serum albumin and 1 m MDPA. Groups of five mice each were sacrificed at 1, 24, 48 and 72 hours and their blood and various tissues prepared and analyzed for associated radioactivity.

The biodistribution of $^{90}$Y-labeled conjugate, having a specific activity of 12.2 mCi/mg antibody, was evaluated in BALB/c mice. Radioincorporations of >90% were obtained and the radiolabeled antibody was purified by HPLC. Tissue deposition of radioactivity was evaluated in the major organs, and the skin, muscle, bone, and urine and feces over 72 hours, and expressed as percent injected dose/g tissue. The results shown in Tables 5-8 and FIG. 24 demonstrate that while the levels of radioactivity associated with the blood dropped from approximately 39.2% injected dose per gram at 1 hour to roughly 15.4% after 72 hours; the levels of radioactivity associated with tail, heart, kidney, muscle and spleen remained fairly constant at 10.2% or less throughout the course of the experiment. Importantly, the radioactivity associated with the bone ranged from 4.4% of the injected dose per gram bone at 1 hour to 3.2% at 72 hours. Taken together, these results suggest that little free yttrium was associated with the conjugate and that little free radiometal was released during the course of the study. These data were used in determining radiation absorbed dose estimates for $^{90}$Y-2B8-MX-DTPA (Table 20).

For tumor localization studies, 2B8-MX-DTPA was prepared and radiolabeled with $^{111}$In to a specific activity of 2.7 mCi/mg. One hundred microliters of labeled conjugate (approximately 24 µCi) were subsequently injected into each of 12 athymic mice bearing Ramos B-cell tumors. Tumors ranged in weight from 0.1 to 1.0 grams. At time points of 0, 24, 48, and 72 hours following injection, 50 µL of blood was removed by retro-orbital puncture, the mice sacrificed by cervical dislocation, and the tail, heart, lungs, liver, kidney, spleen, muscle, femur, and tumor removed. After processing and weighing the tissues, the radioactivity associated with each tissue specimen was determined using a gamma counter and the values expressed as percent injected dose per gram.

Figure 25:
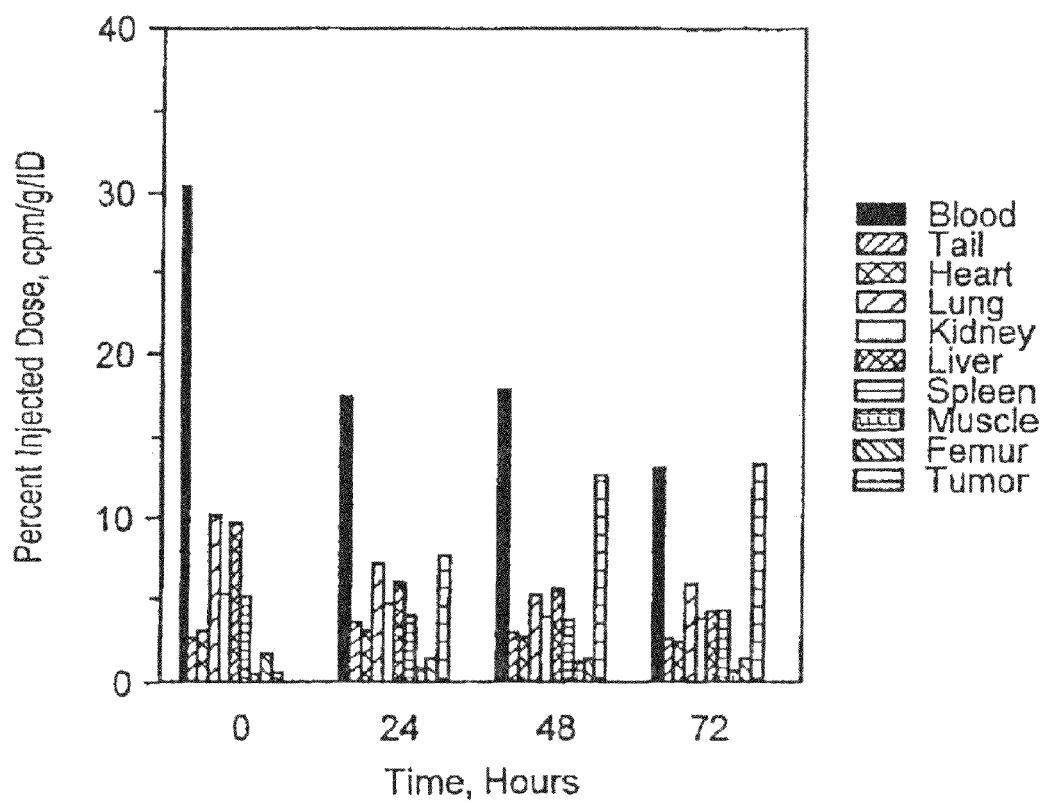
FIG. 25. Athymic mice bearing Ramos B-cell tumors were injected intravenously with 24 µCi of $^{111}$In-2B8-MX-DTPA and groups of three mice each were sacrificed at 0, 24, 48 and 72 hours. Following tissue preparation and determination of associated radioactivity, the percent injected dose per gram tissue values were determined and plotted as shown.

The results (FIG. 25) demonstrate that the tumor concentrations of the $^{111}$In-2B8-MX-DTPA increased steadily throughout the course of the experiment. Thirteen percent of the injected dose was accumulated in the tumor after 72 hours. The blood levels, by contrast, dropped during the experiment from over 30% at time zero to 13% at 72 hours. All other tissues (except muscle) contained between 1.3 and 6.0% of the injected dose per gram tissue by the end of the experiment; muscle tissue contained approximately 13% of the injected dose per gram.

C. Dosimetry

The summary dosimetry data derived from biodistribution studies in normal BALB/c mice and presented in Tables 19 and 20, for the indium- and yttrium-labeled conjugates, respectively, are in agreement with data presented in the literature when compared per millicurie of injected dose (5) and suggest that both the yttrium- and indium-labeled conjugates of 2B8 may be safely evaluated for clinical efficacy in lymphoma patients.

D. Toxicology.

1. 2B8: Single Dose General Safety Test.

Mice and guinea pigs were administered a single intraperitoneal dose of 2B8 (0.5 mL or 5.0 mL, respectively) and observed for seven days. No overt signs of toxicity were detected.

2. 2B8 and 2B8-MX-DTPA: Immunohistology Studies with Human Tissues.

The tissue reactivity of murine monoclonal antibody 2B8 was evaluated using a panel of 32 different human tissues fixed with, acetone. Antibody 2B8 reacts with the anti-CD20 antigen which had a very restricted pattern of tissue distribution, being observed only in a subset of cells in lymphoid tissues including those of hematopoietic origin.

In the lymph node, immunoreactivity was observed in a population of mature cortical B-lymphocytes as well as proliferating cells in the germinal centers. Positive reactivity was also observed in the peripheral blood, B-cell areas of the tonsils, white pulp of the spleen, and with 40-70% of the medullary lymphocytes found in the thymus. Positive reactivity was also seen in the follicles of the lamina propria (Peyer's Patches) of the large intestines. Finally, aggregates or scattered lymphoid cells in the stroma of various organs, including the bladder, breast, cervix, esophagus, lung, parotid, prostate, small intestine, and stomach, were also positive with antibody 2B8.

All simple epithelial cells, as well as the stratified epithelia and squamous epithelia of different organs, were found to be unreactive. Similarly, no reactivity was seen with neuroectodermal cells, including those in the brain, spinal cord and peripheral nerves. Mesenchymal elements, such as skeletal and smooth muscle cells, fibroblasts, endothelial cells, and polymorphonuclear inflammatory cells were also found to be negative.

The tissue reactivity of the 2B8-MX-DTPA conjugate was evaluated using a panel of sixteen human tissues which had been fixed with acetone. As previously demonstrated with the native antibody, the 2B8-MX-DTPA conjugate recognized the CD20 antigen which exhibited a highly restricted pattern of distribution, being found only on a subset of cells of lymphoid origin. In the lymph node, immunoreactivity was observed in the B-cell population. Strong reactivity was seen in the white pulp of the spleen and in the medullary lymphocytes of the thymus. Immunoreactivity was also observed in scattered lymphocytes in the bladder, heart, large intestines, liver, lung, and uterus, and was attributed to the presence of inflammatory cells present in these tissues. As described with the native antibody (above), no reactivity was observed with neuroectodermal cells or with mesenchymal elements.

III. Discussion

The murine monoclonal anti-CD20 antibody 2B8, produced by a clone with the same designation, exhibits an affinity for the B-cell CD20 antigen which may be higher than that observed for the B1 antibody, as determined by competition with antibodies of known specificity for the CD20 antigen, and by Scatchard analysis. Further, immunoprecipitation data suggest that the antigen precipitated by 2B8 appears to be the same antigen as the one precipitated by B1, as both antibodies precipitated a doublet with relative molecular weights of 33 and 35 KD. Cytofluorographic analysis of the specificity of the 2B8 antibody for peripheral blood lymphocytes demonstrates that the antibody reacts specifically with B-cells and has no demonstrated reactivity with T-cells or other types of lymphocytes. Finally, preliminary stability data suggest that the antibody is stable at 30° C. for 12 weeks with no loss of immunoreactivity.

When the 2B8 antibody was conjugated to methylbenzyl diethylenetriamine-pentaacetic acid (MX-DTPA), virtually no reduction in immunoreactivity, relative to the native antibody, was observed. Further, radiolabeling the conjugate with either $^{111}$In or $^{90}$Y produced labeled conjugates with immunoreactivities of 100% and 60%, respectively. Stability studies of $^{111}$In or $^{90}$Y-labeled conjugates incubated in human serum for 96 hours at 37° C. indicated negligible loss of the radiometal during the course of the study, suggesting that the conjugates will be stable when used clinically.

Tumor localization studies in athymic mice using an indium-labeled preparation of 2B8-MX-DTPA demonstrated that increasing amounts of the conjugate bound to the tumor cells during the course of the experiment without unusual accumulations in other tissues. Moreover, dosimetry estimates derived from the biodistribution. Moreover, dosimetry estimates derived from the biodistribution studies are in agreement with data published in the literature. Finally, human tissue cross-reactivity studies with the native and conjugated antibodies indicated that both antibodies recognize an antigen with highly restricted tissue distribution, reacting only with a subset of cells in-lymphoid tissues, including those of hematopoietic origin. Taken together, these results suggest that conjugation did not alter the tissue specificity of the antibody, and that the radiolabeled conjugates are stable in vivo and recognize the CD20 antigen present on the surface of tumors produced experimentally in athymic mice.

When 2B8 was used in a high-dose pharmacology/toxicology study, the antibody produced no significant pharmacotoxic effects in any parameter evaluated, either during or following the study. Similarly, no abnormalities were noted during analysis of the various histopathology specimens examined by light microscopy. Surprisingly, all doses of the antibody used produced marked depletion of circulating B-cells. Circulating B-cell levels did, however, return to roughly normal levels once administration of the antibody ceased. In the single-dose group of monkeys (Group V) the native antibody was cleared from the circulation with an apparent β $t_{1/2}$ value of approximately 4.5 days. Predictably, when this pharmacokinetic study was performed in BALB/c mice the 2B8 antibody was cleared with a β $t_{1/2}$ value of 8.75 days. Thus, taken together, these data suggest that the native antibody may also provide some clinical effect when administered as an adjunct to the radiolabeled conjugates.

Overall our data indicate that the high affinity 2B8 antibody and its MX-DTPA conjugate exhibit a restricted pattern of human tissue reactivity. Moreover, in primates, the native antibody is non-toxic and produces transient clearance of B-cells; however, once the antibody is cleared from the circulation the B-cell levels return reasonably rapidly. Additionally, the indium- and yttrium-labeled 2B8-MX-DTPA conjugates appeared stable in vitro, exhibiting no loss of radiometal during prolonged incubation in human serum. Finally, radiation dose estimates derived from the biodistribution of $^{90}$Y- or $^{111}$In-labeled 2B8-MX-DTPA in BALB/c mice are in agreement, per millicurie of injected dose, with dose estimates derived from human clinical studies using conjugated anti-shared idiotype antibodies radiolabeled with these isotopes.

IV. Summary of Pre-Clinical Development of "Mix-&-Shoot" Radiolabeling Protocol for Preparation of $^{90}$Y-2B8-MX-DTPA A. Introduction A $^{90}$Y-labeled murine monoclonal anti-CD20 antibody (2B8) has been evaluated in a Phase I clinical trial for the treatment of relapsed B-cell lymphoma. The original protocol used for the preparation of the yttrium-labeled antibody used a high performance liquid chromatographic (HPLC) step for removal of non-protein bound radioisotope prior to formulation and administration to patients. Unfortunately, this process is particularly time consuming, resulting in a longer exposure of the antibody to radioisotope in an unprotected state. This results in increased radiolysis of the antibody with a concomitant decrease in immunoreactivity. Additionally, the laborious aspect of the process makes it difficult to prepare more than one dose per day at the radiopharmacy. Simplification of the process would expedite implementation at the clinical site as an alternative to using NIPI Pharmacy Services as a radiopharmacy.

Accordingly, a revised radiolabeling procedure was developed, referred to as the "mix-and-shoot" method, which obviates the need for HPLC purification while maintaining a high radioincorporation and improved retention of immunoreactivity. In vitro stability studies as well as biodistribution studies in mice showed that radiolabeled antibody prepared using the "mix-and-shoot" method is comparable to material produced using the current HPLC process. The results of these pre-clinical studies indicate that this new "mix-&-shoot" protocol can be used to prepare $^{90}$Y-labeled 2B8-MX-DTPA suitable for use in clinical trials.

B. Materials and Methods

Materials

1. Cells

The human lymphoblastic cell lines SB (CD20 positive) and HSB (CD20 negative) were obtained from the American Type Culture Collection and maintained in RPMI-1640 containing 10% fetal bovine serum and supplemented with glutamine.

2. Antibodies

The 2B8 antibody was purified by the Manufacturing department from hollow-fiber bioreactor supernatant using protocols previously described in the IND (BB-IND 4850/4851).

3. Additional Reagents

Yttrium-[90] chloride was obtained from Amersham. All other reagents were obtained from sources described in the appended reports cited below. Reagents used for radiolabeling protocols were processed to remove contaminating heavy metal ions which could compete with-the radioisotopes during the radiolabeling step (see Methods section). Reagents were made under GMP conditions by IDEC's Manufacturing department following established Batch Production Records.

Methods

1. Preparation of 2B8-D4X-DTPA

Clinical-grade MX-DTPA was obtained from Coulter Immunology as the disodium salt in water and stored at −70° C. Conjugate (2B8-MX-DTPA) was prepared by the Manufacturing department. Two different lots of conjugate were used in these studies; both were provided in normal saline at 10 mg/mL. The conjugates were filled in sterile 2 mL polypropylene syringes and stored at 2-8° C.

2. Maintenance of Metal-Free Conditions

All manipulations of reagents were performed to minimize the possibility of metal contamination. Polypropylene or polystyrene plastic containers such as flasks, beakers and graduated cylinders were used. These were washed with Alconox and exhaustively rinsed with Milli-Q water or Water for Irrigation (WFIr) before use. Metal-free pipette tips (Bio-Rad) were used for accurately manipulating small volumes. Larger volumes of reagents were manipulated using sterile, plastic serological pipettes. Reactions were conveniently performed in 1.8 mL screw-top microfuge tubes made from polypropylene.

3. Determination of Radioincorporation

Radioincorporation was determined using instant thin-layer chromatography (ITLC) in triplicate according to SOP SP-13-008. In general, the protocol was as follows: radiolabeled conjugate was diluted 1:20 in 1×PBS containing 1 mM DTPA or 5 mM EDTA, then 1 μ-L spotted 1.5 cm from one end of a 1×5 cm strip of ITLC SG paper (Gelman Sciences). The paper was developed using 10% ammonium acetate in methanol:water (1:1; v/v). The strips were dried, cut in half crosswise, and the radioactivity associated with each section determined by scintillation counting. The radioactivity associated with the bottom half of the strip (protein-associated radioactivity) was expressed as a percentage of the total radioactivity determined by summing the values for both top and bottom halves.

4. "Mix and-Shoot" Protocol for Yttrium-[90]-Labeled 2B8-MX-DTPA

Antibodies were radiolabeled with carrier-free $^{90}$Y chloride pro vided by Amersham in 0.04 M HCl. An aliquot of radioisotope (10-20 mCi/mg antibody) was transferred to a polypropylene tube and 0.02× volume of metalfree 2 M sodium acetate was added to adjust the solution to pH 3.6. 2B8-NaDTPA (0.3 mg; 10.0 mg/mL in normal saline) was added immediately and the solution gently mixed. The solution was checked with pH paper to verify a pH of 3.8-4.1 and incubated for 5 min. The reaction was quenched by transferring the reaction mixture to a separate polypropylene tube containing 1× PBS with 75 mg/mL human serum albumin (HSA) and 1 mM diethylenetriaminepentaacetic acid (DTPA) and gently mixed. The radiolabeled antibody was stored at 2-8° C.

Specific activities were determined by measuring the radioactivity of an appropriate aliquot of the radiolabeled conjugate. This value was corrected for the counter efficiency, related to the protein concentration of the conjugate, determined by absorbance at 280 nm and expressed as mCi/mg proteins.

5. In Vitro Immunoreactivity of Yttrium-[90]-2B8-MX-DTPA

Immunoreactivity of $^{90}$Y-labeled conjugate was determined using SOP #SP13-009 based on a modified version of the whole-cell binding assay described by Lindmo. Increasing concentrations of log phase, CD20-positive SB cells or CD20-negative HSB cells were added to duplicate sets of 1.5 mL polypropylene tubes; final volume of cells, 0.40 mL. The radiolabeled conjugate was diluted to a final antibody concentration of 1-2.5 ng/mL and 0.35 mL was added to each tube. Following a 90 min incubation, the cells were pelleted by centrifugation and the supernatants collected. Radioactivity remaining in the supernatant fraction was determined with a scintillation counter. Data were plotted as the quotient of the total radioactivity added divided by the cell-associated radioactivity versus the inverse of the cell number per tube. The y axis intercept represents the immunoreactive fraction.

6. In Vitro Stability of Clinically-Formulated Yttrium-[90]-2B8-MX-DTPA

The 2B8-MX-DTPA conjugate was radiolabeled with $^{90}$Y and formulated as described in the "mix & shoot" protocol provided above. Two lots of radiolabeled conjugate were prepared; one lot was used for assessing radioincorporation stability and the other lot used to assess retention of immunoreactivity. The formulated conjugates were incubated at 4° C. for 48 hours and aliquots analyzed at time 0, 24 h and 48 hours using non-reducing SDS-PAGE and autoradiography. Immunoreactivity at each time point was assessed using the assay described above.

7. In Vitro Stability of Yttrium-[90]-2B8-NTX-DTPA in Human Serum

The stability of $^{90}$Y-labeled 2B8-MX-DTPA was assessed by incubation in human serum at 37° C. for up to 72 hours. The conjugated antibody was radiolabeled with yttrium-[90] and formulated as described above. The radiolabeled conjugate was diluted 1:10 with normal human serum (non-heatinactivated) and aliquots incubated in plastic tubes at 37° C. At selected times, samples were removed and analyzed by non-reducing SDS-PAGE and autoradiography.

8. Biodistribution of Yttrium-[90]-2B8-MX-DTPA

Yttrium-[90]-labeled 2B8-MX-DTPA was evaluated for tissue biodistribution in eight to ten week old BALB/c mice. The radiolabeled conjugate was prepared and formulated as described above. Mice were injected intravenously with 5 μCi of $^{90}$Y-labeled 2B8-MX-DTPA and groups of five mice were sacrificed at 1, 24, 48, and 72 hours. After sacrifice, the tail, heart, lungs, liver, kidney, spleen, muscle, femur were removed, washed, weighed; a sample of blood and skin were also removed for analysis. Radioactivity associated with each tissue sample was determined by measuring bremstrahlung radiation using a gamma counter and the percent injected dose per gram tissue and percent injected dose per organ determined.

9. Dosimetry

Biodistribution data obtained using mice injected With $^{90}$Y-labeled 2B8-MX-DTPA were used to calculate estimates of the radiation doses absorbed from a 1.0 mCi dose administered to a 70 Kg patient. Estimates were made according to methods adopted by the Medical Internal Radiation Dose (MIRD) Committee of the Society of Nuclear Medicine. These calculations were performed Mr. Phillip Hagan, Nuclear Medicine Service, VA Medical Center, La Jolla, Calif. 92161.

10. Validation of Protocol for Preparation of Clinical Doses of Yttrium-[90]-2B8-MX-DTPA (Reference R&D report titled "Validation of "Mix-and-Shoot" Radiolabeling Protocol for the Preparation of Clinical Doses of $^{90}$Y-2B8-MX-DTPA; author, P. Chinn; dated Apr. 22, 1994).

C. Results

1. Preparation of Yttrium-7[90]-Labeled 2B8-MX-DTPA Using "Mix-&-Shoot" Protocol Preliminary experiments evaluating the kinetics of the radiolabeling reaction with 2B8-MX-DTPA and $^{90}$Y showed that at pH 3.6-4.0, 95% of the radioisotope was incorporated for a reaction time of 5 to 10 min. The reproducibility of this radioincorporation (95.7%±1.7%) was subsequently confirmed in a validation study for the scale-up protocol (Reference R&D report titled "Validation of "Mix-and-Shoot" Radiolabeling Protocol for the Preparation of Clinical Doses of $^{90}$Y-2B8-MX-DTPA; author, P. Chinn; dated Apr. 22, 1994). The preparation of $^{90}$Y-labeled 2B8-MX-DTPA using this "mix-&-shoot" protocol gave a product comparable to that produced with the, HPLC method (see BB-IND 4850/4851). The radiolabeling protocol was found to be reproducible with specific activities typically ranging from 10 to 15 mCi/mg antibody.

The immunoreactivity of the $^{90}$Y-labeled 2B8-MX-DTPA prepared using this protocol was typically greater than 70%, compared with the 55-60% observed for the validations runs for the HPLC protocol (FIG. 26). This difference is probably due to the reduced effects of radiolysis because of the reduced incubation time with the "mix-and-shoot" protocol. This result was typical, and, as discussed below, was representative of the validation runs for the scale-up protocol for preparing clinical doses of the radiolabeled conjugate.

2. In vitro Stability of $^{90}$Y-Labeled 2B8-MX-DTPA

Figure 2:
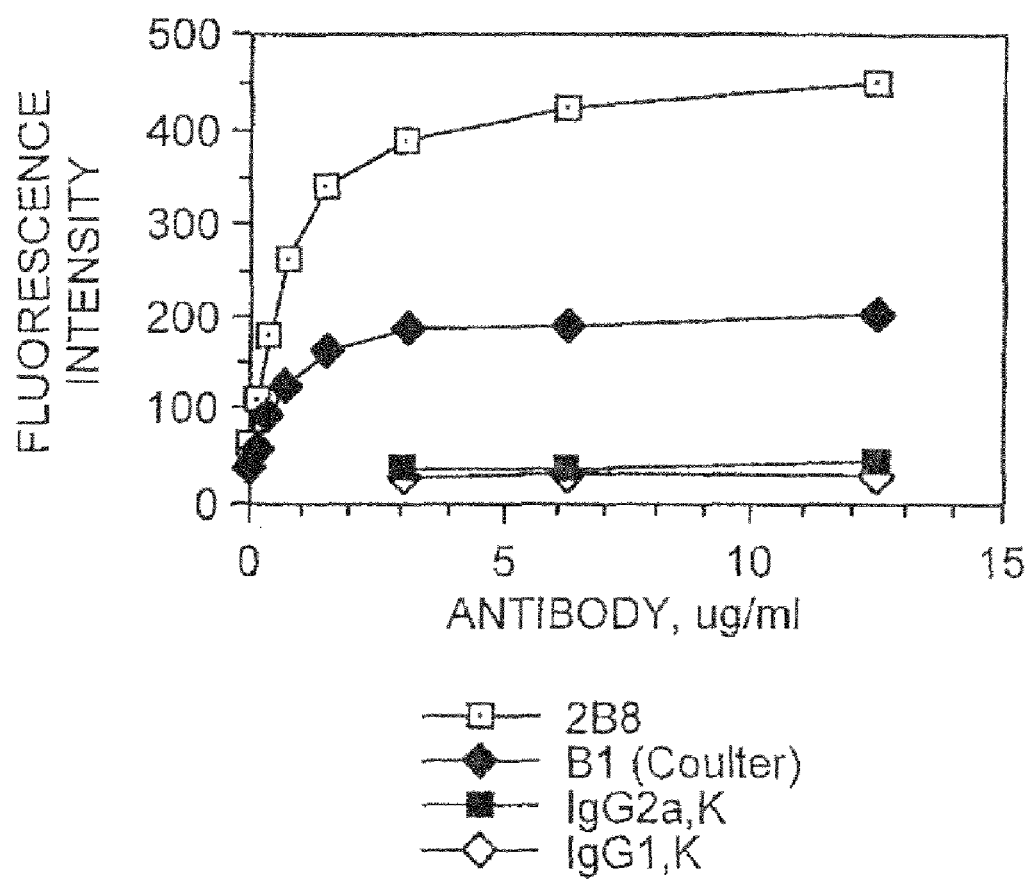
FIG. 2. Increasing amounts of unconjugated 2B8 were analyzed for binding to human B-cells (SB) using FACS analysis. Comparisons were made with a commercially available anti-CD20 monoclonal antibody (B1) and with two irrelevant isotype antibodies. Goat anti-mouse IgG-FITC F(ab)'$_2$ was used as the secondary reagent. The results, show that 2B8 is specific for the CD20 antigen and that it exhibits greater binding than B1.
Figure 4:
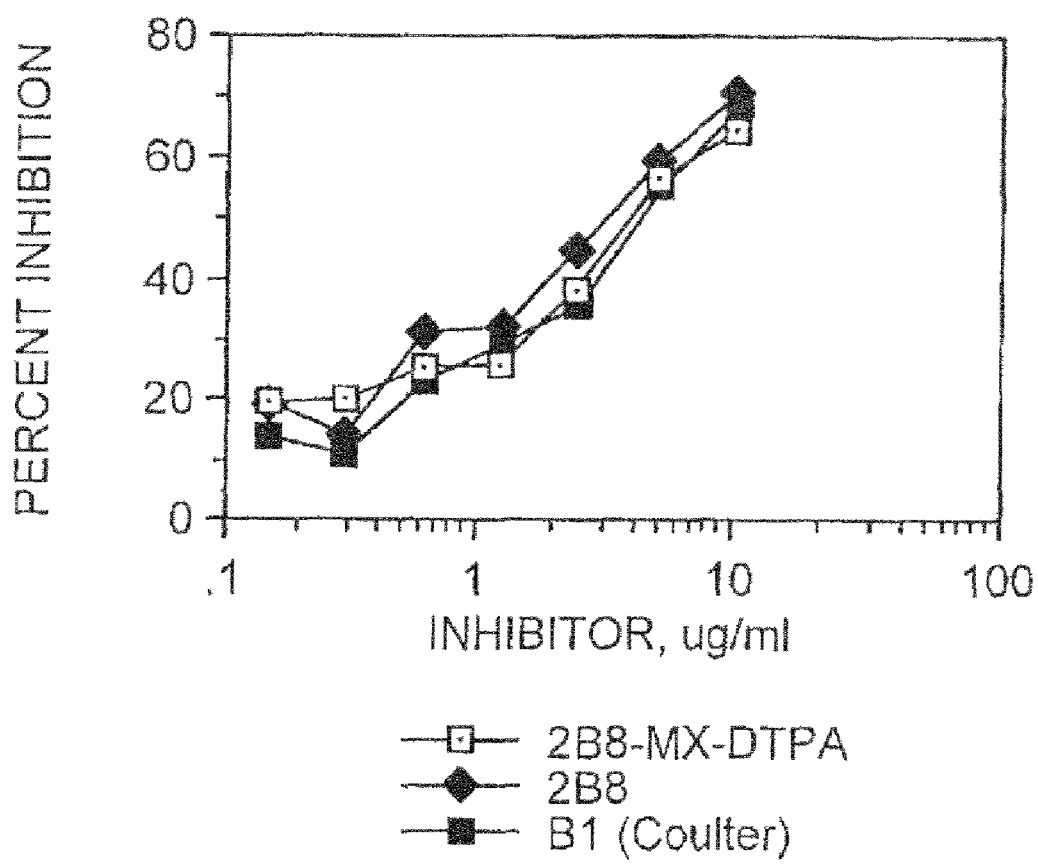
FIG. 4. Immunoreactivity of native 2B8, 2B8-MX-DTPA, and B1. The B1 antibody was radiolabeled as described in the Methods section. Ten nanograms of radiolabeled B1 were mixed with increasing concentrations of the competitor and the mixture added to wells of V&P filter plates containing 100,000 antigen-positive SB cells each; all determinations were performed in triplicate. Following a one hour incubation at ambient temperature, the wells were washed extensively. Subsequently, the filters were dried and the associated radioactivity determined by gamma counting; all values were corrected for background. Values shown are the means of triplicate determinations.

Preliminary experiments with unprotected $^{90}$Y-labeled antibody conjugate prepared using the HPLC process demonstrated that radiolysis caused significant antibody degradation and loss of immunoreactivity. Therefore, a formulation buffer was developed to minimize the effects of radiolysis. Human serum albumin (HSA) was shown to be effective in minimizing. antibody degradation due to radiolysis. An evaluation was made with the radiolabeled conjugate prepared with the "mix-&-shoot" method to confirm the efficacy of the formulation in minimizing radiolysis. The $^{90}$Y-labeled antibody, radiolabeled to a specific activity of 14.5 mCi/mg antibody, was formulated in 1× PBS, pH 7.4 containing 75 mg/mL HSA and 1 mM DTPA. Degradation of the conjugate 2B8-MX-DTPA was evaluated at 0, 24, and 48 hours using SDS-PAGE and autoradiography. FIGS. 2, 3, and 4 show that the radiolabeled conjugate exhibited no significant degradation over a period of 48 h when incubated at 4° C. Instant thin-layer chromatography analysis showed no loss of $^{90}Y$ during the 48 h incubation; these results were corroborated by SDS-PAGE/autoradiographic analysis (Table 28). The immunoreactivity also was relatively constant at >88% (Table 29).

TABLE 28

Stability of "Mix-&-Shoot" $^{90}Y$-2B8-MX-DTPA in PBS Containing Human Serum Albumin and DTPA

| Time (h) | Percent of Conjugate-Associated Radioactivity | |
|---|---|---|
| | ITLC | SDS/PAGE |
| 0 | 92.9 | 96.0 |
| 24 | 95.5 | 95.4 |
| 48 | 91.3 | 94.6 |

TABLE 29

Immunoreactivity of "Mix-&-Shoot" $^{90}Y$-2B8-MX-DTPA in PBS Containing Human Serum Albumin and DTPA

| Time (Hours at 4° C.) | Percent Immunoreactivity |
|---|---|
| 0 | 87.9 |
| 24 | 88.5 |
| 48 | 90.4 |

A clinically-formulated $^{90}Y$-labeled 2B8-MX-DTPA at a specific activity 15.7 mCi/mg was incubated for 72 hours at 37° C. in human serum. Samples analyzed by non-reducing SDS-PAGE and autoradiography (FIG. 30) showed no loss of radioisotope during the course of the incubation period (Table 30). Densitometric scans of the autoradiograms at time zero and 72 h indicated no significant degradation of the radiolabeled conjugate (FIGS. 31 and 32). These results were corroborated by thin-layer chromatographic analyses (Table 30). It should be noted that the radioincorporation for the antibody used in this study was lower than that obtained in the validation studies of the labeling protocol. This lower radioincorporation was due to the reduced quality of the batch of $^{90}Y$ chloride used for this particular preparation of radiolabeled antibody. The lower radioincorporation did not alter the conclusion that the yttrium-labeled conjugate prepared with the "mix-and-shoot" method is stable under these incubation conditions.

TABLE 30

Stability of $^{90}Y$-2B8-MX-DTPA Conjugate Incubated in Human Serum

| Time (Hours at 37° C.) | Percent Conjugate-Associated Radioactivity | |
|---|---|---|
| | ITLC | SDS-PAGE/Autoradiography |
| 0 | 85.7 | 88.8 |
| 24 | 76.4 | 90.0 |
| 72 | 87.6 | 88.7 |

Human serum samples containing $^{90}Y$-2B8-MX-DTPA (specific activity 15.7 mCi/mg) were analyzed for non-protein bound $^{90}Y$ at the times shown using instant thin-layer chromatography strips and SDS-PAGE/autoradiography.

3. Biodistribution Studies with Yttrium-[90] 2B8-MX-DTPA

The biodistribution of the $^{90}Y$-labeled conjugate, with a specific activity of 11.5 mCi/mg antibody and a radioincorporation of >95%, was evaluated in BALB/c mice. Deposition of radioactivity in tissues was evaluated for major organs, skin, muscle, bone, urine and feces over 72 hours and expressed as percent injected dose per g tissue and as percent injected dose per organ. The results shown in Tables 31-34 and FIG. 33 show that the levels of radioactivity associated with the blood decreased from approximately 43% injected dose per gram (% ID/g) at 1 hour to approximately 16% after 72 hours; at 24 h and later, the levels of radioactivity associated with heart, kidney, and spleen remained fairly constant at 4-8%. For lung and liver, radioactivity decreased from 10-12% at 1 h to 8%-10% at 72 h. For the skin, radioactivity was relatively constant at approximately 3% from 24 h through 72 h. The radioactivity in the gastrointestinal tract was constant at 0.5-1% from 24 h to 72 h. Radioactivity for muscle remained approximately 0.6% throughout the course of the study. The uptake of radioactivity by femur (bone) remained less than 4% at all time points indicating that the amount free yttrium in the conjugate preparation was negligible and that little free radiometal was released during the course of the study.

TABLE 31

Distribution of Activity 1.0 Hour Following I.V. Injection of $^{90}Y$-2B8-MX-DTPA Into Normal BALB/c Mice Mean Values ± SD

| Sample | Organ Weight Gram | % ID/ Gram | % ID per Organ |
|---|---|---|---|
| Blood | 1.37 ± 0.053 | 42.74 ± 0.78 | 58.52 ± 1.74 |
| Heart | 0.101 ± 0.01 | 8.03 ± 3.33 | 0.82 ± 0.37 |
| Lung (2) | 0.126 ± 0.01 | 12.44 ± 0.94 | 1.56 ± 0.05 |
| Kidney (1) | 0.129 ± 0.01 | 7.81 ± 1.24 | 0.997 ± 0.10 |
| Liver | 0.899 ± 0.07 | 10.08 ± 1.28 | 9.01 ± 0.52 |
| Spleen | 0.077 ± 0.004 | 10.74 ± 0.96 | 0.823 ± 0.04 |
| Muscle | 7.83 ± 0.28 | 0.44 ± 0.08 | 3.43 ± 0.51 |
| Bone | 2.94 ± 0.11 | 3.44 ± 0.57 | 10.11 ± 1.80 |
| Skin | 2.94 ± 0.11 | 1.46 ± 0.58 | 4.24 ± 1.57 |
| GI Tract | 2.33 ± 0.08 | 1.02 ± 0.19 | 2.36 ± 0.35 |
| Urine | — | — | — |
| Feces | — | — | — |
| | | TOTAL | 94.66 ± 3.47 |

No. Mice = 3
Mean Weight = 19.58 grams ± 0.71 grams

TABLE 32

Distribution of Activity at 24 Hours Following I.V. Injection of $^{90}Y$-2B8-MX-DTA Into Normal BALB/c Mice Mean Values ± SD

| Sample | Organ Weight Gram | % ID/ Gram | % ID per Organ |
|---|---|---|---|
| Blood | 1.55 ± 0.12 | 19.77 ± 2.42 | 30.77 ± 6.04 |
| Heart | 0.105 ± 0.01 | 4.44 ± 0.55 | 0.47 ± 0.08 |
| Lung (2) | 0.127 ± 0.02 | 8.78 ± 1.61 | 1.11 ± 0.21 |
| Kidney (1) | 0.139 ± 0.01 | 5.02 ± 0.52 | 0.69 ± 0.05 |
| Liver | 0.966 ± 0.09 | 8.62 ± 2.73 | 8.20 ± 1.97 |
| Spleen | 0.083 ± 0.01 | 6.75 ± 1.27 | 0.55 ± 0.064 |
| Muscle | 8.83 ± 0.69 | 0.692 ± 0.01 | 6.12 ± 0.52 |
| Bone | 3.31 ± 0.26 | 2.24 ± 0.31 | 7.47 ± 1.53 |
| Skin | 3.31 ± 0.26 | 3.33 ± 0.76 | 10.88 ± 1.76 |
| GI Tract | 2.89 ± 0.43 | 0.73 ± 0.09 | 1.02 ± 0.05 |
| Urine | | | 2.31 |
| Feces | | | 1.23 |
| | | Total: | 73.52 ± 6.18% |

No. Mice = 3
Mean Weight = 22.09 ± 1.73 gram

TABLE 33

Distribution of Activity at 48 Hours Following I.V. Injection of $^{90}$Y-2B8-MX-DTPA Into Normal BALB/c Mice
Mean Values ± SD

| Sample | Organ Weight Gram | % ID/ Gram | % ID per Organ |
|---|---|---|---|
| Blood | 1.50 ± 0.14 | 14.97 ± 5.77 | 22.53 ± 8.48 |
| Heart | 0.104 ± 0.01 | 3.99 ± 1.43 | 0.415 ± 0.16 |
| Lung (2) | 0.122 ± 0.02 | 8.41 ± 1.57 | 1.04 ± 0.31 |
| Kidney (1) | 0.124 ± 0.01 | 3.99 ± 1.62 | 0.49 ± 0.19 |
| Liver | 0.966 ± 0.13 | 6.12 ± 3.21 | 5.69 ± 2.25 |
| Spleen | 0.079 ± 0.01 | 6.05 ± 2.38 | 0.46 ± 0.16 |
| Muscle | 8.59 ± 0.82 | 0.54 ± 0.19 | 4.67 ± 1.67 |
| Bone | 3.22 ± 0.31 | 2.07 ± 0.84 | 6.65 ± 2.56 |
| Skin | 3.22 ± 0.31 | 2.30 ± 0.70 | 7.34 ± 1.95 |
| GI Tract | 2.63 ± 0.40 | 0.652 ± 0.30 | 1.67 ± 0.64 |
| Urine | — | — | 2.83 |
| Feces | — | — | 2.06 |
| TOTAL | | | 57.28 ± 17.60 |

No. Mice = 3
Mean Weight = 21.48 ± 2.05 grams

TABLE 34

Distribution of Activity at 72 Hours Following I.V. Injection of $^{90}$Y-2B8-MX-DTPA Into Normal BALB/c Mice
Mean Values ± SD

| Sample | Organ Weight Gram | % ID/ Gram | % ID per Organ |
|---|---|---|---|
| Blood | 1.45 ± 0.07 | 15.87 ± 4.81 | 23.14 ± 7.26 |
| Heart | 0.093 ± 0.01 | 4.16 ± 1.27 | 0.392 ± 0.13 |
| Lung (2) | 0.123 ± 0.02 | 10.67 ± 3.79 | 1.30 ± 0.45 |
| Kidney (1) | 0.123 ± 0.01 | 4.79 ± 1.03 | 0.596 ± 0.16 |
| Liver | 0.876 ± 0.07 | 7.26 ± 1.79 | 6.39 ± 1.76 |
| Spleen | 0.081 ± 0.01 | 7.37 ± 2.34 | 0.584 ± 0.16 |
| Muscle | 8.30 ± 0.39 | 0.67 ± 0.13 | 5.58 ± 1.22 |
| Bone | 3.11 ± 0.15 | 2.58 ± 0.51 | 8.05 ± 1.76 |
| Skin | 3.11 ± 0.15 | 3.09 ± 0.82 | 9.66 ± 2.68 |
| GI Tract | 2.59 ± 0.20 | 0.79 ± 0.18 | 2.05 ± 0.53 |
| Urine | — | — | 3.56 |
| Feces | — | — | 2.82 |
| TOTAL | | | 65.47 ± 14.0 |

No. Mice = 3
Mean Weight = 20.76 ± 0.97 grams

4. Dosimetry

The radiation absorbed doses for a "standard" 70 Kg human calculated for the $^{90}$Y-labeled conjugate using the mouse biodistribution data (% ID/organ values in Tables 31-34) are presented in Table 35. These results are comparable to results obtained previously using $^{90}$Y-labeled 2B8-MX-DTPA prepared using the HPLC radiolabeling method.

TABLE 35

Radiation Dosimetry Estimates Resulting from the Administration of Yttrium-[90] Labeled 2B8-MX Uniformly Distributed in Standard Man(70 Kg) and Based on Animal Distribution Data Over 72 Hours After Injection

| AMOUNT OF ACTIVITY = | | 1000 MICROCURIES/PATIENT DOSE | |
|---|---|---|---|
| | RADS | | RADS |
| ADRENALS | 0.534 | OVARIES | 0.534 |
| BLADDER WALL | 0.534 | PANCREAS | 0.534 |
| STOMACH WALL | 0.534 | SKELETON | |
| SMALL INTESTINE | 1.158 | CORTICAL BONE | 1.466 |
| UL INTEST. WALL | 1.657 | TRABECULAR BONE | 1.466 |
| LL INTEST. WALL | 2.380 | MARROW (RED) | 4.452 |
| KIDNEYS | 7.015 | MARROW (YELLOW) | 2.096 |
| LIVER | 7.149 | CARTILAGE | 1.466 |
| LUNGS | 2.157 | OTHER CONSTIT. | 1.466 |
| OTHER TISSUES | | SKIN | 6.603 |
| MUSCLE | 2.646 | SPLEEN | 4.973 |
| ADIPOSE | 2.646 | TESTES | 0.534 |
| BLOOD | 2.646 | THYROID | 0.534 |
| BRAIN | 2.112 | UTERUS (NONGRVD) | 0.767 |
| HEART | 2.646 | TOTAL BODY | 1.755 |

Ref: A Schema for Absorbed-dose Calculation for Biologically Distributed Radionuclides, MIRD J. of Nucl. Med./Suppl. #1, 2/68
Calculations Performed Using a Spreadsheet Template in Symphony (Lotus Development Corporation) and Created by Phillip L. Hagan, MS, Nuclear Medicine Service, VA Hospital, San Diego, CA 92161

5. Validation of Protocol for Preparation of Clinical Doses of Yttrium-[90]-2B8-MX-DTPA A total of ten validation lots were prepared at MPI Pharmacy Services, Inc. The results of testing on each lot are summarized in Table 36. The mean value for each test result was calculated and standard deviations noted where appropriate. To evaluate the variability of the process due to different labeling times, lot #1 through #8 were prepared using a 10 min labeling time; lot #9 and #10 were prepared using a reaction time of 5 min. Based on the test results for the ten validation lots, release specifications were established. Release specifications are summarized in Table 37.

TABLE 36

Assay Results for the Ten Validation Lots of $^{90}$Y-Labeled 2B8-MX-DTPA Prepared Using "Mix-&-Shoot"

| | #1 | #2 | #3 | #4 | #5 | #6 | #7 | #8 | #9 | #10 | mean |
|---|---|---|---|---|---|---|---|---|---|---|---|
| % immunoreactivity | 72.8 | 93.3 | 71.7 | 70.2 | 60.6 | 68.2 | 79.5 | 72.4 | 88.2 | 68.5 | 74.5 ± 9.8 |
| endotoxin (Eu/ml) | <0.125 | <0.125 | <0.125 | <0.125 | <0.125 | <0.25 | <0.25 | <0.25 | <0.125 | <0.125 | <0.162 ± 0.06 |
| % radioincorporation | 97.5 | 97.0 | 93.5 | 96.0 | 94.7 | 94.9 | 95.9 | 96.5 | 97.5 | 93.5 | 95.7 ± 1.4 |
| antibody conc. (mg/ml) | 0.122 | 0.102 | 0.088 | 0.128 | 0.134 | 0.119 | 0.093 | 0.088 | 0.111 | 0.096 | 0.108 ± 0.017 |
| radioactivity (mCi/ml) | 1.22 | 1.22 | 0.98 | 1.26 | 1.51 | 1.55 | 1.06 | 0.98 | 1.28 | 1.02 | 1.21 ± 0.21 |
| specific act. (mCi/mg) | 10.0 | 12.0 | 11.2 | 9.8 | 11.3 | 13.0 | 11.3 | 11.1 | 11.5 | 10.7 | 11.2 ± 0.9 |
| vial radioactivity (mCi) | 8.16 | 8.68 | 8.26 | 8.52 | 8.43 | 8.45 | 8.56 | 8.45 | 8.45 | 8.45 | 8.44 ± 0.15 |

TABLE 36-continued

Assay Results for the Ten Validation Lots of $^{90}$Y-Labeled 2B8-MX-DTPA Prepared Using "Mix-&-Shoot"

|  | #1 | #2 | #3 | #4 | #5 | #6 | #7 | #8 | #9 | #10 | mean |
|---|---|---|---|---|---|---|---|---|---|---|---|
| protein conc. (mg/ml) | 76.2 | 76.1 | 73.6 | 73.1 | 72.4 | 76.1 | 76.4 | 74.3 | 71.2 | 74.8 | 74.4 ± 1.8 |
| pH | 6.4 | 6.4 | 6.4 | 6.4 | 6.4 | 6.4 | 6.4 | 6.4 | 6.4 | 6.4 | 6.4 ± 0.0 |
| sterility | pass | pass | pass | pass | pass | pass | pass | pass | pass | pass | |

TABLE 37

Release Specifications for $^{90}$Y-Labeled 2B8-MX-DTPA Prepared Using "Mix-&-Shoot" Protocol

| Test | Specification | Method |
|---|---|---|
| Immunoreactivity | ≧60% | RIA |
| Endotoxin | <5 EU/ml | LAL |
| Radiolabel incorporation | ≧90% | ITLC |
| Antibody conc. | 0.075-0.150 mg/ml | $A_{280}$ |
| Radioact. conc.[1] | ≧6.0 mCi/ml | dose calibration |
| Specific activity[1] | ≧9.0 mCi/mg antibody | $A_{280}$/dose calib. |
| Total vial radioact.[1] | ≧6.0 mCi | dose calibration |
| pH | 6.0-8.0 | pH paper |
| total protein conc. | 65-85 mg/ml | $A_{280}$ |
| sterility testing | passes | CFR 610.12 |

[1](time zero calibration)

D. Discussion

The original radiolabeling protocol for preparing $^{90}$Y-labeled 2B8-MX-DTPA utilized a particularly laborious and time-consuming HPLC purification step for removing non-protein bound $^{90}$Y from the preparation. In order to simplify this process and make it more amenable to use at the clinical site, efforts were directed at eliminating the HPLC step in favor of what has been termed a "mix-and-shoot" protocol. The goal was to identify radiolabeling conditions which would result in a very high radioincorporation of isotope into the conjugate, thereby obviating the need for the purification step. It was discovered that >95% radioincorporation could be-obtained at pH 3.6 with a five to ten minute incubation. An additional benefit of this protocol was increased retention of immunoreactivity (>70%), presumably due to the shorter exposure time of the antibody to the high energy radioisotope before the addition of human serum albumin which provides protection against radiolysis. This retention of immunoreactivity is superior to that previously observed using the HPLC methods Stability studies with $^{90}$Y-labeled conjugate prepared using the "mix-and-shoot" protocol incubated in formulation buffer (1× PBS containing 75 mg/mL human serum albumin and 1 mM DTPA) for up to 48 h at 4° C. showed no loss of radioisotope and complete retention of immunoreactivity. Stability studies conducted with human serum for 72 hours at 37° C. also indicated minimal radioisotope loss. These stability results are comparable to those previously seen with conjugate radiolabeled using the HPLC protocol.

Biodistribution in BALB/c mice using $^{90}$Y-labeled conjugate prepared with the "mix-and-shoot" method indicated no unusual tissue deposition. These results suggested that the radiolabeled antibody was not altered significantly so as to dramatically affect the in vivo characteristics of the antibody. Also, these results are comparable to those obtained previously with the radiolabeled conjugated prepared using the HPLC method of radiolabeling (see BB-IND 4850/4851).

Dosimetry estimates for a "standard" 70 Kg human calculated from the biodistribution data for mice are in agreement with those obtained with conjugate radiolabeled using the HPLC procedure (see BB-IND 4850/4851). Additionally, the dosimetry results are comparable to results obtained for patients enrolled in an on-going clinical trial (IDEC study #1315), when compared per millicurie of injected dose. For six patients in the study, mean values (rads±SD) for whole body, heart, liver, and spleen were 1.40±0.57, 10.50±4.68, 9.89±8.91, and 9.75±6.00, respectively.

Before implementing the "mix-and-shoot" labeling protocol for preparing clinical-grade $^{90}$Y-2B8-MX-DTPA, it was necessary to assess the reproducibility of the protocol. Therefore, ten validation lots were prepared using different lots of $^{90}$Y chloride. For the ten lots prepared, the immunoreactivity values obtained using the "mix-and-shoot" method were in the range of 60.6% to 93.3% with a mean of 74.5% and a median of 72.1%. This retention of immunoreactivity is significantly better than the approximately 60% previously obtained using the current HPLC method (range of 54.9% to 65.1%; mean of 60.2%). The average radioincorporation for the ten lots was 95.7% (range of 93.5% to 97.5%). This value is comparable to that previously seen with the HPLC method (range of 91.7% to 93.7% and a mean of 93.1%). Also, results for endotoxin, antibody concentration, radioactivity concentration, specific activity, total vial radioactivity, total protein concentration, pH, and sterility were comparable for the ten lots. Together, these results confirmed the reproducibility of the "mix-and-shoot" method. In addition, we evaluated the variability of the process due to different labeling times by performing reactions for 5 and 10 minutes. Since there were no significant differences noted for the two reaction times, it was decided that the shorter incubation time would be used in the final protocol.

E. Summary

We have developed a labeling procedure, referred to as the "mix-and-shoot" method, for the preparation of clinical doses of $^{90}$Y-labeled 2B8-MX-DTPA which obviates the need for the currently used high performance liquid chromatographic (HPLC) step for removal of non-protein bound radioisotope. The simplified protocol eliminates this laborious purification step while maintaining a high level of radioisotope incorporation (>95%) and improved retention of immunoreactivity (>70%). The clinically-formulated radiolabeled conjugate was found to be stable in vitro when incubated at 4° C. for 48 hours based on retention of radioisotope and immunoreactivity. Additionally, the radiolabeled conjugate was stable when incubated in human serum at 37° C. for 72 hours. Biodistribution studies in BALB/c mice demonstrated no unusual tissue deposition, including bone. Estimates of radiation absorbed doses to a "standard" 70 Kg human were comparable to those obtained in an on-going clinical trial using $^{90}$Y-labeled 2B8-MX-DTPA. The results of these studies showed that $^{90}$Y-labeled 2B8-MX-DTPA produced using the "mix-and-shoot" protocol was comparable to that prepared using the conventional HPLC process. Validation of the scale-up protocol for preparing clinical-grade radiolabeled conjugate showed that the method was reproducible and that the product was comparable to that produced using the current HPLC method. The results of these pre-clinical studies indicate that this new "mix-&-shoot" protocol can be used to prepare $^{90}$Y-labeled 2B8-MX-DTPA suitable for use in clinical trials.

DETAILED DESCRIPTION OF THE PREFERRED EMBODIMENTS

EXAMPLE 1

Radioincorporation—Kits and Assays

I. Summary

One objective of the present invention was to devise radiolabeling kit protocols for preparation of $^{111}$In and $^{90}$Y-labeled 2B8-MX-DTPA (In2B8 and Y2B8, respectively) and to establish release specifications for clinical products. The radiolabeling kit protocols are reproducible with respect to radioincorporation and binding to antigen-positive SB cells and indicate the suitability of the radiolabeling kit for use in the clinical trials. It is recommended that In2B8 and Y2B8 release specifications for radioincorporation and binding be established at ≧95% and ≧70% respectively.

II. Introduction

A $^{90}$Y-labeled murine monoclonal anti-CD20 antibody (Y2B8) is currently being evaluated in clinical trials for the treatment of relapsed B-cell lymphoma. The yttrium isotope lacks a gamma component making it unsuitable for imaging systems. Therefore, $^{111}$In-labeled 2B8-MX-DTPA (In2B8) will be used to assess tumor localization and dosimetry in patients prior to or after treatment with the yttrium-labeled therapeutic. The protocols used currently for the preparation of Y2B8 and In2B8, referred to as the "mix-&-shoot" methods, produce radiolabeled antibodies suitable for clinical studies. However, simplification of the labeling process would expedite dose preparation in a clinical setting.

The new radiolabeling kit is preferably comprised of four components: 1.) 2B8-MX-DTPA in low-metal normal saline at 2 mg/mL, 2.) 50 mM sodium acetate used to adjust radioisotope solution to appropriate labeling pH, 3.) formulation buffer (1× PBS, pH 7.4 containing 7.5% human serum albumin and 1 mM DTPA), 4.) empty 10 mL glass vial (reaction vial). All components are tested to be sterile and pyrogen-free.

This report summarizes the validation of this radiolabeling kit which is simple and easy to use and which yields radiolabeled antibodies with ≧95% radioincorporation and acceptable retention of binding to antigen-positive cells. Release testing specifications are recommended for the clinical products.

III. Materials and Methods for Radioincorporation
  A. Reagents in Radiolabeling Kit
  1. 2B8-MX-DTPA, IDEC; Lot# 082395RM2
  2. 50 mM Sodium Acetate, low-metal, IDEC; Lot# 082395RM3
  3. Formulation Buffer (1× PBS, pH 7.4 containing 7.5% (w/v) human serum albumin and 1 mM DTPA), IDEC, Lot# 082395RM1
  4. Reaction vial, 10 mL, IDEC
  B. Materials and Equipment
  1. Biodex Tec-Control Radioincorporation Kit, Cat.#151-770
  2. Gloves: powder-free
  3. Sterile polypropylene syringes
  4. Sterile syringe needles
  5. Small tubes with closure; 1.5 ml
  C. Methods
  1. Preparation of Y2B8 and In2B8 Using Radiolabeling Kit
    Kit reagents were prepared and filled into glass septum vials. Type I borosilicate vials (2 or 10 mL) were rinsed with sterile water for injection (WFI) and autoclaved before filling. Butyl rubber septa were rinsed with sterile WFI and autoclaved before use. Reagents were manually filled and crimped in a Class 100 room and tested for pyrogenicity and sterility using USP methods.
    a. Preparation of In2B8

Additional Reagents:
1. Indium-[111]: chloride salt, carrier-free, in HCl.

Precautions:
1. All steps are preferably performed using aseptic technique.
2. Radiolabeling kit components should be allowed to come to room temperature before use.
3. Final product should be administered to patient within 8 hours of completing step 9 below.

In2B8 Radiolabeling Protocol

Procedure
  1. The volume of $^{111}$InCl$_3$ to add to the reaction vial was calculated as follows:
    a. Radioactivity concentration at the time of radiolabeling in mCi/ml:
      $C_0$=Radioactivity concentration at time of calibration (see manufacturer's Certificate of Analysis).
      Δt=Change in time (positive number is post calibration, negative number is pre calibration).

$$\text{Radioactivity Concentration at time of labeling} = \frac{C_0}{e^{0.0103(\Delta t)}}$$

b. Volume of $^{111}$InCl$_3$ to add to the reaction vial:

$$\frac{5.5 \text{ m Ci}}{\text{Radioactivity Concentration at time of labeling}} = \text{Volume to add to reaction vial}$$

2. The volume of 50 mM sodium acetate to be added to the reaction vial was calculated as follows:
    Volume of $^{111}$InCl$_3$ added (Step 1b)×(1.2)=Volume of 50 mM sodium acetate to be added.
  3. The septa of the reaction vial and the 50 mM sodium acetate vial were wiped with alcohol. Using a 1 cc syringe, the calculated volume of 50 mM sodium acetate (Step 2) was transferred to the reaction vial.
  4. The septum of $^{111}$InCl$_3$ source was wiped with alcohol. The vial was vented with a needle fitted with sterile 0.2 μm filter. Using a 1 cc sterile syringe, the required volume (Step 1b) of $^{111}$InCl$_3$ was transferred to the reaction vial. The vial was mixed by inverting several times.
  5. The septum of the 2B8-MX-DTPA vial was wiped with alcohol. Using a 1 cc syringe, 1.0 mL of 2B8-MX-DTPA was slowly transferred to the reaction vial. The vial was mixed by inverting several times.
  6. The reaction was allowed to proceed for 30 minutes±5 minutes at ambient temperature.
  7. The total volume of reaction mixture was calculated by adding together the volume of $^{111}$InCl$_3$ added (Step 4), the volume of 50 mM sodium acetate added (Step 3) and the volume of 2B8-MX-DTPA added (Step 5).

8. The volume of Formulation Buffer to add to the Reaction Vial to obtain a final volume of 10 mL was calculated by subtracting the total amount calculated in step 7 from 10.

9. The Formulation Buffer vial was wiped with alcohol and the vial was vented. Due to the viscosity of the Formulation Buffer, the reaction vial was vented using a needle fitted with a 0.2 μm syringe filter. Using a 10 cc sterile syringe fitted with an appropriate gauge needle, the volume of Formulation Buffer calculated in Step 8 was transferred to the reaction vial. The vent needle was removed from the reaction vial and the vial was mixed by inverting several times (Final Product). This vial was incubated at least 5 minutes prior to doing the "Radioincorporation Assay". The color of the solution was amber and the vial was full, confirming that Formulation Buffer was added.

10. Total radioactivity of the Final Product vial was measured using the appropriate instrumentation set for $^{111}$In measurement.

11. The Final Product was stored immediately at 2°-8° C. for "Binding Assay" and "Radioincorporation Assay".

b. Preparation of Y2B8

Additional Reagents:
1. Yttrium-[90]: chloride salt, carrier-free, in HCl.

Precautions:
1. All steps should be performed using aseptic technique.
2. Radiolabeling kit components should be allowed to come to room temperature before use.
3. The product should be administered to the patient within 8 hours of completing step 8 below.

Y2B8 Radiolabeling Protocol

1. The volume of $^{90}$YCl$_3$ to add to the reaction vial was calculated as follows:
   a. The radioactivity concentration at the time of radiolabeling:
      $C_0$=Radioactivity concentration at time of calibration (see manufacturer's Certificate of Analysis).
      $\Delta t$=Change in time (positive number is post calibration, negative number is pre calibration).

$$\text{Radioactivity Concentration at time of labeling} = \frac{C_0}{e^{0.0108(\Delta t)}}$$

b. The volume of $^{90}$YCl$_3$ to add to the reaction vial:

$$\frac{45 \text{ m Ci}}{\text{Radioactivity Concentration time of labeling}} = \text{Volume added to reaction vial}$$

2. The volume of 50 mM sodium acetate to add to the reaction vial was calculated as follows:
   a. For $^{90}$YCl$_3$ in 0.040 M HCl (Amersham):
      Volume $^{90}$YCl$_3$ (Step 1b)×(0.8)=volume of sodium acetate to add
   b. For $^{90}$YCl$_3$ in 0.050 M HCl (Nordion):
      Volume $^{90}$YCl$_3$ (Step 1b)×(1.0)=volume of sodium acetate to add 3. The septa of the reaction vial and the sodium acetate vial were wiped with alcohol. Using a 1 cc syringe, the calculated volume (Step 1a or 1b) of 50 mM sodium acetate (Step 2) was transferred to the reaction vial. The vial was mixed by inverting several times.

4. The septum of the $^{90}$YCl$_3$ source vial was wiped with alcohol. The vial with a needle fitted with sterile 0.2 μm filter. Using a 1 cc sterile syringe, was vented the required volume (Step 1b) of $^{90}$YCl$_3$ was transferred to the reaction vial. The vial was mixed by inverting several times.

5. The septum of the 2B8-MX-DTPA vial was wiped with alcohol. Using a 3 cc sterile syringe, 1.5 mL of 2B8-MX-DTPA was transferred to the reaction vial. The vial was mixed by inverting several times.

6. The total volume of reaction mixture was calculated by adding the amount of Y-90 chloride added (Step 4), plus the amount of 50 mM sodium acetate added (Step 3), plus the amount of 2B8-MX-DTPA added (Step 5).

7. The volume of Formulation Buffer to add to the Reaction Vial to obtain a final volume of 10 mL was calculated by subtracting the total reaction volume calculated in step 6 from 10.

8. The Formulation Buffer vial was wiped with alcohol and the vial was vented. Due to the viscosity of the Formulation Buffer, the reaction vial using a needle fitted with a 0.20 μm syringe filter. Using a 10 cc sterile syringe fitted with an appropriate gauge needle, the volume of Formulation Buffer calculated in Step 7 was transferred to the reaction vial. The vent needle was removed from the reaction vial and the vial was mixed by inverting several times (Final Product). The vial was incubated at least 5 minutes prior to doing the "Radioincorporation Assay". The color of the solution was amber and the reaction vial was full thereby confirming that Formulation Buffer was added.

9. The total radioactivity of the Final Product vial was measured using the appropriate instrumentation set for measurement of $^{90}$Y.

10. The Final Product was immediately stored at 2°-8° C. until required for patient administration.

11. Immunoreactivity testing:
Using a 1 mL syringe, 0.1 mL was aseptically removed from the reaction vial and transferred to a separate 1.5 mL screwcap tube. The tube was immediately stored at 2°-8° C. for "Binding Assay" and "Radioincorporation Assay".

Validation of the radiolabeling kit protocols was performed at IDEC Pharmaceuticals (San Diego, Calif.), MD Anderson Health Center (Houston, Tex.), Mayo Clinic (Rochester, Minn.), and City of Hope (Duarte, Calif.). All kit components, including clinical-grade 2B8-MX-DTPA, were prepared by IDEC Pharmaceuticals under GMP conditions (Good Manufacturing Conditions according to the Code of Federal Regulations) and determined to be sterile and pyrogen-free.

The radiolabeled antibodies were formulated with 1× PBS containing 7.5% (w/v) human serum albumin (HSA; clinical-grade; Baxter-Hyland) and 1 mM DTPA. Results of the release tests performed on each validation lot are described below.

Six validation lots each of In2B8 and Y2B8 were prepared by five operators. These lots were designated as follows and performed at the following facilities:
In2B8:
  #1: IDEC Pharmaceuticals
  #2: IDEC Pharmaceuticals
  #3: IDEC Pharmaceuticals
  #4: MD Anderson Health Center
  #5: Mayo Clinic
  #6: City of Hope Y2B8:
1: IDEC Pharmaceuticals
2: IDEC Pharmaceuticals
3: IDEC Pharmaceuticals
4: MD Anderson Health Center
5: Mayo Clinic
6: City of Hope 2. Preparation of Lyophilized SB and HSB Cells The human cell lines SB (CD20-positive) and HSB (CD20-negative) were obtained from American Type Culture Collection and cultured in T-flasks using RPMI-1640 containing 10% fetal bovine serum supplemented with 2% glutamine. Cultures were maintained at 37° C. and 5% $CO_2$. Cells were typically split 1:2 every other day and harvested at 0.5-2.5×$10^6$ cells/mL and viability's >80%. Cell concentrations were determined using a hemacytometer and viability determined by trypan blue exclusion.

Cells were harvested at ambient temperature at a cell density of 0.5-2×$10^6$ cells/mL by centrifugation (1300 rpm in a Sorvall centrifuge) and washed twice with 1× HBSS. Pelleted cells were resuspended to 50×$10^6$ cells/mL in 1× HBSS containing 1% (w/v) bovine serum albumin (BSA) and 10% (w/v/) mannitol (lyophilization buffer), 0.5 mL dispensed into 1.5 mL polypropylene microfuge tubes with o-ring gaskets and stored at −70° C., and lyophilized overnight at 30-60 millitorr. Tubes of lyophilized cells were stored desiccated at 2-8° C. and reconstituted in sterile water for assays; tubes of cells lyophilized in microfuge tubes were stored with desiccant.

3. Analytical Assays

The analytical methods used to test the validation lots of In2B8 and Y2B8 are described below. The following assays were performed for each validation lot:
1. Binding Assay using lyophilized SB cells
2. Y2B8/In2B8 Radioincorporation Assay using Biodex Kit
   a. Binding Assays Percent binding was assessed by each operator using lyophilized CD20 positive SB cells according to the following protocols for In2B8 and Y2B8, respectively. These assays provide for a fast and efficient method of confirming that the radiolabeled antibody still recognizes CD20 as an antigen. At one clinical site, CD20-negative HSB cells were also evaluated. Lyophilized cells were prepared and stored according to the above method, "Preparation of Lyophilized SB and HSB Cells".

i. In2B8 Binding Assay

Additional Reagents:
1. Indium-[111]-2B8-MX-DTPA
2. Lyophilized SB cells; three tubes containing 25×$10^6$ cells/tube.
3. Lyophilized HSB cells; three tubes containing 25×$10^6$ cells/tube.
4. Sterile water for irrigation or sterile water for injection.
5. Dilution buffer (1× PBS, pH 7.2-7.4 containing 1% Bovine Serum Albumin (BSA), and 0.02% Sodium Azide 0.2 μm filtered and stored at room temperature.
6. Glass or plastic test tubes for counting radioactivity.

Procedure:

Assay Set-Up (Non-Radioactive Portion)
1. Three tubes of lyophilized SB and HSB cells were obtained.
2. A volume of 0.50 mL of SWFI (sterile water for injection) was added to each tube, and the tubes were vortexed until homogenous suspensions were obtained.
3. Four empty 1.5 mL microfuge tubes. To three of the tubes 0.50 mL of Dilution buffer was added, representing a control with no cells.
4. To the other 1.5 mL microfuge tube, 0.99 mL of Dilution buffer was added; this tube was labeled 1:100.
5. A 50 mL sterile polypropylene tube with cap was obtained and 10 mL of Dilution buffer was added to the tube.

Assay Set-Up (Radioactive Portion)
1. The radiolabeled antibody stored at 2°-8° C. was obtained.
2. A volume of 0.01 mL was withdrawn with a P20 and added to the 1.5 mL microfuge tube containing 0.99 mL of Dilution buffer (1:100 dilution). The tip was rinsed and the tube vortexed gently to mix.
3. A volume 0.20 mL was withdrawn with a P200 from the 1:100 dilution tube and added to the conical tube containing 10 mL of Dilution buffer. The tube was mixed thoroughly.

Assay Protocol
1. A volume of 0.50 mL of the diluted $^{111}$In2B8-MX-DTPA was added to all tubes.
2. The caps were securely tightened on all tubes, and the tubes mixed continuously for 60 minutes.
3. After 60 minutes incubation at ambient temperature, all tubes were centrifuged for 5 minutes at minimum of 2000 g.
4. A volume of 0.75 mL of each supernatant was transferred to tubes appropriate for the counting instrument.
5. The radioactivity in tubes was counted using a gamma counter, adjusting for background.

ii. Y2B8 Binding Assay

Additional Reagents
1. $^{90}$Y2B8-MX-DTPA
2. Lyophilized SB cells
3. Sterile water for irrigation or sterile water for injection
4. Dilution buffer (1× PBS, pH 7.2-7.4 containing 1% Bovine Serum Albumin (BSA), and 0.02% Sodium Azide)

Procedure:

Radiolabeled Antibody Sample Prep
1. The radiolabeled antibody stored at 2°-8° C. was obtained.
2. A volume of 10 μL was withdrawn with a P20 and added to a 1.5 mL microfuge tube containing 990 μL of Dilution buffer (1:100 dilution). The tip was rinsed and the tube was vortexed slightly.
3. A 50 mL sterile polypropylene tube with cap was obtained and 10 mL of Dilution buffer to the tube, using a 10 mL serological pipette.
4. A volume of 35 μL was withdrawn with a P200 from the 1:100 dilution tube and added to the conical tube containing 10 mL of Dilution buffer. Mix thoroughly.

Lyophilized Cell Prep
1. Three tubes of lyophilized SB Cells were obtained.
2. A volume of 0.5 mL of SWFI was added to each tube, and the tubes were vortexed until single cell suspensions were obtained.
3. Three empty 1.5 mL microfuge tubes were obtained; to three of the tubes, 0.5 mL of Dilution buffer was added, representing a control with no cells.

Assay Protocol
1. A volume of 0.5 mL of the diluted $^{90}$Y2B8-MX-DTPA was added to each tube.
2. The tubes were placed on end over mixer for 45 minutes, after making sure caps are securely tightened.

3. After 45 minutes incubation at ambient temperature, the cells were pelleted by microcentrifugation for 5 minutes.
4. A volume of 0.8 mL of the supernatant was transferred to scintillation vials.
5. Scintillation cocktail was added to each vial.
6. The amount of radioactivity in each vial was determined using a scintillation counter, adjusting for background.
    b. Radioincorporation Assay Percent radioincorporation was determined by instant thin-layer chromatography (ITLC) using the Biodex Tec-Control Radiochromatographic Kit according to the following protocol:

Additional Materials and Equipment:
1. $^{111}$In- or $^{90}$Y-radiolabeled 2B8-MX-DTPA
2. Tubes for counting radioactive TLC strips
3. Scissors
4. Sterile syringe, 1 cc
5. Sterile needles, 26 G.
6. Gamma counter or scintillation counter
7. Pipettor Procedure:
1. The entire Biodex Operation Manual should be read first.
2. Each radiolabeled sample in triplicate was tested according to kit instructions; one strip per vial was developed.
3. To spot the radiolabeled sample on the chromatography strip, a pipettor was used to spot 1 μl on the origin line. Alternatively, one small drop dispensed from a 26 G needle attached to a sterile 1 cc syringe may be spotted.
4. Each section was counted for activity using the appropriate counter, i.e., gamma counter for $^{111}$In and a scintillation counter for $^{90}$Y, adjusting for background.
5. The Biodex instructions for calculating the percentage of radiolabeled antibody were followed.

IV. Results

The results of testing on each validation lot of In2B8 or Y2B8 are summarized in Tables 38 and 39.

TABLE 38

Release Assay Results for Y2B8 Validation

| Lot Number | % Radioincorporation | % Binding |
|---|---|---|
| 1 | 99.5 | 78.6 |
| 2 | 99.3 | 87.0 |
| 3 | 99.4 | 85.9 |
| 4 | 99.2 | 81.8 |
| 5 | 99.2 | 79.6 |
| 6 | 96.3 | 80.8 |
| | Mean = 98.8 | Mean = 82.3 |
| | Standard Deviation = 1.24 | Standard Deviation = 3.4 |
| | % CV = 1.25% | CV = 4.2% |

TABLE 39

Release Assay Results for In2B8 Validation Lots

| Lot Number | % Radioincorporation | % Binding |
|---|---|---|
| 1 | 99.4 | 86.2 |
| 2 | 98.7 | 86.8 |
| 3 | 99.3 | 85.8 |
| 4 | 98.3 | 86.7 |
| 5 | 99.0 | 82.1 |
| 6 | 99.3 | 83.0 |
| | Mean = 99.0 | Mean = 85.2 |
| | Standard Deviation = 0.43 | Standard Deviation = 2.06 |
| | % CV = 0.45% | CV = 2.42% |

V. Discussion and Conclusions

To simplify the current radiolabeling methods for In2B8 and Y2B8, a four-component kit was developed. The concentrations of sodium acetate and 2B8-MX-DTPA were reduced to 50 mM and 2 mg/mL, respectively, to allow accurate volume transfers using syringes. All kit components were preferably filled in glass septum vials and tested for sterility and pyrogenicity by IDEC before release, thus eliminating the need for these tests to be performed at the clinical sites. At the site, all reagent manipulations are performed using sterile syringes and needles. Therefore, adherence to aseptic technique customarily found in a radiopharmacy environment insures that the radiolabeled and formulated anti-bodies are suitable for patient administration.

Reproducibility and ruggedness of the radiolabeling protocols for In2B8 and Y2B8 was evaluated by performing several validation runs using different lots of each radioisotope. For the six validation lots of In2B8 prepared, binding ranged from 82.1% to 86.8% with a mean of 85.1%; radioincorporation values for were approximately 99% (range of 98.3% to 99.4%). For the six validation lots of Y2B8 prepared, the percent binding obtained was in the ranged from 78.6% to 87.0% with a mean of 82.3%. Radioincorporation values for Y2B8 averaged 98.8% (range of 96.3% to 99.5%). Together, these results confirm the reproducibility and ruggedness of the radiolabeling kit methods for preparation of both In2B8 and Y2B8. Based on these validation results, it is recommended that release specifications for radioincorporation and binding be established at ≧95% and 270%, respectively, for both In2B8 and Y2B8.

Additionally, because of the increased ease of use and reduced potential for mistakes during preparation, it is recommended that percent binding using lyophilized CD20-positive cells and radioincorporation be used to release test In2B8 and Y2B8 at the clinical sites.

To summarize, these results together indicate that In2B8 and Y2B8 prepared using the radiolabeling kit are suitable for use in the clinical setting. Additionally, for both radiolabeled antibodies, release specifications are established reflecting the results of several validation runs by the five different operators.

EXAMPLE 2

Radioincorporation and Binding—Kits and Assays

I. Summary

The murine anti-CD20-monoclonal antibody designated 2B8 has been cloned in CHO cells to yield a high expression cell line. Specificity of the CHO-derived antibody for CD20-positive human cells was demonstrated by FACS analysis and competitive binding. Negligible binding was observed to human T-cells. The affinity of the antibody for CD20-positive cells was determined to be $1.3 \times 10^{-10}$ M using a competitive binding assay. The antibody was reacted with the chelating agent MX-DTPA to form a conjugate, 2B8-MX-DTPA, with negligible loss of immunoreactivity (affinity value was $4.4 \times 10^{-10}$ M. Optimal chelator conjugation, as determined by measuring radioincorporation of $^{111}$In, was achieved after eight hours reaction. Radiolabeling protocols for 2B8-MX-DTPA were optimized for $^{90}$Y or $^{111}$In with respect to pH and incubation time to insure maximal radioincorporation (≧95%) and retention of immunoreactivity (≧70%). Release specifications for In2B8 and Y2B8 prepared using CHO-derived 2B8-MX-DTPA in clinical trials were recommended for radioincorporation (≧95%) and binding to lyophilized and reconstituted CD20-positive human cells (≧70%). Taken together, these results indicate the suitability of CHO-derived 2B8-MX-DTPA for use in clinical trials.

II. Introduction

The 2B8 antibody previously used was produced in hollow-fiber bioreactors. To reduce the manufacturing costs of this antibody, it has been cloned and expressed in CHO cells to yield a high-expression production cell line. This example describes results of the in vitro characterization of the CHO-derived 2B8 antibody, the conjugated antibody (2B8-MX-DTPA), and the $^{90}$Y and $^{111}$In-labeled antibody products prepared using the clinical radiolabeling kit protocols.

III. Materials and Methods

A. Reagents

The human cell lines SB (CD20-positive) and HSB (CD20-negative) were obtained from American Type Culture Collection and cultured in T-flasks using RPMI-1640 containing 10% fetal bovine serum supplemented with 2% glutamine. Cultures were maintained at 37° C. and 5% $CO_2$. Cells were typically split 1:2 every other day and harvested at 0.5-2.5×$10^6$ cells/mL and viability's >80%. Cell concentrations were determined using a hemacytometer and viability determined by trypan blue exclusion. Specific information on cell lots is recorded in Notebook# 1553 and in the binder titled "Cell Activity Logbook 1995 & 1996" authored by Ron Morena.

CHO-derived 2B8 was produced under GMP conditions in IDEC's manufacturing facility. The antibody was formulated in low-metal normal saline at 11.5 mg/ml. Antibodies were determined to be homogeneous by SDS-PAGE. 2B8-MX-DTPA was produced under GMP conditions according to PSBR-043 from CHO-derived 2B8 and formulated in low-metal saline at 2 mg/mL (Lot #'s 0165A and 0.0165B).

Pharmaceutical-grade $^{111}$In chloride was purchased from Amersham (U.K.) or Cyclotron Products Inc. (Coral Gables, Fla.). Yttrium[90] chloride was obtained from Amersham (U.K.), Nordion International (Kanatta, Canada), or Pacific Northwest National Laboratory (Richland, Wash.). MX-DTPA prepared under GMP was obtained from Hauser Chemical (Boulder, Colo.). Clinical-grade calcium trisodium diethylenetriaminepentaacetic acid (DTPA) was obtained from Heyl (Berlin, Germany). TAG-NHS was obtained from IGEN Inc. (Rockville, Md.). Murine anti-CD19 beads were purchased from Dynal Inc. (Lake Success, N.Y.). Goat anti-mouse FITC-labeled F(ab')$_2$ was purchased from Jackson ImmunoResearch.

Reagents requiring removal of contaminating heavy metals were batch treated with Chelex 100 (BioRad Industries) or with Chelating Sepharose (Pharmacia) by passing solutions through a column. Low-metal stock solutions were diluted with Sterile Water for Irrigation (SWFIr). Solutions were stored in sterile plastic containers.

Additional reagents are described below for specific methods.

B. Materials and Equipment

1. Origen Analyzer; IGEN Inc. Model #1100-1000; IDEC #1492
2. Top-Count scintillation counter; Packard, Model #A9912; IDEC #1329
3. Gamma counter; Isodata, Model # 20-10; IDEC #0628
4. Tec-Control Radiochromatographic Kit, Biodex, Model #151-770
5. Lyophilizer; Virtis, Model Freezemobile 12; IDEC #0458

Additional materials and equipment are described for specific methods.

C. Methods

1. Preparation of Lyophilized SB and HSB Cell

Cells were cultured as described above and harvested at ambient temperature at a cell density of 0.5-2×$10^6$ cells/mL by centrifugation (1300 rpm in a Sorvall centrifuge) and washed twice with 1× HBSS. Pelleted cells were resuspended to 50×$10^6$ cells/mL in 1× HBSS containing 1% (w/v) bovine serum albumin (BSA) and 10% (w/v/) mannitol (lyophilization buffer), 0.5 mL dispensed into 1.5 mL polypropylene microfuge tubes with o-ring gaskets and stored at −70° C., and lyophilized overnight at 30-60 millitorr. Tubes of lyophilized cells were stored desiccated at 2-8° C. and reconstituted in sterile water for assays; tubes of cells lyophilized in microfuge tubes were stored with desiccant.

2. FACS Binding Analysis

Direct binding of antibodies to human B-cells was determined by flow cytometry. Increasing concentrations of antibody were incubated in 1× PBS, pH 7.2, containing 1% (w/v) BSA (binding buffer) with 5×$10^6$ CD20-positive (SB) or CD20-negative (HSB) cells for 30 min. on ice. Cells were washed by centrifugation, resuspended in binding buffer, and incubated with FITC-labeled goat anti-mouse F(ab')$_2$ for 30 min. on ice. After incubation with the secondary reagent, cells were washed by centrifugation and resuspended in 1× PBS containing 1.1% (v/v) formaldehyde to fix cells. Mean fluorescence intensity was determined using flow cytometry.

3. Competitive Binding Assays

Immunoreactivity of 2B8 and 2B8-MX-DTPA was determined by competitive binding to CD20-positive SB cells using the ORIGEN electrochemiluminescent method (Leland and Powell). Log-phase SB cells were harvested from culture and washed twice with 1× HBSS. Cells were diluted in 1× PBS pH 7.2 containing 1% (w/v) bovine serum albumin. In some experiments, lyophilized cells were used after reconstitution with sterile water.

Ruthenium-labeled tracer antibody was prepared by incubating CHO-derived 2B8 (lot #165) in 1× PBS, pH 7.2 with the N-hydroxysuccinimide ester of ruthenium (II) tris-bipyridine chelator (TAG-NHS) at a 15:1 molar ratio of TAG-NHS to antibody. After 1 h incubation at ambient temperature, protected from light, the reaction was quenched with glycine for 10 min. Unreacted TAG was removed by size exclusion chromatography using a Pharmacia PD-10 column equilibrated with 1× PBS. Protein concentration was determined using the Bradford protein assay. TAG incorporation was determined by measuring absorbance at 455 nm. The molar ratio of TAG to protein was calculated to be 3.0.

Assays were performed in 12×75 mm polypropylene tubes. Varying amounts of competing antibody (0.002-17 ug/mL) were incubated in 1× PBS, pH 7.2, containing 1% (w/v) BSA with 0.08 ug/mL TAG-labeled CHO 2B8, 0.08 mg/mL anti-CD19 beads, and 167,000 cells/mL. After incubation at ambient temperature with orbital mixing for 3 h, relative electrochemiluminescence (ECL) was determined using the ORIGEN instrument. Mean ECL values were determined for duplicated samples and plotted vs. competing antibody concentration using Kaleidagraph software. For some experiments, percent inhibition was plotted. Competition curves were fitted and EC 50 values (antibody concentration giving 50% maximal binding) determined using the following 4-parameter program:

$$y=((m1-m4)/(1+(m0/m3)\hat{\ }m2))+m4; m1=; m2=; m3=; m4=$$

m0=independent variable
m1=zero signal response in relative ECL units
m2=curvature parameter m3=EC50 in ug/mL m4=maximum signal response in relative ECL units Average affinity values were calculated from EC50 values and the known concentration of trace antibody using the method of Muller.

4. Preparation of 2B8-MX-DTPA

The chelating agent, 1-isothiocyanatobenzyl-3-methyldiethylenetriaminepentaacetic acid (MX-DTPA) was provided as a dry powder (free-acid) and stored desiccated at −20° or −70° C. Approximately 3 mg of CHO 2B8 antibody in low-metal normal saline were adjusted to pH 8.6 by adding one-tenth volume of 50 mM sodium borate, pH 8.6. Antibody at 10-11 mg/mL was incubated at a 4:1 molar ratio of MX-DTPA to protein by adding MX-DTPA dissolved in 50 mM sodium borate, pH 8.6. After incubation at ambient temperature (2 to 24 h), unreacted chelator was removed from the conjugate by repetitive diafiltration in low-metal normal saline using Centricon 30 spin-filters.

5. Preparation of In2B8 and Y2B8

In2B8 was prepared using the radiolabeling kit protocol as described herein. Antibody was labeled at a specific activity of 3 mCi/mg and formulated to 0.2 mg/mL. Briefly, 0.5 to 2 mCi of $^{111}$In chloride was transferred to a metal-free microfuge tube and adjusted to approximately pH 4.2 using a 1.2× volume of low-metal 50 mM sodium acetate. 2B8-MX-DTPA at 2 mg/mL was added to the indium acetate solution and after incubation at ambient temperature for 30 min., the labeled antibody was formulated to 0.2 mg/mL in 1× PBS, pH 7.2 containing 7.5% (w/v) human serum albumin and 1 mM DTPA (4% to 6% final concentration of HSA). All samples were tested for radioincorporation in triplicate; values were >95%.

Y2B8 was also prepared using a small-scale version of the radiolabeling kit protocol described in Example 1. Antibody was labeled at a specific activity of 15 mCi/mg and formulated to 0.3 mg/mL. Briefly, 0.5 to 2 mCi of $^{90}$Y chloride was transferred to a metal-free microfuge tube and adjusted to approximately pH 4.2 using a 1.2× volume of low-metal 50 mM sodium acetate. 2B8-MX-DTPA at 2 mg/mL was added to the $^{90}$Y acetate solution and after incubation at ambient temperature for 5 min., the labeled antibody was formulated to 0.3 mg/mL in 1×PBS, pH 7.2 containing 7.5% (w/v) human serum albumin and 1 mM DTPA (final concentration of HSA, 4% to 6%). All samples were tested for radioincorporation in triplicate; values were >95%.

The radioactivity concentrations of the final radiolabeled products were calculated based on the amount of radioactivity added to the reaction mixture and by reference to the Certificate of Analysis for the radioisotope. Antibody concentration of the quenched reaction mixtures were calculated from the known amount of antibody added.

For radiolabeling kinetic studies evaluating the effect of pH on radioincorporation and binding, the pH of the reaction mixtures was adjusted. by adding varying amounts of low-metal 50 mM sodium acetate (0.8 to 2.2× volume of radio-isotope solution).

6. Determination of Radioincorporation for In2B8 and Y2B8

The amount of radioactivity associated with the conjugates (radioincorporation) in the final products or incubation samples was determined using a commercially available kit manufactured by Biodex (Tec-Control Radiochromatographic Kit; see Example 1). In general, 1 μL of the test samples were applied in duplicate or triplicate using a micropipetter and developed according to the Biodex instructional insert. Strip halves were counted for radioactivity in glass tubes using an Isodata gamma counter or a Packard Top Count scintillation counter as described below. The radiolabel incorporation was calculated by dividing the amount of radioactivity in the top half of the strip by the total radioactivity found in both top and bottom halves. This value was expressed as a percentage and the mean value determined.

7. Determination of Immunoreactivity of In2B8 and Y2B8

Immunoreactivity was assessed using the method of Lindmo et al and as described above in Example 1.

8. Direct Binding Assay for In2B8 and Y2B8

The same protocols as described herein were used to determine binding to CD20-positive SB cells for In2B8 and Y2B8, respectively. In2B8 and Y2B8 were prepared and formulated as described above. For assay, In2B8 or Y2B8 samples were diluted with assay dilution buffer (1× PBS, pH 7.2, containing 1% (w/v) bovine serum albumin (BSA) to 40 ng/mL and 11 ng/mL, respectively.

Antigen-positive (SB) and antigen-negative (HSB) cells were maintained in RPMI 1640 supplemented with 10% fetal calf serum at 37° C. and 5% $CO_2$. Cells (viability>90% as determined by trypan blue exclusion) were harvested at ambient temperature at a cell density of $0.5-2\times10^6$ cells/mL by centrifugation (1300 rpm in a Sorvall centrifuge) and washed twice with 50 mL 1× HBSS. Pelleted cells were resuspended to $50\times10^6$ cells/mL in prechilled 1× HBSS containing 1% (W/v) bovine serum albumin (BSA) and 10% (w/v/) mannitol (lyophilization buffer). Cell suspensions were dispensed into 1.5 mL polypropylene microfuge tubes with o-ring gaskets at $50\times10^6$ cells/mL (0.5 mL per tube) and lyophilized overnight at 30 to 60 millitorr. Lyophilized cells were stored desiccated at 2-8° C. and reconstituted in sterile water for assays.

Lyophilized SB and HSB cells in 1.5 mL polypropylene tubes were reconstituted to $50\times10^6$ cells/mL using sterile water. Diluted In2B8 or Y2B8 was added to cells, in triplicate, and incubated for 45 to 60 min with end-over-end mixing at ambient temperature, respectively. After incubation, cells were pelleted by centrifugation and cell-bound radioactivity determined by counting samples in an Isodata Gamma Counter or a Packard Top Count scintillation counter as described below. Radioactivity bound (B) to cells was calculated by subtracting the unbound radioactivity (supernatant) from the total radioactivity added. Total radioactivity was determined from the radioactivity counted in tubes without cells. Percent binding was calculated by expressing the bound counts as a percentage of the total counts.

9. Radioactivity Measurement

Radioincorporation samples were counted for 1 min. using an Isodata gamma counter. The counter was set for energy windows of 100-500 KeV and the background adjusted to zero immediately before use for samples using $^{111}$In. The Isodata gamma counter was also used for counting ITLC strips having $^{90}$Y spotted on them. The energy windows for detection of the bremstrulung radiation were 100-1000 KeV.

For the binding assays, $^{90}$Y samples were transferred to 24-well plates and MicroScint 40 cocktail and counted in a Packard TopCount for 1 min using minimum and maximum energy settings. Indium-[111] samples were counted for 1 min. using an Isodata gamma counter. The counter was set for energy-windows of 100-500 KeV and the background adjusted to zero immediately before use.

10. Release Specifications for Clinical Doses of In2B8 and Y2B8

Release specifications for radioincorporation and binding to CD20-positive cells were established by preparing six doses each of In2B8 and Y2B8 using two lots of clinical-grade 2B8-MX-DTPA (lot #'s 0219 and 0220) prepared according to the present invention and filled under GMP conditions. Release assays were performed as described above.

IV. Results

A. Characterization of CHO-Derived 2B8

Using flow cytometric analysis, it was demonstrated that CHO 2B8 binds directly to CD20-positive SB cells without binding to CD20-negative HSB cells (FIG. 34). No significant binding to SB or HSB cells was noted for art irrelevant isotype (γ1κ) antibody (S004).

Binding of CHO 2B8 to CD20-positive cells was evaluated in competition assays using the ORIGEN chemiluminescent detection system. Lyophilized and reconstituted antigen-positive SB cells were incubated with increasing amounts bf antibody in the presence of ruthenium-labeled CHO-2B8 tracer. Results showed that CHO 2B8 inhibits binding to CD20-positive cells to the same extent as the antibody derived from hollow-fiber bioreactors (2B849) (FIG. 35). The EC50 values were determined graphically and the method of Muller (1980) used to calculate average affinity values. The affinity for CHO 2B8 was determined to be $1.3 \times 10^{-10}$ M; the 2B8 antibody derived from hollow-fiber bioreactors gave an affinity value of $2.5 \ 10^{-10}$ M. Non-specific binding was negligible as demonstrated by the lack of competition with the irrelevant isotype antibody, S004.

B. Characterization of CHO-Derived 2B8-MX-DTPA

The 2B8 conjugate (2B8-MX-DTPA) was prepared using a protocol similar to that used for the previously characterized 2B8-49. Reactions were performed using approximately 3 mg of antibody and a 4:1 molar ratio of chelator to antibody. Incubations times of 2, 4, 8, 17, and 24 h were evaluated to determine the reaction time giving acceptable retention of binding to CD20 positive cells and high radioincorporation with $^{111}$In. Competitive binding curves comparing CHO 2B8 to CHO 2B8-MX-DTPA conjugate reacted for 8-24 h were similar indicating that the conjugation process did not significantly alter the binding of the antibody to the CD20 antigen (FIG. 36). Using EC 50 values determined graphically (FIG. 36), affinity constants for the unconjugated and conjugated antibodies ranged from $2.3 \times 10^{-10}$ M to $5.9 \times 10^{-10}$ M (Table 40). Radioincorporation was >95% for conjugation times of 8 to 24 h (Table 30).

TABLE 40

Effect of Conjugation Reaction Time on Radioincorporation and Immunoreactivity of CHO 2B8-MX-DTPA

| Incubation Time (h) | Radioincorporation (%) | Affinity (M) |
| --- | --- | --- |
| 0 | ND | $2.3 \times 10^{-10}$ |
| 2 | 83.5 | ND |
| 4 | 90.5 | ND |
| 8 | 96.1 | $5.9 \times 10^{-10}$ |
| 17 | 97.3 | $5.9 \times 10^{-10}$ |
| 24 | 98.8 | $4.4 \times 10^{-10}$ |

C. Characterization of In2B8 and Y2B8 Prepared From CHO-derived 2B8-MX-DTPA

Indium-[111]-labeled CHO 2B8-MX-DTPA (In2B8) was prepared using the small-scale radiolabeling kit protocol previously described for the hollow-fiber bioreactor-derived antibody (Example 1). Briefly, conjugated antibody (CHO-derived 2B8-MX-DTPA; lot # 0165A) was incubated with $^{111}$In acetate at the indicated pH for 30 minutes at ambient temperature. Reaction mixtures were formulated with PBS, pH 7.2, containing 7.5% (w/v) human serum albumin and 1 mM DTPA. Formulated samples of In2B8 were assayed for radioincorporation using instant thin-layer chromatography. Binding of In2B8 to CD20-positive cells was determined using lyophilized and reconstituted SB cells. For comparison, the conjugate prepared from hybridoma-produced antibody (2B8-49) was incubated with $^{111}$In acetate for 30 min. at pH 4.2 (conditions previously established for this antibody).

Kinetics studies were performed to determine labeling conditions providing maximal retention of binding to CD20-positive cells and high radioincorporation (Tables 41 and 42). Conjugated antibody (CHO-derived 2B8-MX-DTPA) was incubated at ambient temperature with $^{111}$I acetate at pH 4.2 for the times indicated (Table 42).

TABLE 41

In2B8 Radiolabeling Kinetics: Effect of pH on Radioincorporation and Binding to CD20-Positive Cells

| Reaction pH | Radioincorporation (%) | Binding (%) |
| --- | --- | --- |
| 3.0 | 97.7 | 85.3 |
| 3.7 | 98.5 | 83.9 |
| 4.0 | 98.6 | 84.1 |
| 4.3 | 98.0 | 84.0 |
| 4.6 | 98.9 | 83.4 |
| Control (2B8-49) | 99.3 | 86.5 |

TABLE 42

In2B8 Radiolabeling Kinetics: Effect of Incubation Time on Radioincorporation and Binding to CD20-Positive Cells

| | Incubation Time (min) | Radioincorporation (%) | Binding (%) |
| --- | --- | --- | --- |
| pH 2.9: | 15 | 97.2 | 85.3 |
| | 30 | 99.1 | 85.2 |
| | 45 | 97.2 | 84.8 |
| pH 4.6: | 15 | 99.0 | 87.2 |
| | 30 | 97.2 | 86.8 |
| | 45 | 99.4 | 86.3 |
| Control (2B8-49) | | 99.4 | 87.8 |

Results demonstrated that for the range of pH 3.0 to 4.6 and an incubation time of 30 min, >97% radioincorporation of the radioisotope was attained while maintaining binding at approximately 84%. Radioincorporation and binding values were invariant for incubation times of 15 to 45 min for reactions at pH 2.9 to 4.6 (Table 42). Results were comparable to those obtained using the 2B8-49 antibody (Tables 41 and 42).

Yttrium-[90]-labeled antibody was prepared by incubating conjugated antibody (CHO-derived 2B8-MX-DTPA) with $^{90}$Y acetate at the indicated pH for 5 minutes at ambient temperature. Reaction mixtures were formulate in PBS, pH 7.2 containing 7.5% (w/v) human serum albumin and 1 mM DTPA. Formulated samples of Y2B8 were assayed for radioincorporation using instant thin-layer chromatography. Binding of Y2B8 to CD20-positive cells was determined using lyophilized and reconstituted SB cells. For comparison, the conjugate prepared from hybridoma-produced antibody (2B8-49) was incubated with $^{90}$Y acetate for 5 min. at pH 4.2 (conditions previously established for this antibody).

Similar kinetic studies were performed to evaluate the preparation of the $^{90}$Y-labeled antibody (Y2B8). For radiolabeling reactions in the range of pH 3.9 to 4.7 at an incubation time of 5 min, radioincorporation was >96% with >80% retention of binding to CD20-positive cells (Table 43). Similar results were obtained for incubation times of 3, 5, and 10 min for the range of pH 2.9 to 4.6 (Table 44). Then, conjugated antibody (CHO-derived 2B8-MX-DTPA) was incubated at ambient temperature with $^{90}$Y acetate at pH 4.2 for the times indicated (Table 44). Results were comparable to those obtained using the 2B849 antibody (Tables 43 and 44).

TABLE 43

Y2B8 Radiolabeling Kinetics: Effect of pH on Radioincorporation and Binding to CD20-Positive Cells

| Reaction pH | Radioincorporation (%) | Binding (%) |
|---|---|---|
| 3.9 | 98.4 | 80.7 |
| 4.2 | 97.8 | 81.0 |
| 4.4 | 96.1 | 80.0 |
| 4.6 | 97.0 | 80.2 |
| 4.7 | 97.4 | 80.6 |
| Control (2B8-49) | 99.3 | 82.6 |

TABLE 44

Y2B8 Radiolabeling Kinetics: Effect of Incubation Time on Radioincorporation and Binding to CD20-Positive Cells

| Incubation Time (min) | Radioincorporation (%) | Binding (%) |
|---|---|---|
| pH 3.9: 3 | 97.0 | 82.0 |
| 5 | 98.9 | 82.1 |
| 10 | 99.2 | 82.3 |
| pH 4.7: 3 | 97.2 | 82.5 |
| 5 | 96.7 | 81.8 |
| 10 | 97.6 | 81.5 |
| Control (2B8-49) | 99.2 | 84.2 |

Immunoreactivities for In2B8 and Y2B8 prepared from CHO 2B8 were determined using the method of Lindmo et al. Increasing amounts of freshly harvested CD20-positive SB cells were incubated with a fixed amount of In2B8 or Y2B8 under conditions of antigen excess. Reciprocal plot analysis of the binding data allowed immunoreactivities of 80.6% and 72.2% for In2B8 and Y2B8, respectively, to be determined (FIGS. 37 and 38).

D. Release Specifications for CHO-Derived In2B8 and Y2B8

Two lots of clinical-grade In2B8/Y2B8 radiolabeling kits were used to prepare six lots each of In2B8 and Y2B8. In2B8 and Y2B8 were prepared using small-scale versions of the radiolabeling protocols currently used in the clinical trials. Each lot of radiolabeled 2B8-MX-DTPA was tested for radioincorporation and binding to CD20-positive (SB) and CD20-negative (HSB) human cells. These results are summarized in Tables 45 and 46. For the six lots of In2B8 prepared, radioincorporation ranged from 98.9% to 99.3% with a mean of 99.1%. Binding to CD20-positive cells ranged from 81.9% to 85.1% with a mean of 83.6%; binding to CD20-negative cells was <4%. For the six lots of Y2B8 prepared, radioincorporation ranged from 97.4% to 98.7% with a mean of 98.2%. Binding to CD20-positive cells ranged from 81.4% to 82.7% with a mean of 81.9%; binding to CD20-negative cells was <8%.

TABLE 45

Release Assay Results for CHO-Derived In2B8 Prepared Using the Radiolabeling Kit Protocol

| Run # | Radioincorporation (%) | Binding (%) SB Cells | HSB Cells |
|---|---|---|---|
| #1 (Lot #0219) | 99.1 | 81.9 | 2.8 |
| #2 (Lot #0219) | 99.3 | 83.2 | 2.8 |
| #3 (Lot #0219) | 99.2 | 83.6 | 3.7 |
| #4 (Lot #0220) | 99.0 | 83.8 | 2.6 |
| #5 (Lot #0220) | 98.9 | 84.1 | 2.6 |
| #6 (Lot #0220) | 98.9 | 85.1 | 3.3 |
| | Mean = 99.1% | Mean = 83.6% | Mean = 2.9% |
| | SD = 0.2% | SD = 1.1% | SD = 0.4% |

TABLE 46

Release Assay Results for CHO-Derived Y2B8 Prepared Using the Radiolabeling Kit Protocol

| Run # | Radioincorporation (%) | Binding (%) SB Cells | HSB Cells |
|---|---|---|---|
| #1 (Lot #0219) | 98.7 | 82.1 | 7.4 |
| #2 (Lot #0219) | 98.6 | 82.7 | 0.7 |
| #3 (Lot #0219) | 98.3 | 82.2 | 7.2 |
| #4 (Lot #0220) | 97.4 | 81.8 | 1.7 |
| #5 (Lot #0220) | 97.6 | 81.4 | 2.2 |
| #6 (Lot #0220) | 98.4 | 81.4 | 1.1 |
| | Mean = 98.2% | Mean = 81.9% | Mean = 3.4% |
| | SD = 0.5% | SD = 0.5% | SD = 3.1% |

V. Discussion and Conclusions

The anti-CD20 murine monoclonal antibody (2B8) cloned and expressed in CHO cells (CHO-derived 2B8) maintains specificity for CD20-positive human cells as shown by FACS and competitive binding analysis. Binding to human T-cells was minimal. The affinity of the antibody for human CD20-positive cells was determined to be $1.3 \times 10^{-10}$ M using a competitive binding assay. Using the same assay, the 2B8 antibody derived from hollow-fiber bioreactors gave an affinity value of $2.5 \times 10^{-10}$ M.

The CHO 2B8 antibody was reacted with MX-DTPA to form a conjugate, 2B8-MX-DTPA, while maintaining suitable retention of immunoreactivity. Optimal chelator incorporation was determined by measuring radioincorporation with $^{111}$In and was achieved after eight hours incubation at ambient temperature. Radiolabeling protocols for the 2B8-MX-DTPA conjugate were optimized for $^{90}$Y or $^{111}$In with respect to pH and incubation time to insure maximal radioincorporation and retention of immunoreactivity.

The results of several preparations of In2B8 and Y2B8 demonstrate the reproducibility of the radiolabeling protocol used to prepare clinical doses. Based on these radiolabeling results, it is suggested that release specifications for radioincorporation and binding, using lyophilized CD20-positive cells, be established at $\geq 95\%$ and $\geq 70\%$, respectively. Taken together, these results demonstrate the comparability of CHO-derived 2B8 and hollow-fiber-derived 2B8-49, and indicate the suitability of the CHO-derived 2B8-MX-DTPA for use in clinical trials.

Finally, the present invention discloses a labeling procedure, referred to as the "mix-and-shoot" method, for the preparation of clinical doses of radiolabeled antibodies which obviates the need for the currently used high performance liquid chromatographic (HPLC) step for removal of non-protein bound radioisotope. The simplified protocol eliminates this laborious purification step while maintaining a high level of radioisotope incorporation (>95%) and improved retention of immunoreactivity (>70%). The clinically-formulated radiolabeled conjugate was found to be stable in vitro when incubated at 4° C. for 48 hours based on retention of radioisotope and immunoreactivity. Additionally, the radiolabeled conjugate was stable when incubated in human serum at 37° C. for 72 hours. Biodistribution studies in -BALB/c mice demonstrated no unusual tissue deposition, and no significant accumulation in the bone. Estimates of radiation absorbed doses to a "standard" 70 Kg human were comparable to those obtained in an, on-going clinical trial using $^{90}$Y-labeled 2B8-MX-DTPA. The results of these studies showed that $^{90}$Y-labeled 2B8-MX-DTPA produced using the "mix-and-shoot" protocol was comparable to that prepared using the conventional HPLC process. Validation of the scale-up protocol for preparing clinical-grade radiolabeled conjugate showed that the method was reproducible and that the product was comparable to that produced using the current HPLC method. The results of these pre-clinical studies indicate that this new "mix-&-shoot" protocol can be used to prepare $^{90}$Y-labeled 2B8-MX-DTPA suitable for use in clinical trials.

REFERENCES

Each of the following citations is herein incorporated by reference:
1. Adams, R. A., Flowers, A., and Davis, B. J. Direct Implantation and Transplantation of Human Acute Lymphoblastic Leukemia in Hamsters, SB-2. Cancer Research 28: 1121-1125, 1968.
2. Adams, R. A. Formal Discussion: The Role of Transplantation in the Experimental Investigation of Human Leukemia and Lymphoma. Cancer Res. 27(1): 2479-2482, 1967.
3. Lindmo, T., Boven, E., Cuttitta, F., Fedoroko, J., and Bunn, P. A., J. Immunol. Methods, 72: 77-1984.
4. Kozak, R. W., Raubitschek, A., Mirzadeh, S., Brechbiel, M. W., Junghaus, R., Gansow, O. A., and Waldmann, T. A. Cancer Res. (1989) 49: 2639-2644.
5. Parker, B. A., Halpern, S. E., Miller, R. A., Hupf, H., Shawler, D. L., Collins, H. A., Amox, D., White, C. A. and Royston, I. N. Eng. J. Med., submitted.
6. Leland, J. K. and Powell, M. J. J. (1990) Electrochem. Soc. 137, 3127.
7. Muller, R. J. Immunological Methods (1980) 34, 345.
8. Mirzadeh, S., Brechbiel, M. W., Atcher, R. W. and Gansow, O. A. (1990) Bioconjugate Chemistry 1(1), 59.
9. Brechbiel, M. W., Gansow, O. A., Atcher, R. W., Sclom, J., Esteban, J., Simpson, D. E. and Colcher, D. (1986) 25, 2772.

What is claimed:
1. A method for radiolabeling a chelator-conjugated antibody with $^{90}$Y, comprising:
   (i) mixing chelator-conjugated antibody with a solution containing $^{90}$Y; and
   (ii) incubating the mixture for a time between 3 and 10 minutes at appropriate temperature to produce a radiolabeled antibody having sufficient radioincorporation and specific activity of about 3.2 mCi/mg to about 16.7 mCi/mg, without further purification of the radiolabeled antibody from unincorporated radiolabel.
2. The method of claim 1, wherein the chelator is selected from the group consisting of MX-DTPA, phenyl-DTPA, benzyl-DTPA, CHX-DTPA and DOTA.
3. The method of claim 2, wherein the chelator is MX-DTPA.
4. The method of claim 2, wherein the antibody is an anti-CD20 antibody.
5. The method of claim 4, wherein the antibody is a chimeric anti-CD20 antibody.
6. The method of claim 4, wherein the anti-CD20 antibody is 2B8.
7. The method of claim 4, wherein the chelator-conjugated anti-CD20 antibody is 2B8-MX-DTPA.
8. The method of claim 1, wherein the solution containing the radiolabel is adjusted to a pH of about 3 to 6 before it is mixed with the chelator-conjugated antibody.
9. The method of claim 8, wherein the pH is adjusted with a sodium acetate solution.
10. The method of claim 9, wherein the sodium acetate is at a concentration of about 10 to 1000 mM.
11. The method of claim 1, wherein the radiolabeled antibodies produced in step (ii) have at least 70% immunoreactivity.
12. The method of claim 1, wherein the radiolabel is 90Y chloride, and the formulation buffer comprises a radioprotectant that inhibits radiolysis of the 90Y-labeled antibody selected from human serum albumin (HSA) and free-radical scavengers.
13. The method of claim 12, wherein the specific activity of the 90Y -labeled antibodies is in the range of 10-15 mci/mg antibody.
14. The method of claim 12, wherein the volume quantity of 90Y chloride used is between about 5 to 100 mCi divided by the radioactivity concentration at the time of labeling.
15. The method of claim 14, wherein the volume quantity of 90Y chloride used is about 45 mCi divided by the radioactivity concentration at the time of labeling.
16. The method of claim 12, wherein about 1 to 2 ml of MX-DTPA-conjugated antibody at a concentration of about 0.5 to 30 mg/ml is mixed with the radiolabel solution.
17. The method of claim 12, wherein the chelator is MX-DTPA.
18. The method of claim 1, wherein the formulation buffer is added in an amount necessary to achieve a total final volume of about 10 ml to about 50 ml.
19. The method of claim 1, further comprising diluting the radiolabeled antibody to an appropriate concentration in formulation buffer for administration to a human patient.
20. The method of claim 19, wherein the mixture is incubated for 3 minutes.
21. The method of claim 19, wherein the mixture is incubated for 5 minutes.
22. The method of claim 19, wherein the formulation buffer contains physiological saline, a radioprotectant, and unconjugated chelator.
23. The method of claim 22, wherein the radioprotectant is selected from the group consisting of human serum albumin (HSA), ascorbate, ascorbic acid, phenol, sulfites, glutathione, cysteine, gentisic acid, nicotinic acid, ascorbyl palmitate, HOP(:O)H$_2$, glycerol, sodium formaldehyde sulfoxylate, Na$_2$S$_2$O$_5$, Na$_2$S$_2$O$_3$ and SO$_2$.
24. The method of claim 22, wherein the unconjugated chelator is DTPA or EDTA.
25. A method for radiolabeling a chelator-conjugated antibody with 90Y, comprising:
   (i) mixing chelator-conjugated antibody with a solution containing 90Y; and
   (ii) incubating the mixture for 3-10 minutes at an appropriate temperature to produce a radiolabeled antibody having sufficient radioincorporation of at least 95%; and
   (iii) diluting the radiolabeled antibody to an appropriate concentration in formulation buffer for administration to a human patient without further purification of the radiolabeled antibody from unincorporated radiolabel.

26. The method of claim 25, wherein the mixture is incubated for 3 minutes.

27. The method of claim 25, wherein the mixture is incubated for 5 minutes.

* * * * *

UNITED STATES PATENT AND TRADEMARK OFFICE
CERTIFICATE OF CORRECTION

| | |
|---|---|
| PATENT NO. | : 7,608,241 B2 |
| APPLICATION NO. | : 11/033439 |
| DATED | : October 27, 2009 |
| INVENTOR(S) | : Paul Chinn et al. |

It is certified that error appears in the above-identified patent and that said Letters Patent is hereby corrected as shown below:

On the Title Page, Item (*) Notice, please insert --This patent is subject to a terminal disclaimer.--.

Column 3, Line 30, "then-expressed" should read --then expressed--.
Column 4, line 20, "2002), and antibodies" should read --2002), are radiolabeled therapeutic antibodies--.
Column 6, line 56, "is" should read --are--.
Column 7, line 7, "sterile;" should read --sterile,--.
Column 7, line 65, "minimize" should read --minimizes--.
Column 8, line 38, "Although" should read --although--.
Column 9, line 40, "agents. Although other" should read --agents. Other--.
Column 13, line 67, "measure" should read --measured--.
Column 15, line 54, "results, show" should read --results show--.
Column 21, line 12, "defied" should read --defined--.
Column 22, line 14, "(WFIr)" should read --(WFIr),--.
Column 54, line 10, "2B8" should read --2B8,--.
Column 60, line 13, "With" should read --with--.
Column 65, line 43, "be-obtained" should read --be obtained--.
Column 65, line 50, "methods" should read --method.--.
Column 70, line 6, "syringe, was vented the" should read --syringe, the--.
Column 70, line 23, "needle fitted" should read --needle was fitted--.
Column 74, line 16, "was" should read --were--.
Column 77, line 9, "(MX-DTPA)" should read --(MX-DTPA),--.
Column 77, line 51, "were" should read --was--.
Column 77, line 65, "were" should read --was--.
Column 84, line 25, "mci/mg" should read -- mCi/mg--.

Signed and Sealed this
Fifteenth Day of March, 2011

David J. Kappos
*Director of the United States Patent and Trademark Office*